United States Patent
Cameron et al.

(10) Patent No.: US 10,597,648 B2
(45) Date of Patent: *Mar. 24, 2020

(54) ENGINEERED CASCADE COMPONENTS AND CASCADE COMPLEXES

(71) Applicant: Caribou Biosciences, Inc., Berkeley, CA (US)

(72) Inventors: Peter Sean Cameron, San Francisco, CA (US); Sanne Eveline Klompe, New York, NY (US); Samuel Henry Sternberg, New York, NY (US)

(73) Assignee: Caribou Biosciences, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/665,316

(22) Filed: Oct. 28, 2019

(65) Prior Publication Data

US 2020/0048622 A1    Feb. 13, 2020

Related U.S. Application Data

(63) Continuation of application No. 16/420,061, filed on May 22, 2019, now Pat. No. 10,457,922, which is a continuation of application No. 16/262,773, filed on Jan. 30, 2019, now Pat. No. 10,329,547, which is a continuation of application No. 16/104,875, filed on Aug. 17, 2018, now Pat. No. 10,227,576.

(60) Provisional application No. 62/684,735, filed on Jun. 13, 2018.

(51) Int. Cl.
| | |
|---|---|
| C12N 15/11 | (2006.01) |
| C12N 9/22 | (2006.01) |
| C07K 7/06 | (2006.01) |
| C07K 7/08 | (2006.01) |
| C12N 15/90 | (2006.01) |
| C07K 14/00 | (2006.01) |
| C12N 15/113 | (2010.01) |

(52) U.S. Cl.
CPC .......... *C12N 9/22* (2013.01); *C07K 7/06* (2013.01); *C07K 7/08* (2013.01); *C07K 14/00* (2013.01); *C12N 15/11* (2013.01); *C12N 15/113* (2013.01); *C12N 15/902* (2013.01); *C12N 15/907* (2013.01); *C07K 2319/00* (2013.01); *C07K 2319/09* (2013.01); *C07K 2319/21* (2013.01); *C07K 2319/22* (2013.01); *C07K 2319/50* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 8,865,406 B2 | 10/2014 | Zhang et al. |
| 8,993,233 B2 | 3/2015 | Zhang et al. |
| 9,856,497 B2 | 1/2018 | Qi et al. |
| 9,885,026 B2 | 2/2018 | Brouns et al. |
| 9,982,267 B2 | 5/2018 | Del'Guidice et al. |
| 2010/0076057 A1 | 3/2010 | Sontheimer et al. |
| 2013/0130248 A1 | 5/2013 | Haurwitz et al. |
| 2014/0186843 A1 | 7/2014 | Zhang et al. |
| 2014/0294773 A1 | 10/2014 | Brouns et al. |
| 2014/0295556 A1 | 10/2014 | Joung et al. |
| 2014/0302563 A1 | 10/2014 | Doudna et al. |
| 2014/0315985 A1 | 10/2014 | May et al. |
| 2015/0044772 A1 | 2/2015 | Zhao |
| 2015/0133315 A1 | 5/2015 | Jacobson et al. |
| 2015/0152398 A1 | 6/2015 | Doudna et al. |
| 2015/0376586 A1 | 12/2015 | May et al. |
| 2016/0053272 A1 | 2/2016 | Wurtzel et al. |
| 2016/0053304 A1 | 2/2016 | Wurtzel et al. |
| 2016/0186214 A1* | 6/2016 | Brouns .......... C12N 15/62 435/91.5 |
| 2016/0208243 A1 | 7/2016 | Zhang et al. |
| 2016/0215300 A1 | 7/2016 | May et al. |
| 2016/0345578 A1 | 12/2016 | Barrangou et al. |
| 2016/0355796 A1 | 12/2016 | Davidson et al. |
| 2017/0028083 A1 | 2/2017 | Beisel et al. |
| 2017/0080107 A1 | 3/2017 | Chivukula et al. |
| 2017/0151282 A1 | 6/2017 | Discher et al. |
| 2017/0204372 A1 | 7/2017 | Mohler et al. |

(Continued)

FOREIGN PATENT DOCUMENTS

| | | |
|---|---|---|
| WO | WO 2013098244 | 7/2013 |
| WO | WO 2014018423 | 1/2014 |

(Continued)

OTHER PUBLICATIONS (Gleditzsch, D., et al.) Modulating the Cascade architecture of a minimal Type 1-F CRISPR-Cas system. Nucleic Acids Research. Jul. 8, 2016, Epub May 23, 2016, vol. 44, No. 12; pp. 5872-5883;.
(Tsai, Sq et al.,) Dimeric CRISPR RNA-guided FokI nucleases for highly specific genome editing. Nature Biotechnology. Jun. 2014, Epub Apr. 25, 2014, vol. 32, No. 6; pp. 569-576;.
Wright, et al., "Biology and Applications of CRISPR Systems: Harnessing Nature's Toolbox for Genome Engineering," Cell, vol. 164, Jan. 14, 2016.
U.S. Appl. No. 14/997,474, filed Jan. 15, 2016, U.S. Pat. No. 9,885,026, Feb. 6, 2018.

(Continued)

*Primary Examiner* — Catherine S Hibbert
(74) *Attorney, Agent, or Firm* — Barbara G. McClung; Katharina F. S. Stengel

(57) ABSTRACT

The present disclosure provides engineered Class 1 Type I CRISPR-Cas (Cascade) systems that comprise multi-protein effector complexes, nucleoprotein complexes comprising Type I CRISPR-Cas subunit proteins and nucleic acid guides, polynucleotides encoding Type I CRISPR-Cas subunit proteins, and guide polynucleotides. Also, disclosed are methods for making and using the engineered Class 1 Type I CRISPR-Cas systems of the present invention.

20 Claims, 48 Drawing Sheets

Specification includes a Sequence Listing.

(56) References Cited

U.S. PATENT DOCUMENTS

| | | |
|---|---|---|
| 2017/0239370 A1 | 8/2017 | Zhu et al. |
| 2017/0260546 A1 | 9/2017 | Qimron et al. |
| 2017/0283779 A1 | 10/2017 | Holder et al. |
| 2018/0044659 A1 | 2/2018 | Zhu et al. |
| 2018/0049984 A1 | 2/2018 | Brinker et al. |
| 2018/0112228 A1 | 4/2018 | Ecker et al. |
| 2018/0112255 A1 | 4/2018 | Chen et al. |
| 2018/0119121 A1 | 5/2018 | Brouns et al. |
| 2018/0127745 A1 | 5/2018 | Konermann et al. |
| 2018/0148506 A1 | 5/2018 | Png et al. |
| 2018/0148711 A1 | 5/2018 | Finer et al. |
| 2018/0155729 A1 | 6/2018 | Beisel et al. |
| 2018/0161368 A1 | 6/2018 | Odegard |
| 2018/0179522 A1 | 6/2018 | Buckley et al. |
| 2018/0223291 A1 | 8/2018 | Holder et al. |
| 2018/0253563 A1 | 9/2018 | Peck et al. |
| 2018/0273962 A1 | 9/2018 | Kerstetter et al. |
| 2018/0305424 A1 | 10/2018 | Crabtree et al. |

FOREIGN PATENT DOCUMENTS

| | | |
|---|---|---|
| WO | WO 2014093479 | 6/2014 |
| WO | WO 2015155686 | 10/2015 |
| WO | WO 2016053397 | 4/2016 |
| WO | WO 2016077350 | 5/2016 |
| WO | WO2017/066497 | 4/2017 |
| WO | WO 2017066497 | 4/2017 |
| WO | WO 2017219033 | 12/2017 |

OTHER PUBLICATIONS

U.S. Appl. No. 15/802,413, filed Nov. 2, 2017, U.S. Pat. No. 10,435,678, Oct. 8, 2019.
U.S. Appl. No. 16/554,225, filed Aug. 28, 2019.
U.S. Appl. No. 16/104,875, filed Aug. 17, 2019, U.S. Pat. No. 10,227,576, Mar. 12, 2019.
U.S. Appl. No. 16/262,773, filed Jan. 30, 2019, U.S. Pat. No. 10,329,547, Jun. 25, 2019.
U.S. Appl. No. 16/420,061, filed May 22, 2019.
PCT/US2019/036864 filed Jun. 12, 2019.
Beloglazova, N., et al., "Structure and activity of the Cas3 HD nuclease MJ0384, an effector enzyme of the CRISPR interference," EMBO Journal 30(22):4616-4627 (2011; doi:10.1038/emboj.2011.377).
Beloglazova, N., et al., "CRISPR RNA binding and DNA target recognition by purified Cascade complexes from *Escherichia coli*," Nucleic Acids Research 43(1):530-543 (2015; doi:10.1093/nar/gku1285).
Brouns, S., et al., "Small CRISPR RNAs Guide Antiviral Defense in Prokaryotes," Science 321(5891):960-964 (2008; doi:10.1126/science.1159689).
Chen, X., et al., "Fusion Protein Linkers: Property, Design and Functionality," Advanced drug delivery reviews 65(10):1357-1369 (2013; doi:10.1016/j.addr.2012.09.039).
Chichili, V., et al., "Linkers in the structural biology of protein-protein interactions," Protein Science: A Publication of the Protein Society 22(2):153-167 (2013; doi:10.1002/pro.2206).
Choudhury, R., et al., "Engineering RNA endonucleases with customized sequence specificities," Nat. Commun. 3:1147 (2012; doi:10.1038/ncomms2154).
Fu, B., et al., "High-Throughput Characterization of Cascade type I-E CRISPR Guide Efficacy Reveals Unexpected PAM Diversity and Target Sequence Preferences," GENETICS 206(4):1727-1738 (Aug. 1, 2017; doi.org/10.1534/genetics.117.202580).
George, R., et al., "An analysis of protein domain linkers: their classification and role in protein folding," Protein Eng. 15(11):871-9 (Nov. 2003).
Gleditzsch, D., et al., "Modulating the Cascade architecture of a minimal Type I-F CRISPR-Cas system," Nucleic Acids Research 44(12):5872-5882 (2016; doi:10.1093/nar/gkw469).

Guilinger, J,. et al., "Fusion of catalytically inactive Cas9 to FokI nuclease improves the specificity of genome modification," Nat Biotechnol. 32(6):577-582 (Jun. 2014; doi: 10.1038/nbt.2909; Epub Apr. 25, 2014).
Hochstrasser, M., et al., "DNA Targeting by a Minimal CRISPR RNA-Guided Cascade," Molecular cell 63(5):840-851 (2016; doi:10.1016/j.molcel.2016.07.027).
Huo, Y., et al., "Structures of CRISPR Cas3 offer mechanistic insights into Cascade-activated DNA unwinding and degradation," Nature structural & molecular biology 21(9):771-777 (2014; doi:10.1038/nsmb.2875).
Jackson, R., et al., "Crystal structure of the CRISPR RNA-guided surveillance complex from *Escherichia coli*," Science 345(6203):1473-9 (Sep. 19, 2014; doi:10.1126/science.1256328. Epub Aug. 7, 2014).
Jore, M., et al., "Structural basis for CRISPR RNA-guided DNA recognition by Cascade" Nature Structural & Molecular Biology 18:529-537 (2011).
Kim, Y.G., et al., "Site-specific cleavage of DNA-RNA hybrids by zinc finger/FokI cleavage domain fusions," Gene 203(1):43-49 (Dec. 5, 1997).
Klein, J., et al., "Design and characterization of structured protein linkers with differing flexibilities," Protein Engineering, Design & Selection 27(10):325-30 (Oct. 2014; doi:10.1093/protein/gzu043).
Kuznedelov K., et al., "Altered stoichiometry *Escherichia coli* Cascade complexes with shortened CRISPR RNA spacers are capable of interference and primed adaptation," Nucleic Acids Research 44(22):10849-10861 (2016; doi:10.1093/nar/gkw914).
Luo, M., et al., "The CRISPR RNA-guided surveillance complex in *Escherichia coli* accommodates extended RNA spacers," Nucleic Acids Research 44(15):7385-7394 (2016; doi:10.1093/nar/gkw421).
Makarova, K., et al., "Evolution and classification of the CRISPR-Cas systems," Nat. Rev. Microbiol. 9(6): 467-477 (Jun. 2011; doi:10.1038/nrmicro2577).
Makarova, K., et al., "SnapShot: Class 1 CRISPR-Cas Systems," Cell 168(5):946-946.e1 (Feb. 23, 2017; doi: 10.1016/j.cell.2017.02.018).
Mulepati, S., "Structural and Biochemical Analysis of Nuclease Domain of Clustered Regularly Interspaced Short Palindromic Repeat (CRISPR)-associated Protein 3 (Cas3)," Journal of Biological Chemistry 286(36):31896-31903 (2011; doi:10.1074/jbc.M111.270017).
Nishimasu, H., et al., "Structures and mechanisms of CRISPR RNA-guided effector nucleases," Current Opinion in Structural Biology 43:68-78 (Apr. 2017; doi: 10.1016/j.sbi.2016.11.013. Epub Nov. 30, 2016).
Plagens, A., et al., "In vitro assembly and activity of an archaeal CRISPR-Cas type I-A Cascade interference complex," Nucleic Acids Research 42(8):5125-5138 (2014; doi:10.1093/nar/gku120).
Rath, D., et al., "The CRISPR-Cas immune system: biology, mechanisms and applications," Biochimie 117:119-28 (Oct. 2015; doi: 10.1016/j.biochi.2015.03.025. Epub Apr. 10, 2015).
Redding, S., et al., "Surveillance and Processing of Foreign DNA by the *Escherichia coli* CRISPR-Cas System," Cell 163(4):854-865 (Nov. 5, 2015; doi: 10.1016/j.cell.2015.10.003).
Sashital, D., et al., "Mechanism of foreign DNA selection in a bacterial adaptive immune system," Mol. Cell. 46(5):606-15 (Jun. 8, 2012; doi: 10.1016/j.molcel.2012.03.020. Epub Apr. 19, 2012).
Sinkunas, T., et al., "Cas3 is a single-stranded DNA nuclease and ATP-dependent helicase in the CRISPR/Cas immune system," EMBO J. 30(7):1335-1342 (Apr. 6, 2011; doi: 10.1038/emboj.2011.41; Epub Feb. 22, 2011).
Sinkunas, T., et al., "In vitro reconstitution of Cascade-mediated CRISPR immunity in *Streptococcus thermophilus*," EMBO J. 32(3):385-394 Feb. 6, 2013; doi: 10.1038/emboj.2012.352; Epub Jan. 18, 2013).
Sorek, R., et al., "CRISPR-Mediated Adaptive Immune Systems in Bacteria and Archaea," Annu. Rev. Biochem. 82:237-266 (2013; doi: 10.1146/annurev-biochem-072911-172315, Epub Mar. 11, 2013).
Staals, R., et al., "Structure and activity of the RNA-targeting Type III-B CRISPR-Cas complex of Thermus thermophilus," Molecular cell 52(1):135-145 (2013; doi:10.1016/j.molcel.2013.09.013).

(56) References Cited

OTHER PUBLICATIONS

Van der Oost, J., et al., "CRISPR-based adaptive and heritable immunity in prokaryotes," Trends in Biochemical Sciences 34(8):401-407 (2009; doi:10.1016/tibs.2009.05.002; Jul. 29, 2009).

Venclovas, Č., et al., "Structure of Csm2 elucidates the relationship between small subunits of CRISPR-Cas effector complexes," FEBS Lett. 590(10):1521-9 (May 2016; doi: 10.1002/1873-3468.12179 Epub May 5, 2016).

Westra, E., et al., "CRISPR immunity relies on the consecutive binding and degradation of negatively supercoiled invader DNA by Cascade and Cas3," Molecular Cell 46(5):595-605 (2012; doi:10.1016/j.molcel.2012.03.018).

Wiedenheft, B., et al., "Structures of the RNA-guided surveillance complex from a bacterial immune system," Nature 477(7365):486-489 (Sep. 21, 2011; doi: 10.1038/nature10402).

Zhao, H., et al., "Increasing the homogeneity, stability and activity of human serum albumin and interferon-α2b fusion protein by linker engineering," Protein Expr. Purif. 61(1):73-7 (Sep. 2008; doi: 10.1016/j.pep.2008.04.013. Epub May 16, 2008).

\* cited by examiner

FIG. 3

| SEQ ID NO: | Gene/ Protein | Subtype and organism | Type of sequence |
|---|---|---|---|
| SEQ ID NO: 1 | Cas8 | I-E_Escherichia coli K-12 MG1655 | Genomic DNA gene sequence |
| SEQ ID NO: 2 | Cse2 | I-E_Escherichia coli K-12 MG1655 | Genomic DNA gene sequence |
| SEQ ID NO: 3 | Cas7 | I-E_Escherichia coli K-12 MG1655 | Genomic DNA gene sequence |
| SEQ ID NO: 4 | Cas5 | I-E_Escherichia coli K-12 MG1655 | Genomic DNA gene sequence |
| SEQ ID NO: 5 | Cas6 | I-E_Escherichia coli K-12 MG1655 | Genomic DNA gene sequence |
| SEQ ID NO: 6 | Cas8 | I-E_Escherichia coli K-12 MG1655 | E. coli codon-optimized DNA gene sequence |
| SEQ ID NO: 7 | Cse2 | I-E_Escherichia coli K-12 MG1655 | E. coli codon-optimized DNA gene sequence |
| SEQ ID NO: 8 | Cas7 | I-E_Escherichia coli K-12 MG1655 | E. coli codon-optimized DNA gene sequence |
| SEQ ID NO: 9 | Cas5 | I-E_Escherichia coli K-12 MG1655 | E. coli codon-optimized DNA gene sequence |
| SEQ ID NO: 10 | Cas6 | I-E_Escherichia coli K-12 MG1655 | E. coli codon-optimized DNA gene sequence |
| SEQ ID NO: 11 | Cas8 | I-E_Escherichia coli K-12 MG1655 | H. sapiens codon-optimized DNA gene sequence |
| SEQ ID NO: 12 | Cse2 | I-E_Escherichia coli K-12 MG1655 | H. sapiens codon-optimized DNA gene sequence |
| SEQ ID NO: 13 | Cas7 | I-E_Escherichia coli K-12 MG1655 | H. sapiens codon-optimized DNA gene sequence |
| SEQ ID NO: 14 | Cas5 | I-E_Escherichia coli K-12 MG1655 | H. sapiens codon-optimized DNA gene sequence |
| SEQ ID NO: 15 | Cas6 | I-E_Escherichia coli K-12 MG1655 | H. sapiens codon-optimized DNA gene sequence |
| SEQ ID NO: 16 | Cas8 | I-E_Escherichia coli K-12 MG1655 | Protein amino acid sequence |
| SEQ ID NO: 17 | Cse2 | I-E_Escherichia coli K-12 MG1655 | Protein amino acid sequence |
| SEQ ID NO: 18 | Cas7 | I-E_Escherichia coli K-12 MG1655 | Protein amino acid sequence |
| SEQ ID NO: 19 | Cas5 | I-E_Escherichia coli K-12 MG1655 | Protein amino acid sequence |
| SEQ ID NO: 20 | Cas6 | I-E_Escherichia coli K-12 MG1655 | Protein amino acid sequence |
| SEQ ID NO: 21 | Cas3 | I-E_Escherichia coli K-12 MG1655 | Protein amino acid sequence |
| SEQ ID NO: 22 | Cas8 | I-E_Oceanicola sp. HL-35 | Genomic DNA gene sequence |
| SEQ ID NO: 23 | Cse2 | I-E_Oceanicola sp. HL-35 | Genomic DNA gene sequence |
| SEQ ID NO: 24 | Cas7 | I-E_Oceanicola sp. HL-35 | Genomic DNA gene sequence |

FIG. 3 (continued)

| SEQ ID NO: | Gene/ Protein | Subtype and organism | Type of sequence |
|---|---|---|---|
| SEQ ID NO: 25 | Cas5 | I-E_Oceanicola sp. HL-35 | Genomic DNA gene sequence |
| SEQ ID NO: 26 | Cas6 | I-E_Oceanicola sp. HL-35 | Genomic DNA gene sequence |
| SEQ ID NO: 27 | Cas8 | I-E_Oceanicola sp. HL-35 | H. sapiens codon-optimized DNA gene sequence |
| SEQ ID NO: 28 | Cse2 | I-E_Oceanicola sp. HL-35 | H. sapiens codon-optimized DNA gene sequence |
| SEQ ID NO: 29 | Cas7 | I-E_Oceanicola sp. HL-35 | H. sapiens codon-optimized DNA gene sequence |
| SEQ ID NO: 30 | Cas5 | I-E_Oceanicola sp. HL-35 | H. sapiens codon-optimized DNA gene sequence |
| SEQ ID NO: 31 | Cas6 | I-E_Oceanicola sp. HL-35 | H. sapiens codon-optimized DNA gene sequence |
| SEQ ID NO: 32 | Cas8 | I-E_Oceanicola sp. HL-35 | Protein amino acid sequence |
| SEQ ID NO: 33 | Cse2 | I-E_Oceanicola sp. HL-35 | Protein amino acid sequence |
| SEQ ID NO: 34 | Cas7 | I-E_Oceanicola sp. HL-35 | Protein amino acid sequence |
| SEQ ID NO: 35 | Cas5 | I-E_Oceanicola sp. HL-35 | Protein amino acid sequence |
| SEQ ID NO: 36 | Cas6 | I-E_Oceanicola sp. HL-35 | Protein amino acid sequence |
| SEQ ID NO: 37 | CRISPR | I-E_Oceanicola sp. HL-35 | Exemplary minimal CRISPR array |
| SEQ ID NO: 38 | Cas8 | I-E_Pseudomonas sp. S-6-2 | Genomic DNA gene sequence |
| SEQ ID NO: 39 | Cse2 | I-E_Pseudomonas sp. S-6-2 | Genomic DNA gene sequence |
| SEQ ID NO: 40 | Cas7 | I-E_Pseudomonas sp. S-6-2 | Genomic DNA gene sequence |
| SEQ ID NO: 41 | Cas5 | I-E_Pseudomonas sp. S-6-2 | Genomic DNA gene sequence |
| SEQ ID NO: 42 | Cas6 | I-E_Pseudomonas sp. S-6-2 | Genomic DNA gene sequence |
| SEQ ID NO: 43 | Cas8 | I-E_Pseudomonas sp. S-6-2 | H. sapiens codon-optimized DNA gene sequence |
| SEQ ID NO: 44 | Cse2 | I-E_Pseudomonas sp. S-6-2 | H. sapiens codon-optimized DNA gene sequence |
| SEQ ID NO: 45 | Cas7 | I-E_Pseudomonas sp. S-6-2 | H. sapiens codon-optimized DNA gene sequence |
| SEQ ID NO: 46 | Cas5 | I-E_Pseudomonas sp. S-6-2 | H. sapiens codon-optimized DNA gene sequence |
| SEQ ID NO: 47 | Cas6 | I-E_Pseudomonas sp. S-6-2 | H. sapiens codon-optimized DNA gene sequence |
| SEQ ID NO: 48 | Cas8 | I-E_Pseudomonas sp. S-6-2 | Protein amino acid sequence |

FIG. 3 (continued)

| SEQ ID NO: | Gene/Protein | Subtype and organism | Type of sequence |
|---|---|---|---|
| SEQ ID NO: 49 | Cse2 | I-E_Pseudomonas sp. S-6-2 | Protein amino acid sequence |
| SEQ ID NO: 50 | Cas7 | I-E_Pseudomonas sp. S-6-2 | Protein amino acid sequence |
| SEQ ID NO: 51 | Cas5 | I-E_Pseudomonas sp. S-6-2 | Protein amino acid sequence |
| SEQ ID NO: 52 | Cas6 | I-E_Pseudomonas sp. S-6-2 | Protein amino acid sequence |
| SEQ ID NO: 53 | CRISPR | I-E_Pseudomonas sp. S-6-2 | Exemplary minimal CRISPR array |
| SEQ ID NO: 54 | Cas8 | I-E_Salmonella enterica subsp. enterica serovar Muenster strain | Genomic DNA gene sequence |
| SEQ ID NO: 55 | Cse2 | I-E_Salmonella enterica subsp. enterica serovar Muenster strain | Genomic DNA gene sequence |
| SEQ ID NO: 56 | Cas7 | I-E_Salmonella enterica subsp. enterica serovar Muenster strain | Genomic DNA gene sequence |
| SEQ ID NO: 57 | Cas5 | I-E_Salmonella enterica subsp. enterica serovar Muenster strain | Genomic DNA gene sequence |
| SEQ ID NO: 58 | Cas6 | I-E_Salmonella enterica subsp. enterica serovar Muenster strain | Genomic DNA gene sequence |
| SEQ ID NO: 59 | Cas8 | I-E_Salmonella enterica subsp. enterica serovar Muenster strain | H. sapiens codon-optimized DNA gene sequence |
| SEQ ID NO: 60 | Cse2 | I-E_Salmonella enterica subsp. enterica serovar Muenster strain | H. sapiens codon-optimized DNA gene sequence |
| SEQ ID NO: 61 | Cas7 | I-E_Salmonella enterica subsp. enterica serovar Muenster strain | H. sapiens codon-optimized DNA gene sequence |
| SEQ ID NO: 62 | Cas5 | I-E_Salmonella enterica subsp. enterica serovar Muenster strain | H. sapiens codon-optimized DNA gene sequence |
| SEQ ID NO: 63 | Cas6 | I-E_Salmonella enterica subsp. enterica serovar Muenster strain | H. sapiens codon-optimized DNA gene sequence |
| SEQ ID NO: 64 | Cas8 | I-E_Salmonella enterica subsp. enterica serovar Muenster strain | Protein amino acid sequence |
| SEQ ID NO: 65 | Cse2 | I-E_Salmonella enterica subsp. enterica serovar Muenster strain | Protein amino acid sequence |
| SEQ ID NO: 66 | Cas7 | I-E_Salmonella enterica subsp. enterica serovar Muenster strain | Protein amino acid sequence |
| SEQ ID NO: 67 | Cas5 | I-E_Salmonella enterica subsp. enterica serovar Muenster strain | Protein amino acid sequence |

FIG. 3 (continued)

| SEQ ID NO: | Gene/ Protein | Subtype and organism | Type of sequence |
|---|---|---|---|
| SEQ ID NO: 68 | Cas6 | I-E_Salmonella enterica subsp. enterica serovar Muenster strain | Protein amino acid sequence |
| SEQ ID NO: 69 | CRISPR | I-E_Salmonella enterica subsp. enterica serovar Muenster strain | Exemplary minimal CRISPR array |
| SEQ ID NO: 70 | Cas8 | I-E_Atlantibacter hermannii NBRC 105704 | Genomic DNA gene sequence |
| SEQ ID NO: 71 | Cse2 | I-E_Atlantibacter hermannii NBRC 105704 | Genomic DNA gene sequence |
| SEQ ID NO: 72 | Cas7 | I-E_Atlantibacter hermannii NBRC 105704 | Genomic DNA gene sequence |
| SEQ ID NO: 73 | Cas5 | I-E_Atlantibacter hermannii NBRC 105704 | Genomic DNA gene sequence |
| SEQ ID NO: 74 | Cas6 | I-E_Atlantibacter hermannii NBRC 105704 | Genomic DNA gene sequence |
| SEQ ID NO: 75 | Cas8 | I-E_Atlantibacter hermannii NBRC 105704 | H. sapiens codon-optimized DNA gene sequence |
| SEQ ID NO: 76 | Cse2 | I-E_Atlantibacter hermannii NBRC 105704 | H. sapiens codon-optimized DNA gene sequence |
| SEQ ID NO: 77 | Cas7 | I-E_Atlantibacter hermannii NBRC 105704 | H. sapiens codon-optimized DNA gene sequence |
| SEQ ID NO: 78 | Cas5 | I-E_Atlantibacter hermannii NBRC 105704 | H. sapiens codon-optimized DNA gene sequence |
| SEQ ID NO: 79 | Cas6 | I-E_Atlantibacter hermannii NBRC 105704 | H. sapiens codon-optimized DNA gene sequence |
| SEQ ID NO: 80 | Cas8 | I-E_Atlantibacter hermannii NBRC 105704 | Protein amino acid sequence |
| SEQ ID NO: 81 | Cse2 | I-E_Atlantibacter hermannii NBRC 105704 | Protein amino acid sequence |
| SEQ ID NO: 82 | Cas7 | I-E_Atlantibacter hermannii NBRC 105704 | Protein amino acid sequence |
| SEQ ID NO: 83 | Cas5 | I-E_Atlantibacter hermannii NBRC 105704 | Protein amino acid sequence |
| SEQ ID NO: 84 | Cas6 | I-E_Atlantibacter hermannii NBRC 105704 | Protein amino acid sequence |
| SEQ ID NO: 85 | CRISPR | I-E_Atlantibacter hermannii NBRC 105704 | Exemplary minimal CRISPR array |
| SEQ ID NO: 86 | Cas8 | I-E_Geothermobacter sp. EPR-M | Genomic DNA gene sequence |
| SEQ ID NO: 87 | Cse2 | I-E_Geothermobacter sp. EPR-M | Genomic DNA gene sequence |
| SEQ ID NO: 88 | Cas7 | I-E_Geothermobacter sp. EPR-M | Genomic DNA gene sequence |
| SEQ ID NO: 89 | Cas5 | I-E_Geothermobacter sp. EPR-M | Genomic DNA gene sequence |
| SEQ ID NO: 90 | Cas6 | I-E_Geothermobacter sp. EPR-M | Genomic DNA gene sequence |
| SEQ ID NO: 91 | Cas8 | I-E_Geothermobacter sp. EPR-M | H. sapiens codon-optimized DNA gene sequence |
| SEQ ID NO: 92 | Cse2 | I-E_Geothermobacter sp. EPR-M | H. sapiens codon-optimized DNA gene sequence |

FIG. 3 (continued)

| SEQ ID NO: | Gene/ Protein | Subtype and organism | Type of sequence |
|---|---|---|---|
| SEQ ID NO: 93 | Cas7 | I-E_Geothermobacter sp. EPR-M | H. sapiens codon-optimized DNA gene sequence |
| SEQ ID NO: 94 | Cas5 | I-E_Geothermobacter sp. EPR-M | H. sapiens codon-optimized DNA gene sequence |
| SEQ ID NO: 95 | Cas6 | I-E_Geothermobacter sp. EPR-M | H. sapiens codon-optimized DNA gene sequence |
| SEQ ID NO: 96 | Cas8 | I-E_Geothermobacter sp. EPR-M | Protein amino acid sequence |
| SEQ ID NO: 97 | Cse2 | I-E_Geothermobacter sp. EPR-M | Protein amino acid sequence |
| SEQ ID NO: 98 | Cas7 | I-E_Geothermobacter sp. EPR-M | Protein amino acid sequence |
| SEQ ID NO: 99 | Cas5 | I-E_Geothermobacter sp. EPR-M | Protein amino acid sequence |
| SEQ ID NO: 100 | Cas6 | I-E_Geothermobacter sp. EPR-M | Protein amino acid sequence |
| SEQ ID NO: 101 | CRISPR | I-E_Geothermobacter sp. EPR-M | Exemplary minimal CRISPR array |
| SEQ ID NO: 102 | Cas8 | I-E_Methylocaldum sp. 14B | Genomic DNA gene sequence |
| SEQ ID NO: 103 | Cse2 | I-E_Methylocaldum sp. 14B | Genomic DNA gene sequence |
| SEQ ID NO: 104 | Cas7 | I-E_Methylocaldum sp. 14B | Genomic DNA gene sequence |
| SEQ ID NO: 105 | Cas5 | I-E_Methylocaldum sp. 14B | Genomic DNA gene sequence |
| SEQ ID NO: 106 | Cas6 | I-E_Methylocaldum sp. 14B | Genomic DNA gene sequence |
| SEQ ID NO: 107 | Cas8 | I-E_Methylocaldum sp. 14B | H. sapiens codon-optimized DNA gene sequence |
| SEQ ID NO: 108 | Cse2 | I-E_Methylocaldum sp. 14B | H. sapiens codon-optimized DNA gene sequence |
| SEQ ID NO: 109 | Cas7 | I-E_Methylocaldum sp. 14B | H. sapiens codon-optimized DNA gene sequence |
| SEQ ID NO: 110 | Cas5 | I-E_Methylocaldum sp. 14B | H. sapiens codon-optimized DNA gene sequence |
| SEQ ID NO: 111 | Cas6 | I-E_Methylocaldum sp. 14B | H. sapiens codon-optimized DNA gene sequence |
| SEQ ID NO: 112 | Cas8 | I-E_Methylocaldum sp. 14B | Protein amino acid sequence |
| SEQ ID NO: 113 | Cse2 | I-E_Methylocaldum sp. 14B | Protein amino acid sequence |
| SEQ ID NO: 114 | Cas7 | I-E_Methylocaldum sp. 14B | Protein amino acid sequence |
| SEQ ID NO: 115 | Cas5 | I-E_Methylocaldum sp. 14B | Protein amino acid sequence |
| SEQ ID NO: 116 | Cas6 | I-E_Methylocaldum sp. 14B | Protein amino acid sequence |
| SEQ ID NO: 117 | CRISPR | I-E_Methylocaldum sp. 14B | Exemplary minimal CRISPR array |
| SEQ ID NO: 118 | Cas8 | I-E_Methanocella arvoryzae MRE50 | Genomic DNA gene sequence |

FIG. 3 (continued)

| SEQ ID NO: | Gene/ Protein | Subtype and organism | Type of sequence |
|---|---|---|---|
| SEQ ID NO: 119 | Cse2 | I-E_Methanocella arvoryzae MRE50 | Genomic DNA gene sequence |
| SEQ ID NO: 120 | Cas7 | I-E_Methanocella arvoryzae MRE50 | Genomic DNA gene sequence |
| SEQ ID NO: 121 | Cas5 | I-E_Methanocella arvoryzae MRE50 | Genomic DNA gene sequence |
| SEQ ID NO: 122 | Cas6 | I-E_Methanocella arvoryzae MRE50 | Genomic DNA gene sequence |
| SEQ ID NO: 123 | Cas8 | I-E_Methanocella arvoryzae MRE50 | H. sapiens codon-optimized DNA gene sequence |
| SEQ ID NO: 124 | Cse2 | I-E_Methanocella arvoryzae MRE50 | H. sapiens codon-optimized DNA gene sequence |
| SEQ ID NO: 125 | Cas7 | I-E_Methanocella arvoryzae MRE50 | H. sapiens codon-optimized DNA gene sequence |
| SEQ ID NO: 126 | Cas5 | I-E_Methanocella arvoryzae MRE50 | H. sapiens codon-optimized DNA gene sequence |
| SEQ ID NO: 127 | Cas6 | I-E_Methanocella arvoryzae MRE50 | H. sapiens codon-optimized DNA gene sequence |
| SEQ ID NO: 128 | Cas8 | I-E_Methanocella arvoryzae MRE50 | Protein amino acid sequence |
| SEQ ID NO: 129 | Cse2 | I-E_Methanocella arvoryzae MRE50 | Protein amino acid sequence |
| SEQ ID NO: 130 | Cas7 | I-E_Methanocella arvoryzae MRE50 | Protein amino acid sequence |
| SEQ ID NO: 131 | Cas5 | I-E_Methanocella arvoryzae MRE50 | Protein amino acid sequence |
| SEQ ID NO: 132 | Cas6 | I-E_Methanocella arvoryzae MRE50 | Protein amino acid sequence |
| SEQ ID NO: 133 | CRISPR | I-E_Methanocella arvoryzae MRE50 | Exemplary minimal CRISPR array |
| SEQ ID NO: 134 | Cas8 | I-E_Lachnospiraceae bacterium KH1T2 | Genomic DNA gene sequence |
| SEQ ID NO: 135 | Cse2 | I-E_Lachnospiraceae bacterium KH1T2 | Genomic DNA gene sequence |
| SEQ ID NO: 136 | Cas7 | I-E_Lachnospiraceae bacterium KH1T2 | Genomic DNA gene sequence |
| SEQ ID NO: 137 | Cas5 | I-E_Lachnospiraceae bacterium KH1T2 | Genomic DNA gene sequence |
| SEQ ID NO: 138 | Cas6 | I-E_Lachnospiraceae bacterium KH1T2 | Genomic DNA gene sequence |
| SEQ ID NO: 139 | Cas8 | I-E_Lachnospiraceae bacterium KH1T2 | H. sapiens codon-optimized DNA gene sequence |
| SEQ ID NO: 140 | Cse2 | I-E_Lachnospiraceae bacterium KH1T2 | H. sapiens codon-optimized DNA gene sequence |
| SEQ ID NO: 141 | Cas7 | I-E_Lachnospiraceae bacterium KH1T2 | H. sapiens codon-optimized DNA gene sequence |
| SEQ ID NO: 142 | Cas5 | I-E_Lachnospiraceae bacterium KH1T2 | H. sapiens codon-optimized DNA gene sequence |

FIG. 3 (continued)

| SEQ ID NO: | Gene/Protein | Subtype and organism | Type of sequence |
|---|---|---|---|
| SEQ ID NO: 143 | Cas6 | I-E_Lachnospiraceae bacterium KH1T2 | H. sapiens codon-optimized DNA gene sequence |
| SEQ ID NO: 144 | Cas8 | I-E_Lachnospiraceae bacterium KH1T2 | Protein amino acid sequence |
| SEQ ID NO: 145 | Cse2 | I-E_Lachnospiraceae bacterium KH1T2 | Protein amino acid sequence |
| SEQ ID NO: 146 | Cas7 | I-E_Lachnospiraceae bacterium KH1T2 | Protein amino acid sequence |
| SEQ ID NO: 147 | Cas5 | I-E_Lachnospiraceae bacterium KH1T2 | Protein amino acid sequence |
| SEQ ID NO: 148 | Cas6 | I-E_Lachnospiraceae bacterium KH1T2 | Protein amino acid sequence |
| SEQ ID NO: 149 | CRISPR | I-E_Lachnospiraceae bacterium KH1T2 | Exemplary minimal CRISPR array |
| SEQ ID NO: 150 | Cas8 | I-E_Klebsiella pneumoniae strain VRCO0172 | Genomic DNA gene sequence |
| SEQ ID NO: 151 | Cse2 | I-E_Klebsiella pneumoniae strain VRCO0172 | Genomic DNA gene sequence |
| SEQ ID NO: 152 | Cas7 | I-E_Klebsiella pneumoniae strain VRCO0172 | Genomic DNA gene sequence |
| SEQ ID NO: 153 | Cas5 | I-E_Klebsiella pneumoniae strain VRCO0172 | Genomic DNA gene sequence |
| SEQ ID NO: 154 | Cas6 | I-E_Klebsiella pneumoniae strain VRCO0172 | Genomic DNA gene sequence |
| SEQ ID NO: 155 | Cas8 | I-E_Klebsiella pneumoniae strain VRCO0172 | H. sapiens codon-optimized DNA gene sequence |
| SEQ ID NO: 156 | Cse2 | I-E_Klebsiella pneumoniae strain VRCO0172 | H. sapiens codon-optimized DNA gene sequence |
| SEQ ID NO: 157 | Cas7 | I-E_Klebsiella pneumoniae strain VRCO0172 | H. sapiens codon-optimized DNA gene sequence |
| SEQ ID NO: 158 | Cas5 | I-E_Klebsiella pneumoniae strain VRCO0172 | H. sapiens codon-optimized DNA gene sequence |
| SEQ ID NO: 159 | Cas6 | I-E_Klebsiella pneumoniae strain VRCO0172 | H. sapiens codon-optimized DNA gene sequence |
| SEQ ID NO: 160 | Cas8 | I-E_Klebsiella pneumoniae strain VRCO0172 | Protein amino acid sequence |
| SEQ ID NO: 161 | Cse2 | I-E_Klebsiella pneumoniae strain VRCO0172 | Protein amino acid sequence |
| SEQ ID NO: 162 | Cas7 | I-E_Klebsiella pneumoniae strain VRCO0172 | Protein amino acid sequence |
| SEQ ID NO: 163 | Cas5 | I-E_Klebsiella pneumoniae strain VRCO0172 | Protein amino acid sequence |
| SEQ ID NO: 164 | Cas6 | I-E_Klebsiella pneumoniae strain VRCO0172 | Protein amino acid sequence |
| SEQ ID NO: 165 | CRISPR | I-E_Klebsiella pneumoniae strain VRCO0172 | Exemplary minimal CRISPR array |
| SEQ ID NO: 166 | Cas8 | I-E_Pseudomonas aeruginosa DHS01 | Genomic DNA gene sequence |
| SEQ ID NO: 167 | Cse2 | I-E_Pseudomonas aeruginosa DHS01 | Genomic DNA gene sequence |
| SEQ ID NO: 168 | Cas7 | I-E_Pseudomonas aeruginosa DHS01 | Genomic DNA gene sequence |
| SEQ ID NO: 169 | Cas5 | I-E_Pseudomonas aeruginosa DHS01 | Genomic DNA gene sequence |
| SEQ ID NO: 170 | Cas6 | I-E_Pseudomonas aeruginosa DHS01 | Genomic DNA gene sequence |

FIG. 3 (continued)

| SEQ ID NO: | Gene/Protein | Subtype and organism | Type of sequence |
|---|---|---|---|
| SEQ ID NO: 171 | Cas8 | I-E_Pseudomonas aeruginosa DHS01 | H. sapiens codon-optimized DNA gene sequence |
| SEQ ID NO: 172 | Cse2 | I-E_Pseudomonas aeruginosa DHS01 | H. sapiens codon-optimized DNA gene sequence |
| SEQ ID NO: 173 | Cas7 | I-E_Pseudomonas aeruginosa DHS01 | H. sapiens codon-optimized DNA gene sequence |
| SEQ ID NO: 174 | Cas5 | I-E_Pseudomonas aeruginosa DHS01 | H. sapiens codon-optimized DNA gene sequence |
| SEQ ID NO: 175 | Cas6 | I-E_Pseudomonas aeruginosa DHS01 | H. sapiens codon-optimized DNA gene sequence |
| SEQ ID NO: 176 | Cas8 | I-E_Pseudomonas aeruginosa DHS01 | Protein amino acid sequence |
| SEQ ID NO: 177 | Cse2 | I-E_Pseudomonas aeruginosa DHS01 | Protein amino acid sequence |
| SEQ ID NO: 178 | Cas7 | I-E_Pseudomonas aeruginosa DHS01 | Protein amino acid sequence |
| SEQ ID NO: 179 | Cas5 | I-E_Pseudomonas aeruginosa DHS01 | Protein amino acid sequence |
| SEQ ID NO: 180 | Cas6 | I-E_Pseudomonas aeruginosa DHS01 | Protein amino acid sequence |
| SEQ ID NO: 181 | CRISPR | I-E_Pseudomonas aeruginosa DHS01 | Exemplary minimal CRISPR array |
| SEQ ID NO: 182 | Cas8 | I-E_Streptococcus thermophilus strain ND07 | Genomic DNA gene sequence |
| SEQ ID NO: 183 | Cse2 | I-E_Streptococcus thermophilus strain ND07 | Genomic DNA gene sequence |
| SEQ ID NO: 184 | Cas7 | I-E_Streptococcus thermophilus strain ND07 | Genomic DNA gene sequence |
| SEQ ID NO: 185 | Cas5 | I-E_Streptococcus thermophilus strain ND07 | Genomic DNA gene sequence |
| SEQ ID NO: 186 | Cas6 | I-E_Streptococcus thermophilus strain ND07 | Genomic DNA gene sequence |
| SEQ ID NO: 187 | Cas8 | I-E_Streptococcus thermophilus strain ND07 | H. sapiens codon-optimized DNA gene sequence |
| SEQ ID NO: 188 | Cse2 | I-E_Streptococcus thermophilus strain ND07 | H. sapiens codon-optimized DNA gene sequence |
| SEQ ID NO: 189 | Cas7 | I-E_Streptococcus thermophilus strain ND07 | H. sapiens codon-optimized DNA gene sequence |
| SEQ ID NO: 190 | Cas5 | I-E_Streptococcus thermophilus strain ND07 | H. sapiens codon-optimized DNA gene sequence |
| SEQ ID NO: 191 | Cas6 | I-E_Streptococcus thermophilus strain ND07 | H. sapiens codon-optimized DNA gene sequence |
| SEQ ID NO: 192 | Cas8 | I-E_Streptococcus thermophilus strain ND07 | Protein amino acid sequence |
| SEQ ID NO: 193 | Cse2 | I-E_Streptococcus thermophilus strain ND07 | Protein amino acid sequence |
| SEQ ID NO: 194 | Cas7 | I-E_Streptococcus thermophilus strain ND07 | Protein amino acid sequence |

FIG. 3 (continued)

| SEQ ID NO: | Gene/ Protein | Subtype and organism | Type of sequence |
|---|---|---|---|
| SEQ ID NO: 195 | Cas5 | I-E_Streptococcus thermophilus strain ND07 | Protein amino acid sequence |
| SEQ ID NO: 196 | Cas6 | I-E_Streptococcus thermophilus strain ND07 | Protein amino acid sequence |
| SEQ ID NO: 197 | CRISPR | I-E_Streptococcus thermophilus strain ND07 | Exemplary minimal CRISPR array |
| SEQ ID NO: 198 | Cas8 | I-E_Streptomyces sp. S4 | Genomic DNA gene sequence |
| SEQ ID NO: 199 | Cse2 | I-E_Streptomyces sp. S4 | Genomic DNA gene sequence |
| SEQ ID NO: 200 | Cas7 | I-E_Streptomyces sp. S4 | Genomic DNA gene sequence |
| SEQ ID NO: 201 | Cas5 | I-E_Streptomyces sp. S4 | Genomic DNA gene sequence |
| SEQ ID NO: 202 | Cas6 | I-E_Streptomyces sp. S4 | Genomic DNA gene sequence |
| SEQ ID NO: 203 | Cas8 | I-E_Streptomyces sp. S4 | H. sapiens codon-optimized DNA gene sequence |
| SEQ ID NO: 204 | Cse2 | I-E_Streptomyces sp. S4 | H. sapiens codon-optimized DNA gene sequence |
| SEQ ID NO: 205 | Cas7 | I-E_Streptomyces sp. S4 | H. sapiens codon-optimized DNA gene sequence |
| SEQ ID NO: 206 | Cas5 | I-E_Streptomyces sp. S4 | H. sapiens codon-optimized DNA gene sequence |
| SEQ ID NO: 207 | Cas6 | I-E_Streptomyces sp. S4 | H. sapiens codon-optimized DNA gene sequence |
| SEQ ID NO: 208 | Cas8 | I-E_Streptomyces sp. S4 | Protein amino acid sequence |
| SEQ ID NO: 209 | Cse2 | I-E_Streptomyces sp. S4 | Protein amino acid sequence |
| SEQ ID NO: 210 | Cas7 | I-E_Streptomyces sp. S4 | Protein amino acid sequence |
| SEQ ID NO: 211 | Cas5 | I-E_Streptomyces sp. S4 | Protein amino acid sequence |
| SEQ ID NO: 212 | Cas6 | I-E_Streptomyces sp. S4 | Protein amino acid sequence |
| SEQ ID NO: 213 | CRISPR | I-E_Streptomyces sp. S4 | Exemplary minimal CRISPR array |
| SEQ ID NO: 214 | Cas6 | I-B_Fusobacterium nucleatum subsp. animalis 3_1_33 | Genomic DNA gene sequence |
| SEQ ID NO: 215 | Cas8 | I-B_Fusobacterium nucleatum subsp. animalis 3_1_33 | Genomic DNA gene sequence |
| SEQ ID NO: 216 | Cas7 | I-B_Fusobacterium nucleatum subsp. animalis 3_1_33 | Genomic DNA gene sequence |
| SEQ ID NO: 217 | Cas5 | I-B_Fusobacterium nucleatum subsp. animalis 3_1_33 | Genomic DNA gene sequence |
| SEQ ID NO: 218 | Cas6 | I-B_Fusobacterium nucleatum subsp. animalis 3_1_33 | H. sapiens codon-optimized DNA gene sequence |

FIG. 3 (continued)

| SEQ ID NO: | Gene/ Protein | Subtype and organism | Type of sequence |
|---|---|---|---|
| SEQ ID NO: 219 | Cas8 | I-B_Fusobacterium nucleatum subsp. animalis 3_1_33 | H. sapiens codon-optimized DNA gene sequence |
| SEQ ID NO: 220 | Cas7 | I-B_Fusobacterium nucleatum subsp. animalis 3_1_33 | H. sapiens codon-optimized DNA gene sequence |
| SEQ ID NO: 221 | Cas5 | I-B_Fusobacterium nucleatum subsp. animalis 3_1_33 | H. sapiens codon-optimized DNA gene sequence |
| SEQ ID NO: 222 | Cas6 | I-B_Fusobacterium nucleatum subsp. animalis 3_1_33 | Protein amino acid sequence |
| SEQ ID NO: 223 | Cas8 | I-B_Fusobacterium nucleatum subsp. animalis 3_1_33 | Protein amino acid sequence |
| SEQ ID NO: 224 | Cas7 | I-B_Fusobacterium nucleatum subsp. animalis 3_1_33 | Protein amino acid sequence |
| SEQ ID NO: 225 | Cas5 | I-B_Fusobacterium nucleatum subsp. animalis 3_1_33 | Protein amino acid sequence |
| SEQ ID NO: 226 | CRISPR | I-B_Fusobacterium nucleatum subsp. animalis 3_1_33 | Exemplary minimal CRISPR array |
| SEQ ID NO: 227 | Cas6 | I-B_Campylobacter fetus subsp. testudinum Sp3 | Genomic DNA gene sequence |
| SEQ ID NO: 228 | Cas8 | I-B_Campylobacter fetus subsp. testudinum Sp3 | Genomic DNA gene sequence |
| SEQ ID NO: 229 | Cas7 | I-B_Campylobacter fetus subsp. testudinum Sp3 | Genomic DNA gene sequence |
| SEQ ID NO: 230 | Cas5 | I-B_Campylobacter fetus subsp. testudinum Sp3 | Genomic DNA gene sequence |
| SEQ ID NO: 231 | Cas6 | I-B_Campylobacter fetus subsp. testudinum Sp3 | H. sapiens codon-optimized DNA gene sequence |
| SEQ ID NO: 232 | Cas8 | I-B_Campylobacter fetus subsp. testudinum Sp3 | H. sapiens codon-optimized DNA gene sequence |
| SEQ ID NO: 233 | Cas7 | I-B_Campylobacter fetus subsp. testudinum Sp3 | H. sapiens codon-optimized DNA gene sequence |
| SEQ ID NO: 234 | Cas5 | I-B_Campylobacter fetus subsp. testudinum Sp3 | H. sapiens codon-optimized DNA gene sequence |
| SEQ ID NO: 235 | Cas6 | I-B_Campylobacter fetus subsp. testudinum Sp3 | Protein amino acid sequence |
| SEQ ID NO: 236 | Cas8 | I-B_Campylobacter fetus subsp. testudinum Sp3 | Protein amino acid sequence |
| SEQ ID NO: 237 | Cas7 | I-B_Campylobacter fetus subsp. testudinum Sp3 | Protein amino acid sequence |
| SEQ ID NO: 238 | Cas5 | I-B_Campylobacter fetus subsp. testudinum Sp3 | Protein amino acid sequence |
| SEQ ID NO: 239 | CRISPR | I-B_Campylobacter fetus subsp. testudinum Sp3 | Exemplary minimal CRISPR array |
| SEQ ID NO: 240 | Cas6 | I-B_Odoribacter splanchnicus DSM 20712 | Genomic DNA gene sequence |

FIG. 3 (continued)

| SEQ ID NO: | Gene/Protein | Subtype and organism | Type of sequence |
|---|---|---|---|
| SEQ ID NO: 241 | Cas8 | I-B_Odoribacter splanchnicus DSM 20712 | Genomic DNA gene sequence |
| SEQ ID NO: 242 | Cas7 | I-B_Odoribacter splanchnicus DSM 20712 | Genomic DNA gene sequence |
| SEQ ID NO: 243 | Cas5 | I-B_Odoribacter splanchnicus DSM 20712 | Genomic DNA gene sequence |
| SEQ ID NO: 244 | Cas6 | I-B_Odoribacter splanchnicus DSM 20712 | H. sapiens codon-optimized DNA gene sequence |
| SEQ ID NO: 245 | Cas8 | I-B_Odoribacter splanchnicus DSM 20712 | H. sapiens codon-optimized DNA gene sequence |
| SEQ ID NO: 246 | Cas7 | I-B_Odoribacter splanchnicus DSM 20712 | H. sapiens codon-optimized DNA gene sequence |
| SEQ ID NO: 247 | Cas5 | I-B_Odoribacter splanchnicus DSM 20712 | H. sapiens codon-optimized DNA gene sequence |
| SEQ ID NO: 248 | Cas6 | I-B_Odoribacter splanchnicus DSM 20712 | Protein amino acid sequence |
| SEQ ID NO: 249 | Cas8 | I-B_Odoribacter splanchnicus DSM 20712 | Protein amino acid sequence |
| SEQ ID NO: 250 | Cas7 | I-B_Odoribacter splanchnicus DSM 20712 | Protein amino acid sequence |
| SEQ ID NO: 251 | Cas5 | I-B_Odoribacter splanchnicus DSM 20712 | Protein amino acid sequence |
| SEQ ID NO: 252 | CRISPR | I-B_Odoribacter splanchnicus DSM 20712 | Exemplary minimal CRISPR array |
| SEQ ID NO: 253 | Cas5 | I-C_Bacillus halodurans C-125 | Genomic DNA gene sequence |
| SEQ ID NO: 254 | Cas8 | I-C_Bacillus halodurans C-125 | Genomic DNA gene sequence |
| SEQ ID NO: 255 | Cas7 | I-C_Bacillus halodurans C-125 | Genomic DNA gene sequence |
| SEQ ID NO: 256 | Cas5 | I-C_Bacillus halodurans C-125 | H. sapiens codon-optimized DNA gene sequence |
| SEQ ID NO: 257 | Cas8 | I-C_Bacillus halodurans C-125 | H. sapiens codon-optimized DNA gene sequence |
| SEQ ID NO: 258 | Cas7 | I-C_Bacillus halodurans C-125 | H. sapiens codon-optimized DNA gene sequence |
| SEQ ID NO: 259 | Cas5 | I-C_Bacillus halodurans C-125 | Protein amino acid sequence |
| SEQ ID NO: 260 | Cas8 | I-C_Bacillus halodurans C-125 | Protein amino acid sequence |
| SEQ ID NO: 261 | Cas7 | I-C_Bacillus halodurans C-125 | Protein amino acid sequence |
| SEQ ID NO: 262 | CRISPR | I-C_Bacillus halodurans C-125 | Exemplary minimal CRISPR array |
| SEQ ID NO: 263 | Cas5 | I-C_Desulfovibrio vulgaris RCH1 plasmid pDEVAL01 | Genomic DNA gene sequence |
| SEQ ID NO: 264 | Cas8 | I-C_Desulfovibrio vulgaris RCH1 plasmid pDEVAL01 | Genomic DNA gene sequence |

FIG. 3 (continued)

| SEQ ID NO: | Gene/ Protein | Subtype and organism | Type of sequence |
|---|---|---|---|
| SEQ ID NO: 265 | Cas7 | I-C_Desulfovibrio vulgaris RCH1 plasmid pDEVAL01 | Genomic DNA gene sequence |
| SEQ ID NO: 266 | Cas5 | I-C_Desulfovibrio vulgaris RCH1 plasmid pDEVAL01 | H. sapiens codon-optimized DNA gene sequence |
| SEQ ID NO: 267 | Cas8 | I-C_Desulfovibrio vulgaris RCH1 plasmid pDEVAL01 | H. sapiens codon-optimized DNA gene sequence |
| SEQ ID NO: 268 | Cas7 | I-C_Desulfovibrio vulgaris RCH1 plasmid pDEVAL01 | H. sapiens codon-optimized DNA gene sequence |
| SEQ ID NO: 269 | Cas5 | I-C_Desulfovibrio vulgaris RCH1 plasmid pDEVAL01 | Protein amino acid sequence |
| SEQ ID NO: 270 | Cas8 | I-C_Desulfovibrio vulgaris RCH1 plasmid pDEVAL01 | Protein amino acid sequence |
| SEQ ID NO: 271 | Cas7 | I-C_Desulfovibrio vulgaris RCH1 plasmid pDEVAL01 | Protein amino acid sequence |
| SEQ ID NO: 272 | CRISPR | I-C_Desulfovibrio vulgaris RCH1 plasmid pDEVAL01 | Exemplary minimal CRISPR array |
| SEQ ID NO: 273 | Cas5 | I-C_Geobacillus thermocatenulatus strain KCTC 3921 | Genomic DNA gene sequence |
| SEQ ID NO: 274 | Cas8 | I-C_Geobacillus thermocatenulatus strain KCTC 3921 | Genomic DNA gene sequence |
| SEQ ID NO: 275 | Cas7 | I-C_Geobacillus thermocatenulatus strain KCTC 3921 | Genomic DNA gene sequence |
| SEQ ID NO: 276 | Cas5 | I-C_Geobacillus thermocatenulatus strain KCTC 3921 | H. sapiens codon-optimized DNA gene sequence |
| SEQ ID NO: 277 | Cas8 | I-C_Geobacillus thermocatenulatus strain KCTC 3921 | H. sapiens codon-optimized DNA gene sequence |
| SEQ ID NO: 278 | Cas7 | I-C_Geobacillus thermocatenulatus strain KCTC 3921 | H. sapiens codon-optimized DNA gene sequence |
| SEQ ID NO: 279 | Cas5 | I-C_Geobacillus thermocatenulatus strain KCTC 3921 | Protein amino acid sequence |
| SEQ ID NO: 280 | Cas8 | I-C_Geobacillus thermocatenulatus strain KCTC 3921 | Protein amino acid sequence |
| SEQ ID NO: 281 | Cas7 | I-C_Geobacillus thermocatenulatus strain KCTC 3921 | Protein amino acid sequence |

FIG. 3 (continued)

| SEQ ID NO: | Gene/Protein | Subtype and organism | Type of sequence |
|---|---|---|---|
| SEQ ID NO: 282 | CRISPR | I-C_Geobacillus thermocatenulatus strain KCTC 3921 | Exemplary minimal CRISPR array |
| SEQ ID NO: 283 | Cas8 | I-F_Vibrio cholerae strain L15 | Genomic DNA gene sequence |
| SEQ ID NO: 284 | Cas5 | I-F_Vibrio cholerae strain L15 | Genomic DNA gene sequence |
| SEQ ID NO: 285 | Cas7 | I-F_Vibrio cholerae strain L15 | Genomic DNA gene sequence |
| SEQ ID NO: 286 | Cas6 | I-F_Vibrio cholerae strain L15 | Genomic DNA gene sequence |
| SEQ ID NO: 287 | Cas8 | I-F_Vibrio cholerae strain L15 | H. sapiens codon-optimized DNA gene sequence |
| SEQ ID NO: 288 | Cas5 | I-F_Vibrio cholerae strain L15 | H. sapiens codon-optimized DNA gene sequence |
| SEQ ID NO: 289 | Cas7 | I-F_Vibrio cholerae strain L15 | H. sapiens codon-optimized DNA gene sequence |
| SEQ ID NO: 290 | Cas6 | I-F_Vibrio cholerae strain L15 | H. sapiens codon-optimized DNA gene sequence |
| SEQ ID NO: 291 | Cas8 | I-F_Vibrio cholerae strain L15 | Protein amino acid sequence |
| SEQ ID NO: 292 | Cas5 | I-F_Vibrio cholerae strain L15 | Protein amino acid sequence |
| SEQ ID NO: 293 | Cas7 | I-F_Vibrio cholerae strain L15 | Protein amino acid sequence |
| SEQ ID NO: 294 | Cas6 | I-F_Vibrio cholerae strain L15 | Protein amino acid sequence |
| SEQ ID NO: 295 | CRISPR | I-F_Vibrio cholerae strain L15 | Exemplary minimal CRISPR array |
| SEQ ID NO: 296 | Cas8 | I-F_Klebsiella oxytoca strain ICU1-2b | Genomic DNA gene sequence |
| SEQ ID NO: 297 | Cas5 | I-F_Klebsiella oxytoca strain ICU1-2b | Genomic DNA gene sequence |
| SEQ ID NO: 298 | Cas7 | I-F_Klebsiella oxytoca strain ICU1-2b | Genomic DNA gene sequence |
| SEQ ID NO: 299 | Cas6 | I-F_Klebsiella oxytoca strain ICU1-2b | Genomic DNA gene sequence |
| SEQ ID NO: 300 | Cas8 | I-F_Klebsiella oxytoca strain ICU1-2b | H. sapiens codon-optimized DNA gene sequence |
| SEQ ID NO: 301 | Cas5 | I-F_Klebsiella oxytoca strain ICU1-2b | H. sapiens codon-optimized DNA gene sequence |
| SEQ ID NO: 302 | Cas7 | I-F_Klebsiella oxytoca strain ICU1-2b | H. sapiens codon-optimized DNA gene sequence |
| SEQ ID NO: 303 | Cas6 | I-F_Klebsiella oxytoca strain ICU1-2b | H. sapiens codon-optimized DNA gene sequence |
| SEQ ID NO: 304 | Cas8 | I-F_Klebsiella oxytoca strain ICU1-2b | Protein amino acid sequence |
| SEQ ID NO: 305 | Cas5 | I-F_Klebsiella oxytoca strain ICU1-2b | Protein amino acid sequence |
| SEQ ID NO: 306 | Cas7 | I-F_Klebsiella oxytoca strain ICU1-2b | Protein amino acid sequence |

FIG. 3 (continued)

| SEQ ID NO: | Gene/Protein | Subtype and organism | Type of sequence |
|---|---|---|---|
| SEQ ID NO: 307 | Cas6 | I-F_Klebsiella oxytoca strain ICU1-2b | Protein amino acid sequence |
| SEQ ID NO: 308 | CRISPR | I-F_Klebsiella oxytoca strain ICU1-2b | Exemplary minimal CRISPR array |
| SEQ ID NO: 309 | Cas8 | I-F_Pseudomonas aeruginosa UCBPP-PA14 | Genomic DNA gene sequence |
| SEQ ID NO: 310 | Cas5 | I-F_Pseudomonas aeruginosa UCBPP-PA14 | Genomic DNA gene sequence |
| SEQ ID NO: 311 | Cas7 | I-F_Pseudomonas aeruginosa UCBPP-PA14 | Genomic DNA gene sequence |
| SEQ ID NO: 312 | Cas6 | I-F_Pseudomonas aeruginosa UCBPP-PA14 | Genomic DNA gene sequence |
| SEQ ID NO: 313 | Cas8 | I-F_Pseudomonas aeruginosa UCBPP-PA14 | H. sapiens codon-optimized DNA gene sequence |
| SEQ ID NO: 314 | Cas5 | I-F_Pseudomonas aeruginosa UCBPP-PA14 | H. sapiens codon-optimized DNA gene sequence |
| SEQ ID NO: 315 | Cas7 | I-F_Pseudomonas aeruginosa UCBPP-PA14 | H. sapiens codon-optimized DNA gene sequence |
| SEQ ID NO: 316 | Cas6 | I-F_Pseudomonas aeruginosa UCBPP-PA14 | H. sapiens codon-optimized DNA gene sequence |
| SEQ ID NO: 317 | Cas8 | I-F_Pseudomonas aeruginosa UCBPP-PA14 | Protein amino acid sequence |
| SEQ ID NO: 318 | Cas5 | I-F_Pseudomonas aeruginosa UCBPP-PA14 | Protein amino acid sequence |
| SEQ ID NO: 319 | Cas7 | I-F_Pseudomonas aeruginosa UCBPP-PA14 | Protein amino acid sequence |
| SEQ ID NO: 320 | Cas6 | I-F_Pseudomonas aeruginosa UCBPP-PA14 | Protein amino acid sequence |
| SEQ ID NO: 321 | CRISPR | I-F_Pseudomonas aeruginosa UCBPP-PA14 | Exemplary minimal CRISPR array |
| SEQ ID NO: 322 | Cas7 | I-Fv2_Shewanella putrefaciens CN-32 | Genomic DNA gene sequence |
| SEQ ID NO: 323 | Cas5 | I-Fv2_Shewanella putrefaciens CN-32 | Genomic DNA gene sequence |
| SEQ ID NO: 324 | Cas6 | I-Fv2_Shewanella putrefaciens CN-32 | Genomic DNA gene sequence |
| SEQ ID NO: 325 | Cas7 | I-Fv2_Shewanella putrefaciens CN-32 | H. sapiens codon-optimized DNA gene sequence |
| SEQ ID NO: 326 | Cas5 | I-Fv2_Shewanella putrefaciens CN-32 | H. sapiens codon-optimized DNA gene sequence |
| SEQ ID NO: 327 | Cas6 | I-Fv2_Shewanella putrefaciens CN-32 | H. sapiens codon-optimized DNA gene sequence |
| SEQ ID NO: 328 | Cas7 | I-Fv2_Shewanella putrefaciens CN-32 | Protein amino acid sequence |
| SEQ ID NO: 329 | Cas5 | I-Fv2_Shewanella putrefaciens CN-32 | Protein amino acid sequence |
| SEQ ID NO: 330 | Cas6 | I-Fv2_Shewanella putrefaciens CN-32 | Protein amino acid sequence |
| SEQ ID NO: 331 | CRISPR | I-Fv2_Shewanella putrefaciens CN-32 | Exemplary minimal CRISPR array |
| SEQ ID NO: 332 | Cas7 | I-Fv2_Acinetobacter sp. 869535 | Genomic DNA gene sequence |
| SEQ ID NO: 333 | Cas5 | I-Fv2_Acinetobacter sp. 869535 | Genomic DNA gene sequence |

FIG. 3 (continued)

| SEQ ID NO: | Gene/ Protein | Subtype and organism | Type of sequence |
|---|---|---|---|
| SEQ ID NO: 334 | Cas6 | I-Fv2_Acinetobacter sp. 869535 | Genomic DNA gene sequence |
| SEQ ID NO: 335 | Cas7 | I-Fv2_Acinetobacter sp. 869535 | H. sapiens codon-optimized DNA gene sequence |
| SEQ ID NO: 336 | Cas5 | I-Fv2_Acinetobacter sp. 869535 | H. sapiens codon-optimized DNA gene sequence |
| SEQ ID NO: 337 | Cas6 | I-Fv2_Acinetobacter sp. 869535 | H. sapiens codon-optimized DNA gene sequence |
| SEQ ID NO: 338 | Cas7 | I-Fv2_Acinetobacter sp. 869535 | Protein amino acid sequence |
| SEQ ID NO: 339 | Cas5 | I-Fv2_Acinetobacter sp. 869535 | Protein amino acid sequence |
| SEQ ID NO: 340 | Cas6 | I-Fv2_Acinetobacter sp. 869535 | Protein amino acid sequence |
| SEQ ID NO: 341 | CRISPR | I-Fv2_Acinetobacter sp. 869535 | Exemplary minimal CRISPR array |
| SEQ ID NO: 342 | Cas7 | I-Fv2_Vibrio cholerae HE48 | Genomic DNA gene sequence |
| SEQ ID NO: 343 | Cas5 | I-Fv2_Vibrio cholerae HE48 | Genomic DNA gene sequence |
| SEQ ID NO: 344 | Cas6 | I-Fv2_Vibrio cholerae HE48 | Genomic DNA gene sequence |
| SEQ ID NO: 345 | Cas7 | I-Fv2_Vibrio cholerae HE48 | H. sapiens codon-optimized DNA gene sequence |
| SEQ ID NO: 346 | Cas5 | I-Fv2_Vibrio cholerae HE48 | H. sapiens codon-optimized DNA gene sequence |
| SEQ ID NO: 347 | Cas6 | I-Fv2_Vibrio cholerae HE48 | H. sapiens codon-optimized DNA gene sequence |
| SEQ ID NO: 348 | Cas7 | I-Fv2_Vibrio cholerae HE48 | Protein amino acid sequence |
| SEQ ID NO: 349 | Cas5 | I-Fv2_Vibrio cholerae HE48 | Protein amino acid sequence |
| SEQ ID NO: 350 | Cas6 | I-Fv2_Vibrio cholerae HE48 | Protein amino acid sequence |
| SEQ ID NO: 351 | CRISPR | I-Fv2_Vibrio cholerae HE48 | Exemplary minimal CRISPR array |

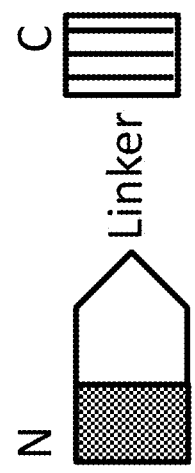
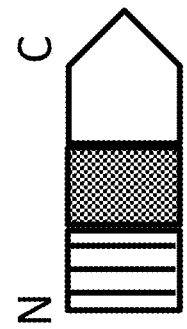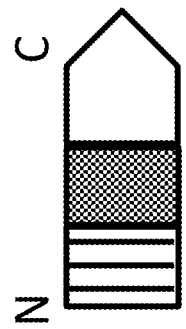
FIG. 4A  FIG. 4B

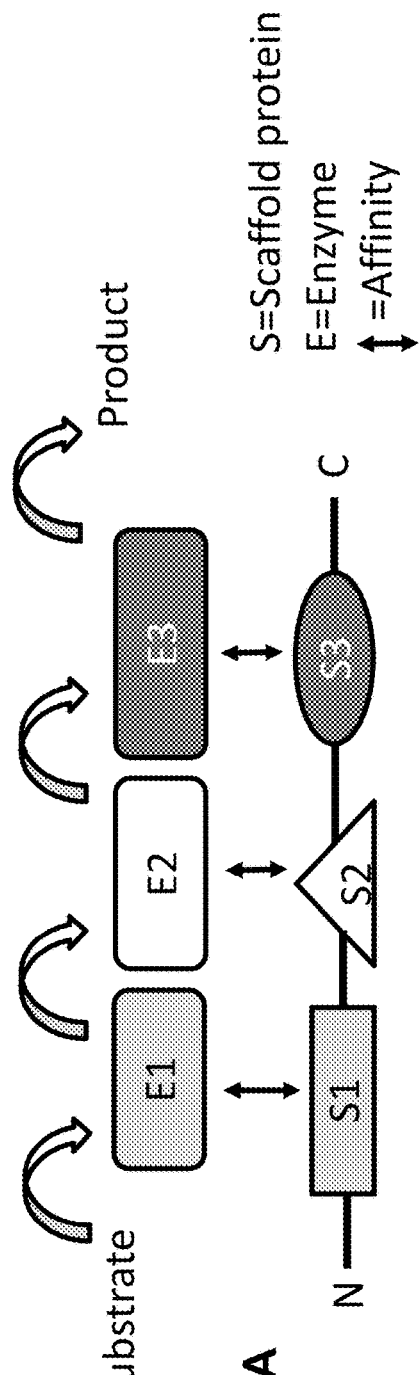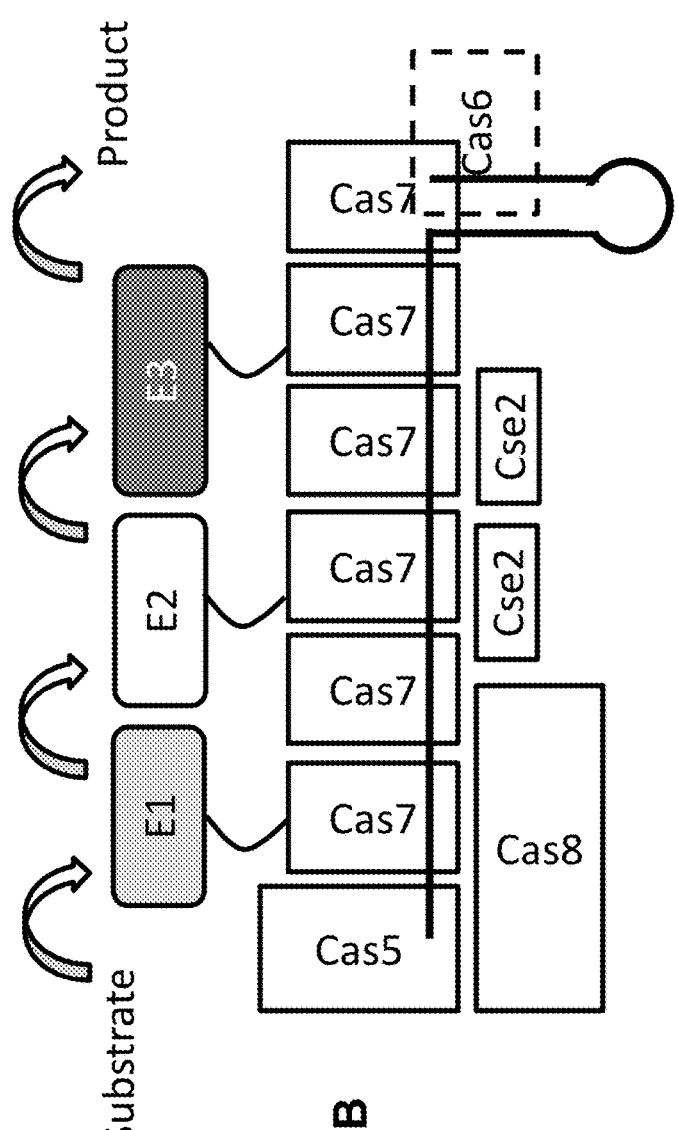
FIG. 12A
FIG. 12B

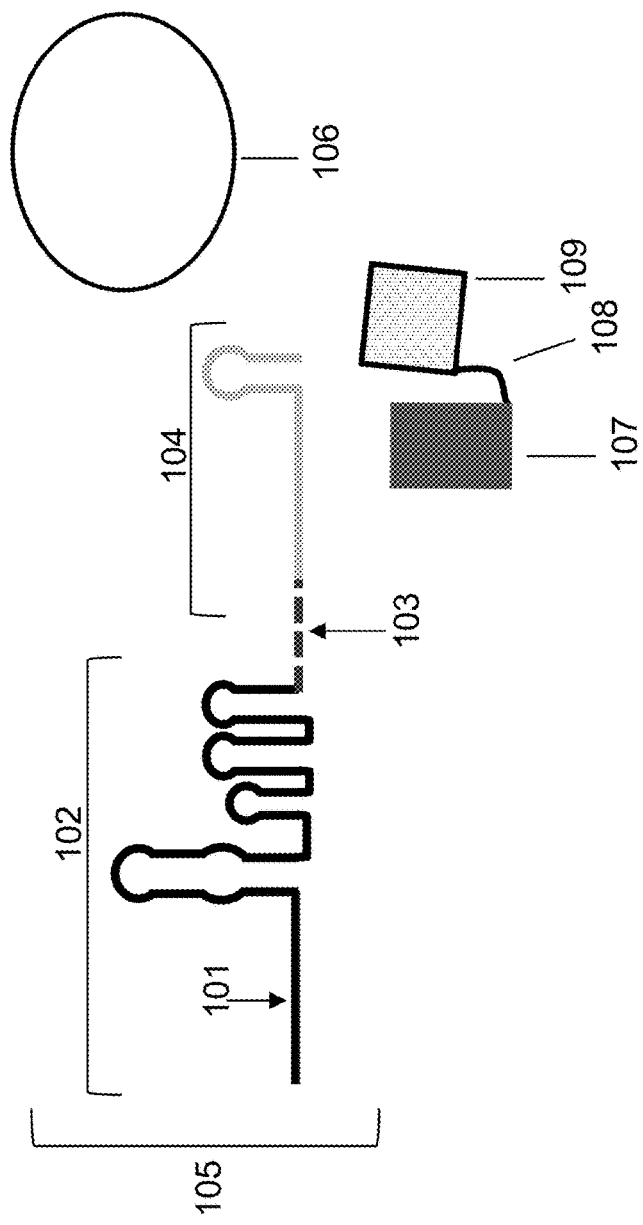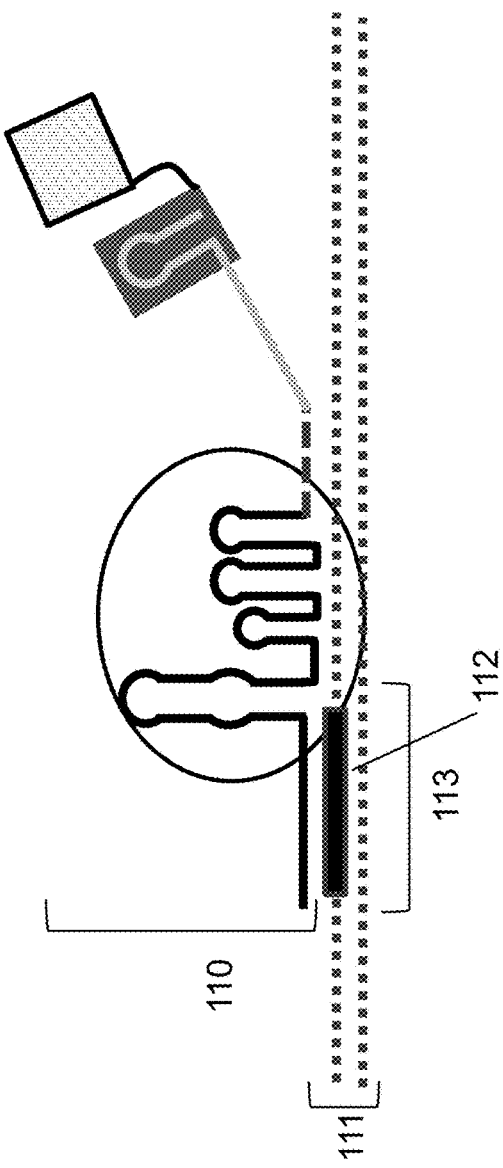
FIG. 13A
FIG. 13B

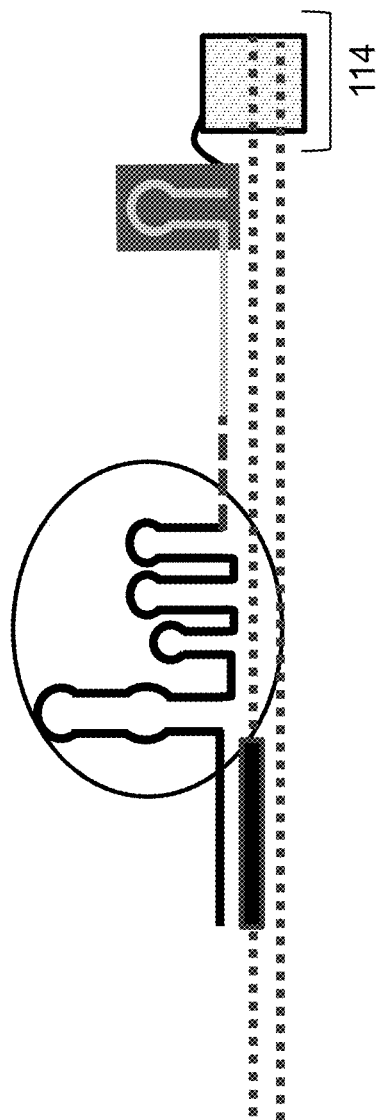

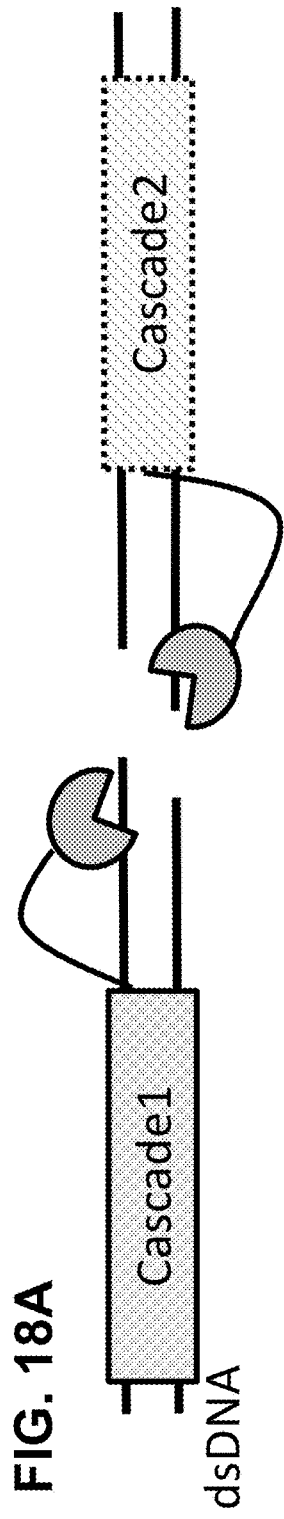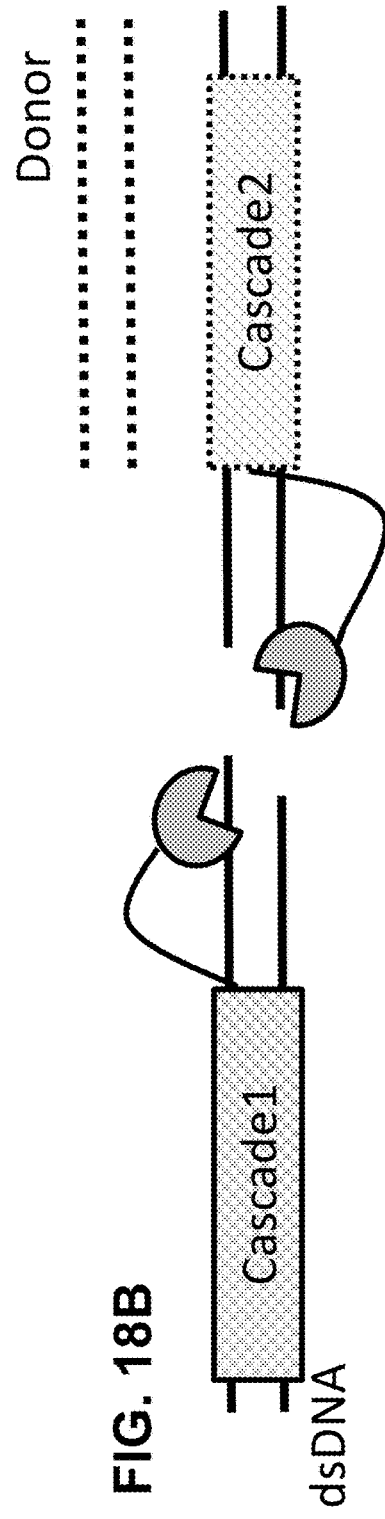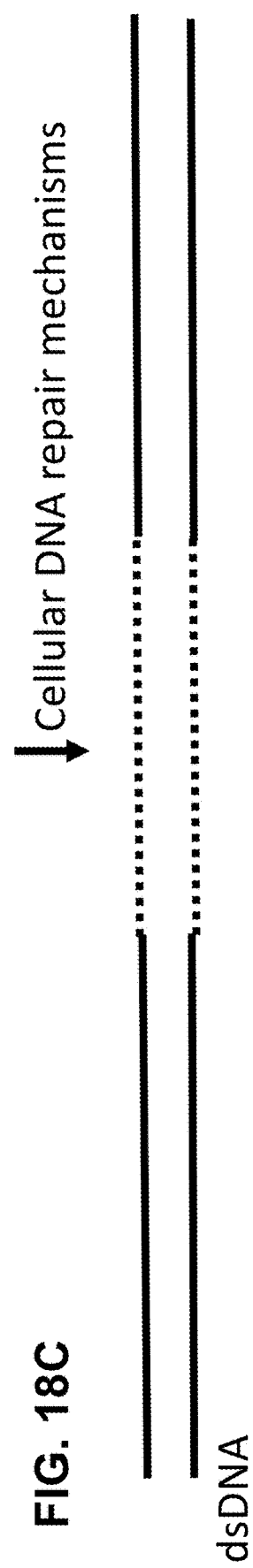

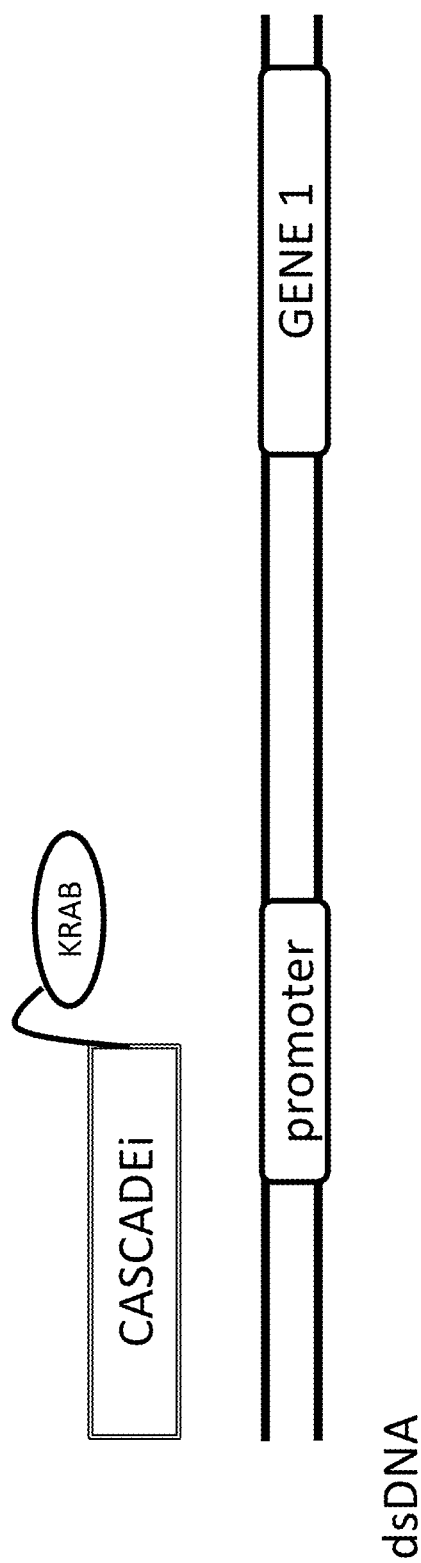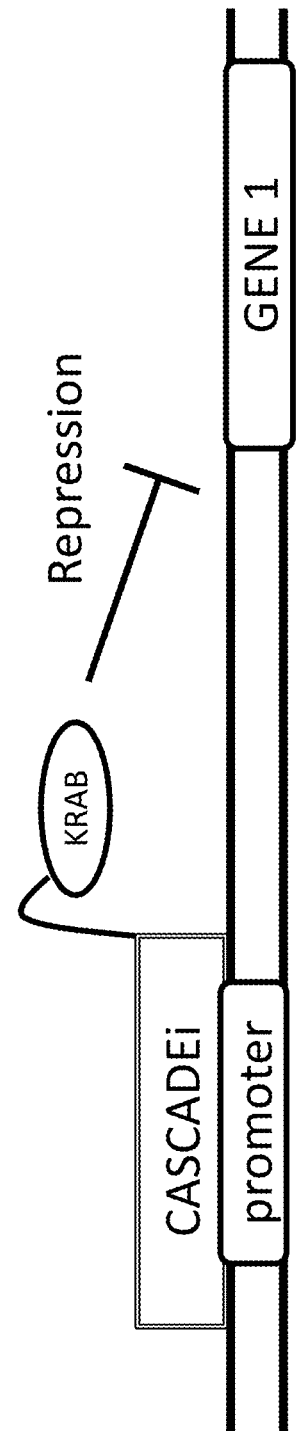
FIG. 21A
FIG. 21B

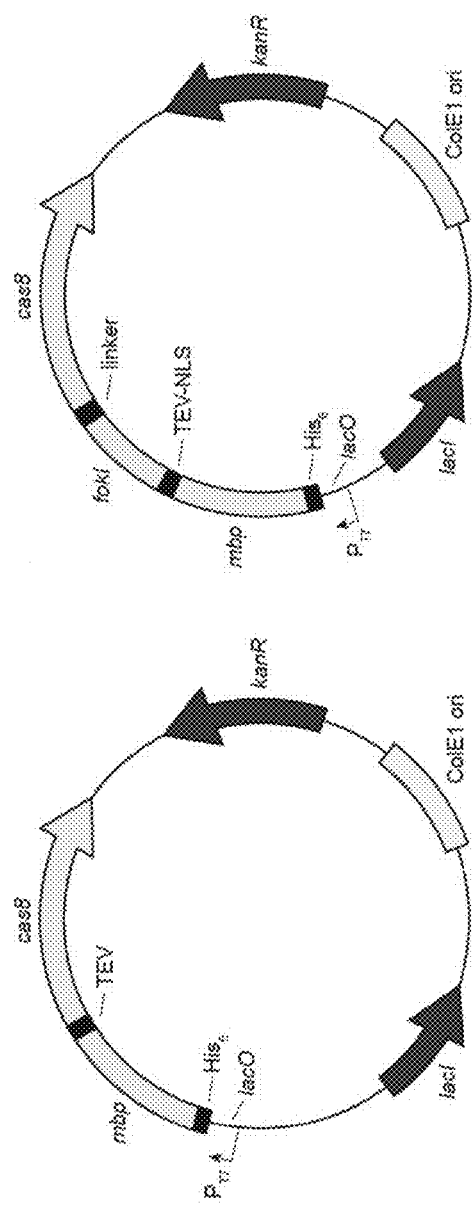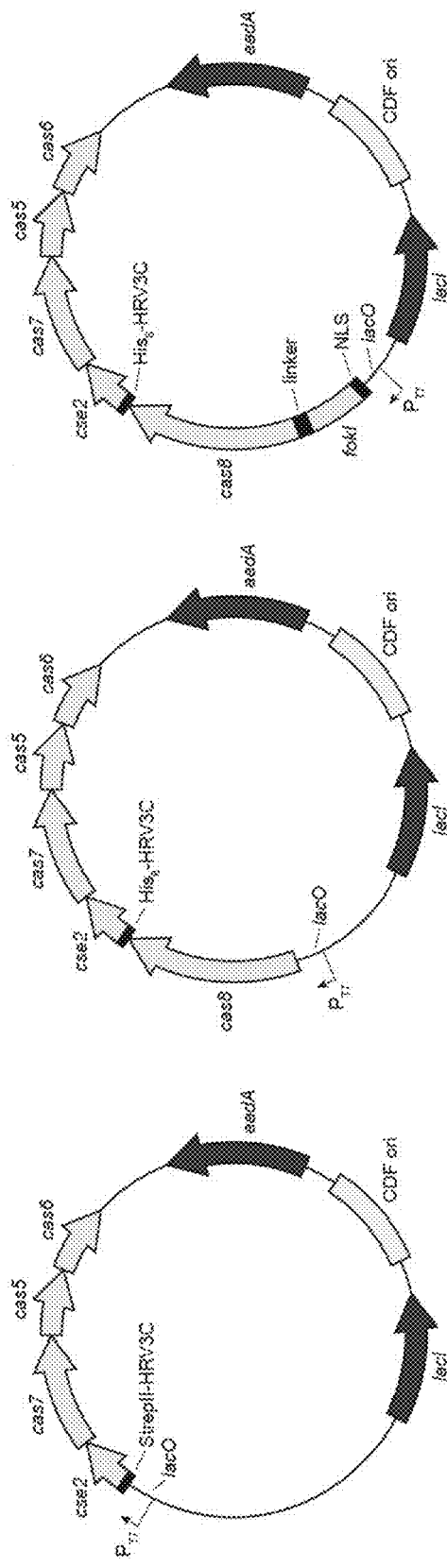
FIG. 24A  FIG. 24B  FIG. 24C  FIG. 24D  FIG. 24E

|    | 5    | 10   | 15   | 17   | 20   | 30   | 40   | 50   |
|----|------|------|------|------|------|------|------|------|
| 14 | 0.07 | 0.03 | 0.03 | 0.04 | 0.06 | 0.03 | 0.04 | 0.04 |
| 16 | 0.11 | 0.02 | 0.05 | 0.09 | 0.04 | 0.04 | 0.07 | 0.04 |
| 18 | 0.04 | 0.02 | 0.04 | 0.05 | 0.02 | 0.07 | 0.01 | 0.03 |
| 20 | 0.01 | 0.00 | 0.04 | 0.14 | 0.04 | 0.11 | 0.02 | 0.06 |
| 22 | 0.04 | 0.03 | 0.17 | 1.03 | 0.09 | 0.05 | 0.06 | 0.05 |
| 24 | 0.03 | 0.03 | 0.10 | 0.36 | 0.14 | 0.10 | 0.08 | 0.06 |
| 26 | 0.12 | 0.04 | 0.09 | 0.24 | 0.06 | 0.02 | 0.08 | 0.06 |
| 28 | 0.13 | 0.01 | 0.17 | 0.14 | 0.21 | 0.12 | 0.01 | 0.16 |
| 30 | 0.10 | 0.10 | 0.24 | 1.38 | 0.83 | 0.54 | 0.71 | 0.35 |
| 32 | 0.10 | 1.14 | 2.17 | 5.67 | 5.11 | 2.39 | 2.04 | 1.26 |
| 34 | 0.06 | 0.09 | 0.24 | 1.70 | 1.02 | 0.62 | 0.60 | 0.38 |
| 36 | 0.04 | 0.04 | 0.05 | 0.16 | 0.21 | 0.25 | 0.55 | 0.48 |
| 38 | 0.02 | 0.00 | 0.02 | 0.02 | 0.00 | 0.01 | 0.00 | 0.01 |
| 40 | 0.77 | 0.08 | 0.26 | 0.80 | 0.12 | 0.24 | 0.33 | 0.18 |
| 42 | 0.04 | 0.04 | 0.12 | 1.08 | 0.43 | 0.38 | 0.73 | 0.40 |
| 44 | 0.02 | 0.01 | 0.03 | 0.08 | 0.08 | 0.12 | 0.16 | 0.19 |
| 46 | 0.01 | 0.02 | 0.01 | 0.98 | 0.02 | 0.03 | 0.01 | 0.02 |
| 48 | 0.08 | 0.06 | 0.07 | 0.08 | 0.05 | 0.05 | 0.07 | 0.08 |
| 50 | 0.04 | 0.02 | 0.05 | 0.03 | 0.05 | 0.07 | 0.05 | 0.09 |
| 52 | 0.05 | 0.10 | 0.05 | 0.10 | 0.08 | 0.12 | 0.09 | 0.13 |
| 54 | 0.04 | 0.05 | 0.01 | 0.06 | 0.03 | 0.04 | 0.05 | 0.02 |
| 56 | 0.18 | 0.03 | 0.14 | 0.09 | 0.01 | 0.02 | 0.00 | 0.05 |
| 58 | 0.09 | 0.09 | 0.05 | 0.11 | 0.16 | 0.13 | 0.11 | 0.26 |
| 60 | 0.02 | 0.02 | 0.07 | 0.07 | 0.13 | 0.01 | 0.01 | 0.11 |

FIG. 32B

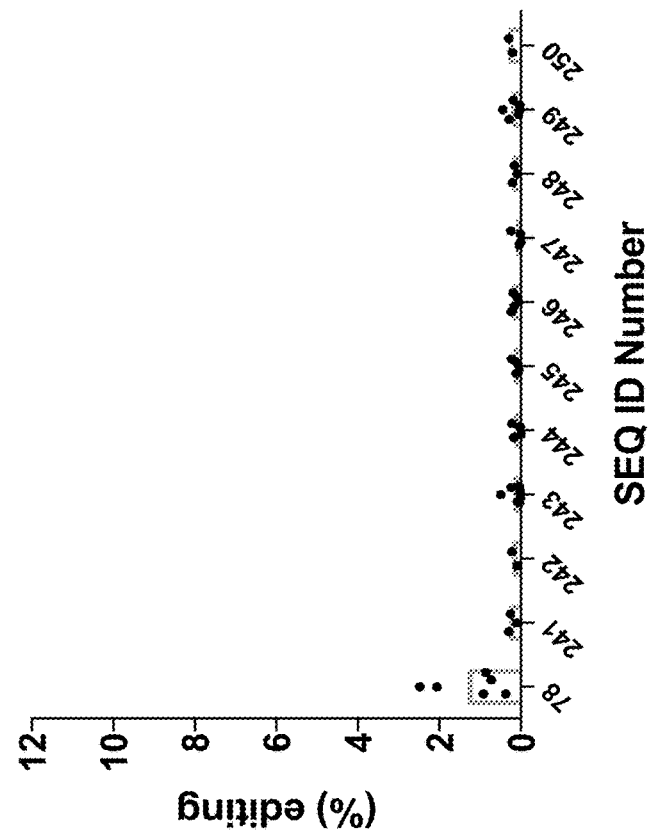
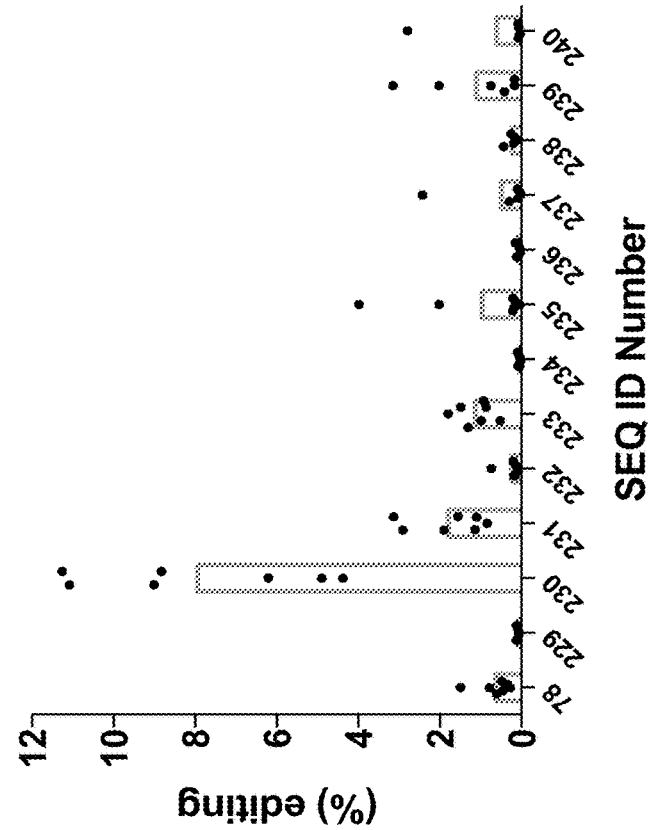
FIG. 34B
FIG. 34A

ENGINEERED CASCADE COMPONENTS AND CASCADE COMPLEXES

CROSS-REFERENCE TO RELATED APPLICATIONS

This application is a continuation of U.S. patent application Ser. No. 16/420,061, filed 22 May 2019, now allowed, which is a continuation of U.S. patent application Ser. No. 16/262,773, filed 30 Jan. 2019, now U.S. Pat. No. 10,329,547, which is a continuation of U.S. patent application Ser. No. 16/104,875, filed 17 Aug. 2018, now U.S. Pat. No. 10,227,576, which claims the benefit of U.S. Provisional Patent Application Ser. No. 62/684,735, filed 13 Jun. 2018, now expired, the contents of which are herein incorporated by reference in their entirety.

STATEMENT REGARDING FEDERALLY SPONSORED RESEARCH OR DEVELOPMENT

Not applicable.

SEQUENCE LISTING

The present application contains a Sequence Listing that has been submitted electronically in ASCII format and is hereby incorporated by reference in its entirety. The ASCII copy, created on 7 Oct. 2019 is named CBI032-13_ST25.txt and is 2.2 MB in size.

TECHNICAL FIELD

The present disclosure relates generally to engineered Class 1 Type I CRISPR-Cas (Cascade) systems that comprise multi-protein effector complexes, nucleoprotein complexes comprising Type I CRISPR-Cas subunit proteins and nucleic acid guides, polynucleotides encoding Type I CRISPR-Cas subunit proteins, and guide polynucleotides. The disclosure also relates to compositions and methods for making and using the engineered Type I CRISPR-Cas systems of the present invention.

BACKGROUND

Clustered regularly interspaced short palindromic repeats (CRISPR) and CRISPR-associated proteins (Cas) constitute CRISPR-Cas systems. The CRISPR-Cas systems provide adaptive immunity against foreign polynucleotides in bacteria and archaea (see, e.g., Barrangou, R., et al., Science 315:1709-1712 (2007); Makarova, K. S., et al., Nature Reviews Microbiology 9:467-477 (2011); Garneau, J. E., et al., Nature 468:67-71 (2010); Sapranauskas, R., et al., Nucleic Acids Research 39:9275-9282 (2011); Koonin, E. V., et al., Curr. Opin. Microbiol. 37:67-78 (2017)). Various CRISPR-Cas systems in their native hosts are capable of DNA targeting (Class 1 Type I; Class 2 Type II and Type V), RNA targeting (Class 2 Type VI), and joint DNA and RNA targeting (Class 1 Type III) (see, e.g., Makarova, K. S., et al., Nat. Rev. Microbiol. 13(11):722-736 (2015); Shmakov, S., et al., Nat. Rev. Microbiol. 15:169-182 (2017); Abudayyeh, O. O., et al., Science 353:1-17 (2016)).

The classification of CRISPR-Cas systems has had many iterations. Koonin, E. V., et al., (Curr. Opin. Microbiol. 37:67-78 (2017)) proposed a classification system that takes into consideration the signature cas genes specific for individual types and subtypes of CRISPR-Cas systems. The classification also considered sequence similarity between multiple shared Cas proteins, the phylogeny of the best conserved Cas protein, gene organization, and the structure of the CRISPR array. This approach provided a classification scheme that divides CRISPR-Cas systems into two distinct classes: Class 1 comprising a multiprotein effector complex (Type I (CRISPR-associated complex for antiviral defense ("Cascade") effector complex), Type III (Cmr/Csm effector complex), and Type IV); and Class 2 comprising a single effector protein (Type II (Cas9), Type V (Cas12a, previously referred to as Cpf1), and Type VI (Cas13a, previously referred to as C2c2)). In the Class 1 systems, Type I is the most common and diverse, Type III is more common in archaea than bacteria, and Type IV is least common.

The Type I systems comprise the signature Cas3 protein. The Cas3 protein has helicase and DNase domains responsible for DNA target sequence cleavage. To date, seven subtypes of the Type I system have been identified (i.e., Type I-A, I-B, I-C, I-D, I-E, I-F (and variants for I-F (e.g., I-Fv1, I-Fv2), and I-U) that have a variable number of cas genes. Type I cas genes include, but are not limited to, the following: cas7, cas5, cas8, cse2, csa5, cas3, cast, cas4, cas1, and cash. Examples of organisms having Type I systems are as follows: I-A, *Archaeoglobus fuldgidus*; I-B, *Clostridium kluyveri*; I-C, *Bacillus halodurans*; I-U, *Geobacter sulfurreducens*; I-D, Cyanothece sp. 8802; I-E, *Escherichia coli* K12; I-F, *Yersinia* pseudo-tuberculosis; I-F variant, *Shewanella putrefaciens* CN-32 (Koonin, E. V., et al., Curr. Opin. Microbiol. 37:67-78 (2017)).

Type I systems typically encode proteins that combine with a CRISPR RNA (crRNA or "guide RNA") to form a Cascade complex. These complexes comprise multiple proteins and a CRISPR RNA (crRNA), which are transcribed from this CRISPR locus. In Type I systems, primary processing of a pre-crRNA is catalyzed by Cash. This typically results in a crRNA with a 5' handle of 8 nucleotides, a spacer region, and a 3' handle; both 5' and 3' handles are derived from the repeat sequence. In some systems, the 3' handle forms a stem-loop structure; in other systems, secondary processing of the 3' end of crRNA is catalyzed by ribonuclease(s) (van der Oost, J., et al., Nature Reviews Microbiology 12:479-492 (2014)).

The Cascade effector complexes of the Type I CRISPR-Cas systems comprise a backbone having paralogous Repeat-Associated Mysterious Proteins (RAMPs; e.g., Cas7 and Cas5 proteins) containing the RNA Recognition Motif (RRM) fold and additional "large" and "small" subunit proteins (see, e.g., Koonin, E. V., et al., Curr. Opin. Microbiol. 37:67-78, FIG. 2 (2017)). These Cascade effector complexes typically have a Cas5 subunit protein and several Cas7 subunit proteins. Such Cascade effector complexes also comprise the guide RNA. The Cascade effector complexes comprise the various subunit proteins arranged in an asymmetric fashion along the length of the guide RNA. The Cas5 subunit protein and the large subunit protein (Cas8 protein) are positioned at one end of the complex, enveloping the 5' end of the guide RNA. Several copies of the small subunit protein interact with the guide RNA backbone, which is bound to multiple copies of the Cas7 subunit protein. The Cas6 subunit protein, another RAMP protein, is associated with the Cascade effector complex primarily through association with the 3' handle (repeat region) of the crRNA. The Cas6 subunit protein usually functions as the repeat-specific RNase involved in pre-crRNA processing; however, in Type I-C systems, Cas5 functions as the repeat-specific RNase and there is no Cas6.

The primary sequences of the CRISPR-Cas Type I Cascade subunit proteins have little sequence identity; however, the presence of homologous RAMP modules and the overall structural similarity of the multiprotein effector complexes supports a common origin of these effector complexes (Koonin, E. V., et al., Curr. Opin. Microbiol. 37:67-78 (2017)).

The adaptive immunity mechanism of action in the Type I CRISPR-Cas systems involves essentially three phases: adaptation, expression, and interference. In the adaptation phase, a foreign DNA or RNA infects the host and proteins encoded by various cas genes bind regions of the infecting DNA or RNA. Such regions are called protospacers. A protospacer adjacent motif (PAM) is a short nucleotide sequence (e.g., 2 to 6 base pair DNA sequence) that is adjacent to the protospacer. PAM sequences are typically recognized by a Cas1 subunit protein/Cas2 subunit protein complex, wherein the active PAM-sensing site is associated with the Cas1 subunit proteins (Jackson, S. A., et al., Science 356:356(6333) (2017)).

In the expression phase, the CRISPR array comprising multiple spacer-repeat elements is transcribed as a single transcript. Individual spacer repeat elements are processed by an endonuclease (e.g., Type I, a Cas6 protein; and Type I-C, a Cas5 protein) into individual crRNAs. Cas subunit proteins are expressed and associate with the crRNA to form a Cascade effector complex.

The Cascade effector complex scans foreign polynucleotides infecting the host to identify DNA complementary to the spacer. In Type I systems, interference occurs when the effector complex identifies a sequence complementary to the spacer that is adjacent a PAM; and the Cas3 protein is recruited to the DNA-bound Cascade effector complex to cleave and progressively digest the foreign polynucleotide.

Makarova, K. S., et al., (Cell 168:946 (2017)) provide a summary of genes, homologs, Cascade complexes, and mechanisms of action for Type I CRISPR-Cas systems.

Although CRISPR-Cas systems have been used for genome editing, there remains a need to improve editing efficiency and editing fidelity of these systems.

SUMMARY OF THE INVENTION

The present invention generally relates to compositions comprising engineered Type I CRISPR-Cas effector complexes, modified guide polynucleotides, and combinations thereof.

One embodiment of the present invention is a composition comprising:

a first engineered Type I CRISPR-Cas effector complex comprising, a first Cse2 subunit protein, a first Cas5 subunit protein, a first Cas6 subunit protein, and a first Cas7 subunit protein, a first fusion protein comprising a first Cas8 subunit protein and a first FokI, wherein the N-terminus of the first Cas8 subunit protein or the C-terminus of the first Cas8 subunit protein is covalently connected by a first linker polypeptide to the C-terminus or N-terminus, respectively, of the first FokI, and wherein the first linker polypeptide has a length of between 10 amino acids to 40 amino acids, and a first guide polynucleotide comprising a first spacer capable of binding a first nucleic acid target sequence; and a second engineered Type I CRISPR-Cas effector complex comprising, a second Cse2 subunit protein, a second Cas5 subunit protein, a second Cas6 subunit protein, and a second Cas7 subunit protein, a second fusion protein comprising a second Cas8 subunit protein and a second FokI, wherein the N-terminus of the second Cas8 subunit protein or the C-terminus of the second Cas8 protein is covalently connected by a second linker polypeptide to the C-terminus or N-terminus, respectively, of the second FokI, and wherein the second linker polypeptide has a length of between 10 amino acids to 40 amino acids, and a second guide polynucleotide comprising a second spacer capable of binding a second nucleic acid target sequence, wherein a protospacer adjacent motif (PAM) of the second nucleic acid target sequence and a PAM of the first nucleic acid target sequence have an interspacer distance between 20 base pairs (bp) to 42 bp.

In some embodiments, the length of the first linker polypeptide and/or the second linker polypeptide is a length of between about 15 amino acids and about 30 amino acids, or between about 17 amino acids and about 20 amino acids. In one embodiment, the length of the first linker polypeptide and the second linker polypeptide are the same.

Interspacer distances between the second nucleic acid target sequence and the first nucleic acid target sequence include, but are not limited to, between about 22 bp to about 40 bp, between about 26 bp to about 36 bp, between about 29 bp to about 35 bp, or between about 30 bp to about 34 bp.

The first FokI and the second FokI can be monomeric subunits that are capable of associating to form a homodimer, or distinct subunits that are capable of associating to form a heterodimer.

In some embodiments, the N-terminus of the first Cas8 subunit protein is covalently connected by the first linker polypeptide to the C-terminus of the first FokI, the C-terminus of the first Cas8 subunit protein is covalently connected by a first linker polypeptide to the N-terminus of the first FokI, the N-terminus of the second Cas8 subunit protein is covalently connected by the second linker polypeptide to the C-terminus of the second FokI, the C-terminus of the second Cas8 subunit protein is covalently connected by a second linker polypeptide to the N-terminus of the second FokI, and combinations thereof. The first Cas8 subunit protein and the second Cas8 subunit protein can each comprise a Cas8 subunit protein having a different sequence or both the first and the second Cas8 subunit protein can comprise identical amino acid sequences.

Similarly, the first Cse2 subunit protein and the second Cse2 subunit protein can each comprise different or identical Cse2 subunit protein amino acid sequences, the first Cas5 subunit protein and the second Cas5 subunit protein can each comprise different or identical Cas5 subunit protein amino acid sequences, the first Cas6 subunit protein and the second Cas6 subunit protein can each comprise different or identical Cas6 subunit protein amino acid sequences, the first Cas7 subunit protein and the second Cas7 subunit protein can each comprise different or identical Cas7 subunit protein amino acid sequences, and combinations thereof.

In a preferred embodiment, the guide polynucleotides comprise RNA.

Additional embodiments of the present invention will be readily apparent to those of ordinary skill in the art in view of the disclosures herein.

BRIEF DESCRIPTION OF THE FIGURES

The Figures are not proportionally rendered, nor are they to scale. The locations of indicators are approximate.

FIG. 3 presents information related to SEQ ID NO:1 to SEQ ID NO:351.

FIG. 4A and FIG. 4B present examples of circularly permuted proteins.

FIG. 12A and FIG. 12B illustrate examples of substrate channels.

FIG. 13A, FIG. 13B, and FIG. 13C present a generalized illustration of site-directed recruitment of a functional protein domain fused to a Cascade subunit protein by a dCas9:NATNA complex.

FIG. 16A, FIG. 16B, FIG. 16C, FIG. 17A, FIG. 17B, FIG. 17C, FIG. 18A, FIG. 18B, FIG. 18C, FIG. 19A, FIG. 19B, FIG. 19C, FIG. 19D, FIG. 20A, FIG. 20B, FIG. 21A, and FIG. 21B present examples of engineered Type I CRISPR-Cas effector complexes of the present invention and methods of use thereof.

FIG. 24A, FIG. 24B, FIG. 24C, FIG. 24D, FIG. 24E, FIG. 25, FIG. 26, FIG. 27, and FIG. 28 present schematic diagrams of a variety of Cascade component expression systems.

FIG. 29, FIG. 30, FIG. 31, FIG. 32A, FIG. 32B, FIG. 33, FIG. 34A, FIG. 34B, and FIG. 35 present data related to genome editing of the engineered Cascade systems of the present invention.

INCORPORATION BY REFERENCE

Figure 1A:
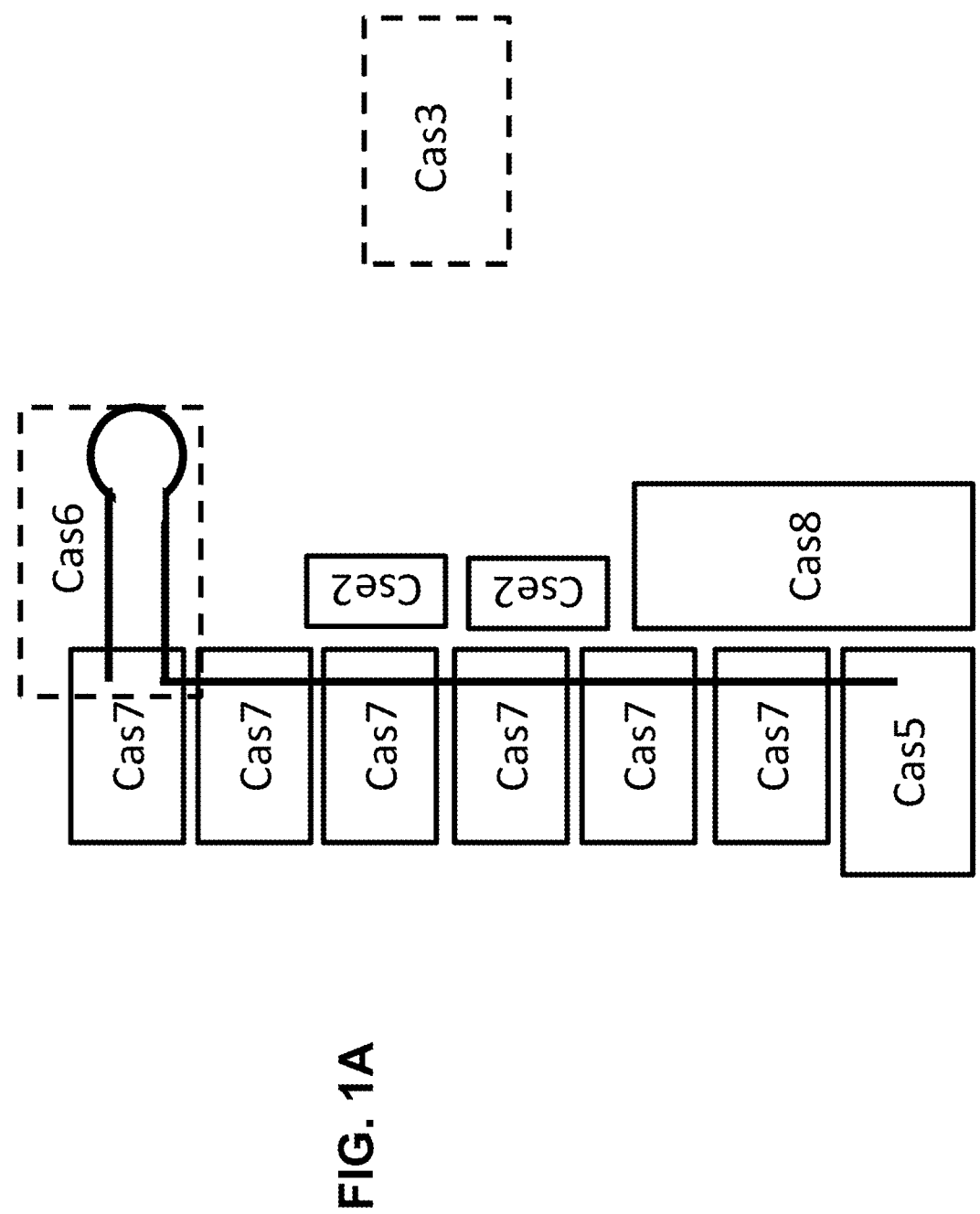
FIG. 1A present a generalized illustration of a Type I CRISPR-Cas effector complex.

All patents, publications, and patent applications cited in the present Specification are herein incorporated by reference as if each individual patent, publication, or patent application was specifically and individually indicated to be incorporated by reference in its entirety for all purposes.

DETAILED DESCRIPTION OF THE INVENTION

It is to be understood that the terminology used herein is for the purpose of describing particular embodiments only, and is not intended to be limiting. As used in the present Specification and the Claims, the singular forms "a," "an," and "the" include plural referents unless the context clearly dictates otherwise. Thus, for example, reference to "a polynucleotide" includes one or more polynucleotides, and reference to "a vector" includes one or more vectors.

Unless defined otherwise, all technical and scientific terms used herein have the same meaning as commonly understood by one of ordinary skill in the art to which the invention pertains. Although other methods and materials similar, or equivalent, to those described herein can be useful in the present invention, preferred materials and methods are described herein.

In view of the teachings of the present Specification and the Examples, one of ordinary skill in the art can apply conventional techniques of immunology, biochemistry, chemistry, molecular biology, microbiology, cell biology, genomics, and recombinant polynucleotides, as taught, for example, by the following standard texts: Cellular and Molecular Immunology, Ninth Edition, A. K. Abbas., et al., Elsevier (2017), ISBN 978-0323479783; Cancer Immunotherapy Principles and Practice, First Edition, L. H. Butterfield, et al., Demos Medical (2017), ISBN 978-1620700976; Janeway's Immunobiology, Ninth Edition, Kenneth Murphy, Garland Science (2016), ISBN 978-0815345053; Clinical Immunology and Serology: A Laboratory Perspective, Fourth Edition, C. Dorresteyn Stevens, et al., F. A. Davis Company (2016), ISBN 978-0803644663; Antibodies: A Laboratory Manual, Second edition, E. A. Greenfield, Cold Spring Harbor Laboratory Press (2014), ISBN 978-1-936113-81-1; Culture of Animal Cells: A Manual of Basic Technique and Specialized Applications, Seventh Edition, R. I. Freshney, Wiley-Blackwell (2016), ISBN 978-1118873656; Transgenic Animal Technology, Third Edition: A Laboratory Handbook, C. A. Pinkert, Elsevier (2014), ISBN 978-0124104907; The Laboratory Mouse, Second Edition, H. Hedrich, Academic Press (2012), ISBN 978-0123820082; Manipulating the Mouse Embryo: A Laboratory Manual, Fourth Edition, R. Behringer, et al., Cold Spring Harbor Laboratory Press (2013), ISBN 978-1936113019; PCR 2: A Practical Approach, M. J. McPherson, et al., IRL Press (1995), ISBN 978-0199634248; Methods in Molecular Biology (Series), J. M. Walker, ISSN 1064-3745, Humana Press; RNA: A Laboratory Manual, D. C. Rio, et al., Cold Spring Harbor Laboratory Press (2010), ISBN 978-0879698911; Methods in Enzymology (Series), Academic Press; Molecular Cloning: A Laboratory Manual (Fourth Edition), M. R. Green, et al., Cold Spring Harbor Laboratory Press (2012), ISBN 978-1605500560; Bioconjugate Techniques, Third Edition, G. T. Hermanson, Academic Press (2013), ISBN 978-0123822390; Methods in Plant Biochemistry and Molecular Biology, W. V. Dashek, CRC Press (1997), ISBN 978-0849394805; Plant Cell Culture Protocols (Methods in Molecular Biology), V. M. Loyola-Vargas, et al., Humana Press (2012), ISBN 978-1617798177; Plant Transformation Technologies, C. N. Stewart, et al., Wiley-Blackwell (2011), ISBN 978-0813821955; Recombinant Proteins from Plants (Methods in Biotechnology), C. Cunningham, et al., Humana Press (2010), ISBN 978-1617370212; Plant Genomics: Methods and Protocols (Methods in Molecular Biology), W. Busch, Humana Press (2017), ISBN 978-1493970018; Plant Biotechnology: Methods in Tissue Culture and Gene Transfer, R. Keshavachandran, et al., Orient Blackswan (2008), ISBN 978-8173716164.

Clustered regularly interspaced short palindromic repeats (CRISPR) and related CRISPR-associated proteins (Cas proteins) constitute CRISPR-Cas systems (see, e.g., Barrangou, R., et al., Science 315:1709-1712 (2007)).

As used herein, "Cas protein," "CRISPR-Cas protein," and "CRISPR-Cas subunit protein," and "Cas subunit protein," unless otherwise identified, all refer to Class 1 Type I CRISPR-Cas proteins. Typically, for use in aspects of the present invention, Cas subunit proteins are capable of interacting with one or more cognate polynucleotides (most typically, a crRNA) to form a Type I effector complex (most typically, a ribonucleoprotein complex). Genes encoding Cas subunit proteins are listed in Table 1.

TABLE 1

Type I CRISPR-Cas Proteins

| Role | Universal family name* | Alternative designation | Reported stoichiometry (when present) |
|---|---|---|---|
| RNA 5' cap, PAM recognition, duplex unwinding | Cas5 | CasD, Cas5e, Csc1, Csy2, Csf3, Cas1822 | 1 |
| PAM recognition, duplex unwinding, Cas3 recruitment | Cas8 | Large subunit, CasA, Cse1, Cas8a, Cas8b, Cas8c, Cas8e, Cas8f, Csy1 | 1 |
| R-loop stabilization | Cse2 | Small subunit, CasB, Cas11 | 2 |
| Backbone | Cas7 | CasC, Cse4, Csc2, Csy3, Csf2, Cas1821, Cst2/DevR | 3-6 |
| RNA 3' cap | Cas6 | CasE, Cse3, Cas6e, Cas6f, Csy4 | 1 |
| DNA cleavage | Cas3 | Cas3', Cas3" | 1 |

*As defined by Makarova, K. S., et al., Nat. Rev. Microbiol. 13(11): 722-736 (2015); Koonin, E. V., et al., Curr Opin Microbiol. 37: 67-78 (2017).

The terms "Type I CRISPR-Cas effector complex," "Cascade complex," "Type I CRISPR-Cas nucleoprotein complex," and "Type I complexes" are used interchangeably herein. The terms "Cascade RNP complex" and "Type I ribonucleoprotein (RNP) complex" refer to a Cascade complex specifically comprising a crRNA (versus a more generic guide polynucleotide, as described below). An example of a wild-type Type I CRISPR-Cas effector complex is illustrated in FIG. 1A. FIG. 1A is adapted from Makarova, K. S., et al., (Cell 168:946 (2017); and Makarova, K., et al., Nature reviews Microbiology 13(11):722-736 (2015)). doi:10.1038/nrmicro3569.). FIG. 1A illustrates six Cas7 proteins, a Cas5 protein, a Cas8 protein, two Cse2 proteins, a Cas6 protein, and a crRNA associated as a Cascade complex. The complex is capable of binding a nucleic acid target sequence. After association of a wild-type Cas3 with the complex, the Cascade complex is capable of cleavage of a nucleic acid target sequence. As noted in Table 1, the total number of some Cas subunit proteins can vary in Cascade complexes.

"Cas3" and "Cas3 protein" are used interchangeably herein to refer to Type I CRISPR-Cas3 proteins, modifications, and variants thereof. The Type I CRISPR-Cas effector complexes bind foreign DNA complementary to the crRNA guide and recruit Cas3, a trans-acting nuclease-helicase required for target degradation. Cas3 proteins have motifs characteristic of helicases from superfamily 2 and contain a DEAD/DEAH box region and a conserved C-terminal domain. Cas3 proteins and variants thereof are known in the art (see, e.g., Westra, E. R., et al., Mol Cell. 46(5): 595-605 (2012); Sinkunas, T., et al., EMBO J. 30(7):1335-1342 (2011); Beloglazova, N., et al., EMBO J. 30:4616-4627 (2011); Mulepati, S., et al., J. Biol. Chem. 286:31896-31903 (2011)). As used herein, dCas3* is a mutated Cas3 protein that does not have any nuclease activity and/or helicase activity.

The term "nuclease" as used herein refers to an enzyme capable of cleaving the phosphodiester bonds, such as those connecting two nucleotides, as found in double-stranded (ds) nucleic acids (e.g., dsDNA, genomic DNA (gDNA), dsRNA), single-stranded (ss) nucleic acids (e.g., ssDNA, RNA) or hybrid dsRNA/DNA. An "endonuclease" typically can effect ss-(nicks) or ds-breaks in its target molecules. One example of a DNA endonuclease is a FokI enzyme. "FokI endonuclease" and "FokI" are used interchangeably herein and refer to a FokI enzyme, FokI homologs, enzymatically active domain(s) of FokI enzymes, and variants of FokI enzymes. FokI dimerization is typically required for DNA cleavage. Dimers of FokI can comprise two monomeric subunits that associate to form a homodimer or two distinct monomeric subunits that associate to form a heterodimer (see, e.g., Bitinaite, J., et al., Proceedings of the National Academy of Sciences 95(18):10570-10575 (1998); Ramalingam, S., et al., Journal of Molecular Biology, 405(3):630-641 (2011)). One example of a FokI variant is the Sharkey variant described by Guo, et al. (Guo, J., et al., J. Mol. Biol. 400:96-107 (2010)). Additional DNA and RNA nucleases are known in the art.

Figure 1B:
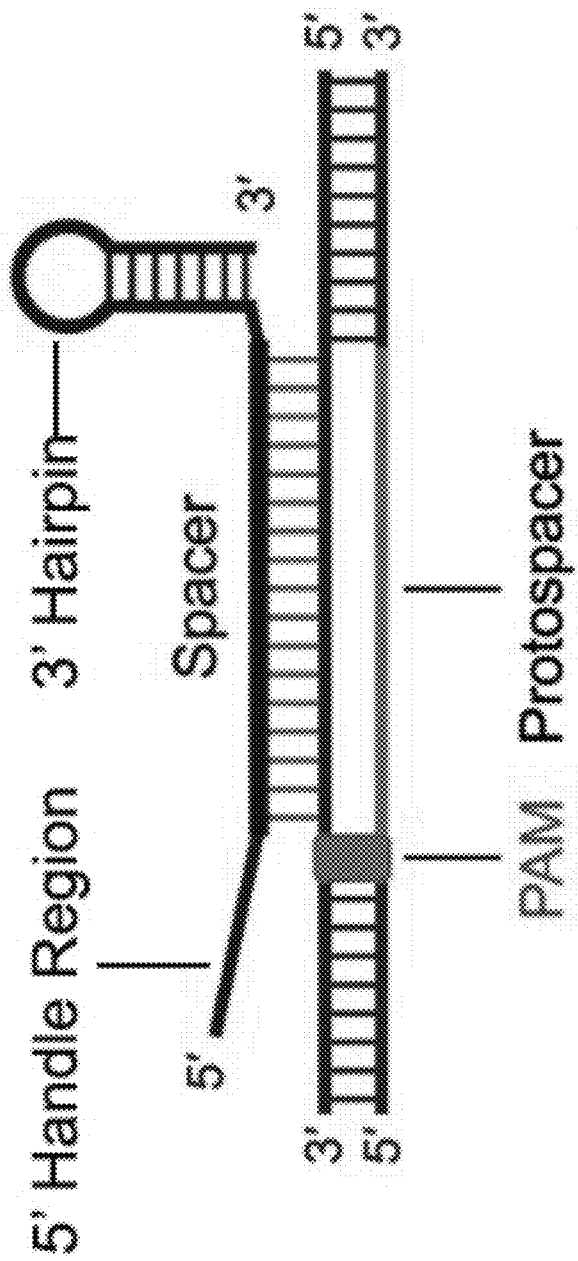
FIG. 1B presents a generalized illustration of a Type I CRISPR-Cas crRNA.

"CRISPR RNA," "crRNA," and "guide RNA," as used herein, refer to one or more RNAs with which Cas subunit proteins are capable of interacting to form a Type I effector complex that guides the complex to preferentially bind a nucleic acid target sequence in a polynucleotide (relative to a polynucleotide that does not comprise the nucleic acid target sequence). "Guide" and "guide polynucleotide" as used herein refer to the polynucleotide component of Type I effector complexes and can comprise ribonucleotide bases (e.g., RNA), deoxyribonucleotide bases (e.g., DNA), combinations of ribonucleotide bases and deoxyribonucleotide bases, nucleotides, nucleotide analogs, modified nucleotides, and the like, as well as synthetic, naturally occurring, and non-naturally occurring modified backbone residues or linkages, for example, as described herein. An example of a Type I CRISPR-Cas crRNA associated with a nucleic acid target sequence through the crRNA spacer is illustrated in FIG. 1B. FIG. 1B is adapted from Hochstrasser, M. L., et al., Molecular Cell 63(5):840-851 (2016). In FIG. 1B, the PAM associated with the nucleic acid target sequence and the 5' and 3' strands of a double-stranded nucleic acid are illustrated (FIG. 1B, vertical lines represent hydrogen bonds). A guide polynucleotide typically comprises a 5' handle region (FIG. 1B, 5' Handle Region), a spacer region (FIG. 1B, Spacer) comprising a seed region, and a 3' hairpin comprising two hydrogen-bonded repeat regions (FIG. 1B, 3' Hairpin; horizontal lines represent hydrogen bonds). FIG. 1B illustrates the Cascade complex spacer bound to the nucleic acid target sequences (FIG. 1B, vertical lines represent hydrogen bonds). FIG. 1B also illustrates the protospacer region (FIG. 1B, protospacer). The spacer can comprise a region of the crRNA between about 6 to about 56 nucleotides, wherein the spacer is complementary to a nucleic acid target sequence in a polynucleotide. The spacer length can be modified to fine-tune Cascade activity in Type I-E CRISPR-Cas systems. Cascade complexes can incorporate an extra Cas7 subunit with every 6 nucleotides added to the crRNA spacer and an extra Cse2 subunit with every 12 nucleotides added to the spacer (Luo, M. L., et al., Nucleic Acids Research. 44(15):7385-7394 (2016)). The spacer typically comprises a region of between about 32 to about 36 nucleotides.

The terms "spacer," "spacer sequence," and "nucleic acid target binding sequence" are used interchangeably herein.

As used herein, a "stem element" or "stem structure" refers to two strands of nucleic acids that are known or predicted to form a double-stranded region (the "stem element"). A "stem-loop element" or "stem-loop structure" refers to a stem structure wherein 3'-end sequences of one strand are covalently bonded to 5'-end sequences of the second strand by a nucleotide sequence of typically single-stranded nucleotides ("a stem-loop element nucleotide sequence"). In some embodiments, the loop element comprises a loop element nucleotide sequence of between about 3 and about 20 nucleotides in length, preferably between about 4 and about 10 nucleotides in length. In preferred embodiments, a loop element nucleotide sequence is a single-stranded nucleotide sequence of unpaired nucleic acid bases that do not interact through hydrogen bond formation to create a stem element within the loop element nucleotide sequence. The term "hairpin element" is also used herein to refer to stem-loop structures. Such structures are well known in the art. The base pairing may be exact; however, as is known in the art, a stem element does not require exact base pairing. Thus, the stem element may include one or more base mismatches or non-paired bases. An example of a stem-loop structure in a guide polynucleotide is illustrated in FIG. 1B.

A "linker element nucleotide sequence," "linker nucleotide sequence," and "linker polynucleotide" are used interchangeably herein and refer to either a single-stranded nucleic acid sequence or a double-stranded nucleic acid sequence of one or more nucleotides covalently attached to a first nucleic acid sequence (e.g., 5'-linker nucleotide sequence-first nucleic acid sequence-3'). In some embodiments, a linker nucleotide sequence connects two separate nucleic acid sequences to form a single polynucleotide (e.g., 5'-first nucleic acid sequence-linker nucleotide sequence-second nucleic acid sequence-3'). Other examples of linker nucleotide sequences include, but are not limited to, 5'-first nucleic acid sequence-linker nucleotide sequence-3' and 5'-linker nucleotide sequence-first first nucleic acid sequence-linker nucleotide sequence-3'. In some embodiments, the linker element nucleotide sequence can be a single-stranded nucleotide sequence of unpaired nucleic acid bases that do not interact with each other through hydrogen bond formation to create a secondary structure (e.g., a stem-loop structure) within the linker element nucleotide sequence. In some embodiments, two linker element nucleotide sequences can interact with each other through hydrogen bonding between the two linker element nucleotide sequences. In some embodiments, a linker polynucleotide encodes a "linker polypeptide." Such a linker polynucleotide typically connects the 3' end of a first polynucleotide encoding a first polypeptide to the 5' end of a second polynucleotide encoding a second polypeptide to form a single polynucleotide that encodes a fusion protein comprising N-the first polypeptide-the linker polypeptide-the second polypeptide-C. In some embodiments of the present invention, more than two polypeptide sequences can be connected in tandem by linker polypeptides (e.g., N-a first polypeptide-a first linker polypeptide-a second polypeptide-a second linker polypeptide-a third polypeptide-C). Linker polypeptide, "linker polypeptide sequence," "amino acid linker sequence," and "linker sequence" are used interchangeably herein.

As used herein, a "connecting nucleotide sequence" refers to a single-stranded nucleic acid sequence linker sequence that covalently connects a first nucleic acid sequence and a second nucleic acid sequence.

Figure 2A:
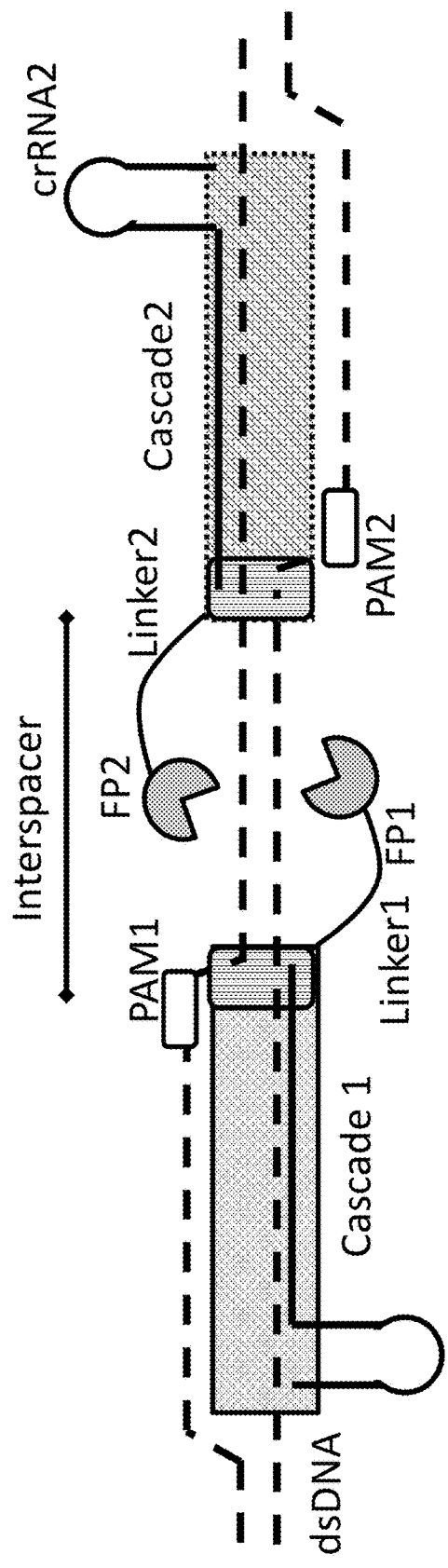
FIG. 2A, FIG. 2B, and FIG. 2C present illustrative examples of two engineered Type I CRISPR-Cas effector complexes with fusion domains bound to neighboring spacer sequences.
Figure 2B:
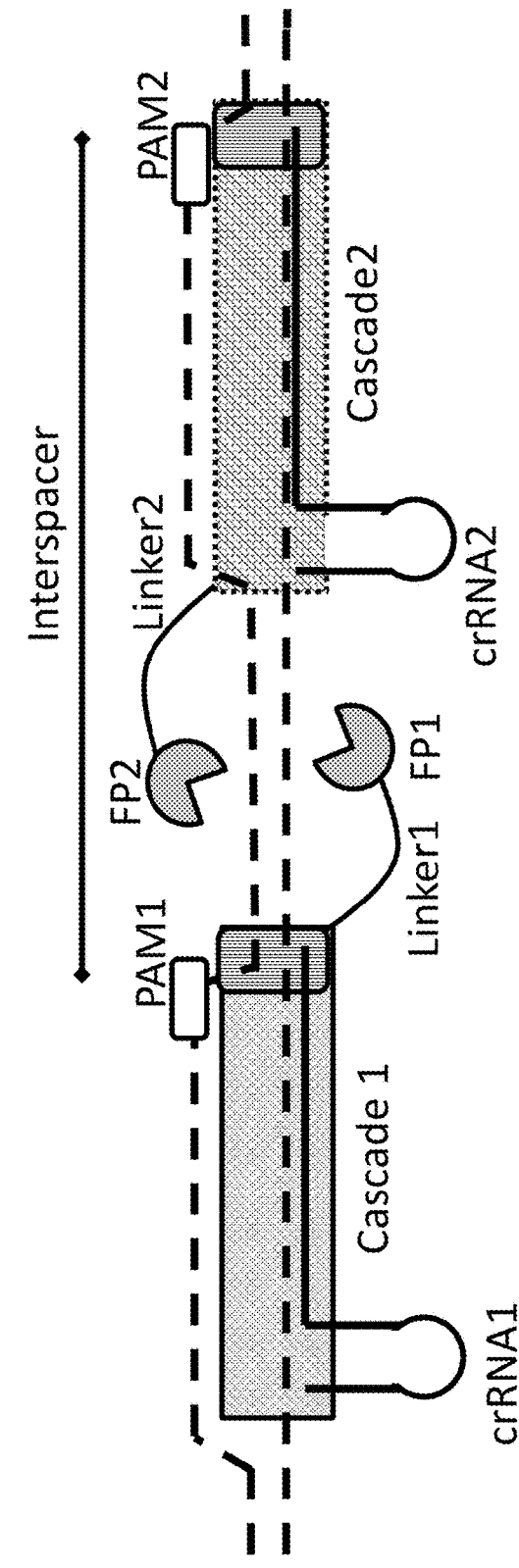
Figure 2C:
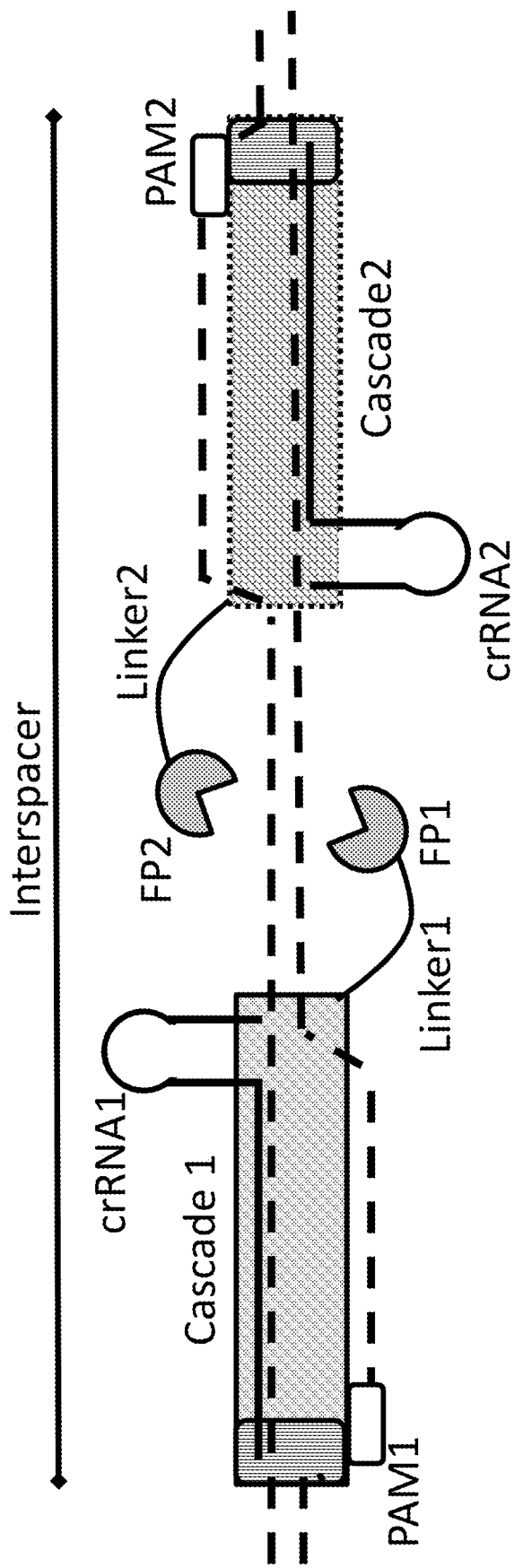

As used herein, the terms "interspacer," "interspacer region," and "interspacer distance" are used interchangeably and refer to the distance between a PAM of a first nucleic acid target sequence (e.g., a first DNA target sequence) and a PAM of a second nucleic acid target sequence (e.g., a second DNA target sequence) typically in a PAM-in orientation, wherein a first Type I CRISPR-Cas effector complex comprises a first spacer capable of binding the first nucleic acid target sequence, and a second Type I CRISPR-Cas effector complex comprises a second spacer capable of binding the second nucleic acid target sequence. FIG. 2A, FIG. 2B, and FIG. 2C present illustrative examples of two Type I CRISPR-Cas effector complexes ("Cascade1" comprising "crRNA1" and "Cascade2" comprising "crRNA2") comprising fusion proteins ("FP1" and "FP2"; e.g., FokI) connected with each Cascade complex through linker polynucleotides ("Linker1" and "Linker2"), wherein the CRISPR-Cas effector complexes are bound to neighboring nucleic acid target sequences on double-stranded DNA ("dsDNA"). PAM sequences associated with each nucleic acid target sequence are indicated ("PAM1," open box, and "PAM2," open box)). FIG. 2A illustrates an interspacer (shown as a double-arrowheaded line) between two target sites in a PAM-in (PAM-in/PAM-in) configuration. FIG. 2B illustrates an interspacer (shown as a double-arrowheaded line) between two target sites in a PAM-in/PAM-out configuration. FIG. 2C illustrates an interspacer between two target sites in the PAM-out (PAM-out/PAM-out) configuration. FIG. 2A, FIG. 2B, and FIG. 2C also illustrate the separation of the two strands of the dsDNA. A Cascade complex recognizes a dsDNA target sequence adjacent a PAM. PAM sequences are recognized by Cse1. Base pairing between the crRNA and complementary target DNA strand results in an R-loop with the displaced non-complementary target DNA strand (Beloglazova, N., et al., Nucleic Acids Research 43(1):530-543 (2015)).

As used herein, the term "cognate" typically refers to a group of Cas subunit proteins (e.g., Cse2, Cas5, Cash, Cas7, and Cas8) and one or more guide polynucleotides (e.g., a Type I CRISPR-Cas RNA) that are capable of forming a nucleoprotein complex capable of site-directed binding to a nucleic acid target sequence complementary to a spacer present in one of the one or more guide polynucleotides.

The terms "wild-type," "naturally occurring," and "unmodified" are used herein to mean the typical (or most common) form, appearance, phenotype, or strain existing in nature; for example, the typical form of cells, organisms, polynucleotides, proteins, macromolecular complexes, genes, RNAs, DNAs, or genomes as they occur in, and can be isolated from, a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," "non-naturally occurring," "non-natural," and "non-native" are interchangeable and indicate intentional human manipulation.

"Covalent bond," "covalently attached," "covalently bound," "covalently linked," "covalently connected," and "molecular bond" are used interchangeably herein and refer to a chemical bond that involves the sharing of electron pairs between atoms. Examples of covalent bonds include, but are not limited to, phosphodiester bonds, phosphorothioate bonds, disulfide bonds and peptide bonds (—CO—NH—).

"Non-covalent bond," "non-covalently attached," "non-covalently bound," "non-covalently linked," "non-covalent interaction," and "non-covalently connected" are used interchangeably herein and refer to any relatively weak chemical bond that does not involve sharing of a pair of electrons. Multiple non-covalent bonds often stabilize the conformation of macromolecules and mediate specific interactions between molecules. Examples of non-covalent bonds include, but are not limited to, hydrogen bonding, ionic interactions (e.g., $Na^+Cl^-$), van der Waals interactions, and hydrophobic bonds.

As used herein, "hydrogen bonding," "hydrogen-base pairing," and "hydrogen bonded" are used interchangeably and refer to canonical hydrogen bonding and non-canonical hydrogen bonding including, but not limited to, "Watson-Crick-hydrogen-bonded base pairs" (W-C-hydrogen-bonded base pairs or W-C hydrogen bonding); "Hoogsteen-hydrogen-bonded base pairs" (Hoogsteen hydrogen bonding); and "wobble-hydrogen-bonded base pairs" (wobble hydrogen bonding). W-C hydrogen bonding, including reverse W-C hydrogen bonding, refers to purine-pyrimidine base pairing, e.g., adenine:thymine, guanine:cytosine, and uracil:adenine. Hoogsteen hydrogen bonding, including reverse Hoogsteen hydrogen bonding, refers to a variation of base pairing in nucleic acids wherein two nucleobases, one on each strand, are held together by hydrogen bonds in the major groove. This non-W-C hydrogen bonding can allow a third strand to wind around a duplex and form triple-stranded helices. Wobble hydrogen bonding, including reverse wobble hydrogen bonding, refers to a pairing between two nucleotides in RNA molecules that does not follow Watson-Crick base pair rules. There are four major wobble base pairs: guanine:uracil, inosine (hypoxanthine):uracil, inosine-adenine, and inosine-cytosine. Rules for canonical hydrogen bonding and non-canonical hydrogen bonding are known to those of ordinary skill in the art (see, e.g., The RNA World, Third Edition (Cold Spring Harbor Monograph Series), R. F. Gesteland, Cold Spring Harbor Laboratory Press (2005), ISBN 978-0879697396; The RNA World, Second Edition (Cold Spring Harbor Monograph Series), R. F. Gesteland, et al., Cold Spring Harbor Laboratory Press (1999), ISBN 978-0879695613; The RNA World (Cold Spring Harbor Monograph Series), R. F. Gesteland, et al., Cold Spring Harbor Laboratory Press (1993), ISBN 978-0879694562 (see, e.g., Appendix 1: Structures of Base Pairs Involving at Least Two Hydrogen Bonds, I. Tinoco); Principles of Nucleic Acid Structure, W. Saenger, Springer International Publishing AG (1988), ISBN 978-0-387-90761-1; Principles of Nucleic Acid Structure, First Edition, S. Neidle, Academic Press (2007), ISBN 978-01236950791).

"Connect," "connected," and "connecting" are used interchangeably herein and refer to a covalent bond or a non-covalent bond between two macromolecules (e.g., polynucleotides, proteins, and the like).

As used herein, the terms "nucleic acid sequence," "nucleotide sequence," and "oligonucleotide" are interchangeable and refer to a polymeric form of nucleotides. As used herein, the term "polynucleotide" refers to a polymeric form of nucleotides that has one 5' end and one 3' end, and can comprise one or more nucleic acid sequences. A "circular polynucleotide" refers to a polynucleotide having a covalent bond between its 5' end and 3' end, thus forming the circular polynucleotide. The nucleotides may be deoxyribonucleotides (DNA), ribonucleotides (RNA), analogs thereof, or combinations thereof, and may be of any length. Polynucleotides may perform any function and may have various secondary and tertiary structures. The terms encompass known analogs of natural nucleotides and nucleotides that are modified in the base, sugar, and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include, but are not limited to, fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. Also encompassed are nucleic acids comprising modified backbone residues or linkages, that are synthetic, naturally occurring, and/or non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (LNA™) (Exiqon, Inc., Woburn, Mass.) nucleosides, glycol nucleic acid, bridged nucleic acids, and morpholino structures.

Peptide-nucleic acids (PNAs) are synthetic homologs of nucleic acids wherein the polynucleotide phosphate-sugar backbone is replaced by a flexible pseudo-peptide polymer, and nucleobases are linked to the polymer. PNAs have the capacity to hybridize with high affinity and specificity to complementary sequences of RNA and DNA.

In phosphorothioate nucleic acids, the phosphorothioate (PS) bond substitutes a sulfur atom for a non-bridging oxygen in the polynucleotide phosphate backbone. This modification makes the internucleotide linkage resistant to nuclease degradation. In some embodiments, phosphorothioate bonds are introduced between the last 3 to 5 nucleotides at the 5'-end or 3'-end sequences of a polynucleotide sequence to inhibit exonuclease degradation. Placement of phosphorothioate bonds throughout an entire oligonucleotide helps reduce degradation by endonucleases, as well.

Threose nucleic acid (TNA) is an artificial genetic polymer. The backbone structure of TNA comprises repeating threose sugars linked by phosphodiester bonds. TNA polymers are resistant to nuclease degradation. TNA can self-assemble by base-pair hydrogen bonding into duplex structures.

Linkage inversions can be introduced into polynucleotides through use of "reversed phosphoramidites" (see, e.g., www.ucalgary.ca/dnalab/synthesis/-modifications/linkages). A 3'-3' linkage at a terminus of a polynucleotide stabilizes the polynucleotide to exonuclease degradation by creating an oligonucleotide having two 5'-OH termini but lacking a 3'-OH terminus. Typically, such polynucleotides have phosphoramidite groups on the 5'-OH position and a dimethoxytrityl (DMT) protecting group on the 3'-OH position. Normally, the DMT protecting group is on the 5'-OH and the phosphoramidite is on the 3'-OH.

Polynucleotide sequences are displayed herein in the conventional 5' to 3' orientation unless otherwise indicated.

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., BLAST, CS-BLAST, PSI-BLAST, FASTA, HMMER, L-ALIGN, and the like) available through the worldwide web at sites including, but not limited to, GENBANK (www.ncbi.nlm.nih.gov/genbank/) and EMBL-EBI (www.ebi.ac.uk). Sequence identity between two polynucleotides or two polypeptide sequences is generally calculated using the standard default parameters of the various methods or computer programs. A high degree of sequence identity, as used herein, between two polynucleotides or two polypeptides is typically between about 90% identity and 100% identity, for example, about 90% identity or higher, preferably about 95% identity or higher, more preferably about 98% identity or higher. A moderate degree of sequence identity, as used herein, between two polynucleotides or two polypeptides is typically between about 80% identity to about 85% identity, for example, about 80% identity or higher, preferably about 85% identity. A low degree of sequence identity, as used herein, between two polynucleotides or two polypeptides is typically between about 50% identity and 75% identity, for example, about 50% identity, preferably about 60% identity, more preferably about 75% identity. For example, a Cas protein (e.g., Type I-E Cse2, Cas5, Cas6, Cas7, and/or Cas8) comprising amino acid substitutions can have a low degree of sequence identity, a moderate degree of sequence identity, or a high degree of sequence identity over its length to a reference Cas protein (e.g., wild-type Type I-E Cse2, Cas5, Cas6, Cas7, and/or Cas8, respectively). As another example, a guide polynucleotide can have a low degree of sequence identity, a moderate degree of sequence identity, or a high degree of sequence identity over its length compared with a reference wild-type guide polynucleotide that complexes with the reference Cas proteins (e.g., a guide polynucleotide that forms a complex with a Type I-E Cse2, Cas5, Cas6, Cas7, and/or Cas8).

As used herein, "hybridization" "hybridize," or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5'C to 10° C. below $T_m$; moderate stringency, approximately 0.16M to approximately 0.33M salt, hybridization temperature 20° C. to 29° C. below $T_m$; and low stringency, approximately 0.33M to approximately 0.82M salt, hybridization temperature 40° C. to 48° C. below $T_m$. $T_m$ of duplex nucleic acid sequences is calculated by standard methods well known in the art (see, e.g., Maniatis, T., et al., Molecular Cloning: A Laboratory Manual, Cold Spring Harbor Laboratory Press: New York (1982); Casey, J., et al., Nucleic Acids Research 4:1539-1552 (1977); Bodkin, D. K., et al., Journal of Virological Methods 10(1):45-52 (1985); Wallace, R. B., et al., Nucleic Acids Research 9(4):879-894 (1981)). Algorithm prediction tools to estimate $T_m$ are also widely available. High stringency conditions for hybridization typically refer to conditions under which a polynucleotide complementary to a target sequence predominantly hybridizes with the target sequence and substantially does not hybridize to non-target sequences. Typically, hybridization conditions are of moderate stringency, preferably high stringency.

As used herein, "complementarity" refers to the ability of a nucleic acid sequence to form hydrogen bond(s) with another nucleic acid sequence (e.g., through canonical Watson-Crick base pairing). A percent complementarity indicates the percentage of residues in a nucleic acid sequence that can form hydrogen bonds with a second nucleic acid sequence. If two nucleic acid sequences have 100% complementarity, the two sequences are perfectly complementary, i.e., all of the contiguous residues of a first polynucleotide hydrogen bond with the same number of contiguous residues in a second polynucleotide.

As used herein, "binding" refers to a non-covalent interaction between macromolecules (e.g., between a protein and a polynucleotide, between a polynucleotide and a polynucleotide, between a protein and a protein, and the like). Such non-covalent interaction is also referred to as "associating" or "interacting" (e.g., if a first macromolecule interacts with a second macromolecule, the first macromolecule binds to second macromolecule in a non-covalent manner). Some portions of a binding interaction may be sequence-specific (the terms "sequence-specific binding," "sequence-specifically bind," "site-specific binding," and "site specifically binds" are used interchangeably herein). Sequence-specific binding, as used herein, typically refers to one or more guide polynucleotides capable of forming a complex with Type I CRISPR-Cas subunit proteins (e.g., Cse2, Cas5, Cash, Cas7, and Cas8) to cause the protein to bind a nucleic acid sequence (e.g., a DNA sequence) comprising a nucleic acid target sequence (e.g., a DNA target sequence) preferentially relative to a second nucleic acid sequence (e.g., a second DNA sequence) without the nucleic acid target binding sequence (e.g., the DNA target binding sequence). All components of a binding interaction do not need to be sequence-specific, such as contacts of a protein with phosphate residues in a DNA backbone. Binding interactions can be characterized by a dissociation constant (Kd). "Binding affinity" refers to the strength of the binding interaction. An increased binding affinity is correlated with a lower Kd.

As used herein, effector complexes are said to "target" a polynucleotide if such a complex binds or cleaves a polynucleotide in the nucleic acid target sequence within the polynucleotide.

As used herein, a "double-strand break" (DSB) refers to both strands of a double-stranded segment of DNA being severed. In some instances, if such a break occurs, one strand can be said to have a "sticky end" wherein nucleotides are exposed and not hydrogen bonded to nucleotides on the other strand. In other instances, a "blunt end" can occur wherein both strands remain fully base paired with each other.

"Donor polynucleotide," "donor oligonucleotide," and "donor template" are used interchangeably herein and can be a double-stranded polynucleotide (e.g., DNA), a single-stranded polynucleotide (e.g., DNA or RNA), or a combination thereof. Donor polynucleotides can comprise homology arms flanking the insertion sequence (e.g., DSBs in the DNA). The homology arms on each side can vary in length (e.g., 1-50 bases, 50-100 bases, 100-200 bases, 200-300 bases, 300-500 bases, 500-1000 bases). Homology arms can be symmetric or asymmetric in length. Parameters for the design and construction of donor polynucleotides are well known in the art (see, e.g., Ran, F., et al., Nature Protocols 8(11):2281-2308 (2013); Smithies, O., et al., Nature 317: 230-234 (1985); Thomas, K., et al., Cell 44:419-428 (1986);

Wu, S., et al., Nature Protocols 3:1056-1076 (2008); Singer, B., et al., Cell 31:25-33 (1982); Shen, P., et al., Genetics 112:441-457 (1986); Watt, V., et al., Proceedings of the National Academy of Sciences of the United States of America 82:4768-4772 (1985); Sugawara, N., et al., Journal of Molecular Cell Biology 12(2):563-575 (1992); Rubnitz, J., et al., Journal of Molecular Cell Biology 4(11):2253-2258 (1984); Ayares, D., et al., Proceedings of the National Academy of Sciences of the United States of America 83(14):5199-5203 (1986); Liskay, R., et al., Genetics 115 (1):161-167 (1987)).

As used herein, "homology-directed repair" (HDR) refers to DNA repair that takes place in cells, for example, during repair of a DSB in genomic DNA. HDR requires nucleotide sequence homology and uses a donor or template polynucleotide to repair the sequence wherein the DSB (e.g., within a DNA target sequence) occurred. The donor polynucleotide generally has the requisite sequence homology with the sequence flanking the DSB so that the donor polynucleotide can serve as a suitable template for repair. HDR results in the transfer of genetic information from, for example, the donor polynucleotide to the DNA target sequence. HDR may result in alteration of the DNA target sequence (e.g., insertion, deletion, or mutation) if the donor polynucleotide sequence differs from the DNA target sequence and part or all of the donor polynucleotide is incorporated into the DNA target sequence. In some embodiments, an entire donor polynucleotide, a portion of the donor polynucleotide, or a copy of the donor polynucleotide is integrated at the site of the DNA target sequence. For example, a donor polynucleotide can be used for repair of the break in the DNA target sequence, wherein the repair results in the transfer of genetic information from the donor polynucleotide at the site or in close proximity of the break in the DNA. Accordingly, new genetic information may be inserted or copied at a DNA target sequence.

A "genomic region" is a segment of a chromosome in the genome of a host cell that is present on either side of the nucleic acid target sequence site or, alternatively, also includes a portion of the nucleic acid target sequence site. The homology arms of the donor polynucleotide have sufficient homology to undergo homologous recombination with the corresponding genomic regions. In some embodiments, the homology arms of the donor polynucleotide share significant sequence homology to the genomic region immediately flanking the nucleic acid target sequence site; it is recognized that the homology arms can be designed to have sufficient homology to genomic regions farther from the nucleic acid target sequence site.

As used herein, "non-homologous end joining" (NHEJ) refers to the repair of a DSB in DNA by direct ligation of one terminus of the break to the other terminus of the break without a requirement for a donor polynucleotide. NHEJ is a DNA repair pathway available to cells to repair DNA without the use of a repair template. NHEJ in the absence of a donor polynucleotide often results in nucleotides being randomly inserted or deleted at the site of the DSB.

"Microhomology-mediated end joining" (MMEJ) is pathway for repairing a DSB in genomic DNA. MMEJ involves deletions flanking a DSB and alignment of microhomologous sequences internal to the break site before joining. MMEJ is genetically defined and requires the activity of, for example, CtIP, Poly(ADP-Ribose) Polymerase 1 (PARP1), DNA polymerase theta (Pol θ), DNA Ligase 1 (Lig 1), or DNA Ligase 3 (Lig 3). Additional genetic components are known in the art (see, e.g., Sfeir, A., et al., Trends in Biochemical Sciences 40:701-714 (2015)).

As used herein, "DNA repair" encompasses any process whereby cellular machinery repairs damage to a DNA molecule contained in the cell. The damage repaired can include ss-breaks or DSBs. At least three mechanisms exist to repair DSBs: HDR, NHEJ, and MMEJ. "DNA repair" is also used herein to refer to DNA repair resulting from human manipulation, wherein a target locus is modified, e.g., by inserting, deleting, or substituting nucleotides, all of which represent forms of genome editing.

As used herein, "recombination" refers to a process of exchange of genetic information between two polynucleotides.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, transcription start sites, repressor binding sequences, stem-loop structures, translational initiation sequences, internal ribosome entry sites (IRES), translation leader sequences, transcription termination sequences (e.g., polyadenylation signals and poly-U sequences), translation termination sequences, primer binding sites, and the like.

Regulatory elements include those that direct constitutive, inducible, and repressible expression of a nucleotide sequence in many types of host cells and those that direct expression of the nucleotide sequence only in certain host cells (e.g., tissue-specific regulatory sequences). In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart, M., et al., Cell 41:521-530 (1985)), the SV40 promoter, the dihydrofolate reductase promoter, the (β-actin promoter, the phosphoglycerol kinase (PGK) promoter, and the EF1α promoter. It will be appreciated by those skilled in the art that the design of an expression vector may depend on such factors as the choice of the host cell to be transformed, the level of expression desired, and the like. A vector can be introduced into host cells to thereby produce transcripts, proteins, or peptides, including fusion proteins or peptides, encoded by nucleic acid sequences as described herein.

"Gene," as used herein, refers to a polynucleotide sequence comprising exon(s) and related regulatory sequences. A gene may further comprise intron(s) and/or untranslated region(s) (UTR(s)).

As used herein, the term "operably linked" refers to polynucleotide sequences or amino acid sequences placed into a functional relationship with one another. For example, regulatory sequences (e.g., a promoter or enhancer) are "operably linked" to a polynucleotide encoding a gene product if the regulatory sequences regulate or contribute to the modulation of the transcription of the polynucleotide. Operably linked regulatory elements are typically contiguous with the coding sequence. However, enhancers can function if separated from a promoter by up to several kilobases or more. Accordingly, some regulatory elements may be operably linked to a polynucleotide sequence but not contiguous with the polynucleotide sequence. Similarly, translational regulatory elements contribute to the modulation of protein expression from a polynucleotide.

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product(s)." Expression may include splicing the mRNA in a eukaryotic cell, if the polynucleotide is derived from genomic DNA.

As used herein, the term "modulate" refers to a change in the quantity, degree or amount of a function. For example, a Type I CRISPR nucleoprotein complex, as disclosed herein, may modulate the activity of a promoter sequence by binding to a nucleic acid target sequence at or near the promoter or a transcriptional start site or regulator site. Depending on the action occurring after binding, the Type I CRISPR nucleoprotein complex can induce, enhance, suppress, or inhibit transcription of a gene operatively linked to the promoter sequence. Thus, "modulation" of gene expression includes both gene activation and gene repression.

Modulation can be assayed by determining any characteristic directly or indirectly affected by the expression of the target gene. Such characteristics include, for example, changes in RNA or protein levels, protein activity, product levels, expression of the gene, or activity level of reporter genes. Accordingly, the terms "modulating expression," "inhibiting expression," and "activating expression" of a gene can refer to the ability of a Type I CRISPR nucleoprotein complex to change, activate, or inhibit transcription of a gene.

"Vector" and "plasmid," as used herein, refer to a polynucleotide vehicle to introduce genetic material into a cell. Vectors can be linear or circular. Vectors can contain a replication sequence capable of effecting replication of the vector in a suitable host cell (e.g., an origin of replication). Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art. The four major types of vectors are plasmids, viral vectors, cosmids, and artificial chromosomes. Typically, vectors comprise an origin of replication, a multicloning site, and/or a selectable marker. An expression vector typically comprises an expression cassette.

As used herein, "expression cassette" refers to a polynucleotide construct generated using recombinant methods or by synthetic means and comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in a vector to form an expression vector.

As used herein, a "targeting vector" is a recombinant DNA construct typically comprising tailored DNA arms, homologous to genomic DNA, that flank elements of a target gene or nucleic acid target sequence (e.g., a DSB). A targeting vector comprises a donor polynucleotide. Elements of the target gene can be modified in a number of ways, including deletions and/or insertions. A defective target gene can be replaced by a functional target gene, or in the alternative a functional gene can be knocked out. Optionally, the donor polynucleotide of a targeting vector comprises a selection cassette comprising a selectable marker that is introduced into the target gene. Targeting regions adjacent or within a target gene can be used to affect regulation of gene expression.

As used herein, the term "between" is inclusive of end values in a given range (e.g., between 1 and 50 nucleotides in length includes 1 nucleotide and 50 nucleotides; between 5 amino acids and 50 amino acids in length includes 5 amino acids and 50 amino acids).

As used herein, the term "amino acid" (aa) refers to natural and synthetic (unnatural) amino acids, including amino acid analogs, modified amino acids, peptidomimetics, glycine, and D or L optical isomers.

As used herein, the terms "peptide," "polypeptide," "protein," and "subunit protein" are interchangeable and refer to polymers of amino acids. A polypeptide may be of any length. It may be branched or linear, it may be interrupted by non-amino acids, and it may comprise modified amino acids. The terms also refer to an amino acid polymer that has been modified through, for example, acetylation, disulfide bond formation, glycosylation, lipidation, phosphorylation, pegylation, biotinylation, cross-linking, and/or conjugation (e.g., with a labeling component or ligand). Polypeptide sequences are displayed herein in the conventional N-terminal to C-terminal orientation, unless otherwise indicated.

Polypeptides and polynucleotides can be made using routine techniques in the field of molecular biology (see, e.g., standard texts discussed above). Furthermore, essentially any polypeptide or polynucleotide is available from commercial sources.

The terms "fusion protein" and "chimeric protein," as used herein, refer to a single protein created by joining two or more proteins, protein domains, or protein fragments or circular permuted polypeptides that do not naturally occur together in a single protein. In some embodiments, a linker polynucleotide can be used to connect a first protein, protein domains, or protein fragments, or circular permuted polypeptides to a second protein, protein domains, or protein fragments or circular permuted polypeptides. For example, a fusion protein can comprise a Type I CRISPR-Cas protein (e.g., Cas8, Cas3) and a functional domain from another protein (e.g., FokI; see, e.g., U.S. Pat. No. 9,885,026, issued 6 Feb. 2018). The modification to include such domains in fusion proteins may confer additional activity on engineered Type I CRISPR-Cas proteins. Such activities can include nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, and/or myristoylation activity or demyristoylation activity that modifies a polypeptide associated with nucleic acid target sequence (e.g., a histone).

In some embodiments, a fusion protein can comprise epitope tags (e.g., histidine tags, HA tags, FLAG® (Sigma Aldrich, St. Louis, Mo.) tags, Myc tags, nuclear localization signal (NLS) tags, SunTag), reporter protein sequences (e.g., glutathione-S-transferase, beta-galactosidase, luciferase, green fluorescent protein, cyan fluorescent protein, yellow fluorescent protein), and/or nucleic acid sequence binding domains (e.g., a DNA binding domain or an RNA binding domain).

A fusion protein can also comprise activator domains (e.g., heat shock transcription factors, NFKB activators) or repressor domains (e.g., a KRAB domain). As described by Lupo, A., et al., Current Genomics 14(4):268-278 (2013), the KRAB domain is a potent transcriptional repression module and is located in the amino-terminal sequence of most C2H2 zinc finger proteins (see, e.g., Margolin, J., et al., Proceedings of the National Academy of Sciences of the United States of America 91:4509-4513 (1994); Witzgall, R., et al., Proceedings of the National Academy of Sciences of the United States of America 91:4514-4518 (1994)). The KRAB domain typically binds to co-repressor proteins and/or transcription factors via protein-protein interactions, causing transcriptional repression of genes to which KRAB zinc finger proteins (KRAB-ZFPs) bind (see, e.g., Friedman J. R., et al., Genes & Development 10:2067-2678 (1996)). In some embodiments, linker nucleic acid sequences are used to join the two or more proteins, protein domains, or protein fragments.

As used herein "CASCADEa" (Cascade activation) is a CRISPR method or system wherein the method or system activates the expression of a gene within the locus of the target nucleic acid sequence. For the recruitment of endogenous transcription factors, one or more subunit proteins in a Cascade complex and/or the guide polynucleotide is typically fused to an effector domain (e.g., VP16 or VP64). In some embodiments, the guide polynucleotide can be fused 5' or 3' to a nucleotide effector domain such as an MS2 binding RNA that also recruits transcription factors. Fusions comprising one or more Cascade subunit proteins and the guide polynucleotide can be combined.

As used herein "CASCADE" (Cascade inhibition) is a CRISPR method or system wherein the CRISPR method or system downregulates the expression of a gene within the locus of the target nucleic acid sequence. For the recruitment of endogenous repression factors, one or more subunit proteins in a Cascade complex and/or the guide polynucleotide is typically fused to an effector domain (e.g., KRAB). In some embodiments, the guide polynucleotide can be fused 5' or 3' to a nucleotide effector domain that also recruits transcription factors. Fusions comprising one or more Cascade subunit proteins and the guide polynucleotide can be combined.

A "moiety," as used herein, refers to a portion of a molecule. A moiety can be a functional group or describe a portion of a molecule with multiple functional groups (e.g., that share common structural aspects). The terms "moiety" and "functional group" are typically used interchangeably; however, a "functional group" can more specifically refer to a portion of a molecule that comprises some common chemical behavior.

The term "affinity tag," as used herein, typically refers to one or more moieties that increases the binding affinity of one macromolecule for another, for example, to facilitate formation of an engineered Type I CRISPR-Cas nucleoprotein complex. In some embodiments, an affinity tag can be used to increase the binding affinity of one Cas subunit protein for another Cas subunit protein (e.g., a first Cas7 protein for a second Cas7 protein). In some embodiments, an affinity tag can be used to increase the binding affinity of one or more Cas subunit proteins for a cognate guide polynucleotide. Some embodiments of the present invention introduce one or more affinity tags to the N-terminal of a Cas subunit protein sequence, to the C-terminal of a Cas subunit protein sequence, to a position located between the N-terminal and C-terminal of a Cas subunit protein sequence, or to combinations thereof. In some embodiments of the present invention, one or more guide polynucleotide comprises an affinity tag that increases binding affinity of the guide polynucleotide with one or more Cas subunit proteins. A wide variety of affinity tags are disclosed in U.S. Published Patent Application No. 2014-0315985, published 23 Oct. 2014. Ligands and ligand-binding moieties are paired affinity tags.

As used herein, a "cross-link" is a bond that links one polymer chain (e.g., a polynucleotide or polypeptide) to another. Such bonds can be covalent bonds or ionic bonds. In some embodiments, one polynucleotide can be bound to another polynucleotide by cross linking the polynucleotides. In other embodiments, a polynucleotide can be cross linked to a polypeptide. In additional embodiments, a polypeptide can be cross linked to a polypeptide.

The term "cross-linking moiety," as used herein, typically refers to a moiety suitable to provide cross linking between two macromolecules. A cross-linking moiety is another example of an affinity tag.

As used herein, a "host cell" generally refers to a biological cell. A cell is the basic structural, functional, and/or biological unit of an organism. A cell can originate from any organism having one or more cells. Examples of host cells include, but are not limited to, a prokaryotic cell, eukaryotic cell, a bacterial cell, an archaeal cell, a cell of a single-cell eukaryotic organism, a cell of a eukaryotic organism, a protozoal cell, a cell from a plant (e.g., cells from plant crops (such as soy, tomatoes, sugar beets, pumpkin, hay, *cannabis*, tobacco, plantains, yams, sweet potatoes, cassava, potatoes, wheat, sorghum, soybean, rice, corn, maize, oil-producing *Brassica* (e.g., oil-producing rapeseed and canola), cotton, sugar cane, sunflower, millet, and alfalfa), fruits, vegetables, grains, seeds, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. agardh*, and the like), seaweeds (e.g., kelp), a fungal cell (e.g., a yeast cell or a cell from a mushroom), an animal cell, a cell from an invertebrate animal (e.g., fruit fly, cnidarian, echinoderm, nematode, and the like), a cell from a vertebrate animal (e.g., fish, amphibian, reptile, bird, or mammal), a cell from a mammal (e.g., a pig, a cow, a goat, a sheep, a rodent, a rat, a mouse, a non-human primate, a human, and the like). Furthermore, a cell can be a stem cell or a progenitor cell. In some embodiments, a host cell is a non-human cell. In some embodiments, a host cell is a human cell outside of a human body, wherein in particular embodiments the human cell is not introduced into a human body.

As used herein, "stem cell" refers to a cell that has the capacity for self-renewal, i.e., the ability to go through numerous cycles of cell division while maintaining the undifferentiated state. Stem cells can be totipotent, pluripotent, multipotent, oligopotent, or unipotent. Stem cells can be embryonic, fetal, amniotic, adult, or induced pluripotent stem cells.

As used herein, "induced pluripotent stem cell" refers to a type of pluripotent stem cell that is artificially derived from a non-pluripotent cell, typically a somatic cell. In some embodiments, the somatic cell is a human somatic cell. Examples of somatic cells include, but are not limited to, dermal fibroblasts, bone marrow-derived mesenchymal cells, cardiac muscle cells, keratinocytes, liver cells, stomach cells, neural stem cells, lung cells, kidney cells, spleen cells, and pancreatic cells. Additional examples of somatic cells include cells of the immune system, including but not limited to, B cells, dendritic cells, granulocytes, innate lymphoid cells, megakaryocytes, monocytes/macrophages, myeloid-derived suppressor cells, natural killer (NK) cells, T cells, thymocytes, and hematopoietic stem cells.

"Plant," as used herein, refers to whole plants, plant organs, plant tissues, germplasm, seeds, plant cells, and progeny of the same. Plant cells include, without limitation, cells from seeds, suspension cultures, embryos, meristematic regions, callus tissue, leaves, roots, shoots, gametophytes, sporophytes, pollen, and microspores. Plant parts include differentiated and undifferentiated tissues including, but not limited to, roots, stems, shoots, leaves, pollens, seeds, tumor tissue, and various forms of cells and culture (e.g., single cells, protoplasts, embryos, and callus tissue). The plant tissue may be in plant or in a plant organ, tissue, or cell culture. "Plant organ" refers to plant tissue or a group of tissues that constitute a morphologically and functionally distinct part of a plant.

"Subject," as used herein, refers to any member of the phylum Chordata, including, without limitation, humans and other primates, including non-human primates such as rhesus macaques, chimpanzees, and other monkey and ape species; farm animals, such as cattle, sheep, pigs, goats, and horses; domestic mammals, such as dogs and cats; laboratory animals, including rabbits, mice, rats, and guinea pigs; birds, including domestic, wild, and game birds, such as chickens, turkeys and other gallinaceous birds, ducks, and geese; and the like. The term does not denote a particular age or gender. Thus, the term includes adult, young, and newborn individuals as well as male and female. In some embodiments, a host cell is derived from a subject (e.g., stem cells, progenitor cells, or tissue-specific cells). In some embodiments, the subject is a non-human subject.

As used herein, "transgenic organism" refers to an organism that contains genetic material into which DNA from an unrelated organism has been artificially introduced. The term includes the progeny (any generation) of a transgenic organism, provided that the progeny has the genetic modification. In some embodiments, the transgenic organism is a non-human transgenic organism.

As used herein, "isolated" can refer to a molecule (e.g., a polynucleotide or a polypeptide) that, by human intervention, exists apart from its native environment and is therefore not a product of nature. An isolated polynucleotide or polypeptide can exist in a purified form and/or can exist in a non-native environment such as, for example, in a recombinant cell.

As used herein, a "substrate channel" refers to the direct transfer of a reactant from one enzymatic reaction to another enzymatic reaction without first diffusing into the bulk environment (Wheeldon, I., et al., Nat. Chem. 8(4):299-309 (2016)). Intermediates of these enzymatic steps are not in equilibrium with the bulk solution, which enables the increased efficiencies and yields in enzymatic processes. Frequently, enzymes in naturally occurring metabolic processes have evolved means of co-localization and assembly into controlled aggregates.

As used herein, "substrate channel element" refers to a component of a metabolic pathway. In some embodiments, a substrate channel element is an enzyme that catalyzes a chemical reaction.

As used herein, "substrate channel complex" refers to multiple substrate channel elements that are co-localized together via some means.

As used herein, an "RNA scaffold" refers to an RNA molecule that peptides can use as a substrate for binding.

In a first aspect, the present invention relates to engineered polynucleotides encoding Cascade components including, but not limited to, Cascade subunit proteins and Cascade guide polynucleotides.

In one embodiment, the present invention relates to engineered polynucleotides encoding Cascade components that are derived from Cascade Type I-E systems. Exemplary polynucleotide constructs comprising Cascade proteins and Cascade crRNAs are presented in Example 1. Example 1, Table 10, and SEQ ID NO:1 through SEQ ID NO:20 (FIG. 3) present polynucleotide DNA sequences of genes encoding the five subunit proteins of Type I-E Cascade, specifically from *E. coli* strain K-12 MG1655, as well as the amino acid sequences of the resulting protein components. The polynucleotide sequences were derived from *E. coli* genomic DNA and were codon optimized specifically for expression in *E. coli*, and/or codon optimized specifically for expression in eukaryotic cells (e.g., human cells). When this polynucleotide is transcribed into a precursor crRNA and processed by the Cascade RNA endonuclease, a mature crRNA is produced that functions as a guide RNA to target complementary DNA sequences in the genome. The minimal CRISPR array comprises two repeat sequences (underlined in the CRISPR array sequences presented in Example 1) flanking an exemplary spacer sequence, which represents the guide portion of the crRNA. RNA processing by the Cascade endonuclease generates a crRNA with repeat sequences on both the 5' and 3' ends, flanking the guide sequence. One of ordinary skill in the art, in view of the teachings of the present Specification and the Examples, can select appropriate spacer sequences to target binding of a Cascade complex to a chosen target sequence (e.g., in genomic DNA).

Polynucleotide sequences encoding Cascade components from additional bacterial or archaeal species can be identified and designed following the guidance of the present Specification and using bioinformatics tools such as BLAST and PSI-BLAST to locate, as an example, homologs of Cascade subunit genes from *E. coli* strain K-12 MG1655, and then inspecting the flanking genomic neighborhood of the Cascade gene to locate and identify genes of the remaining Cascade subunit proteins (see, e.g., Example 14, Example 15). Because Cascade genes co-occur as conserved operons, they are typically arranged in a consistent order, within the same Type I subtype, facilitating their identification and selection for follow-up analysis and experimentation. As an example, additional Type I-E systems can be identified by locating Cas8 homologs, identifying promising bacterial species for homologous Cascade testing, and then obtaining or designing polynucleotide sequences encoding the Cas8 and other protein components of the Cascade from those homologous CRISPR-Cas systems.

Polynucleotide DNA sequences of genes encoding the five subunit proteins of Cascade from twelve species (these species are listed in Table 2) with Cascade complexes homologous to those derived from *E. coli* strain K-12 MG1655, and the amino acid sequences of the resulting protein components, as well as exemplary minimal CRISPR arrays, are presented as SEQ ID NO:22 through SEQ ID NO:213 (FIG. 3). The polynucleotide sequences for the proteins were derived from the genomic DNA of the host bacterium, and were codon optimized specifically for expression in *E. coli*, and/or codon optimized specifically for expression in eukaryotic cells (e.g., human cells). The polynucleotide DNA sequences encoding corresponding minimal CRISPR arrays were based on repeat sequences derived from the 12 species and can be used to generate mature crRNA that function as guide RNAs. In Table 2, the minimal CRISPR array comprises two repeat sequences (lower case, underlined) flanking an exemplary "spacer" sequence, which represents the guide portion of the crRNA. RNA processing by the endonuclease Cascade subunit generates a crRNA with repeat sequences on both the 5' and 3' ends, flanking the guide sequence.

In another embodiment, the present invention relates to engineered polynucleotide sequences encoding Cascade components from additional bacterial or archaeal species, within other Type I subtypes; including, but not limited, to Types I-B, I-C, I-F, and variants of I-F, which can be identified and designed following the guidance of the present Specification and by using bioinformatics tools such as BLAST and PSI-BLAST to locate homologs of Cascade genes from hallmark systems typifying each subtype (see, e.g., Makarova, K. S., et al., Nat. Rev. Microbiol. 13(11): 722-736 (2015); Koonin, E. V., et al., Curr Opin Microbiol. 37:67-78 (2017)). After identifying desirable homologs, the flanking genomic neighborhoods of the Cascade gene can be inspected to locate and identify genes of the remaining Cascade subunit proteins as disclosed herein. As an example, additional Type I-F systems can be identified by locating Cas8 homologs (and additional Type I-F variant 2 systems can be identified by locating Cas5 homologs) and identifying promising bacterial species for homologous Cas-

TABLE 2

Minimal CRISPR Arrays

| SEQ ID NO: | Species | Minimal CRISPR repeat |
|---|---|---|
| SEQ ID NO: 37 | I-E_*Oceanicola* sp. HL-35 | ctgttccccgcacacgcggggatgaaccgGGTTCT TCGATCTGCGCATCCATGATGCCGC Cctgttccccgcacacgcggggatgaaccg |
| SEQ ID NO: 53 | I-E_*Pseudomonas* sp. S-6-2 | gtgttccccgcacctgcggggatgaaccGGGCCG GGGCGTTTGCGCTGTCAGGGGCGT CCCgtgttccccgcacctgcggggatgaaccg |
| SEQ ID NO: 69 | I-E_*Salmonella enterica* sub sp. *enterica* serovar Muenster strain | gtgttccccgcgccagcggggataaaccgCAGCTT TAGCATCGGTCGACAGCCCATCTG GCgtgttccccgcgccagcggggataaaccg |
| SEQ ID NO: 85 | I-E_*Atlantibacter hermannii* NBRC 105704 | gtgttccccgcgccagcggggataaaccgTTTTAA AACAGGATGTGGCCCGCCTGGTGC TGgtgttccccgcgccagcggggataaaccg |
| SEQ ID NO: 101 | I-E_*Geothermobacter* sp. EPR-M | ctgttccccgcacccgcggggatgaaccgGTCATC TATTTTTAATGGACGATATTTTTCA Actgttccccgcacccgcggggatgaaccg |
| SEQ ID NO: 117 | I-E_*Methylocaldum* sp. 14B | ctgttccccacgtacgtggggatgaaccgACGGCG TAATGGTAATTGTTAGCCGACAAG TTctgttccccacgtacgtggggatgaaccg |
| SEQ ID NO: 133 | I-E_*Methanocella arvoryzae* MRE50 | aaagtccccacaggcgtgggggtgaaccgTGATC AGTAACCCGGTCACCATTAAACAG ATTaaagtccccacaggcgtgggggtgaaccg |
| SEQ ID NO: 149 | I-E_*Lachnospiraceae bacterium* KH1T2 | gtattccccacgcacgtggrggtaaatcCGCTGAG TTTAATTACGCAGCGGAAGCCGGA GCGgtattccccacgcacgtgggggtaaatc |
| SEQ ID NO: 165 | I-E_*Klebsiella pneumoniae* strain VRC00172 | gtatccccacacgcgtgggggtgtttcCGGCTCTT TTTTATCTCCTTCATCCTTCGCTATgt cttcccacacgcgtgggggtgtttc |
| SEQ ID NO: 181 | I-E_*Pseudomonas aeruginosa* DHS01 | gtgttccccacatgcgtggggatgaaccgGGCACC ATCGGCGCCATTGACCGCGCGCTG AAGgtgttccccacatgcgtggggatgaaccg |
| SEQ ID NO: 197 | I-E_*Streptococcus thermophilus* strain ND07 | gttttccccgcacacgcgggggtgatccTATACCT ATATCAATGGCCTCCCACGCATAA GCgttttccccgcacacgcgggggtgatcc |
| SEQ ID NO: 213 | I-E_*Streptomyces* sp. S4 | gtcggccccgcacccgcggggatgctccAATGGC CGAGGACGACGGCGATCTGGCCAC GGACgtcggccccgcacccgcggggatgctcc | cade testing, and then obtaining or designing polynucleotide sequences encoding the Cas8, Cas5, and other protein components of the Cascade from those homologous CRISPR-Cas systems.

Polynucleotide DNA sequences of genes encoding the three, four, or five subunit proteins of Cascade from Types I-B, I-C, I-F, and I-F variant 2 from twelve additional homologous Cascade complexes, and the amino acid sequences of the resulting protein components, as well as exemplary minimal CRISPR arrays, are presented as SEQ ID NO:214 through SEQ ID NO:351 (FIG. 3). The polynucleotide sequences for the subunit proteins were derived from the genomic DNA of the host bacterium, and were codon optimized specifically for expression in *E. coli*, and/or codon optimized specifically for expression in eukaryotic cells (e.g., human cells). The polynucleotide DNA sequences encoding corresponding minimal CRISPR arrays were based on repeat sequences derived from the twelve species and can be used to generate mature crRNA that function as guide RNAs. In Table 3 the minimal CRISPR array comprises two repeat sequences (lower case, underlined) flanking an exemplary "spacer" sequence, which represents the guide portion of the crRNA. RNA processing by the endonuclease Cascade subunit generates a crRNA with repeat sequences on both the 5' and 3' ends, flanking the guide sequence.

TABLE 3

Minimal CRISPR Arrays

| SEQ ID NO: | Species | Minimal CRISPR repeat |
|---|---|---|
| SEQ ID NO: 226 | I-B_*Fusobacterium nucleatum* subsp. *animalis* 3_1_33 | atgaactgtaaacttgaaaagttttgaaatGTTGACAA ATATTCAGATAATTTTTCAAAATCTT TTatgaactgtaaacttgaaaagttttgaaat |
| SEQ ID NO: 239 | I-B_*Campylobacter fetus* subsp. *testudinum* Sp3 | gtttgctaatgacaatatttgtgttaaaacAAGCGTAG CACCAAAAGAAGCGTATGAAAGCAT AGgtttgctaatgacaatatttgtgttaaaac |
| SEQ ID NO: 252 | I-B_*Odoribacter splanchnicus* DSM 20712 | cttttaattgaactaaggtagaattgaaacTAGGAATA AACCGTACCCAACCACGTAGCCATA TACGcttttaattgaactaaggtagaattgaaac |
| SEQ ID NO: 262 | I-C_*Bacillus halodurans* C-125 | gtcgcactcttcatgggtgcgtggattgaaatCCTTTG ACGGAGAGGGGAACAGGAAATTAG AGAAGgtcgcactcttcatgggtgcgtggattgaaat |
| SEQ ID NO: 272 | I-C_*Desulfovibrio vulgaris* RCH1 plasmid pDEVAL01 | gtcgcccccacgcgggggcgtggattgaaacCAGTC TCGTTACCCTGTCGCGGAGGGCGTCG ATgtcgcccccacgcgggggcgtggattgaaac |
| SEQ ID NO: 282 | I-C_*Geobacillus thermocatenulatus* strain KCTC 3921 | gttgcaccgggctattaagccgggtgaggattgaaacTA TATCACACAGCTTCTTAGTATCATCG ACAACACGTgttgcacccggctattaagccgggtg aggattgaaac |
| SEQ ID NO: 295 | I-F_*Vibrio cholerae* strain L15 | gttcactgccgtacaggcagcttagaaaAATATGCA GGGGTTTGAAACGCTCGATGTTATgtt cactgccgtacaggcagcttagaaa |
| SEQ ID NO: 308 | I-F_*Klebsiella oxytoca* strain ICU1-2b | gttcactgccgtacaggcagcttagaaaAAAAACTG AGCGGCCGCAGAATGAAGTTGTAAgt tcactgccgtacaggcagcttagaaa |
| SEQ ID NO: 321 | I-F_*Pseudomonas aeruginosa* UCBPP-PA14 | gttcactgccgtgtagggcagctaagaaaACCACCCG CTACCACCGGCAGCCGCACCGGCCgtt cactgccgtgtagggcagctaagaaa |
| SEQ ID NO: 331 | I-Fv2_*Shewanella putrefaciens* CN-32 | gttcaccgccgcacaggcggcttagaaaTCAACCA AATCATAAATTGCGCGACCACATTGg ttcaccgccgcacaggcggcttagaaa |
| SEQ ID NO: 341 | I-Fv2_*Acinetobacter* sp. 869535 | gttcactgccatataggcagcttagaaaATCGTTTTT TCATACGAGATTCGAAACGGACAgttc actgccatataggcagcttagaaa |
| SEQ ID NO: 351 | I-Fv2_*Vibrio cholerae* HE48 | gttcactgccgcacaggcagcttagaaaTAACCGGA GGCGTACACTCGATAGAGGCAGCGgt tcactgccgcacaggcagcttagaaa |

Example 19 describes the design and testing of multiple Cascade complex homologs, each comprising a Cas subunit protein-FokI fusion protein, to evaluate the efficiency of genome editing for each Cascade complex.

In a second aspect, the present invention relates to modified Cascade subunit proteins. Cascade subunit proteins suitable for modification include, but are not limited to, Cascade subunit proteins of the species described herein.

In one embodiment, the present invention relates to engineered circular permutations of Cascade subunit proteins. Such circular permutations of a Cascade subunit protein result in a protein structure having different connectivity of the original linear sequence of amino acids of the Cascade subunit protein, but having an overall similar three-dimensional shape (see, e.g., Bliven, S., et al., PLoS Comput. Biol. 8(3):e1002445 (2012)). Circular permutations of Cascade subunit proteins can have a number of advantages. For example, a circular permutation of a Cas7 subunit protein can create a new N-terminus and a new C-terminus designed to be positioned for connection with an additional polypeptide sequence to form a fusion protein or linker region without disturbing the Cas7 protein fold or the Cascade complex assembly. Three examples of circular permutations of Cas7 (circularly permuted Cas7, cpCas7) are illustrated in FIG. 4A and FIG. 4B. In FIG. 4A and FIG. 4B, three portions of the protein are shown: a N-terminal portion of the native protein (vertical stripes), a central portion of the native protein (grey shading), and a C-terminal portion of the native protein (no shading). FIG. 4A illustrates relocation of a N-terminal portion of the native protein to the C-terminal position of the cpCas7, wherein the N-terminal portion of the native protein is now at the N-terminal end of the cpCas7 and is connected to the central portion of the native protein by a linker polypeptide. FIG. 4B illustrates relocation of a C-terminal portion of the native protein to the N-terminal position of the cpCas7, wherein the C-terminal portion of the native protein is now at the N-terminal end of the cpCas7 and is connected to the central portion of the native protein by a linker polypeptide.

The data in Example 10 show that purification of Cascade complexes comprising circularly-permuted Cas7 subunit protein variants demonstrate that circularly-permuted Type I-E CRISPR-Cas subunit proteins can be successfully used to form Cascade complexes having essentially the same composition (based on molecular weight) as Cascade complexes comprising wild-type proteins.

In another embodiment, the present invention relates to Cascade subunit proteins fused to additional polypeptide sequences to create fusion proteins, as well as polynucleotides encoding such fusion proteins. Additional polypeptide sequences can include, but are not limited to, proteins, protein domains, protein fragments, and functional domains. Examples of such additional polypeptide sequences include, but are not limited to, sequences derived from transcription activator or repressor domains, and nucleotide deaminases (e.g., a cytidine deaminase or an adenine deaminase such as described in Komor et. al., Nature 553:420-424 (2016); Koblan et. al., Nat Biotechnol. 2018 May 29-doi: 10.1038/nbt.4172). Additional functional domains for fusion proteins are presented herein.

An additional polypeptide sequence can be fused to any of the Cascade subunit proteins wherein the additional polypeptide sequence is encoded by an additional polynucleotide sequence that is typically appended to either the 5' or 3' end of a polynucleotide comprising the coding sequence of a Cascade subunit protein. In some embodiments, additional polynucleotide sequences that encode amino acid linkers connect a Cascade subunit protein to the additional polypeptide sequences of interest. In some embodiments, the polynucleotide sequences for the fusion protein partner and the linker sequence can be derived from naturally occurring genomic DNA sequences or may be codon optimized for bacterial expression in E. coli or eukaryotic expression in mammalian cells (e.g., human cells). Examples of fusions proteins comprising affinity tags (e.g., His6, Strep-tag® II (IBA GMBH LLC, Göttingen, Germany)), nuclear localization signal or sequence (NLS), maltose binding protein, and FokI are presented in Example 1. Exemplary amino acid linker sequences are also disclosed in Example 1.

Example 11 describes Cascade subunit protein-FokI fusions, as well as Cascade subunit protein fusions to cytidine deaminases, endonucleases, restriction enzymes, a nuclease/helicase, or domains thereof. Example 11 describes Cascade subunit protein fusions with other Cascade subunit proteins, as well as Cascade subunit protein fusions with other Cascade subunit fusion proteins and an enzymatic protein domain. In some embodiments, a Type I CRISPR subunit protein can be evaluated in silico for the ability to be used to generate protein fusions at the N-terminus, C-terminus, or positions between the N-terminus and the C-terminus. In some embodiments, a Type I CRISPR subunit protein can be linked to one or more fusion domains at the N-terminus, C-terminus, or positions between the N-terminus and the C-terminus using one or more polypeptide linkers. Examples of polypeptide linkers are set forth in Examples 1, 11, 18, and 19.

Figure 5B:
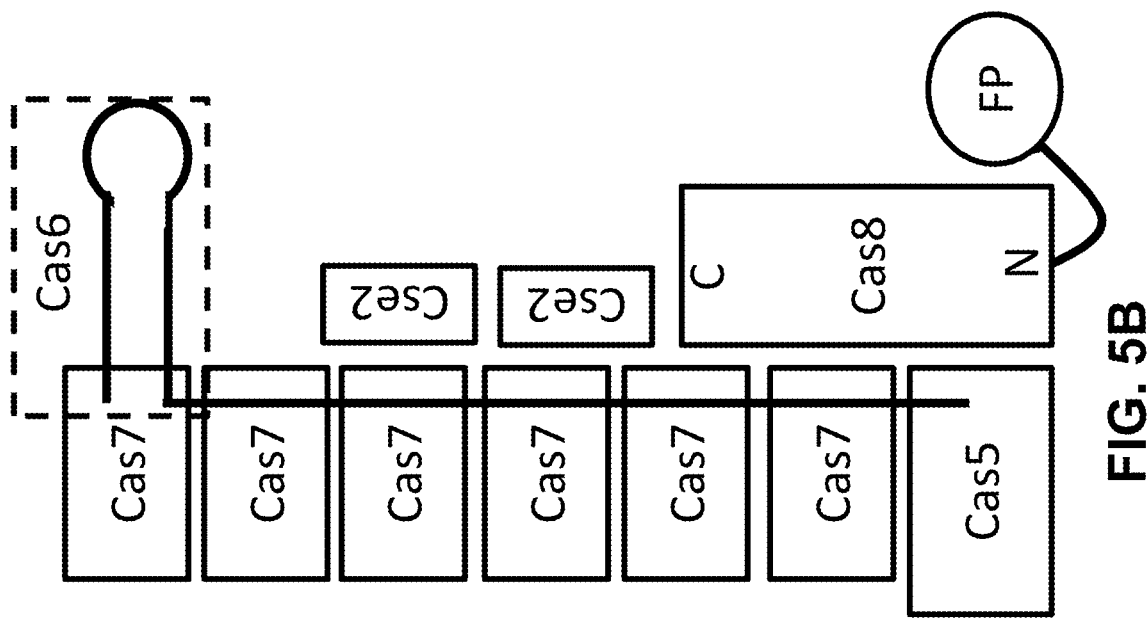
FIG. 5A, FIG. 5B, FIG. 6A, FIG. 6B, FIG. 7A, FIG. 7B, FIG. 7C, FIG. 8A, FIG. 8B, FIG. 9, FIG. 10, FIG. 11A, and FIG. 11B illustrate a variety of examples of engineered Type I CRISPR-Cas effector complexes of the present invention.
Figure 5A:
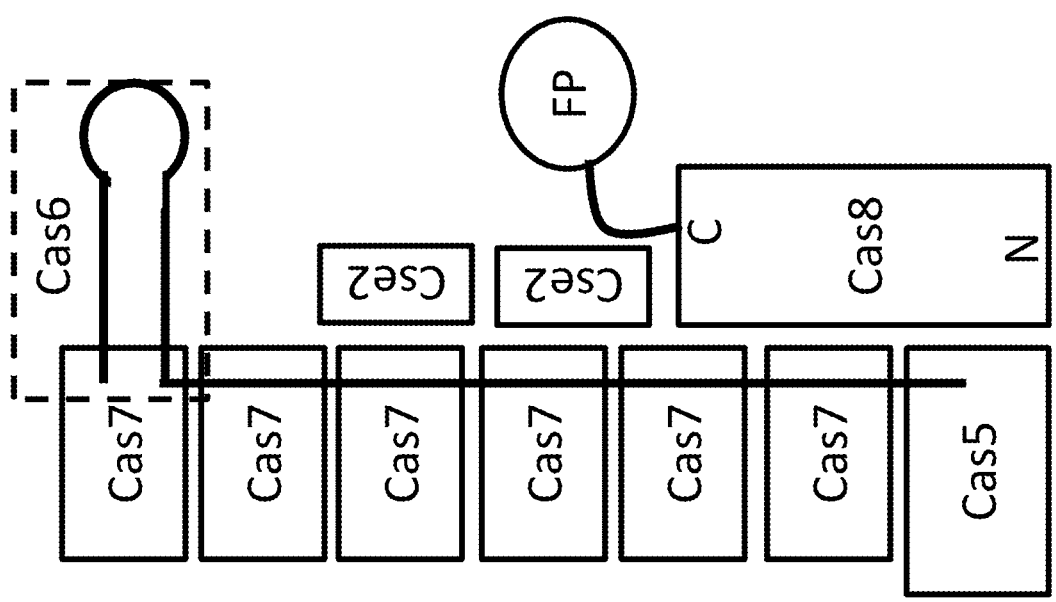

FIG. 5A and FIG. 5B illustrate Cascade complexes comprising a Cas8 subunit protein fused to an additional protein sequence (e.g., a FokI). FIG. 5A shows an example of the additional protein sequence ("FP") connected with the C-terminus of a Cas8 subunit protein using a linker polypeptide. FIG. 5B shows an example of the additional protein sequence ("FP") connected with the N-terminus of a Cas8 subunit protein using a linker polypeptide. Example 11A describes in silico design, cloning, expression, and purification of a Type I-E Cas8 fused N-terminally with a FokI nuclease domain.

Figure 6B:
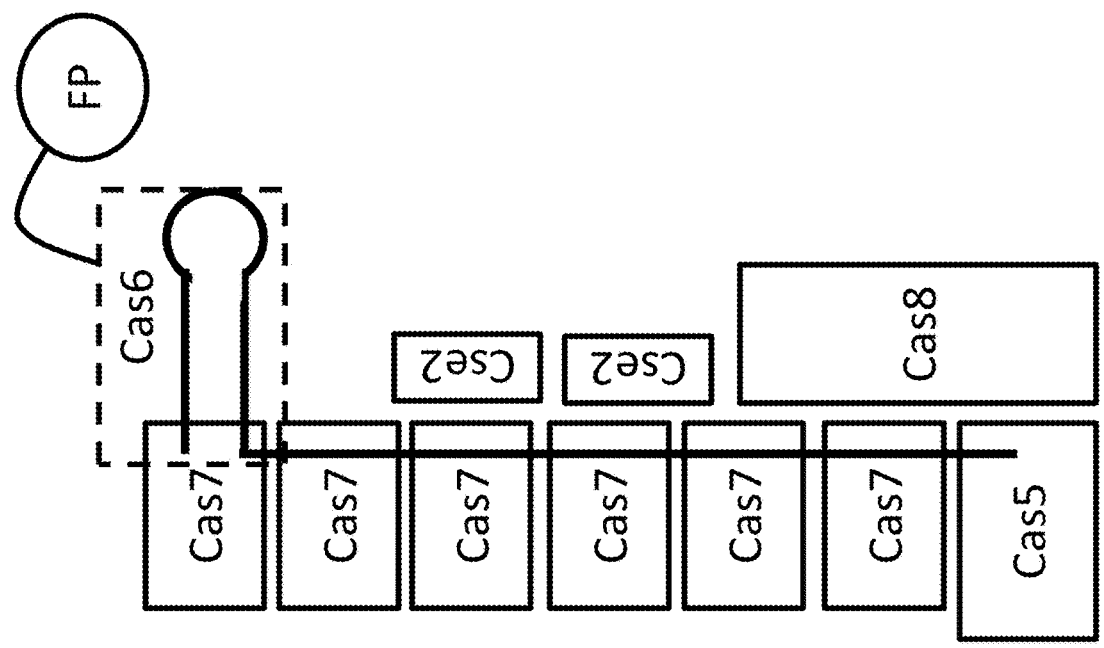
Figure 6A:
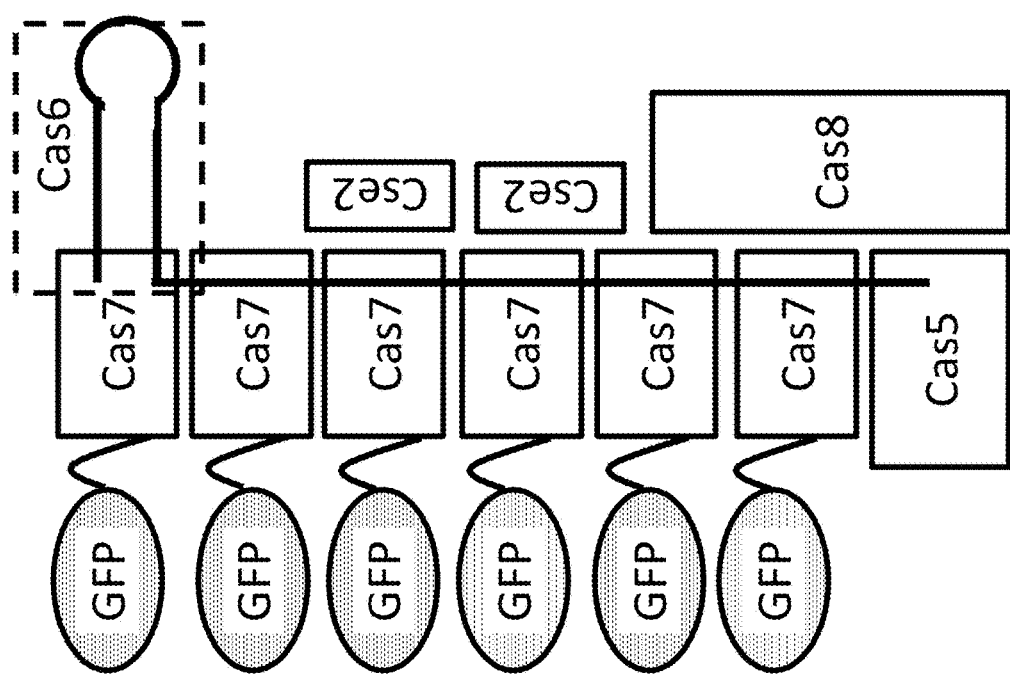

FIG. 6A and FIG. 6B illustrate additional examples of Cascade complexes comprising a Cascade subunit protein fused to an additional protein sequence. FIG. 6A shows an example of a detectable moiety (e.g., a green fluorescent protein, GFP) fused to each of six Cas7 subunit proteins, each via a linker polypeptide. Such a Cascade complex can be useful for detection of binding of the complex to a nucleic acid target sequence by providing significant signal amplification as a result of the presence of the multiple detectable moieties associated with the Cascade complex. FIG. 6B shows an example of an additional protein sequence ("FP") connected with Cas6 subunit protein using a linker polypeptide.

Examples of fusion proteins containing E. coli Type I-E Cascade subunit proteins include, but are not limited to, the following: the same subunit (e.g., Cse2_linker_Cse2), circularly permuted subunits (e.g., cpCas7_linker_cpCas7_linker_cpCas7_linker_cpCas7_linker_cpCas7_linker_cpCas7), a Type I-E Cascade protein fused to a nuclease (e.g., FokI_linker_Cas8, Cas3_linker_Cas8, Cas6_linker FokI, S1Nuclease_linker_Cse2_linker_Cse2), a Type I-E Cascade protein fused to a cytidine deaminase (e.g., Cas8_linker_AID, Cse2_linker_Cse2_linker APOBEC3G), and a Type I-E Cascade protein fused one or more other Type I-E Cascade proteins (e.g., Cas6_linker_cpCas7_linker_cpCas7__linker_cpCas7_linker_cpCas7_linker_cpCas7_linker_cpCas7, cpCas7_linker_cpCas7_linker_cpCas7_linker_cpCas7_linker_cpCas7_linker_cpCas7_linker_Cas5, Cas6_linker_cpCas7_linker_cpCas7_linker_cpCas7_linker_cpCas7_linker_cpCas7_linker_cp Cas7_linker_Cas5).

Figure 7C:
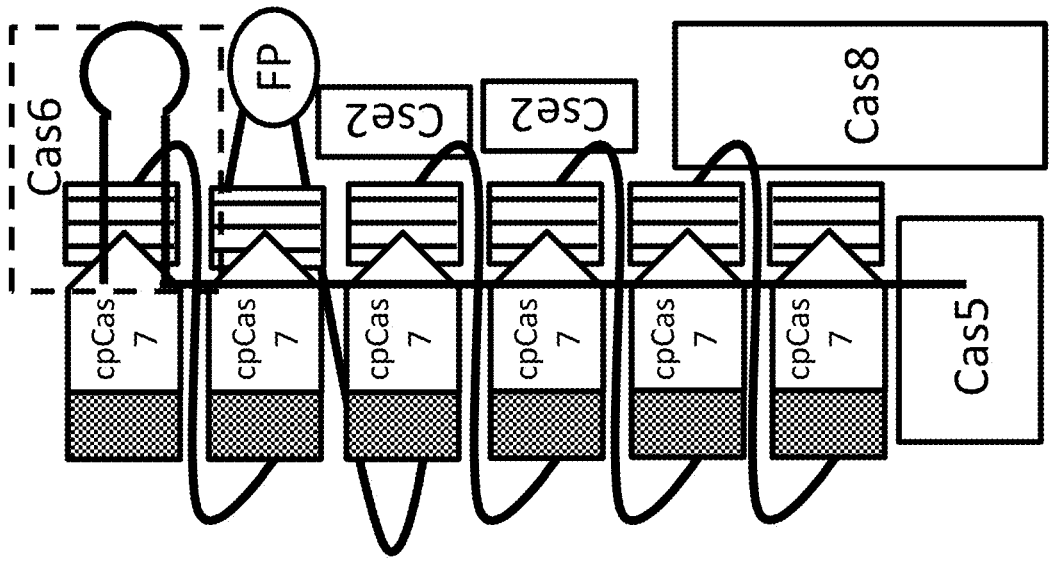
Figure 7B:
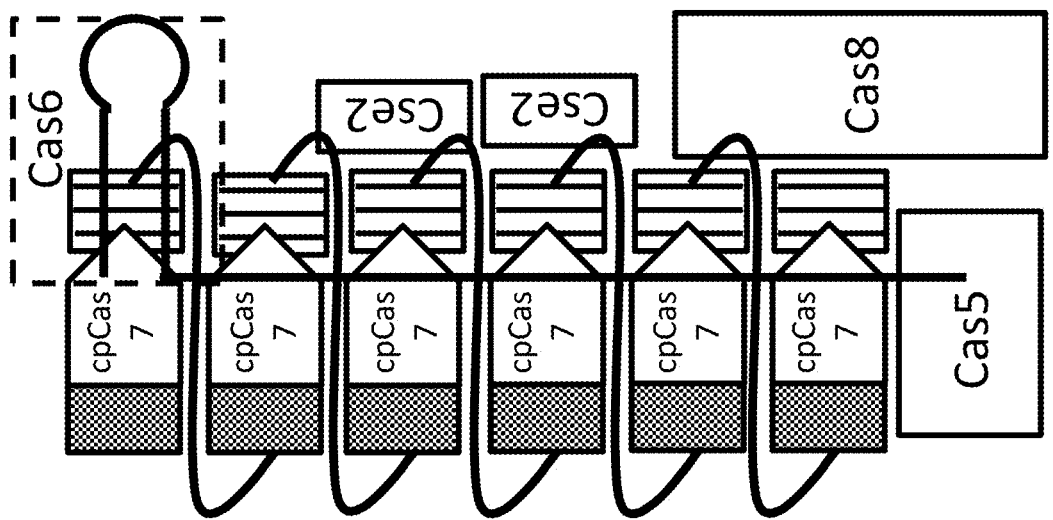
Figure 7A:
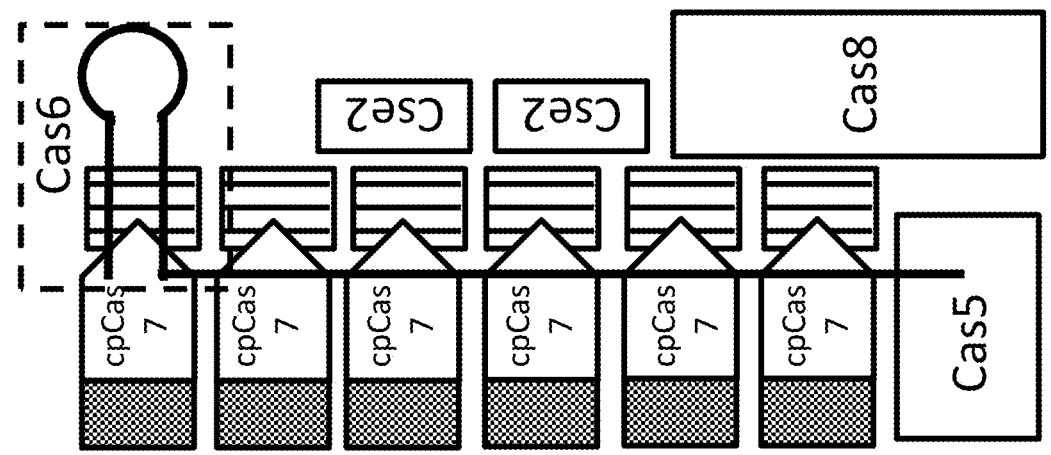

FIG. 7A, FIG. 7B, and FIG. 7C present illustrations of modified Type I CRISPR-Cas effector complexes that contain cpCas7 (compare FIG. 4A)). FIG. 7A presents a Cascade complex comprising six individual cpCas7 subunit proteins. FIG. 7B presents a Cascade complex comprising six fused cpCas7 subunit proteins, wherein the C-terminus of a cpCas7 subunit protein is connected with the N-terminus of an adjacent cpCas7 subunit protein using a linker polypeptide. FIG. 7C presents an embodiment wherein the Cascade complex comprises six fused cpCas7 subunit proteins (a "backbone"), wherein the C-terminus of the first cpCas7 subunit protein is connected with the N-terminus of the second cpCas7 subunit protein using a linker polypeptide, the C-terminus of the second cpCas7 subunit protein is connected with the N-terminus of a different protein sequence ("FP") (e.g., a cytidine deaminase) using a linker polypeptide and the C-terminus of this protein coding sequence is connected with the N-terminus of the third cpCas7 using a linker polypeptide. One advantage of such a fused backbone of cpCas7 subunit proteins is that an additional protein sequence can be introduced at a specific location along the backbone to provide access of the additional protein sequence to different locations along the length of the nucleic acid target sequence to which the guide directs binding of the Cascade complex.

Figure 8B:
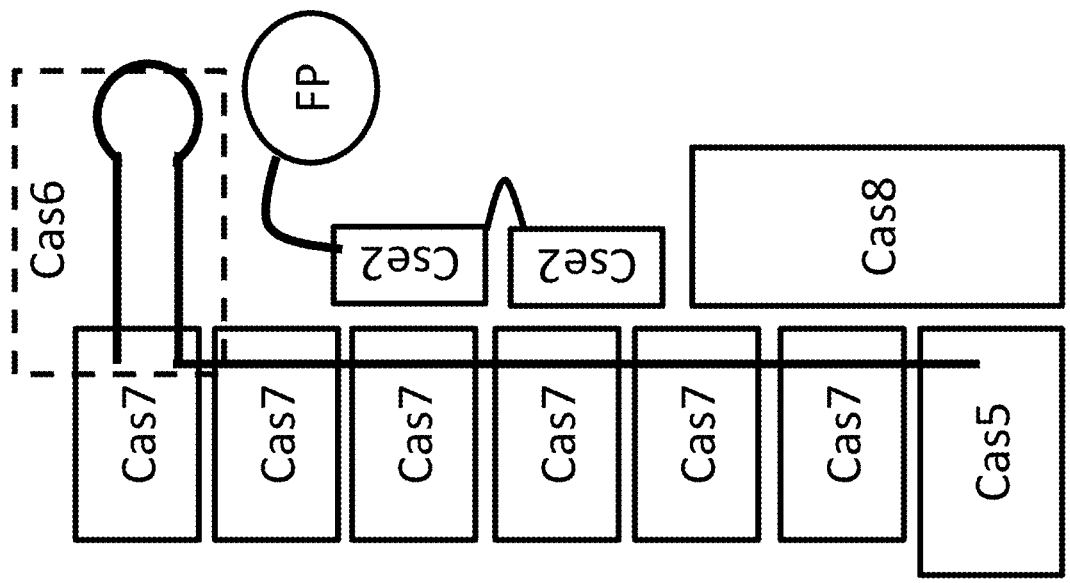
Figure 8A:
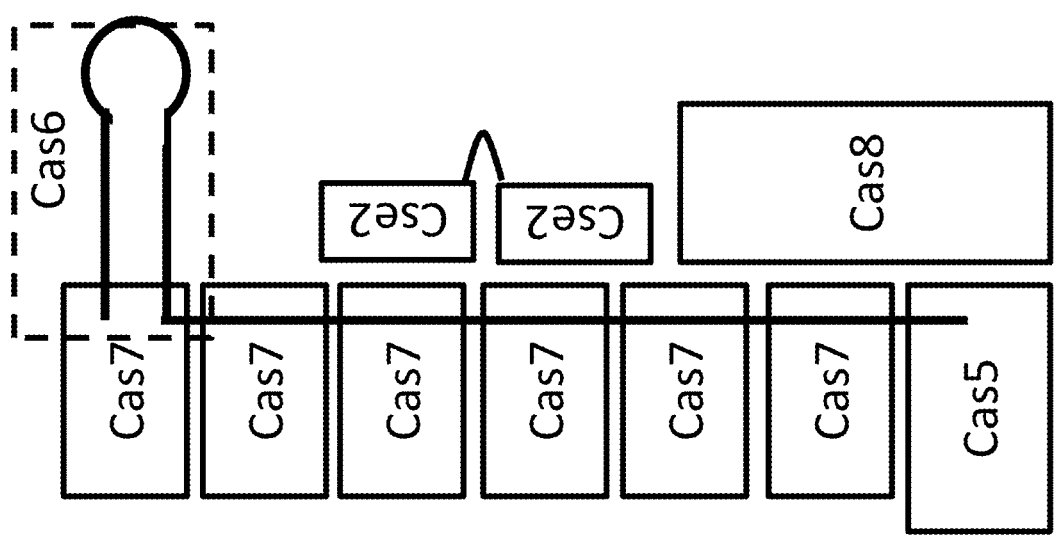

FIG. 8A and FIG. 8B illustrate further embodiments of modified Type I CRISPR-Cas effector complexes comprising fusion proteins. FIG. 8A shows a Cascade complex comprising a Cse2-Cse2 fusion protein. In silico design, cloning, expression, purification, and electrophoretic mobility shift assays are described in Example 11B and Example 11C Cascade complexes comprising Cse2-Cse2 fusion proteins. FIG. 8B shows a Cascade complex comprising a Cse2-Cse2 fusion protein connected with an additional protein sequence ("FP"). Example 11D describes in silico design, cloning, expression, and purification of a Cse2-Cse2 protein fused to a cytidine deaminase.

In some embodiments, one or more nuclear localization signals can be added at the engineered N-terminus or C-terminus of a Cascade protein subunit (e.g., a Cas8-FokI fusion protein, a cpCas7 protein, or a Cse2-Cse2 fusion protein).

In some embodiments of fusion polypeptides, linker polypeptides connect two or more protein coding sequences. The length of exemplary linker polypeptides are described in the Examples. Typically, linker lengths include, but are not limited to, between about 10 amino acids to about 40 amino acids, between about 15 amino acids and about 30 amino acids, and between about 17 amino acids and about 20 amino acids. The amino acid composition of linker polypeptides typically comprises amino acids that are polar, small, and/or charged (e.g., Gly, Ala, Leu, Val, Gln, Ser, Thr, Pro, Glu, Asp, Lys, Arg, His, Asn, Cys, Tyr). Following the guidance of the present Specification, the linker polypeptide is designed to provide appropriate spacing and positioning of the functional domain and the Cascade protein within the fusion protein (Chichili, C., et al., Protein Science 22(2): 153-167 (2013); Chen, X., et al., 65(10):1357-1369 (2013); George, R., et al., Protein Engineering, Design and Selection 15:(11):871-879 (2002)). Additional examples of linker polypeptides useful in the practice of the present invention are linker polypeptides identified that connect coding sequences of Cascade proteins to each other in organisms comprising Cascade systems (e.g., the linker polypeptide that connects Cas8 to Cas3 in *Streptomyces griseus* as described by Westra, E. R., et al., Mol Cell. 46(5): 595-605 (2012)).

Fusion protein coding DNA sequences can be codon optimized for expression in a selected organism such as bacteria, archae, plants, fungi, or mammalian cells. Codon-optimizing programs are widely available. such as on the Integrated DNA Technologies website (www.idtdna.com/CodonOpt), or through Genscript® services (Genscript, Piscataway, N.J.). To facilitate cloning into the recipient expression vector, additional sequences overlapping with the vector compatible for SLIC cloning (Li, M., et al., Methods Mol. Biol. 852:51-59 (2012)) can be appended at the 5' and 3' ends of the DNA sequence.

In other embodiments, Cascade subunit proteins can be fused to transcription activation and/or repression domains. In some embodiments, a fusion protein can comprise activator domains (e.g., heat shock transcription factors, NFKB activators, VP16, and VP64 (Eguchi, A. et. al., PNAS 113(51):E8257-E8266 (2016); Perez-Pinera, P. et. al., Nature Methods 10(10):973-6 (2013); Gilbert, L. A., et. al. Cell 159(3):647-61 (2014)) or repressor domains (e.g., a KRAB domain). In some embodiments, linker nucleic acid sequences are used to join the two or more coding sequences for proteins, protein domains, or protein fragments.

Figure 9:
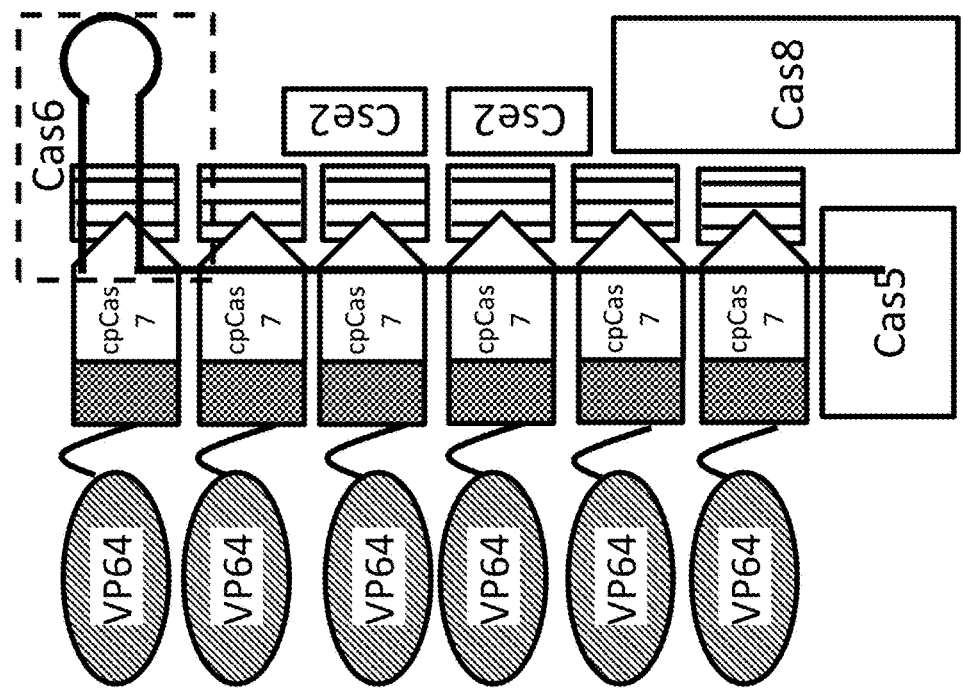

Cascade complexes comprising Type I CRISPR-Cas subunit proteins fused to transcription activators can be used to activate the expression of the gene. The target locus can contain a transcriptional start site (TSS) that typically harbors one or more binding site for the transcriptional activation machinery (factors) of a cell. FIG. 9 illustrates a Cascade complex comprising six fusion proteins comprising a cpCas7 connected via a linker polypeptide to the transcriptional activator VP64. Such modification of a Cascade complex converts the complex into a flexible tool for transcriptional activation of a gene (CASCADEa), wherein targeting a selected gene is achieved by selection of a guide sequence that directs binding of the Cascade complex to one or more regulatory elements (e.g., a TSS) of the selected gene. Example 12 describes the design of a *E. coli* Type I-E cp-Cas7 protein fused to a VP64 activation domain to confer transcriptional activation activity to the Cascade complex.

In addition, Cascade complexes comprising Type I CRISPR-Cas subunit proteins fused to transcription repressors can be used to repress the expression of the gene. The target locus can comprise transcriptional regulatory elements. In one embodiment, a Cascade subunit protein can be connected to a KRAB domain via a linker polypeptide. A Cascade complex comprising the Cascade subunit protein/KRAB domain fusion can convert the complex into a flexible tool for transcriptional repression of a gene (CASCADEi), wherein targeting a selected gene is achieved by selection of a guide sequence that directs binding of the Cascade complex to one or more regulatory elements of the selected gene.

In additional embodiments, Cascade subunit proteins can be fused to affinity tags.

Figure 10:
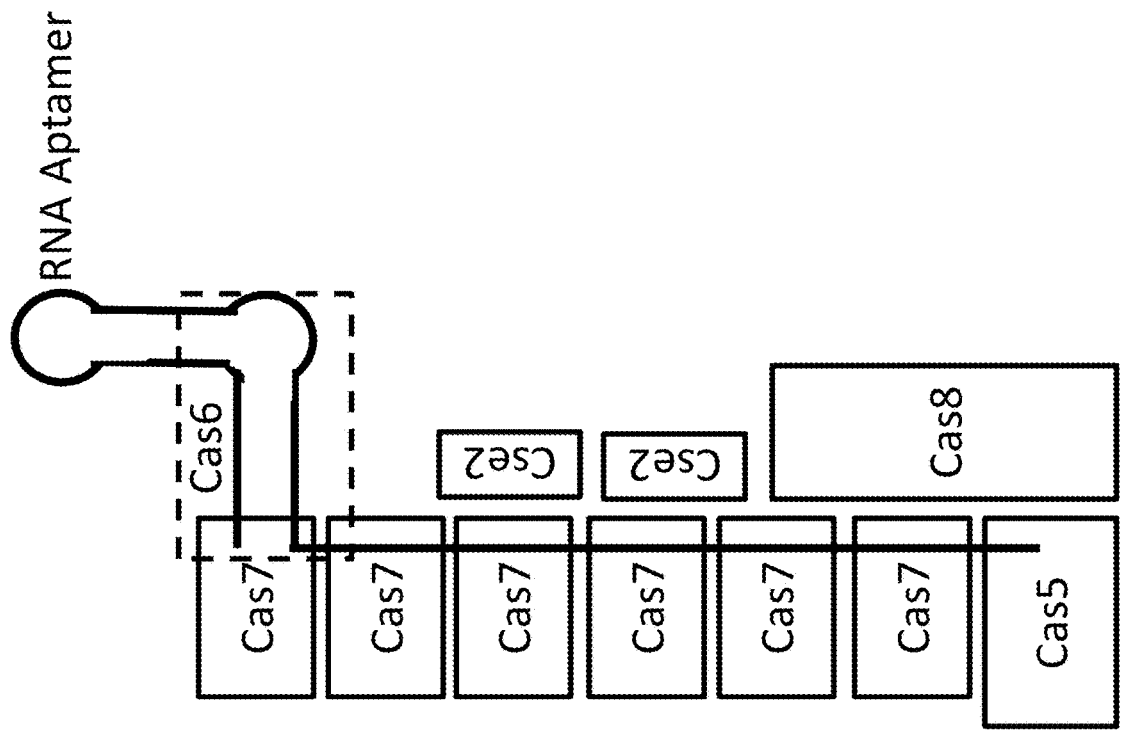

In other embodiments of the present invention, Type I CRISPR-Cas guide polynucleotides can be modified by insertion of a selected polynucleotide element or modification of a nucleotides at selected positions within the guide polynucleotides (e.g., substitution of a DNA moiety for a RNA moiety). Such embodiments include, but are not limited to, Type I CRISPR-Cas guide polynucleotides 5', 3' or internally fused to one or more nucleotide effector domain (e.g., an MS2 or MS2-P65-HSF1 binding RNA or Aptamer that recruits transcription factors). FIG. 10 illustrates a Type I CRISPR guide polynucleotide comprising an RNA aptamer introduced into the 3' hairpin of the guide.

Figure 11B:
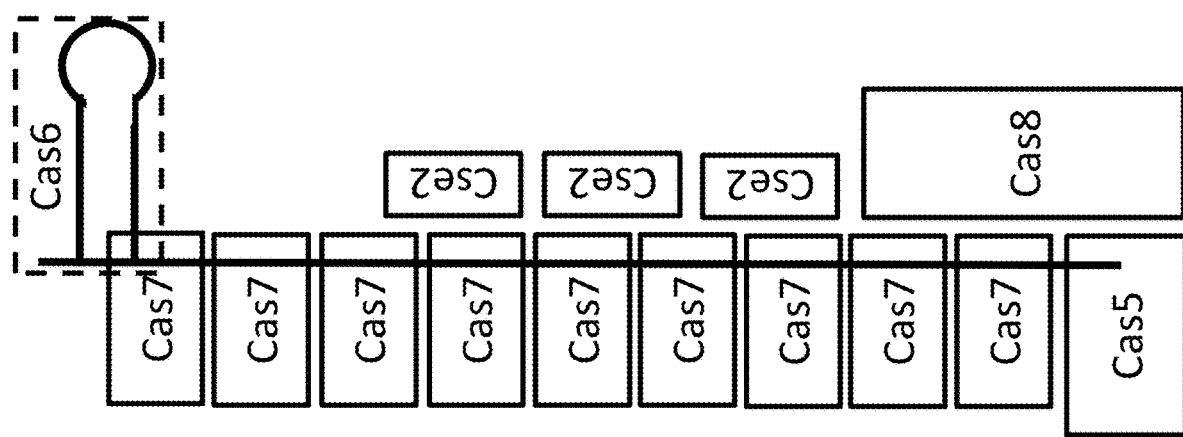
Figure 11A:
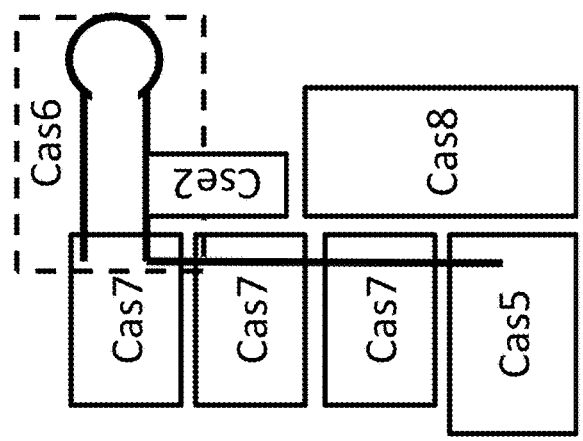

The length of Type I CRISPR-Cas guides can also be modified, typically by lengthening or shortening the Cas7 subunit protein and Cse2 subunit protein binding region. FIG. 11A illustrates a Cascade complex with three Cas7 subunits, one Cse2 subunit and a shortened crRNA. FIG. 11B illustrates a Cascade complex with nine Cas7 subunits, three Cse2 subunit and a lengthened crRNA.

Example 16 describes the generation and testing of modifications of Type I CRISPR-Cas guide crRNAs and the suitability of the modified guides for use in constructing engineered Type I CRISPR-Cas effector complexes.

In a third aspect, the present invention relates to nucleic acid sequences encoding one or more engineered Cascade components, as well as expression cassettes, vectors, and recombinant cells comprising nucleic acid sequences encoding one or more engineered Cascade components. Some embodiments of the third aspect of the invention include one or more polypeptide encoding all the components of a selected Cascade system (e.g., Cse2, Cas5, Cash, Cas7, and Cas8 proteins, and one or more cognate guides), wherein the components are capable of forming an effector complex. Typically, when more than one cognate guide is expressed, the guides have different spacer sequences to direct binding to different nucleic acid target sequences. Such embodiments include, but are not limited to, expression cassettes, vectors, and recombinant cells.

In one embodiment, the present invention relates to one or more expression cassettes comprising one or more nucleic acid sequences encoding one or more engineered Cascade components. Expression cassettes typically comprise a regulatory sequence involved in one or more of the following: regulation of transcription, post-transcriptional regulation, or regulation of translation. Expression cassettes can be introduced into a wide variety of organisms including, but not limited to, bacterial cells, yeast cells, plant cells, and mammalian cells (including human cells). Expression cassettes typically comprise functional regulatory sequences corresponding to the organism(s) into which they are being introduced.

A further embodiment of the present invention relates to vectors, including expression vectors, comprising one or more nucleic acid sequences encoding one or more one or more engineered Cascade components. Vectors can also include sequences encoding selectable or screenable markers. Furthermore, nuclear targeting sequences can also be added, for example, to Cascade subunit proteins. Vectors can also include polynucleotides encoding protein tags (e.g., poly-His tags, hemagglutinin tags, fluorescent protein tags, and bioluminescent tags). The coding sequences for such protein tags can be fused to, for example, one or more nucleic acid sequences encoding a Cascade subunit protein.

General methods for construction of expression vectors are known in the art. Expression vectors for host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, and viral vectors (including lentivirus, retrovirus, adenovirus, herpes simplex virus I or II, parvovirus, reticuloendotheliosis virus, and adeno-associated virus (AAV) vectors) for cell transformation and gene expression and methods to easily allow cloning of such polynucleotides. Illustrative plant transformation vectors include those derived from a Ti plasmid of *Agrobacterium tumefaciens* (Lee, L. Y., et al., Plant Physiology 146(2):325-332 (2008)). Also useful and known in the art are *Agrobacterium rhizogenes* plasmids. For example, SNAPGENE™ (GSL Biotech LLC, Chicago, Ill.; snapgene.com/resources/plasmid_files/your_time_is_valuable/) provides an extensive list of vectors, individual vector sequences, and vector maps, as well as commercial sources for many of the vectors.

In order to express and purify recombinant Cascade in a bacterial expression system, vectors can be designed that encode Cascade subunit proteins, as well as a minimal CRISPR arrays comprising guide sequences of interest. Accordingly, one aspect of the present invention includes such expression systems. In one embodiment, the Cascade complex is expressed off of three distinct plasmid vectors, which collectively encode the following components: a Cas8 protein; Cse2, Cas7, Cas5, and Cas6 proteins; and a CRISPR crRNA. In some embodiments, the expression plasmid encoding Cas8 comprises the natural, genomic DNA gene sequence and, in other embodiments, the expression plasmid can encode Cas8 that is codon optimized for expression in a chosen cell type. Similarly, the expression plasmid encoding Cse2, Cas7, Cas5, and Cas6 can contain the natural, genomic DNA gene sequences or can contain gene sequences that have been codon optimized for expression in a chosen cell type. In some embodiments, the entire Cascade subunit protein coding operon can be placed downstream of a single transcriptional promoter, such that the different proteins are all translated from a single polycistronic transcript. In additional embodiments, the gene encoding the Cascade subunit proteins can be separated from each other, with intervening transcriptional terminators and promoters.

The expression plasmid encoding the crRNA may contain as few as two repeats flanking a single spacer sequence, downstream of an appropriate transcriptional promoter, or may contain many repeats flanking multiple spacer sequences, of either the same exact guide sequence or multiple distinct guide sequences. Coordinated expression of the CRISPR and the Cascade subunits, in particular the Cas6 subunit, lead to processing of long precursor crRNAs into the mature length crRNA, each one of which comprises fragments of a single repeat on the 5' and 3' ends of the crRNA, and a single spacer sequence in the middle.

An alternative strategy to express the complete Cascade complex in *E. coli* uses two plasmids: one plasmid that encodes the entire Cas8-Cse2-Cas7-Cas5-Cas6 operon on a single expression plasmid and one encoding the CRISPR crRNA. In this case, the 5' end of the Cse2 gene, which normally overlaps with the 3' end of the Cas8 gene, is separated spatially from the 3' end of the Cas8 gene, in order to append a polynucleotide sequence encoding an affinity tag and/or protease recognition sequence.

Example 2 describes two types of bacterial expression plasmid systems for the Cascade proteins: the first type comprises two plasmids, a first plasmid encoding the Cas8 protein and a second encoding the 4 subunit proteins of the CasBCDE complex (cse2-cas7-cas5-cas6 operon); and the second type comprises an expression plasmid encoding all 5 subunit proteins of the Cascade complex (cas8-cse2-cas7-cas5-cash operon). Cognate CRISPR arrays are also described.

In order to facilitate purification of Cascade complexes, an affinity tag can be appended onto the Cse2 subunit, such as an N-terminal Strep-II tag or a hexahistidine (His6) tag. Furthermore, an amino acid sequence recognized by a protease, such as TEV protease or the HRV3C protease can be inserted between the affinity tag and the native N-terminus of the Cse2 subunit, such that biochemical cleavage of the sequence with the protease after initial purification liberates the affinity tag from the final recombinant Cascade complex. The affinity tag may also be placed on other subunits, or left on the Cse2 subunit and combined with additional affinity tags on other subunits. Examples of Cascade subunit proteins comprising affinity tags are set forth in Example 1, Example 2, and Example 3.

For Type I-E Cascade systems, a strain of *E. coli* can be transformed with plasmids encoding the CRISPR crRNA as well as the Cse2-Cas7-Cas5-Cas6 genes, protein expression induced, and a Cascade complex that is lacking the Cas8 subunit can be produced. This Cascade complex typically is referred to as a Cas8-minus Cascade complex, or alternatively as a CasBCDE complex (Jore, M., et al., Nat. Struct. Mol. Biol. 18(5):529-536 (2011)). This purified complex can be biochemically combined with separately purified Cas8 to reconstitute full Cascade (Sashital, D. G., et al., Mol. Cell 46(5):606-615 (2012)).

Table 4 presents exemplary sequences of bacterial expression plasmids encoding the minimal CRISPR array, Cas8, Cse2-Cas7-Cas5-Cas6 constructs, and Cas8-Cse2-Cas7-Cas5-Cas6 constructs, containing different tags and designs. Plasmids that encode Cascade complexes and Cascade complexes from homologous Type I systems can be designed similarly as the exemplary expression plasmid sequences for the Type I-E found in *E. coli* K-12 MG1655 following the guidance of the present Specification. Table 4 additionally contains sequences of expression plasmids expressing Cas8-Cse2-Cas7-Cas5-Cas6 as well as FokI fusions to either the Cas8 gene or the Cas6 gene, for the production of nuclease-Cascade fusions for gene editing experiments.

TABLE 4

Vectors for Production of Cascade Effector Complexes

| SEQ ID NO: | Description | Effector complex species of origin | Type of sequence |
|---|---|---|---|
| SEQ ID NO: 352 | minimal CRISPR array | I-E_*Escherichia coli* K-12 MG1655 | Spacer sequence targets J3 |
| SEQ ID NO: 353 | minimal CRISPR array | I-E_*Escherichia coli* K-12 MG1655 | Spacer sequence targets CCR5.1 |
| SEQ ID NO: 354 | minimal CRISPR array (J3/L3) | I-E_*Escherichia coli* K-12 MG1655 | Dual-guide spacer sequence targets J3 and L3 |
| SEQ ID NO: 355 | minimal CRISPR array (Hsa07) | I-E_*Escherichia coli* K-12 MG1655 | Dual-guide spacer sequence targets Hsa07 |
| SEQ ID NO: 356 | His6-MBP-TEV-Cas8 | I-E_*Escherichia coli* K-12 MG1655 | Derived from genomic DNA, with appended tags |
| SEQ ID NO: 357 | StrepII-HRV3C-Cse2__Cas7__Cas5__Cas6 | I-E_*Escherichia coli* K-12 MG1655 | Derived from genomic DNA, with appended tags |
| SEQ ID NO: 358 | Cas8__His6-HRV3C-Cse2__Cas7__Cas5__Cas6 | I-E_*Escherichia coli* K-12 MG1655 | Derived from genomic DNA, with appended tags |
| SEQ ID NO: 359 | FokI-30aa-Cas8__His6-HRV3C-Cse2__Cas7__Cas5__Cas6 | I-E_*Escherichia coli* K-12 MG1655 | Derived from genomic DNA, with appended tags |
| SEQ ID NO: 360 | FokI-30aa-Cas8__His6-HRV3C-Cse2__Cas7__Cas5__NLS-Cas6 | I-E_*Escherichia coli* K-12 MG1655 | Derived from genomic DNA, with appended tags |
| SEQ ID NO: 361 | FokI-30aa-Cas8__His6-HRV3C-Cse2__Cas7-NLS__Cas5__Cas6 | I-E_*Escherichia coli* K-12 MG1655 | Derived from genomic DNA, with appended tags |
| SEQ ID NO: 362 | Cas8__His6-HRV3C-Cse2__Cas7__Cas5__Cas6-20aa-FokI | I-E_*Escherichia coli* K-12 MG1655 | Derived from genomic DNA, with appended tags |

Table 5 contains the sequences of single polypromoter bacterial expression plasmids encoding all 5 subunit proteins together with the crRNA from a single bacterial expression plasmid. In this design, each gene is separated from the other genes it flanks upstream and downstream with a transcriptional promoter and terminator. Additional sequences can be introduced that encode an affinity tag and/or protease recognition tag, as well as a fusion to a nuclease protein, in order to generate a Cascade-nuclease fusion for gene editing.

TABLE 5

Vectors for Production of Cascade Effector Complexes

| SEQ ID NO: | Description | Effector complex species of origin | Type of sequence |
|---|---|---|---|
| SEQ ID NO: 363 | Polypromoter, Cas5__Cas3__Cse2__Cas7__Cas6__Cas8__CRISPR(J3) | I-E_*Escherichia coli* K-12 MG1655 | Derived from genomic DNA, with appended tags |
| SEQ ID NO: 364 | Polypromoter, Cas5__Cas3__Cse2__Cas7__CRISPR(J3)__Cas6__Cas8 | I-E_*Escherichia coli* K-12 MG1655 | Derived from genomic DNA, with appended tags |
| SEQ ID NO: 365 | Polypromoter(EcoCO), CRISPR(J3/L3)__Cse2__Cas7__Cas5__Cas8__Cas6 | I-E_*Escherichia coli* K-12 MG1655 | *E. coli* codon-optimized DNA gene sequences |
| SEQ ID NO: 366 | Polypromoter(EcoCO), CRISPR(J3/L3)__Cse2__Cas7__Cas5__Cas8__FokI-30aa-Cas6 | I-E_*Escherichia coli* K-12 MG1655 | *E. coli* codon-optimized DNA gene sequences |
| SEQ ID NO: 367 | Polypromoter(EcoCO), CRISPR(J3/L3)__Cse2__Cas7__Cas5__Cas6__FokI-30aa-Cas8 | I-E_*Escherichia coli* K-12 MG1655 | *E. coli* codon-optimized DNA gene sequences |

Additional bacterial expression plasmids can be designed encoding homologous Cascade complexes from other Type I subtypes and other bacterial or archaeal organisms based on the design criteria herein. Such expression plasmids can be designed with genomic DNA sequences for the Cascade genes, or they can be designed with gene sequences that have been codon optimized for expression in *E. coli* or other bacterial strains.

In order to express Cascade or effectors fusions to Cascade in mammalian cells, such as human cells, eukaryotic expression plasmid vectors were designed to enable expression of the relevant proteins and RNA components by eukaryotic transcription and translation machinery. In one embodiment, Cascade can be generated in mammalian cells by encoding each of the protein components on a separate expression vector driven by a eukaryotic promoter (e.g., a cytomegalovirus (CMV) promoter), and encoding the crRNA on a separate expression vector driving by a RNA Polymerase III promoter (e.g., the human U6 promoter). The CRISPR RNA can be encoded with a minimal CRISPR array containing at least two repeats flanking one or more spacer sequences that function as the guide portion of the mature crRNA. The construct generating CRISPR RNA can be designed with additional sequences flanking the outermost repeats in the minimal array. Processing of the precursor CRISPR RNA is enabled by the RNA processing subunit of the Cascade complex (Cas6 subunit protein), which can be expressed from a separate plasmid.

Table 6 contains the sequences of individual eukaryotic expression plasmids for each protein of the *E. coli* Type I-E Cascade complex. Cas8 subunit can be fused to additional effector nuclease domains, such as the FokI nuclease (Example 1 and Example 3). Table 6 also contains the sequences of expression plasmids for the crRNA component of Cascade, encoding two separate dual-guide crRNAs, whereby three repeat sequences flank two spacer spacers. Each of the protein-coding genes can be appended to polynucleotide sequences that append nuclear localization signals (NLS), affinity tags, and linker sequences connecting those tags. Other fusions to any of the Cascade subunit proteins can be encoded by additional polynucleotide sequences that typically are appended to either the 5' or 3' coding sequence, including additional polynucleotide sequences that encode amino acid linkers connecting to the Cascade subunit protein to additional polypeptide sequences of interest. Examples of candidate fusions proteins are described herein.

TABLE 6

Vectors for Production of Cascade Effector Complexes

| SEQ ID NO: | Description | Effector complex species of origin | Type of sequence |
|---|---|---|---|
| SEQ ID NO: 368 | Cas8, HsCO | I-E_*Escherichia coli* K-12 MG1655 | Homo sapiens codon-optimized DNA gene sequence |
| SEQ ID NO: 369 | NLS-Cas8, HsCO | I-E_*Escherichia coli* K-12 MG1655 | Homo sapiens codon-optimized DNA gene sequence |
| SEQ ID NO: 370 | NLS-HA-FokI-30aa-Cas8, HsCO | I-E_*Escherichia coli* K-12 MG1655 | Homo sapiens codon-optimized DNA gene sequence |
| SEQ ID NO: 371 | NLS-Cse2, HsCO | I-E_*Escherichia coli* K-12 MG1655 | Homo sapiens codon-optimized DNA gene sequence |
| SEQ ID NO: 372 | NLS-Cas7, HsCO | I-E_*Escherichia coli* K-12 MG1655 | Homo sapiens codon-optimized DNA gene sequence |
| SEQ ID NO: 373 | Cas5, HsCO | I-E_*Escherichia coli* K-12 MG1655 | Homo sapiens codon-optimized DNA gene sequence |
| SEQ ID NO: 374 | NLS-Cas5, HsCO | I-E_*Escherichia coli* K-12 MG1655 | Homo sapiens codon-optimized DNA gene sequence |
| SEQ ID NO: 375 | Cas6, HsCO | I-E_*Escherichia coli* K-12 MG1655 | Homo sapiens codon-optimized DNA gene sequence |
| SEQ ID NO: 376 | NLS-Cas6, HsCO | I-E_*Escherichia coli* K-12MG1655 | Homo sapiens codon-optimized DNA gene sequence |
| SEQ ID NO: 377 | NLS-V5-FokI-30aa-Cas8, HsCO | I-E_*Escherichia coli* K-12 MG1655 | Homo sapiens codon-optimized DNA gene sequence |
| SEQ ID NO: 378 | Cas3-NLS, HsCO | I-E_*Escherichia coli* K-12 MG1655 | Homo sapiens codon-optimized DNA gene sequence |
| SEQ ID NO: 379 | CRISPR(Hsa07) | I-E_*Escherichia coli* K-12 MG1655 | Homo sapiens codon-optimized DNA gene sequence |

In order to express components of the Cascade complex on fewer expression vectors, polycistronic expression vectors can be constructed, whereby a single promoter (e.g., CMV promoter) drives expression of multiple coding sequence simultaneously that are separated by a *Thosea asigna* virus 2A sequence. 2A viral peptide sequences induce ribosomal skipping, thus enabling multiple protein-coding genes to be concatenated within a single polycistronic construct for expression in eukaryotic cells. Thus, polycistronic vectors can be designed that encode 4 or 5 subunits of the Cascade complex on a single transcript driven by a single promoter. Table 7 contains the sequences of eukaryotic polycistronic expression plasmids that can be combined with a CRISPR RNA expression plasmid to produce functional Cascade in mammalian cells.

TABLE 7

Vectors for Production of Cascade Effector Complexes

| SEQ ID NO: | Description | Effector complex species of origin | Type of sequence |
|---|---|---|---|
| SEQ ID NO: 380 | Polycistronic(HsCO), NLS-Cas7_NLS-Cse2_NLS-Cas5_NLS-Cas6 | I-E_*Escherichia coli* K-12 MG1655 | *Homo sapiens* codon-optimized DNA gene sequence |
| SEQ ID NO: 381 | Polycistronic(HsCO), NLS-Cas7_NLS-Cse2_NLS-Cas5_NLS-Cas6_NLS-Cas8 | I-E_*Escherichia coli* K-12 MG1655 | *Homo sapiens* codon-optimized DNA gene sequence |
| SEQ ID NO: 382 | Polycistronic(HsCO), NLS-Cas7_NLS-Cse2_NLS-Cas5_NLS-Cas6_NLS-FokI-30aa-Cas8 | I-E_*Escherichia coli* K-12 MG1655 | *Homo sapiens* codon-optimized DNA gene sequence |
| SEQ ID NO: 383 | Polycistronic(HsCO), NLS-Cas7_NLS-Cse2_NLS-Cas5_NLS-Cas6_NLS-FokI-30aa-Cas8, no epitope tags | I-E_*Escherichia coli* K-12 MG1655 | *Homo sapiens* codon-optimized DNA gene sequence |
| SEQ ID NO: 384 | Polycistronic(HsCO), NLS-Cas7_NLS-Cse2_NLS-Cas5_NLS-FokI-30aa-Cas6_NLS-Cas8, no epitope tags | I-E_*Escherichia coli* K-12 MG1655 | *Homo sapiens* codon-optimized DNA gene sequence |

In some embodiments, the CRISPR RNA is encoded within the 3' untranslated region (UTR) of a protein-coding gene, whose expression is driven by a RNA Polymerase II promoter (e.g., CMV promoter) to produce a transcript. In such embodiments, the minimal CRISPR array is designed to exist downstream of a protein coding gene such as Cash, Cas7, or a reporter gene (e.g., an enhanced green fluorescent protein, eGFP), and is separated from the protein coding sequence by a MALAT1 triplex sequence that has previously been shown to confer stability to the upstream transcript. The minimal CRISPR array is processed by the RNA processing subunit of Cascade (typically expressed using a different plasmid), an endonuclease that cleaves the minimal CRISPR array, and a break is introduced into the transcript, and the triplex sequence protects the 3' end of the upstream protein-coding gene from premature exonucleolytic degradation. Table 8 contains sequences of three polynucleotide sequences, whereby the CRISPR array is cloned downstream of either Cash, Cas7, or eGFP, and expression of the entire fusion sequence is driven by a CMV promoter.

TABLE 8

Vectors for Production of Minimal CRISPR Arrays

| SEQ ID NO: | Description | Effector complex species of origin | Type of sequence |
|---|---|---|---|
| SEQ ID NO: 385 | eGFP_MALAT1-triplex_CRISPR (Hsa07) | I-E_*Escherichia coli* K-12 MG1655 | *Homo sapiens* codon-optimized DNA gene sequence |
| SEQ ID NO: 386 | NLS-Cas7_MALAT1-triplex_CRISPR (Hsa07) | I-E_*Escherichia coli* K-12 MG1655 | *Homo sapiens* codon-optimized DNA gene sequence |
| SEQ ID NO: 387 | NLS-Cas6_MALAT1-triplex_CRISPR (Hsa07) | I-E_*Escherichia coli* K-12 MG1655 | *Homo sapiens* codon-optimized DNA gene sequence |

In some embodiments, the CRISPR RNA array is encoded on the same vector as the polycistronic construct driving expression of the 5 Cascade subunits; the combination of these two elements generates an all-in-one vector that produces all functional subunits (both protein and RNA) of the Cascade complex, together with any nuclease or effector domains fused to one of the Cascade subunits. Table 9 contains two representative sequences of these all-in-one polynucleotide sequences that encode all the respective components to produce functional FokI-Cascade RNPs in mammalian cells.

TABLE 9

Vectors for Production of Cascade Effector Complexes

| SEQ ID NO: | Description | Effector complex species of origin | Type of sequence |
|---|---|---|---|
| SEQ ID NO: 388 | hU6_CRISPR(Hsa07)_F, CMV_NLS-Cas7_NLS-Cse2_NLS-Cas5_NLS-Cas6_NLS-FokI-30aa-Cas8 | I-E_*Escherichia coli* K-12 MG1655 | *Homo sapiens* codon-optimized DNA gene sequence |
| SEQ ID NO: 389 | hU6_CRISPR(Hsa07)_R, CMV_NLS-Cas7_NLS-Cse2_NLS-Cas5_NLS-Cas6_NLS-FokI-30aa-Cas8 | I-E_*Escherichia coli* K-12 MG1655 | *Homo sapiens* codon-optimized DNA gene sequence |

Example 3 describes expression systems using separate plasmids expressing each Cascade subunit protein and minimal CRISPR array, expression systems wherein multiple Cascade subunit protein coding sequences are expressed from a single promoter, and an expression system wherein a single plasmid Cascade expression system was constructed to express the entire Cas8-Cse2-Cas7-Cas5-Cash operon and a minimal CRISPR array for use in mammalian cells.

One of ordinary skill in the art following the guidance of the present Specification can design additional mammalian expression vectors encoding other Cascade complexes analogously to the examples provided the *E. coli* Type I-E Cascade complex.

In a fourth aspect, the present invention relates to production of engineered Type I CRISPR-Cas effector complexes by introduction of plasmids encoding one or more components of the engineered Type I CRISPR-Cas effector complexes into host cells. Transformed host cells (or recombinant cells) or the progeny of cells that have been transformed or transfected using recombinant DNA techniques can comprise one or more nucleic acid sequences encoding one or more component of an engineered Type I CRISPR-Cas effector complex. Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, microprojectile bombardment, direct microinjection, and nanoparticle-mediated delivery. In one embodiment of the present invention, polynucleotides encoding components of engineered Type I CRISPR-Cas effector complexes are introduced into bacterial cells (e.g., *E. coli*).

Example 4 describes a method for introduction and expression of Cas8 protein coding sequences, as well as coding sequences for components of engineered Type I CRISPR-Cas effector complexes for bacterial production of such complexes using *E. coli* expression systems.

A variety of exemplary host cells disclosed herein can be used to produce recombinant cells using an engineered Cascade effector complex. Such host cells include, but are not limited to, a plant cell, a yeast cell, a bacterial cell, an insect cell, an algal cell, and a mammalian cell.

For ease of discussion, "transfection" is used below to refer to any method of introducing polynucleotides into a host cell.

In some embodiments, a host cell is transiently or non-transiently transfected with nucleic acid sequences encoding one or more component of a Type I CRISPR-Cas effector complex. In some embodiments, a cell is transfected as it naturally occurs in a subject. In some embodiments, a cell that is transfected is first removed from a subject, e.g., a primary cell or progenitor cell. In some embodiments, the primary cell or progenitor cell is cultured and/or is returned after ex vivo transfection to the same subject or to a different subject.

Example 9 illustrates the design and delivery of *E. coli* Type I-E Cascade complexes comprising FokI fusion proteins to facilitate genome editing in human cells. The Example describes the delivery of plasmid vectors expressing Cascade complex components into eukaryotic cells.

In a fifth aspect, the present invention relates to the purification of engineered Type I CRISPR-Cas effector complexes from cells and uses of such complexes. Engineered Type I CRISPR-Cas effector complexes are produced in a host cell. The engineered Type I CRISPR-Cas effector complexes (in this case Cascade ribonucleoprotein (RNP) complexes) are purified from cell lysates.

Example 5 describes purification of *E. coli* Type I-E Cascade RNP complexes produced by overexpression in bacteria as described in Example 4. The method uses immobilized metal affinity chromatography followed by size exclusion chromatography. The Example also describes methods that can be used to assess the quality of purified Cascade RNP products. Examples are presented illustrating the purification of Cas8, Cas7, Cas6, Cas5, and Cse2 Cascade RNP complexes, Cascade complexes comprising Cas7, Cas6, Cas5, and Cse2 proteins, and FokI-Cas8 fusion proteins.

The purified, engineered Type I CRISPR-Cas effector complexes can also be used directly in biochemical assays (e.g., binding and/or cleavage assays). Example 6 describes production of dsDNA target sequences for use in in vitro DNA binding or cleavage assays. The Example describes three methods to produce target sequences, including annealing of synthetic ssDNA oligonucleotides, PCR amplification of selected nucleic acid target sequences from genomic DNA, as well as cloning of nucleic acid target sequences into bacterial plasmids. The dsDNA target sequences were used in Cascade binding or cleavage assays.

The site-specific binding of and/or cutting by one or more engineered Type I CRISPR-Cas effector complexes can be confirmed, if necessary, using an electrophoretic mobility shift assay (see, e.g., Garner, M., et al., Nucleic Acids Research 9(13):3047-3060 (1981); Fried, M., et al., Nucleic Acids Research 9(23):6505-6525 (1981); Fried, M., Electrophoresis 10:366-376 (1989); Gagnon, K., et al., Methods Molecular Biology 703:275-2791 (2011); Fillebeen, C., et al., J. Vis. Exp. (94), e52230, doi:10.3791/52230 (2014)), or the biochemical cleavage assay described in Example 7.

The data presented in Example 7 demonstrate that engineered Type I CRISPR-Cas effector complexes can exhibited nearly quantitative DNA cleavage, as evidenced by conversion of a supercoiled, circular plasmid substrate into a cleaved, linear form.

In another embodiment, the complexes are introduced directly into a cell, as an alternative to expressing one or more nucleic acid sequences encoding one or more components of engineered Type I CRISPR-Cas effector complexes in a cell. The purified, engineered Type I CRISPR-Cas effector complexes can be directly introduced into cells. Methods to introduce the components into a cell include electroporation, lipofection, particle gun technology, and microprojectile bombardment.

Example 8 illustrates the design and delivery of E. coli Type I-E Cascade complexes comprising Cas subunit protein-FokI fusion proteins to human cells. The data in the Example demonstrate delivery of pre-assembled Cascade RNPs into target cells and effective genome editing in human cells.

In some embodiments, the engineered Type I CRISPR-Cas effector complexes described herein can be used to generate non-human transgenic organisms by site specifically introducing a selected polynucleotide sequence (e.g., a portion of a donor polynucleotide) at a DNA target locus in the genome to generate a modification of the genomic DNA. The transgenic organism can be an animal or a plant.

A transgenic animal is typically generated by introducing engineered Type I CRISPR-Cas effector complexes into a zygote cell. A basic technique, described with reference to making transgenic mice (see, e.g., Cho, A., et al., "Generation of Transgenic Mice," Current Protocols in Cell Biology, CHAPTER.Unit-19.11 (2009)) involves five basic steps: first, preparation of a system, as described herein, including a suitable donor polynucleotide; second, harvesting of donor zygotes; third, microinjection of the system into the mouse zygote; fourth, implantation of microinjected zygotes into pseudo-pregnant recipient mice; and fifth, performing genotyping and analysis of the modification of the genomic DNA established in founder mice. The founder mice will pass the genetic modification to any progeny. The founder mice are typically heterozygous for the transgene. Mating between these mice will produce mice that are homozygous for the transgene 25% of the time.

Methods for generating transgenic plants are also well known and can be applied using engineered 1 Type I CRISPR-Cas effector complexes. A generated transgenic plant, for example using *Agrobacterium*-mediated transformation, typically contains one transgene inserted into one chromosome. It is possible to produce a transgenic plant that is homozygous with respect to a transgene by sexually mating (i.e., selfing) an independent segregant transgenic plant containing a single transgene to itself. Typical zygosity assays include, but are not limited to, single nucleotide polymorphism assays and thermal amplification assays that distinguish between homozygotes and heterozygotes.

In a sixth aspect, the present invention relates to use of engineered Type I CRISPR-Cas effector complexes to create substrate channels. In some embodiments, fusion proteins comprising substrate channel elements and Cas7 subunit proteins are constructed. These Cas7 fusion proteins are then assembled into an engineered Type I CRISPR-Cas effector complex (e.g., comprising Cse2, Cas5, Cas6, Cas7-substrate channel element fusions, and Cas8). In some embodiments, the crRNA of the engineered Type I CRISPR-Cas effector complex can be extended to accommodate additional Cas7 subunits (Luo, M., et al., Nucleic Acids Research 44:7385-7394 (2016)). Different substrate elements can be fused to Cas7 and then mixed at the desired stoichiometry. When these various Cas7 subunits assemble into a complete Type I CRISPR-Cas effector complex, co-localization of substrate elements can improve the efficacy of substrate channeling.

In some embodiments, an RNA scaffold is constructed such that multiple Cas7-substrate channel element fusions can bind to it in the absence of other Type I CRISPR-Cas effector complex components.

Substrate channel elements can be fused to the N-terminus of Cas7 and/or the C-terminus of Cas7. In addition, circular permutations of Cas7 can be fused to substrate channel elements.

FIG. 12A and FIG. 12B presents illustrations of substrate channels consisting of three consecutive enzymes in a pathway. Substrate channels facilitate the passing of intermediary metabolic products directly to the active site of the consecutive enzyme in the metabolic pathway chain without release into the extra channel space. FIG. 12A illustrates a typical arrangement of an engineered substrate channel. Enzymes E1, E2, and E3 are linked covalently or non-covalently to a scaffold protein (S1, S2, S3) matrix. The substrate is then processed to the product without release to the extra channel space. FIG. 12B illustrates one embodiment of the present invention comprising a modified Type I CRISPR-Cas effector complex that carries Enzymes E1, E2, and E3 as fusion proteins to Cas7 subunit proteins, thus creating a substrate channel. cpCas7 proteins and backbones formed of cpCas7 proteins can also be useful in the practice of this aspect of the present invention.

In other embodiments, substrate channel elements can be fused to Cas6. The Cas6 subunit of Cascade complexes recognizes specific RNA hairpin structures. An RNA scaffold can be constructed that is composed of multiple Cas6 RNA hairpin structures concatenated together. Cas6 peptides from different Cascade complexes have different recognition sequences. Accordingly, RNA scaffolds can be constructed from multiple orthogonal Cas6 RNA hairpins. By fusing different substrate channel elements to orthogonal Cas6 peptides, substrate channel complexes can be assembled in specific stoichiometry.

Substrate channel elements can be fused to the N-terminus of Cas6 and/or the C-terminus of Cas6. In addition, circular permutations of Cas6 can be fused to substrate channel elements.

In some embodiments, a heterologous metabolic pathway of interest can be expressed in a model organism, such as *E. coli*. When genes are heterologously expressed, the genes can be codon optimized to express the genes more efficiently.

In one embodiment, the metabolic pathway of interest is the mevalonate pathway from *Saccharomyces cerevisiae*. Substrate channel elements of this pathway include, but are not limited to, acetoacetyl-CoA-thioase (AtoB), hydroxymethylglutaryl-CoA synthase (HMGS), and hydroxy-methylglutaryl-CoA reductase (HMGR).

In another embodiment, the metabolic pathway of interest is the glycerol synthesis pathway from *S. cerevisiae*. Substrate channel elements of this pathway include, but are not limited to, glycerol-3-phosphate dehydrogenase (GPD1) and glycerol-3-phosphate phosphatase (GPP2).

In yet another embodiment, the metabolic pathway of interest is the starch hydrolysis pathway from *Clostridium stercorarium*. Substrate channel elements of this pathway include, but are not limited to, CelY and CelZ.

In an additional embodiment, the metabolic pathway of interest is the glucose phosphotransferase pathway from *E.*

*coli*. Substrate channel elements of this pathway include, but are not limited to, trehalose-6-phosphate synthetase (TPS) and trehalose-6-phosphate phosphatase (TPP).

In a seventh aspect, the present invention relates to site-directed recruitment of functional domains fused to Cascade subunit proteins by complexes comprising a Class 2 Type II Cas9 protein and a nucleic acid-targeting nucleic acid (NATNA; see e.g., U.S. Pat. No. 9,260,752, issued 16 Feb. 2016; U.S. Pat. No. 9,580,727, issued 28 Feb. 2017; U.S. Pat. No. 9,677,090, issued 13 Jun. 2017; U.S. Pat. No. 9,771,600, issued 26 Sep. 2017; U.S. Pat. No. 9,816,093, issued 14 Nov. 2017). Functional domains are disclosed herein and include, but are not limited to, protein domains having enzymatic function, capable of transcriptional activation, or capable of transcriptional repression. Example 13 describes a method of modifying a Class 2 Type II CRISPR sgRNA, crRNA, tracrRNA, or crRNA and tracrRNA sequences with a Class 1 Type I CRISPR repeat stem sequence, allowing for the recruitment of one or more Cascade subunit proteins to a Type II CRISPR Cas protein/ guide RNA complex binding site.

FIG. 13A, FIG. 13B, and FIG. 13C present a generalized illustration of the site-directed recruitment of a functional protein domain fused to a Cascade subunit protein by a dCas9:NATNA complex to a target site. A Class 2 Type II CRISPR NATNA (FIG. 13A, 102) comprising a spacer sequence (FIG. 13A, 101) is covalently linked through a linker nucleic acid sequence (FIG. 13A, 103) to a Class 1 Type I CRISPR repeat stem sequence (FIG. 13A, 104). The Type II CRISRP NATNA covalently linked to the Type I CRISPR repeat stem sequence (FIG. 13A, 105) is capable of binding to a Type II dCas9 (FIG. 13A, 106) and a Type I Cascade subunit protein (e.g., Cas6; FIG. 13A, 107) which is fused though a linker sequence (FIG. 13A, 108) to a functional protein domain (e.g., an enzymatic domain, a transcriptional activation or repression domain; FIG. 13A, 109) to form an RNP complex. This RNP complex (FIG. 13B, 110) is capable of targeting a double-stranded DNA (FIG. 13B, 111) comprising a target sequence (FIG. 13B, 112) complementary to the Type II CRISPR NATNA spacer sequence (FIG. 13A, 101). Target recognition by the RNP complex results in hybridization (FIG. 13B, 113) between the spacer sequence (FIG. 13A, 101) and the target sequence (FIG. 13B, 112). Localization of the Cascade subunit-functional domain fusion protein to the DNA allows for modification of the DNA by the functional protein domain or transcriptional regulation of an adjacent gene (FIG. 13C, 114).

In an eighth aspect, the present invention relates to compositions comprising engineered Type I CRISPR-Cas effector complexes, modified guide polynucleotides, and combinations thereof. In some embodiments, the engineered Type I CRISPR-Cas effector complex comprises an associated Cas3 fusion protein.

An embodiment of this aspect of the present invention relates to a composition comprising two engineered Type I CRISPR-Cas effector complexes each comprising a spacer and a fusion protein comprising a Cas subunit and an endonuclease (e.g., a FokI; see e.g., the Cascade complexes of FIG. 2A, FIG. 2B, and FIG. 2C), wherein at least two parameters are varied to modulate genome editing efficiency. Such parameters include:

the length of a linker polypeptide used to produce the fusion protein comprising a Cas subunit protein and the endonuclease (e.g., FokI); and the length of the interspacer distance between the nucleic acid target sequences to which the spacers are capable of binding.

Guidance is provided herein regarding the amino acid composition and sequence linker polypeptides.

One embodiment of this aspect of the present invention is a composition comprising:

a first engineered Type I CRISPR-Cas effector complex comprising, a first Cse2 subunit protein, a first Cas5 subunit protein, a first Cas6 subunit protein, and a first Cas7 subunit protein, a first fusion protein comprising a first Cas8 subunit protein and a first FokI, wherein the N-terminus of the first Cas8 subunit protein or the C-terminus of the first Cas8 subunit protein is covalently connected by a first linker polypeptide to the C-terminus or N-terminus, respectively, of the first FokI, and wherein the first linker polypeptide has a length of between 10 amino acids to 40 amino acids, and a first guide polynucleotide comprising a first spacer capable of binding a first nucleic acid target sequence; and a second engineered Type I CRISPR-Cas effector complex comprising, a second Cse2 subunit protein, a second Cas5 subunit protein, a second Cas6 subunit protein, and a second Cas7 subunit protein, a second fusion protein comprising a second Cas8 subunit protein and a second FokI, wherein the N-terminus of the second Cas8 subunit protein or the C-terminus of the second Cas8 protein is covalently connected by a second linker polypeptide to the C-terminus or N-terminus, respectively, of the second FokI, and wherein the second linker polypeptide has a length of between 10 amino acids to 40 amino acids, and a second guide polynucleotide comprising a second spacer capable of binding a second nucleic acid target sequence, wherein a protospacer adjacent motif (PAM) of the second nucleic acid target sequence and a PAM of the first nucleic acid target sequence have an interspacer distance between 20 bp 42 bp.

Examples of such a first engineered Type I CRISPR-Cas effector complex bound to a first nucleic acid target sequence and a second engineered Type I CRISPR-Cas effector complex bound to a second nucleic acid target sequence are illustrated in FIG. 2A, FIG. 2B, and FIG. 2C.

In some embodiments, the length of the first linker polypeptide and/or the second linker polypeptide is a length of between about 15 amino acids and about 30 amino acids, or between about 17 amino acids and about 20 amino acids. In one embodiment, the length of the first linker polypeptide and the second linker polypeptide are the same.

The first Cas8 subunit protein and the second Cas8 subunit protein can each comprise identical amino acid sequences of the Cas8 subunit protein.

Similarly, the first Cse2 subunit protein and the second Cse2 subunit protein can each comprise identical amino acid sequences of the Cse2 subunit protein, the first Cas5 subunit protein and the second Cas5 subunit protein can each comprise identical amino acid sequences of the Cas5 subunit protein, the first Cas6 subunit protein and the second Cas6 subunit protein can each comprise identical amino acid sequences of the Cas6 subunit protein, the first Cas7 subunit protein and the second Cas7 subunit protein can each comprise identical amino acid sequences of the Cas7 subunit protein, and combinations thereof.

Typically, the N-terminus of the first Cas8 subunit protein is covalently connected by the first linker polypeptide to the C-terminus of the first FokI, the C-terminus of the first Cas8 subunit protein is covalently connected by a first linker polypeptide to the N-terminus of the first FokI, the N-terminus of the second Cas8 subunit protein is covalently connected by the second linker polypeptide to the C-terminus of the second FokI, the C-terminus of the second Cas8 subunit protein is covalently connected by a second linker polypeptide to the N-terminus of the second FokI, and combinations thereof.

Embodiments of this aspect of the present invention include embodiments wherein the length between the second nucleic acid target sequence and the first nucleic acid target sequence is an interspacer distance between about 22 bp to about 40 bp, between about 26 bp to about 36 bp, between about 29 bp to about 35 bp, or between about 30 bp to about 34 bp.

The first FokI and the second FokI can be monomeric subunits that are capable of associating to form a homodimer, or distinct subunits that are capable of associating to form a heterodimer.

In a preferred embodiment, the guide polynucleotides comprise RNA.

In some embodiments, genomic DNA comprises the PAM of the second nucleic acid target sequence and the PAM of the first nucleic acid target sequence.

In some embodiments, the engineered Type I CRISPR-Cas effector complexes are based on Type I CRISPR-Cas effector complexes of one or more organisms selected from the group consisting of *Salmonella enterica, Geothermobacter* sp. EPR-M, *Methanocella arvoryzae* MRE50, *Streptococcus thermophilus* (strain ND07)), *S. thermophilus, Pseudomonas* sp. S-6-2 and *E. coli*. In preferred embodiments, the engineered Type I CRISPR-Cas effector complexes are based on Type I CRISPR-Cas effector complexes of *S. thermophilus, Pseudomonas* sp. S-6-2, and/or *E. coli*.

The data presented in Example 18 and Example 20 demonstrate that varying the length of the linker polypeptide used to produce the fusion protein comprising the Cas subunit protein and the FokI and/or varying the length of the interspacer distance between the nucleic acid target sequences to which the spacers are capable of binding facilitate modulation of genome editing efficiency in cells.

Figure 14A:
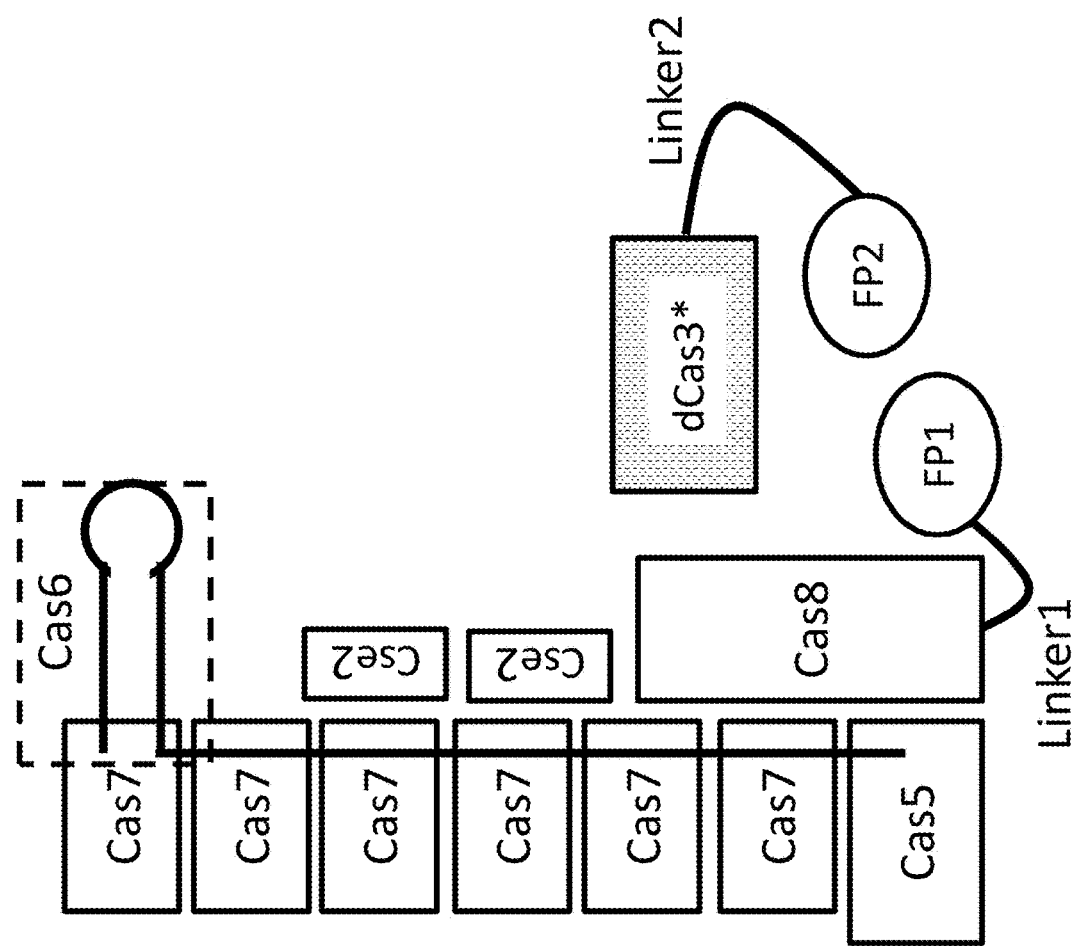
Figures 15A, 15B, 15C:
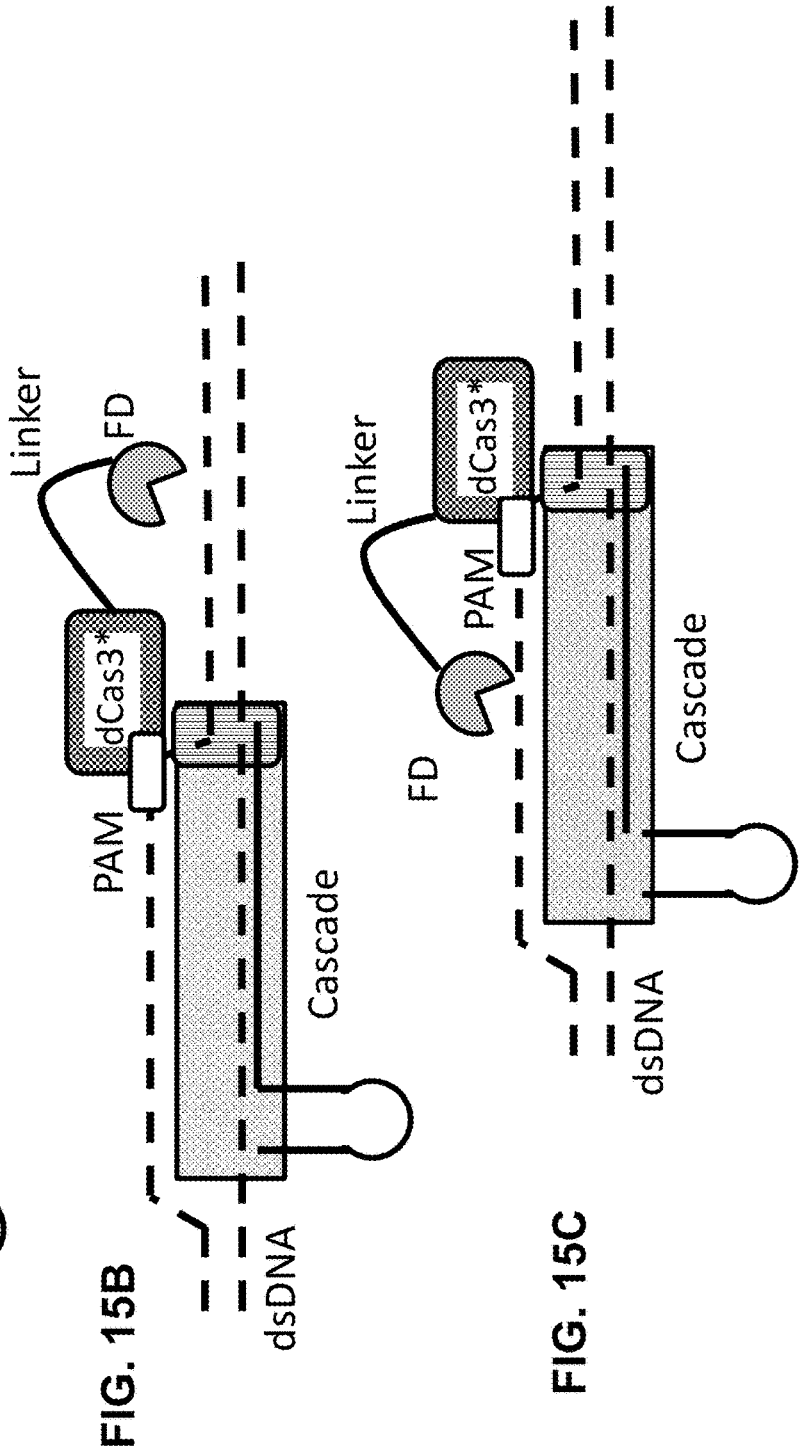

In yet another embodiment, the present invention relates to an engineered Type I CRISPR-Cas effector complex comprising a first fusion protein that comprises a Cascade subunit protein (e.g., a Cas8 subunit protein) and a first functional domain (e.g., FokI), and a second fusion protein that comprises a dCas3* protein and a second functional domain (e.g., FokI). The engineered Type I CRISPR-Cas effector complex comprising the first functional domain (e.g., FokI) (FIG. 14A, Cas8-linker1-FP1 fusion) can bind DNA and can then recruit the dCas3*-second functional domain (e.g., FokI) fusion protein (FIG. 14A, dCas3*-linker2-FP2). In the case where the first functional domain (FIG. 14A, Cas8-linker1-FP1 fusion) and the second functional domain (FIG. 14A, dCas3*-linker2-FP2) comprise subunits of a dimeric protein, the dCas3*-second functional domain (e.g., FokI) fusion protein binds the engineered Type I CRISPR-Cas effector complex comprising the first functional domain (e.g., FokI) facilitating dimerization of the first functional domain and the second functional domain (FIG. 14A). FIG. 15A illustrates the binding to dsDNA of an engineered Type I CRISPR-Cas effector complex (FIG. 15A, Cascade) comprising the first functional domain (FIG. 15A, FD1) connected to a Cas subunit protein (FIG. 15A, striped box) via a linker polypeptide (FIG. 15A, Linker 1) and a dCas3* connected to a second functional domain (FIG. 15A, FD2) via a linker polypeptide (FIG. 15A, Linker 2) associated with the Cascade complex; thus bringing FD1 and FD2 into proximity and facilitating the interaction of FD1 and FD2. Binding of the Cascade complex involves a single PAM sequence (FIG. 15A, PAM, open box). In the case of the functional domain being a dimeric endonuclease (e.g., FokI), the proximity of FD1 and FD2 facilitates formation of a functional dimer.

One advantage of this embodiment of the present invention is a single Cascade complex (recognizing a single PAM sequence) can be used to cleave a double-stranded nucleic acid target sequence, versus using two FokI-Cascade complexes (FIG. 15A compare FIG. 2A, FIG. 2B, and FIG. 2C). Using two FokI-Cascade complexes requires two PAM sequences in the proper orientation (FIG. 2A, FIG. 2B, and FIG. 2C), which can limit selection of proximal nucleic acid target sequences.

The length and/or composition of the linker polypeptide used to produce the fusion protein comprising a Cas subunit protein and an endonuclease (e.g., FokI), as well as the length and/or composition of the linker polypeptide used to produce the fusion protein comprising a dCas3*protein and an endonuclease can be varied to modulate genome editing efficiency. Example 21 describes the design and testing of multiple Cas3-FokI linker compositions and lengths and FokI-Cas8 linker compositions and lengths for modulation of genome editing efficiency.

Figure 14B:
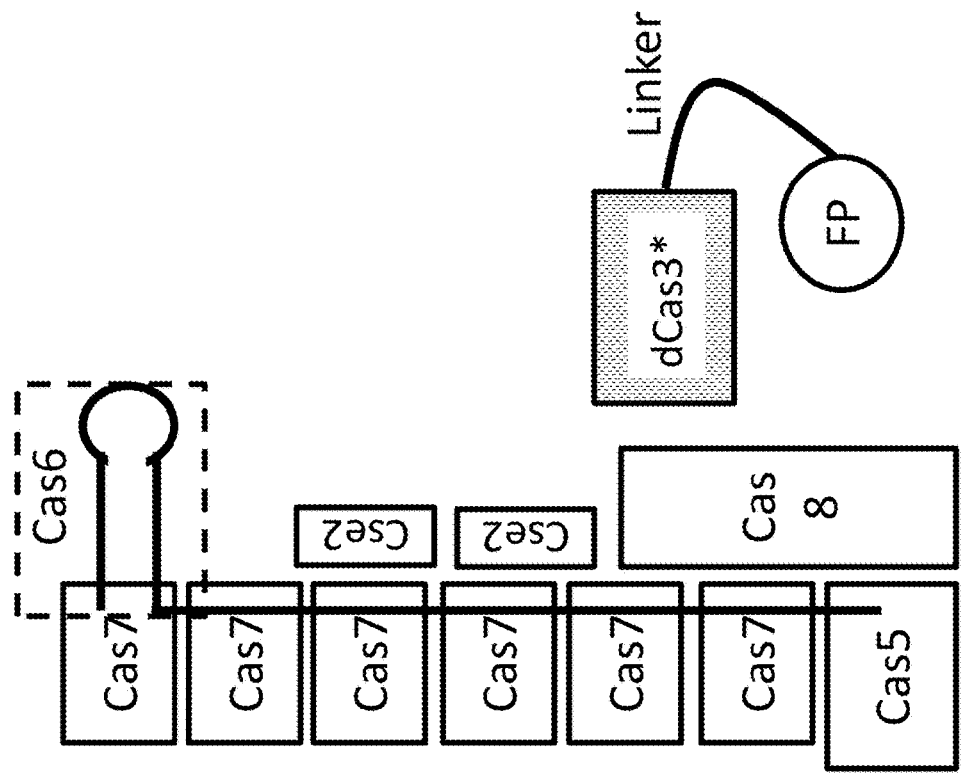
FIG. 14A, FIG. 14B, FIG. 15A, FIG. 15B, and FIG. 15C illustrate examples of engineered Type I CRISPR-Cas effector complexes of the present invention.

Another embodiment of this aspect of the invention comprises an engineered Type I CRISPR-Cas effector complex and a fusion protein comprising a dCas3*protein and a functional domain (e.g., cytidine deaminase) connected by a linker polypeptide (FIG. 14B, dCas3*, Linker, and FP). The engineered Type I CRISPR-Cas effector complex can bind DNA and recruit the dCas3*-functional domain (e.g., cytidine deaminase) fusion protein. This embodiment can facilitate site-specific targeting of a nucleic acid target sequence for modification by, or interaction with, a functional domain. In the case of cytidine deaminase, an engineered Type I CRISPR-Cas effector complex and a fusion protein that comprises a dCas3* protein and cytidine deaminase can be used for site-specific base editing in a nucleic acid target sequence. FIG. 15B illustrates an example of an engineered Type I CRISPR-Cas effector complex (FIG. 15B, Cascade) comprising a fusion protein comprising a dCas3* protein (FIG. 15B, dCas3*) connected with a functional domain (FIG. 15B, FD) via a linker polypeptide (FIG. 15B, Linker), wherein the complex is bound to dsDNA. In FIG. 15B, contact of the functional domain with dsDNA is facilitated. FIG. 15C illustrates another example of an engineered Type I CRISPR-Cas effector complex (FIG. 15C, Cascade) comprising a fusion protein comprising a dCas3* protein (FIG. 15C, dCas3*) connected with a functional domain (FIG. 15C, FD) via a linker polypeptide (FIG. 15C, Linker), wherein the complex is bound to dsDNA. In FIG. 15C, contact of the functional domain with ssDNA is facilitated.

Some embodiments of the invention can use an engineered Type I CRISPR-Cas effector complex and mutant form of Cas3 lacking ATPase and/or helicase activity (e.g., the Cas3 can be a nickase). The engineered Type I CRISPR-Cas effector complexes can bind DNA and then recruit the ATPase or helicase mutant form of Cas3. This embodiment can facilitate site-specific cleavage of genomic DNA by a mutant form of Cas3.

Additional functional domains and proteins that can be used to construct fusion proteins with Type I CRISPR-Cas subunit proteins are described in the present Specification and Examples. Linker polypeptide compositions and lengths for Cas3-linker polypeptide-functional domain fusion proteins can be evaluated following the guidance of Example 21 and the present Specification to evaluate effects on the performance of the functional domain.

In a ninth aspect, the present invention relates to methods of using engineered Type I CRISPR-Cas effector complexes.

In one embodiment, the present invention includes a method of binding a nucleic acid target sequence in a polynucleotide (e.g., dsDNA) comprising providing one or more engineered Type I CRISPR-Cas effector complexes for introduction into a cell or a biochemical reaction and introducing the engineered Type I CRISPR-Cas effector complex(es) into the cell or biochemical reaction, thereby facilitating contact of the engineered Type I CRISPR-Cas effector complex(es) with the polynucleotide. In one embodiment, a first engineered Type I CRISPR-Cas effector complex comprises a guide complementary to a first nucleic acid target sequence in the polynucleotide and a second engineered Type I CRISPR-Cas effector complex comprises a guide complementary to a second nucleic acid target sequence in the polynucleotide. In another embodiment, an engineered Type I CRISPR-Cas effector complex comprises a guide complementary to a nucleic acid target sequence in the polynucleotide and further comprises a dCas3*fusion protein capable of associating with the complex. Contact of the complex(es) with the polynucleotide results in binding of the engineered Type I CRISPR-Cas effector complex(es) to the nucleic acid target sequence(s) in the polynucleotide. In one embodiment, a first engineered 1 Type I CRISPR-Cas effector complex binds to a first nucleic acid target sequence and a second engineered Type I CRISPR-Cas effector complex binds to a second nucleic acid target sequence in the polynucleotide. In another embodiment, an engineered Type I CRISPR-Cas effector complex binds to a nucleic acid target sequence in the polynucleotide, and the effector complex comprises a dCas3*fusion protein associated with the complex.

Such methods of binding a nucleic acid target sequence can be carried out in vitro (e.g., in a biochemical reaction or in cultured cells; in some embodiments, the cultured cells are human cultured cells that remain in culture and are not introduced into a human); in vivo (e.g., in cells of a living organism, with the proviso that, in some embodiments, the organism is a non-human organism); or ex vivo (e.g., cells removed from a subject, with the proviso that, in some embodiments, the subject is a non-human subject).

A variety of methods are known in the art to evaluate and/or quantitate interactions between nucleic acid sequences and polypeptides including, but not limited to, the following: immunoprecipitation (ChIP) assays, DNA electrophoretic mobility shift assays (EMSA), DNA pull-down assays, and microplate capture and detection assays. Commercial kits, materials, and reagents are available to practice many of these methods and, for example, can be obtained from the following suppliers: Thermo Scientific (Wilmington, Del.), Signosis (Santa Clara, Calif.), Bio-Rad (Hercules, Calif.), and Promega (Madison, Wis.). A common approach to detect interactions between a polypeptide and a nucleic acid sequence is EMSA (see, e.g., Hellman L. M., et al., Nature Protocols 2(8):1849-1861 (2007)).

Figure 16A:
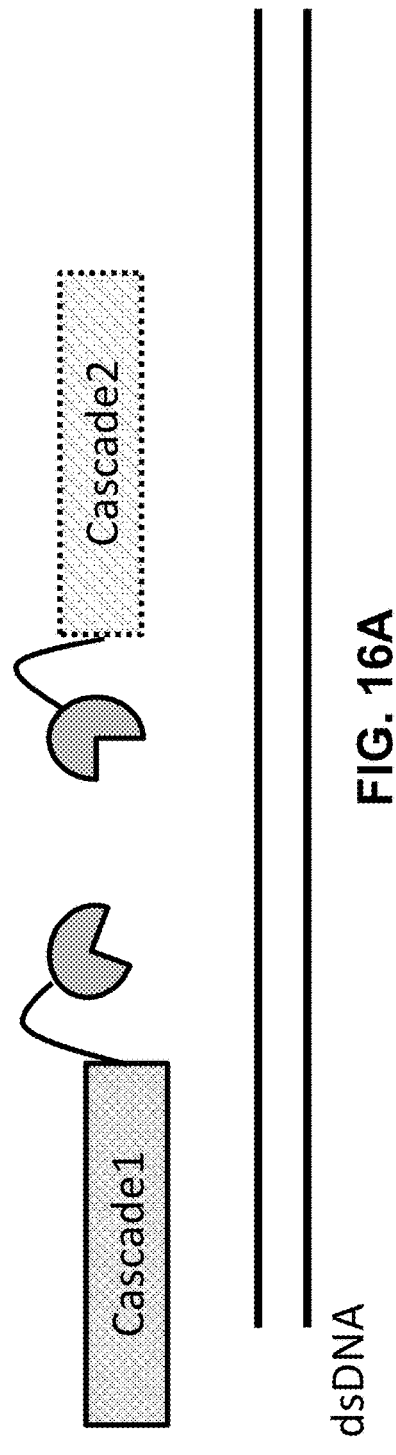
Figure 16B:
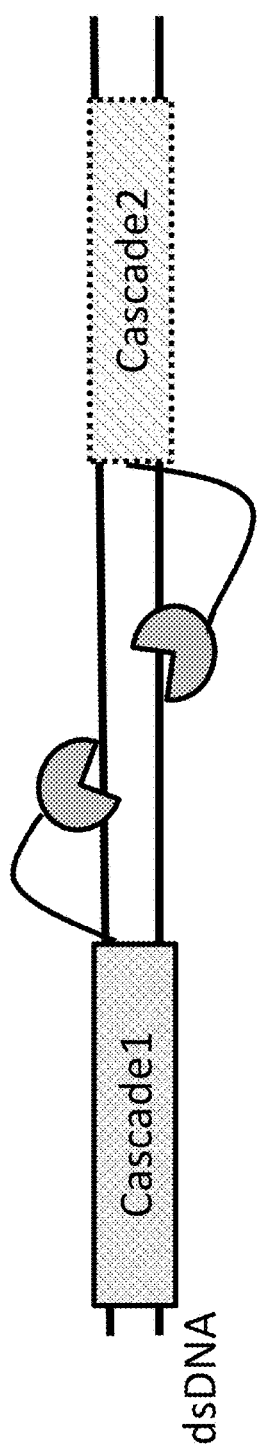
Figure 16C:
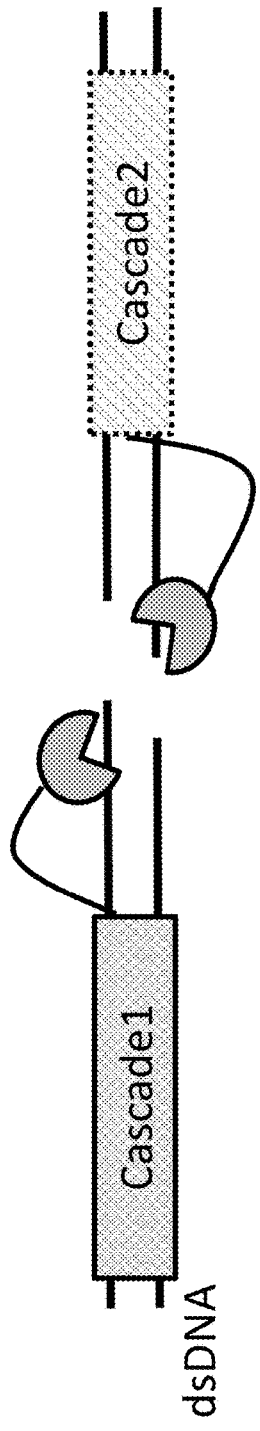

In another embodiment, the present invention includes a method of cutting a nucleic acid target sequence in a polynucleotide (e.g., a single-strand cut in dsDNA or double-strand cut in dsDNA) comprising providing one or more engineered Type I CRISPR-Cas effector complexes for introduction into a cell or biochemical reaction, and introducing the engineered Type I CRISPR-Cas effector complex(es) into the cell or biochemical reaction, thereby facilitating contact of the engineered Type I CRISPR-Cas effector complex(es) with the polynucleotide. In one embodiment, a first engineered Type I CRISPR-Cas effector complex comprising a guide complementary to a first nucleic acid target sequence in the polynucleotide and a first nuclease domain (e.g., FokI) (FIG. 16A, Cascade1), and a second engineered Type I CRISPR-Cas effector complex comprising a guide complementary to a second nucleic acid target sequence in the polynucleotide and a second nuclease domain (e.g., FokI) (FIG. 16A, Cascade 2) are introduced into the cell or biochemical reaction. In another embodiment, an engineered Type I CRISPR-Cas effector complex comprising a guide complementary to a nucleic acid target sequence in the polynucleotide and a first nuclease domain (e.g., FokI) (FIG. 17A, Cascade), and a dCas3*-second nuclease domain (e.g., FokI) fusion protein (FIG. 17A, dCas3) capable of associating with the complex are introduced into the cell or biochemical reaction. The contacting results in cutting of the nucleic acid target sequence(s) in the polynucleotide (e.g., a dsDNA) by the engineered Type I CRISPR-Cas effector complex(es). In one embodiment, the first engineered 1 Type I CRISPR-Cas effector complex binds to the first nucleic acid target sequence in dsDNA (FIG. 16B, Cascade1) and cleaves the first strand of a dsDNA (FIG. 16C, Cascade1), and the second engineered Type I CRISPR-Cas effector complex binds to the second nucleic acid target sequence in dsDNA (FIG. 16B, Cascade2) and cleaves the second strand of a dsDNA (FIG. 16C, Cascade2). In another embodiment, the engineered Type I CRISPR-Cas effector complex binds to a nucleic acid target sequence in dsDNA (FIG. 17B, Cascade) and cleaves the first strand of a dsDNA (FIG. 17C, Cascade), and the dCas3*fusion protein associates with the complex (FIG. 17B, dCas3*) and cleaves the second strand of the dsDNA (FIG. 17C, dCas3*).

In an additional embodiment of the method of cutting a nucleic acid target sequence in a polynucleotide, a donor polynucleotide can also be introduced into a cell to facilitate incorporation of at least a portion of the donor polynucleotide into genomic DNA of the cell. FIG. 18A illustrates an example of both strands of a dsDNA being cleaved by a first engineered Type I CRISPR-Cas effector complex comprising a guide complementary to a first nucleic acid target sequence in the polynucleotide and a first nuclease domain (e.g., FokI) (FIG. 18A, Cascade1), and a second engineered Type I CRISPR-Cas effector complex comprising a guide complementary to a second nucleic acid target sequence in the polynucleotide and a second nuclease domain (e.g., FokI) (FIG. 18A, Cascade 2). FIG. 18B illustrates a donor polynucleotide comprising homology arms complementary to DNA sequences adjacent the double-strand cut site (FIG. 18B, Donor, dashed lines). FIG. 18C illustrates incorporation of a portion of the donor polynucleotide (FIG. 18C dashed lines) at the double-strand cut site. Incorporation of the donor polynucleotide is mediated by cellular DNA repair mechanisms (e.g., homology-directed repair).

In other embodiments, an engineered Type I CRISPR-Cas effector complex comprising a guide complementary to a first nucleic acid target sequence in a polynucleotide and a first nuclease domain can be paired with a second component comprising a second nuclease domain, wherein the second component is capable of binding to a second nucleic acid target sequence in the polynucleotide. Examples of such second components include, a transcription activator-like effector nuclease (TALEN) comprising the second nuclease domain, a zinc finger comprising the second nuclease domain, or a dCas9/NATNA complex comprising the second nuclease domain.

In some embodiments, the nucleic acid target sequence is dsDNA (e.g., genomic) DNA. In some embodiments, the nucleic acid target sequence is double-stranded and one or both of the strands is cut. Such methods of cutting a nucleic acid target sequence can be carried out in vitro, in vivo, or ex vivo.

Figures 19A, 19B, 19C, 19D:
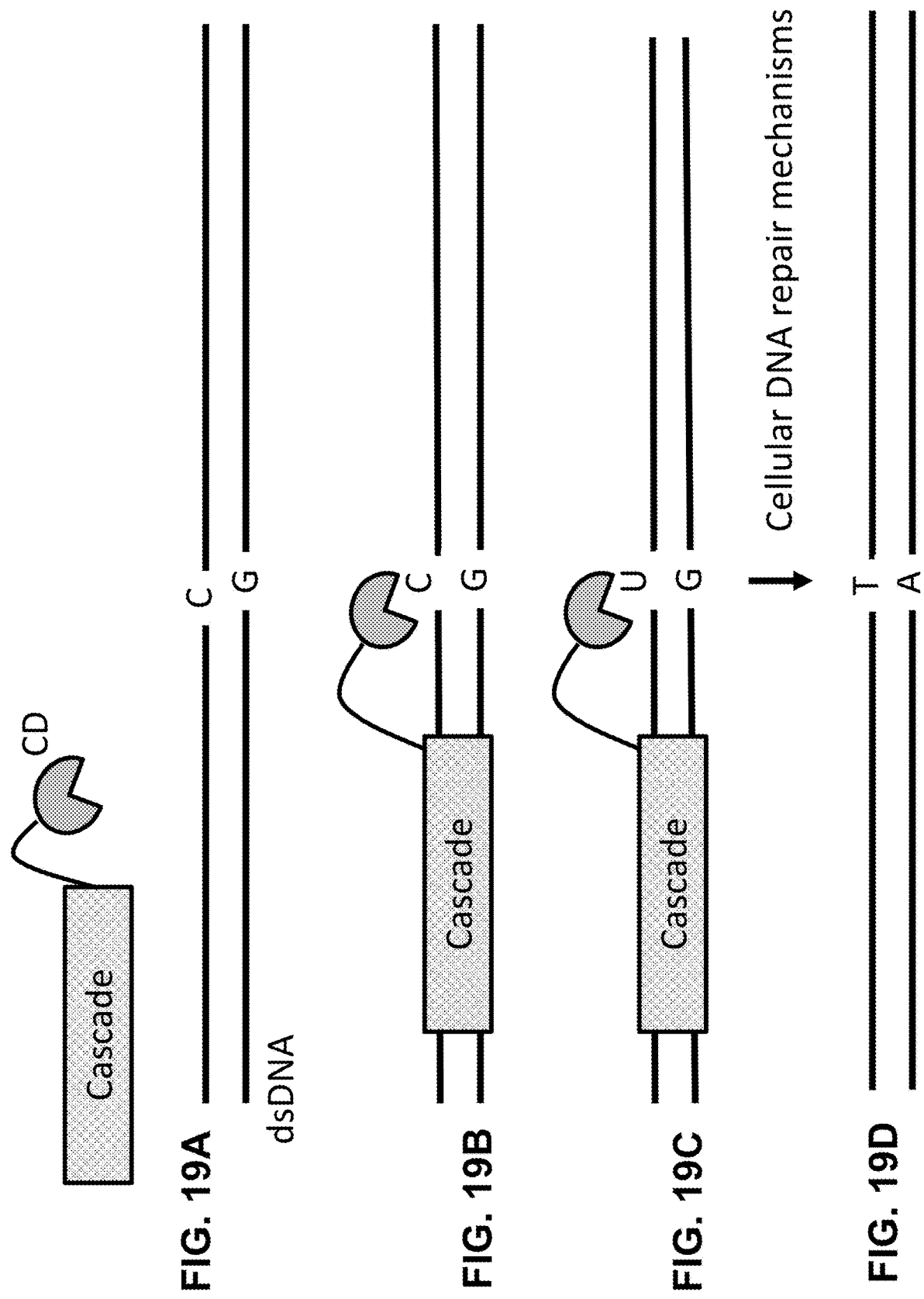

In yet another embodiment, the present invention includes a method of modifying one or more nucleic acid target sequences in a polynucleotide (e.g., DNA) in a cell or biochemical reaction comprising providing one or more engineered Type I CRISPR-Cas effector complexes (e.g., comprising a Cas subunit protein-cytidine deaminase fusion protein) for introduction into the cell or the biochemical reaction, and introducing the engineered Type I CRISPR-Cas effector complex(es) into the cell or biochemical reaction, thereby facilitating contact of the engineered Type I CRISPR-Cas effector complex(es) with the polynucleotide resulting in binding of the engineered Type I CRISPR-Cas effector complex(es) to the nucleic acid target sequence(s) in the polynucleotide that facilitates modification of the nucleic acid target sequence(s) (e.g., C-to-T, G-to-A, A-to-G, and T-to-C). FIG. 19A to FIG. 19D illustrate an example of using a Cascade complex comprising a Cas subunit protein-linker polypeptide-cytidine deaminase fusion protein (Cascade/CD complex) to modify a target nucleotide in genomic DNA of a cell. The Cascade/CD complex (FIG. 19A) is introduced into the cell. The Cascade/CD complex comprises a guide complementary to a DNA target sequence adjacent a target cytosine (FIG. 19B, FIG. 19C). The Cascade/CD complex binds the DNA target sequence (FIG. 19B) and the cytidine deaminase converts the cytosine to a uracil (FIG. 19C). Cellular repair mechanisms can then repair the uracil to a thymidine, and change the mismatched guanidine to adenine (FIG. 19D).

In yet another embodiment, the present invention includes methods of modulating in vitro or in vivo transcription, for example, transcription of a gene comprising regulatory element sequences. Such methods comprise providing one or more engineered Type I CRISPR-Cas effector complexes (e.g., comprising a Cas subunit protein-transcription factor fusion protein) for introduction into the cell or the biochemical reaction, and introducing the engineered Type I CRISPR-Cas effector complex(es) into the cell or biochemical reaction, thereby facilitating contact of the engineered Type I CRISPR-Cas effector complex(es) with the regulatory element sequences resulting in binding of the engineered Type I CRISPR-Cas effector complex(es) to the regulatory element sequences thereby facilitating modulating in vitro or in vivo transcription of the gene comprising the regulatory element sequences.

Figure 20B:
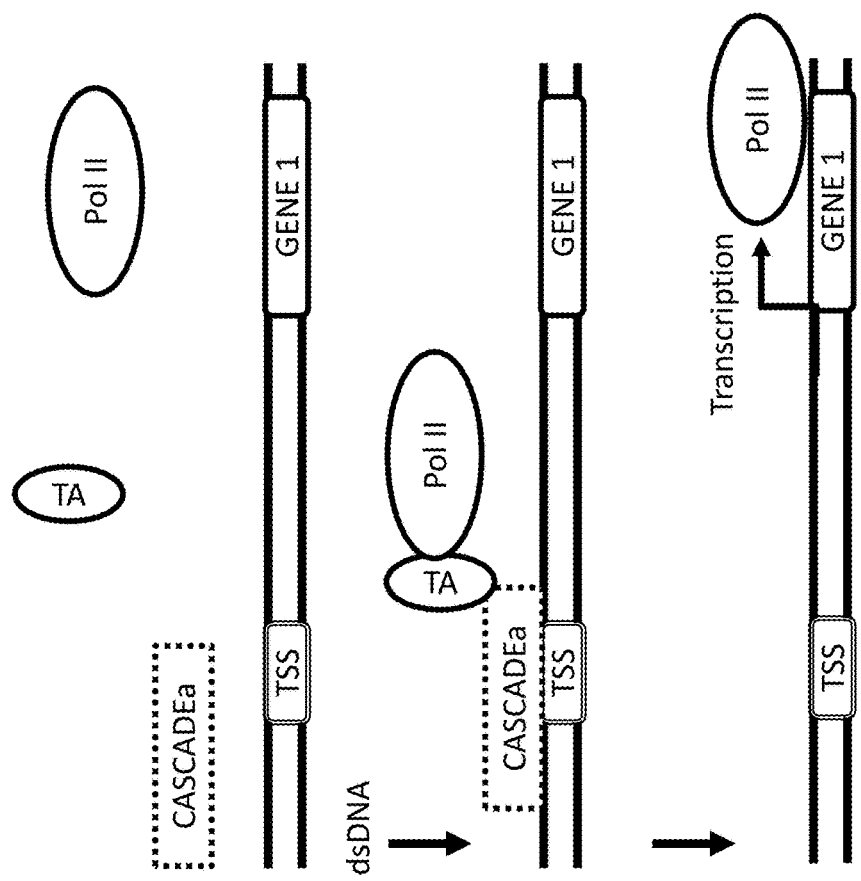
Figure 20A:
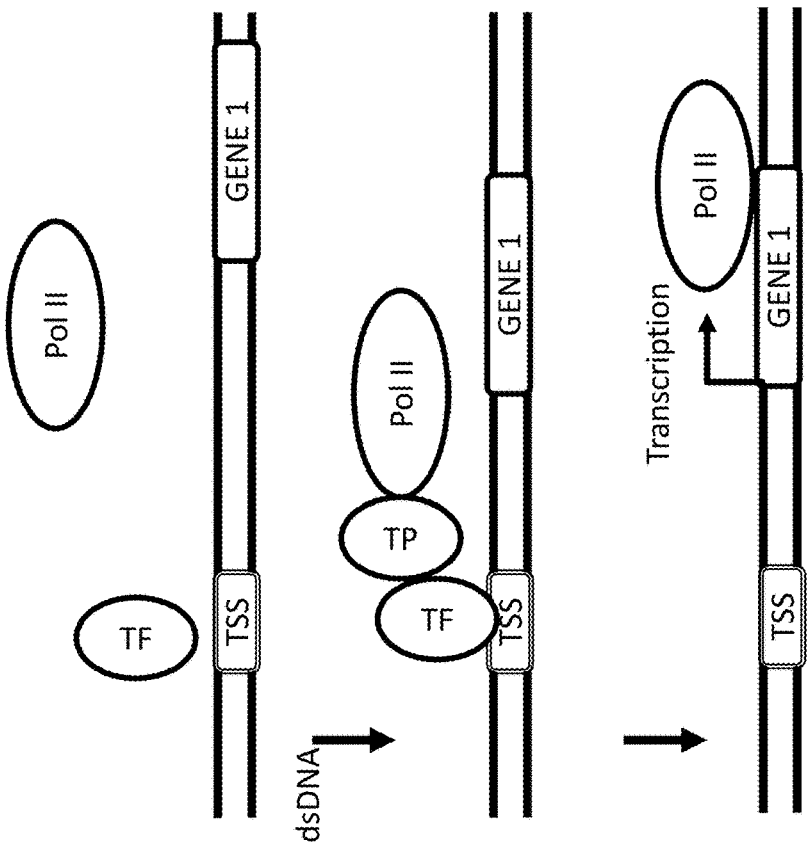

FIG. 20A and FIG. 20B present general illustrations of examples for the transcriptional activation of a generic gene ("GENE1"). FIG. 20A provides an overview of transcriptional regulation of an endogenous gene in a eukaryotic cell. In FIG. 20A, the two dark parallel lines represent double-stranded DNA, the location of Gene 1 (FIG. 20A, GENE 1) is indicated, as well as the transcriptional start site (FIG. 20A, TSS) associated with Gene 1. In the first panel of FIG. 20A, a transcription factor (FIG. 20A, TF) that is needed for the transcriptional activation of Gene 1 and polymerase II (FIG. 20A, Pol II) are illustrated as not yet associated with Gene1-TSS. The second panel illustrates association of the TF with its cognate TSS. The TF then recruits a transcription activation protein (TP) that then recruits RNA Polymerase II (Pol II). Typically, in eukaryotes the TF factor and the TP form a complex comprising multiple proteins and possibly other molecules. The third panel illustrates the resulting transcription of Gene 1 by Pol II. This type of transcriptional activation is typically dependent on TF(s) that are specific to the expression of a gene(s). FIG. 20B presents an illustration of one embodiment of the present invention, wherein a Cascade complex is modified with a protein or factor (FIG. 20B, CASCADEa) that attracts one or more components in the cells responsible for transcriptional activation (Transcriptional Activation factor; FIG. 20B, TA). An example of one such protein or factor is the protein vp64. CASCADEa comprises a guide that is capable of binding at or near the TSS (FIG. 20B, TSS). In FIG. 20B, the two dark parallel lines represent double-stranded DNA, the location of Gene 1 (FIG. 20B, GENE 1) is indicated, as well as the transcriptional start site (TSS) associated with Gene 1. In the first panel of FIG. 20B, CASCADEa and polymerase II (FIG. 20B, Pol II) are illustrated as not yet associated with Gene1-TSS. The second panel illustrates association of CASCADEa with its target, the TSS. The CASCADEa then recruits a transcription activation protein (FIG. 20B, TA) that then recruits RNA Polymerase II (FIG. 20B, Pol II). The third panel illustrates the resulting transcription of Gene 1 by Pol II. One advantage of this embodiment of the present invention is that transcriptional activation of a gene is not dependent on endogenous transcription factors that bind to the TSS of the gene, rather the TSS of a gene can be targeted by selection of an appropriate Cascade guide.

FIG. 21A and FIG. 21B present a general illustration of an example for the transcriptional repression of a generic gene (FIG. 21 A, GENE 1) using a Cascade complex comprising a Cas subunit protein-KRAB domain fusion and a guide (FIG. 21A, CASCADEi) complementary to regulatory sequences (FIG. 21A, promoter) associated with GENE 1. Binding of CASCADEi to the regulatory sequences (FIG. 21B) results in transcriptional repression of GENE 1.

In yet another aspect, the present invention relates to using Type I CRISPR systems and Cas3 to delete nucleic acid target sequences in a 3' to 5' manner. This method can be used to make long range deletions of a specific length and can be useful for creation of gene knockouts.

Figures 22A, 22B, 22C, 22D:
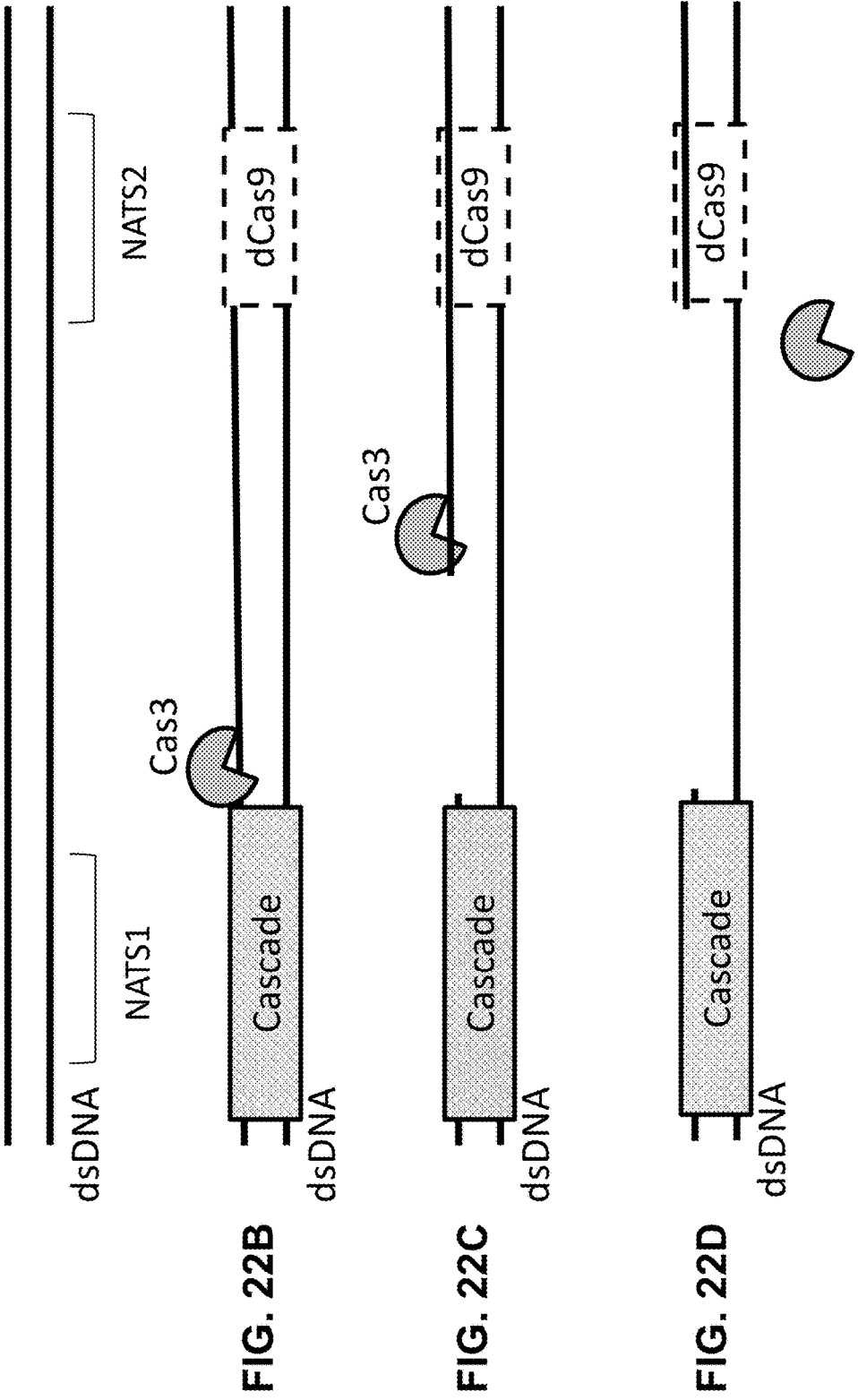
FIG. 22A, FIG. 22B, FIG. 22C, FIG. 22D, FIG. 23A, FIG. 23B, FIG. 23C, and FIG. 23D illustrate embodiments of the present invention that use a Cas3 protein comprising active endonuclease activity.

In one embodiment, a region of a target polynucleotide (e.g., genomic DNA) can be deleted using a combination of a Cascade complex comprising a guide complementary to a first nucleic acid target sequence in the target polynucleotide and a dCas9/NATNA complex wherein the NATNA comprises a spacer sequence complementary to a second nucleic acid target sequence in the target polynucleotide. The first and second nucleic acid target sequences are selected to flank the nucleic acid target sequence targeted for deletion. A Cas3 protein comprising an active endonuclease activity associates with the Cascade complex and then progressively deletes a single strand of the dsDNA comprising the nucleic acid target sequence targeted for deletion. When the Cas3 protein collides with the dCas9/NATNA complex, the Cas3 nuclease activity can be stopped at the second nucleic acid target sequence by the dCas9/NATNA complex. FIG. 22A to FIG. 22D illustrate an example of a Cas3 deletion of a nucleic acid target sequence. FIG. 22A shows a dsDNA comprising nucleic acid target sequence 1 (FIG. 22A, NATS1) and nucleic acid target sequence 2 (FIG. 22A, NATS2) that flank the nucleic acid target sequence targeted for deletion. FIG. 22A shows the Cascade complex comprising a guide complementary to NATS1 (FIG. 22A, Cascade), the Cas3 protein (FIG. 22A, Cas3), and the dCas9/NATNA complex comprising a spacer complementary to NATS2 (FIG. 22A, dCas9). FIG. 22B shows binding of the Cascade complex to NATS1, association of the Cas3 protein with the Cascade complex, and binding of the dCas9/

NATNA complex to NATS2. FIG. 22C illustrates the progressive deletion by Cas3 of a single strand of the nucleic acid target sequence targeted for deletion. FIG. 22D shows the dissociation of the Cas3 protein from the dsDNA at the position of the dCas9/NATNA complex bound to NATS2.

Figure 23A:
Figure 23B:
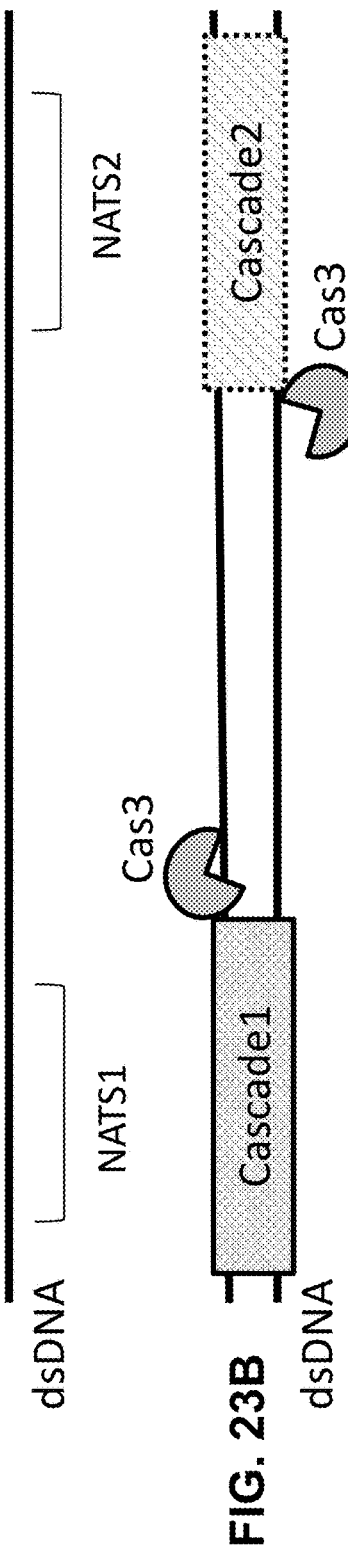
Figure 23C:
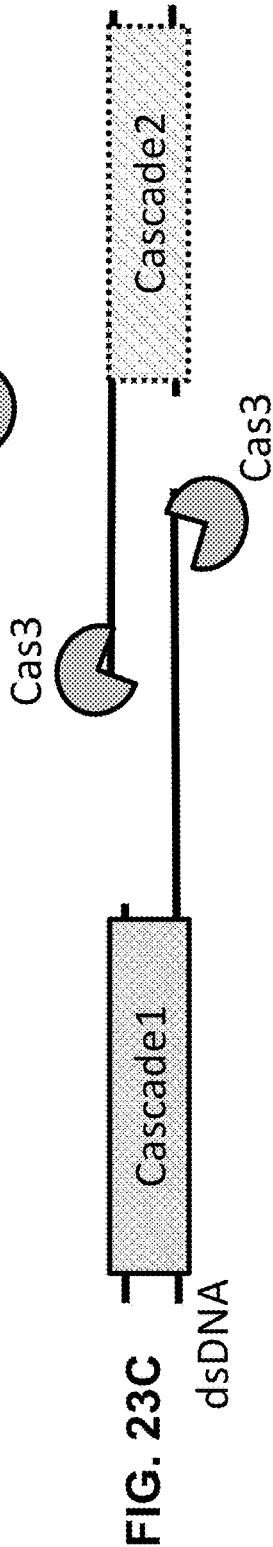
Figure 23D:
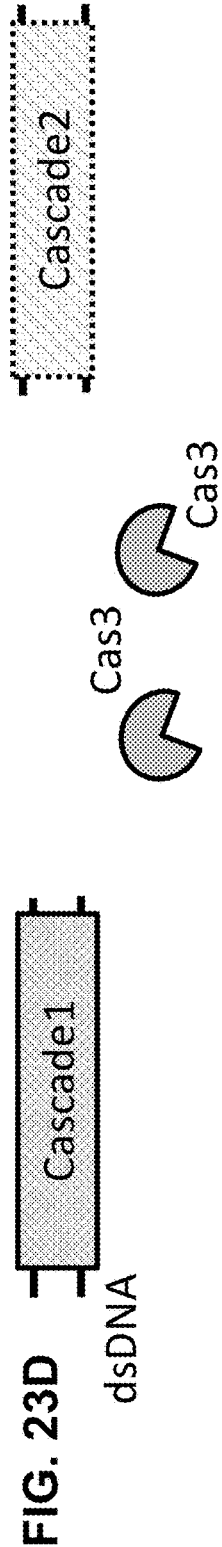

In another embodiment, a region of a target polynucleotide (e.g., genomic DNA) can be deleted using a combination of a first Cascade complex comprising a guide complementary to a first nucleic acid target sequence in the target polynucleotide and a second Cascade complex comprising a guide complementary to a second nucleic acid target sequence in the target polynucleotide. The first and second nucleic acid target sequences are selected to flank the nucleic acid target sequence targeted for deletion. Cas3 proteins comprising active endonuclease activity associate with each Cascade complex and then progressively delete both strands of the nucleic acid target sequence targeted for deletion. When each Cas3 protein collides with one of the Cascade complexes, the Cas3 nuclease activity can be stopped at the first and second nucleic acid target sequences by the Cascade complexes. FIG. 23A to FIG. 23D illustrate an example of a Cas3 deletion of both strands of a nucleic acid target sequence. FIG. 23A shows a dsDNA comprising nucleic acid target sequence 1 (FIG. 23A, NATS1) and nucleic acid target sequence 2 (FIG. 23A, NATS2) that flank the nucleic acid target sequence targeted for deletion. FIG. 23A shows the first Cascade complex comprising a guide complementary to NATS1 (FIG. 23A, Cascade1), the Cas3 proteins (FIG. 23A, Cas3), and the second Cascade complex comprising a guide complementary to NATS2 (FIG. 23A, Cascade2). FIG. 23B shows binding of the Cascade complexes to NATS1 and NATS2, as well as association of the Cas3 proteins with the Cascade complexes. FIG. 23C illustrates the progressive deletion by Cas3 of both strands of the nucleic acid target sequence targeted for deletion. FIG. 23D shows the dissociation of the Cas3 proteins from the dsDNA at the positions of the Cascade complexes bound to NATS1 and NATS2.

The engineered Type I CRISPR-Cas effector complexes, as described herein, can be incorporated into a kit. In some embodiments, a kit includes a package with one or more containers holding the kit elements, as one or more separate compositions or, optionally if the compatibility of the components allows, as admixture. In some embodiments, a kit also comprises one or more of the following excipients: a buffer, a buffering agent, a salt, a sterile aqueous solution, a preservative, and combinations thereof. Illustrative kits can comprise one or more engineered Type I CRISPR-Cas effector complexes and one or more excipients, or one or more nucleic acid sequences encoding one or more components of engineered Type I CRISPR-Cas effector complexes.

Furthermore, kits can further comprise instructions for using engineered Type I CRISPR-Cas effector complex compositions.

Another aspect of the invention relates to methods of making or manufacturing one or more engineered Type I CRISPR-Cas effector complexes, or components thereof. In one embodiment, a method of making or manufacturing comprises production of engineered Type I CRISPR-Cas effector complexes in a cell and purification of the engineered Type I CRISPR-Cas effector complexes from cell lysates.

Engineered Type I CRISPR-Cas effector complex compositions can further comprise a detectable label, such as a moiety that can provide a detectable signal. Examples of detectable labels include, but are not limited to, an enzyme, a radioisotope, a member of a specific binding pair, a fluorophore (FAM), a fluorescent protein (green fluorescent protein (GFP), red fluorescent protein, mCherry, tdTomato), a DNA or RNA aptamer together with a suitable fluorophore (enhanced GFP (eGFP), "Spinach"), a quantum dot, an antibody, and the like. A large number and variety of suitable detectable labels are well-known to one of ordinary skill in the art.

Cells comprising engineered Type I CRISPR-Cas effector complexes, cells modified through the use of engineered Type I CRISPR-Cas effector complexes, or progeny of such cells can be used as pharmaceutical compositions formulated, for example, with a pharmaceutically acceptable excipient. Illustrative excipients include carriers, stabilizers, diluents, dispersing agents, suspending agents, thickening agents, and the like. The pharmaceutical compositions can facilitate administration of engineered Type I CRISPR-Cas effector complexes to a subject. Pharmaceutical compositions can be administered in therapeutically effective amounts by various forms and routes including, for example, intravenous, subcutaneous, intramuscular, oral, aerosol, parenteral, ophthalmic, and pulmonary administration.

Embodiments of the present invention include, but are not limited to, the following.

Embodiment 1. A composition comprising:
a first engineered Class 1 Type I CRISPR-Cas effector complex comprising,
a first Cse2 subunit protein, a first Cas5 subunit protein, a first Cas6 subunit protein, and a first Cas7 subunit protein,
a first fusion protein comprising a first Cas8 subunit protein and a first FokI, wherein the N-terminus of the first Cas8 subunit protein or the C-terminus of the first Cas8 subunit protein is covalently connected by a first linker polypeptide to the C-terminus or N-terminus, respectively, of the first FokI, and wherein the first linker polypeptide has a length of between 10 amino acids to 40 amino acids, and
a first guide polynucleotide comprising a first spacer capable of binding a first nucleic acid target sequence; and
a second engineered Class 1 Type I CRISPR-Cas effector complex comprising,
a second Cse2 subunit protein, a second Cas5 subunit protein, a second Cas6 subunit protein, and a second Cas7 subunit protein,
a second fusion protein comprising a second Cas8 subunit protein and a second FokI, wherein the N-terminus of the second Cas8 subunit protein or the C-terminus of the second Cas8 subunit protein is covalently connected by a second linker polypeptide to the C-terminus or N-terminus, respectively, of the second FokI, and wherein the second linker polypeptide has a length of between 10 amino acids to 40 amino acids, and
a second guide polynucleotide comprising a second spacer capable of binding a second nucleic acid target sequence, wherein a protospacer adjacent motif (PAM) of the second nucleic acid target sequence and a PAM of the first nucleic acid target sequence have an interspacer distance between 20 bp to 42 bp.

Embodiment 2. The composition of embodiment 1, wherein the first linker polypeptide has a length of between 15 amino acids and 30 amino acids.

Embodiment 3. The composition of embodiment 2, wherein the first linker polypeptide has a length of between 17 amino acids and 20 amino acids.

Embodiment 4. The composition of any one of embodiments 1-3, wherein the second linker polypeptide has a length of between 15 amino acids and 30 amino acids.

Embodiment 5. The composition of embodiment 4, wherein the second linker polypeptide has a length of between 17 amino acids and 20 amino acids.

Embodiment 6. The composition of any preceding embodiment, wherein the length of the first linker polypeptide and the second linker polypeptide are the same.

Embodiment 7. The composition of any preceding embodiment, wherein the second nucleic acid target sequence and the first nucleic acid target sequence each has an interspacer distance between 22 bp to 40 bp.

Embodiment 8. The composition of embodiment 7, wherein the second nucleic acid target sequence and the first nucleic acid target sequence each has an interspacer distance between 26 bp to 36 bp.

Embodiment 9. The composition of embodiment 8, wherein the second nucleic acid target sequence and the first nucleic acid target sequence each has an interspacer distance between 29 bp to 35 bp.

Embodiment 10. The composition of embodiment 9, wherein the second nucleic acid target sequence and the first nucleic acid target sequence each has an interspacer distance between 30 bp to 34 base bp.

Embodiment 11. The composition of any preceding embodiment, wherein the first FokI and the second FokI are monomeric subunits capable of associating to form a homodimer.

Embodiment 12. The composition of any one of embodiments 1-10, wherein the first FokI and the second FokI are distinct monomeric subunits capable of associating to form a heterodimer.

Embodiment 13. The composition of any preceding embodiment, wherein the N-terminus of the first Cas8 subunit protein is covalently connected by the first linker polypeptide to the C-terminus of the first FokI.

Embodiment 14. The composition of any one of embodiments 1-12, wherein the C-terminus of the first Cas8 subunit protein is covalently connected by a first linker polypeptide to the N-terminus of the first FokI.

Embodiment 15. The composition of any preceding embodiment, wherein the N-terminus of the second Cas8 subunit protein is covalently connected by the second linker polypeptide to the C-terminus of the second FokI.

Embodiment 16. The composition of any one of embodiments 1-14, wherein the C-terminus of the second Cas8 subunit protein is covalently connected by a second linker polypeptide to the N-terminus of the second FokI.

Embodiment 17. The composition of any preceding embodiment, wherein the first Cas8 subunit protein and the second Cas8 subunit protein each comprises identical amino acid sequences.

Embodiment 18. The composition of any preceding embodiment, wherein the first Cse2 subunit protein and the second Cse2 subunit protein each comprises identical amino acid sequences, the first Cas5 subunit protein and the second Cas5 subunit protein each comprises identical amino acid sequences, the first Cas6 subunit protein and the second Cas6 subunit protein each comprises identical amino acid sequences, and the first Cas7 subunit protein and the second Cas7 subunit protein each comprises identical amino acid sequences.

Embodiment 19. The composition of any preceding embodiment, wherein the first guide polynucleotide comprises RNA.

Embodiment 20. The composition of any preceding embodiment, wherein the second guide polynucleotide comprises RNA.

Embodiment 21. The composition of any preceding embodiment, wherein genomic DNA comprises the PAM of the second nucleic acid target sequence and the PAM of the first nucleic acid target sequence.

Embodiment 22. A cell comprising: the composition of any preceding embodiment.

Embodiment 23. The cell of embodiment 22, wherein genomic DNA of the cell comprises the PAM of the second nucleic acid target sequence and the PAM of the first nucleic acid target sequence.

Embodiment 24. The cell of embodiment 22 or 23, wherein the cell is a prokaryotic cell.

Embodiment 25. The cell of embodiment 22 or 23, wherein the cell is a eukaryotic cell.

Embodiment 26. One or more nucleic acid sequences encoding the first Cse2 subunit protein, the first Cas5 subunit protein, the first Cas6 subunit protein, the first Cas7 subunit protein, the first fusion protein, and the first guide polynucleotide of any one of embodiments 1-21.

Embodiment 27. One or more nucleic acid sequences encoding the second Cse2 subunit protein, the second Cas5 subunit protein, the second Cas6 subunit protein, the second Cas7 subunit protein, the second fusion protein, and the second guide polynucleotide of any one of embodiments 1-21.

Embodiment 28. One or more expression cassettes comprising the one or more nucleic acid sequences of embodiment 26, embodiment 27, or embodiment 26 and embodiment 27.

Embodiment 29. One or more vectors comprising the one or more expression cassettes of embodiment 28.

Embodiment 30. A method of binding a polynucleotide comprising the first nucleic acid target sequence and the second nucleic acid target sequence, the method comprising:

providing the composition of any one of embodiments 1-21 for introduction into a cell or a biochemical reaction; and introducing the composition into the cell or the biochemical reaction, thereby facilitating contact of the first engineered Class 1 Type I CRISPR-Cas effector complex with the first nucleic acid target sequence and contact of the second engineered Class 1 Type I CRISPR-Cas effector complex with the second nucleic acid target sequence, resulting in binding of the first engineered Class 1 Type I CRISPR-Cas effector complex with the first nucleic acid target sequence and binding of the second engineered Class 1 Type I CRISPR-Cas effector complex with the second nucleic acid target sequence in the polynucleotide.

Embodiment 31. The method of embodiment 30, wherein genomic DNA comprises the polynucleotide.

Embodiment 32. A method of cutting a polynucleotide comprising the first nucleic acid target sequence and the second nucleic acid target sequence, the method comprising:

providing the composition of any one of embodiments 1-21 for introduction into a cell or a biochemical reaction; and introducing the composition into the cell or the biochemical reaction, thereby facilitating contact of the first engineered Class 1 Type I CRISPR-Cas effector complex with the first nucleic acid target sequence and contact of the engineered second Class 1 Type I CRISPR-Cas effector complex with the second nucleic acid target sequence, resulting in cutting of the first nucleic acid target sequence by the first engineered Class 1 Type I CRISPR-Cas effector complex and cutting of the second nucleic acid target sequence by the second engineered Class 1 Type I CRISPR-Cas effector complex.

Embodiment 33. The method of embodiment 32, wherein genomic DNA comprises the polynucleotide.

Embodiment 34. A kit comprising: the composition of any one of embodiments 1-21; and a buffer.

Embodiment 35. A kit comprising: the one or more nucleic acid sequences of embodiment 26, embodiment 27, or embodiment 26 and embodiment 27; and a buffer.

Embodiment 36. A composition comprising:
an engineered Class 1 Type I CRISPR-Cas effector complex comprising,
a Cse2 subunit protein, a Cas5 subunit protein, a Cas6 subunit protein, and a Cas7 subunit protein,
a first fusion protein comprising a Cas8 subunit protein and a first FokI, wherein the N-terminus of the first Cas8 subunit protein or the C-terminus of the first Cas8 subunit protein is covalently connected by a first linker polypeptide to the C-terminus or N-terminus, respectively, of the first FokI, and
a guide polynucleotide comprising a spacer capable of binding a nucleic acid target sequence; and
a second fusion protein comprising an engineered Class 1 Type I CRISPR-Cas3 fusion protein comprising a dCas3*protein and a second FokI, wherein the N-terminus of the dCas3* protein or the C-terminus of the dCas3* protein is covalently connected by a second linker polypeptide to the C-terminus or N-terminus, respectively, of the second FokI, and wherein the first linker polypeptide has a length of between 10 amino acids to 40 amino acids, effector complex comprising, Embodiment 37. The composition of embodiment 36, wherein the first linker polypeptide has a length of between 5 amino acids to 40 amino acids.

Embodiment 38. The composition of embodiment 36, wherein the first linker polypeptide has a length of between 5 amino acids to 40 amino acids.

Embodiment 39. A cell comprising: the composition of any one of embodiments 36 to 38.

Embodiment 40. The cell of embodiment 39, wherein the cell is a prokaryotic cell.

Embodiment 41. The cell of embodiment 39, wherein the cell is a eukaryotic cell.

Embodiment 42 One or more nucleic acid sequences encoding the Cse2 subunit protein, the Cas5 subunit protein, the Cas6 subunit protein, the Cas7 subunit protein, the first fusion protein, and the guide polynucleotide of any one of embodiments 36 to 38.

Embodiment 43. One or more nucleic acid sequences encoding the second fusion protein of any one of embodiments 36 to 38.

Embodiment 44. One or more expression cassettes comprising the one or more nucleic acid sequences of embodiment 42, embodiment 43, or embodiment 42 and embodiment 43.

Embodiment 45. One or more vectors comprising the one or more expression cassettes of embodiment 44.

Embodiment 46. A method of binding a polynucleotide comprising the nucleic acid target sequence, the method comprising:
providing the composition of any one of embodiments 36 to 38 for introduction into a cell or a biochemical reaction; and
introducing the composition into the cell or the biochemical reaction, thereby facilitating contact of the engineered Class 1 Type I CRISPR-Cas effector complex with the nucleic acid target sequence and contact of the second fusion protein with the engineered Class 1 Type I CRISPR-Cas effector complex, resulting in binding of the engineered Class 1 Type I CRISPR-Cas effector complex and the second fusion protein to the nucleic acid target sequence in the polynucleotide.

Embodiment 47. The method of embodiment 46, wherein genomic DNA comprises the polynucleotide.

Embodiment 48. A method of cutting a polynucleotide comprising the nucleic acid target sequence, the method comprising:
providing the composition of any one of embodiments 36 to 38 for introduction into a cell or a biochemical reaction; and
introducing the composition into the cell or the biochemical reaction, thereby facilitating contact of the first engineered Class 1 Type I CRISPR-Cas effector complex with the first nucleic acid target sequence and contact of the engineered second Class 1 Type I CRISPR-Cas effector complex with the second nucleic acid target sequence, and
introducing the composition into the cell or the biochemical reaction, thereby facilitating contact of the second engineered Class 1 Type I CRISPR-Cas effector complex with the nucleic acid target sequence and contact of the second fusion protein with the engineered Class 1 Type I CRISPR-Cas effector complex, resulting in cutting of the nucleic acid target sequence by the engineered Class 1 Type I CRISPR-Cas effector complex and the second fusion protein.

Embodiment 49. The method of embodiment 48, wherein genomic DNA comprises the polynucleotide.

Embodiment 50. A kit comprising: the composition of any one of embodiments 36 to 38; and a buffer.

Embodiment 51. A kit comprising: the one or more nucleic acid sequences of embodiment 42, embodiment 43, or embodiment 42 and embodiment 43; and a buffer.

Although preferred embodiments of the present invention have been shown and described herein, it will be obvious to those skilled in the art that such embodiments are provided by way of example only. From the present Specification and the Examples, one skilled in the art can ascertain essential characteristics of this invention, and without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are illustrated in the following Examples. Efforts have been made to ensure accuracy with respect to numbers used (e.g., amounts, concentrations, percent changes, and the like) but some experimental errors and deviations should be accounted for. Unless indicated otherwise, temperature is in degrees Centigrade and pressure is at or near atmospheric. It should be understood that these Examples are given by way of illustration only and are not intended to limit the scope of the present invention.

Example 1

In Silico Design of Polynucleotides Encoding Cascade Components

This Example provides a description of the design of polynucleotide components encoding Cascade using gene, protein, and CRISPR sequences derived from a Type I-E CRISPR-Cas system.

Table 10 presents polynucleotide DNA sequences of genes encoding the five proteins of Cascade from Type I-E, specifically from *E. coli* strain K-12 MG1655, as well as the amino acid sequences of the resulting protein components. Genomic sequences were obtained from NCBI Reference Sequence NZ_CP014225.1. In the Table, polynucleotide sequences were either amplified from *E. coli* genomic DNA or manufacturer-produced polynucleotides encoding Cascade protein components that were codon optimized specifically for expression in *E. coli* and also for expression in human cells.

TABLE 10

Cas Protein DNA and Amino Acid Sequences

| Protein | Type of sequence | DNA coding sequence | Amino acid sequence |
| --- | --- | --- | --- |
| Cas8 | genomic | SEQ ID NO: 1 | SEQ ID NO: 16 |
| Cse2 | genomic | SEQ ID NO: 2 | SEQ ID NO: 17 |
| Cas7 | genomic | SEQ ID NO: 3 | SEQ ID NO: 18 |
| Cas5 | genomic | SEQ ID NO: 4 | SEQ ID NO: 19 |
| Cas6 | genomic | SEQ ID NO: 5 | SEQ ID NO: 20 |
| Cas8 | *E. coli* codon-optimized | SEQ ID NO: 6 | SEQ ID NO: 16 |
| Cse2 | *E. coli* codon-optimized | SEQ ID NO: 7 | SEQ ID NO: 17 |
| Cas7 | *E. coli* codon-optimized | SEQ ID NO: 8 | SEQ ID NO: 18 |
| Cas5 | *E. coli* codon-optimized | SEQ ID NO: 9 | SEQ ID NO: 19 |
| Cas6 | *E. coli* codon-optimized | SEQ ID NO: 10 | SEQ ID NO: 20 |
| Cas8 | *H. sapiens* codon-optimized | SEQ ID NO: 11 | SEQ ID NO: 16 |
| Cse2 | *H. sapiens* codon-optimized | SEQ ID NO: 12 | SEQ ID NO: 17 |
| Cas7 | *H. sapiens* codon-optimized | SEQ ID NO: 13 | SEQ ID NO: 18 |
| Cas5 | *H. sapiens* codon-optimized | SEQ ID NO: 14 | SEQ ID NO: 19 |
| Cas6 | *H. sapiens* codon-optimized | SEQ ID NO: 15 | SEQ ID NO: 20 |

In addition, several fusion proteins comprising Cascade proteins were designed. Table 11 presents polynucleotide DNA sequences of genes encoding Cascade protein fusion proteins, as well as the amino acid sequences of the resulting protein components. In most instances, fusion proteins described in Table 11 include short tri-amino acid linkers connecting the two polypeptide sequences within the fusion construct; this linker typically comprises glycine-glycine-serine (GGS) or glycine-serine-glycine (GSG). The exact tri-amino acid linker sequences used in each particular fusion protein can be found in the full-length amino acid sequence in Table 11.

TABLE 11

Cascade Fusion Protein Sequences

| Cascade protein | Heterologous polypeptide | Heterologous polypeptide fused to the N- or C-terminus of the Cascade protein | DNA coding sequence | Expression system for DNA coding sequence | Amino acid sequence |
| --- | --- | --- | --- | --- | --- |
| Cse2 | Strep-tag® II-HRV3C | N | SEQ ID NO: 390 | *E. coli* | SEQ ID NO: 391 |
| Cse2 | His6-HRV3C | N | SEQ ID NO: 392 | *E. coli* | SEQ ID NO: 393 |
| Cse2 | NLS | N | SEQ ID NO: 394 | Mammalian | SEQ ID NO: 395 |
| Cas5 | NLS | N | SEQ ID NO: 396 | Mammalian | SEQ ID NO: 397 |
| Cas6 | NLS | N | SEQ ID NO: 398 | *E. coli* | SEQ ID NO: 399 |
| Cas6 | NLS-HA | N | SEQ ID NO: 400 | *E. coli* | SEQ ID NO: 401 |
| Cas6 | NLS | N | SEQ ID NO: 402 | Mammalian | SEQ ID NO: 403 |
| Cas7 | NLS | C | SEQ ID NO: 404 | *E. coli* | SEQ ID NO: 405 |
| Cas7 | HA-NLS | C | SEQ ID NO: 406 | *E. coli* | SEQ ID NO: 407 |
| Cas7 | NLS | N | SEQ ID NO: 408 | Mammalian | SEQ ID NO: 409 |
| Cas8 | His6-MBP-TEV | N | SEQ ID NO: 410 | *E. coli* | SEQ ID NO: 411 |
| Cas8 | His6-MBP-TEV-NLS-FokI-linker | N | SEQ ID NO: 412 | *E. coli* | SEQ ID NO: 413 |
| Cas8 | NLS | N | SEQ ID NO: 414 | Mammalian | SEQ ID NO: 415 |
| Cas8 | NLS-HA-FokI-linker | N | SEQ ID NO: 416 | Mammalian | SEQ ID NO: 417 |

The His6 (hexahistidine; SEQ ID NO:418) and Strep-tag™ II (GE Healthcare Bio-Sciences, Pittsburgh, Pa.) (SEQ ID NO:419) peptide tags on the Cse2 protein, when co-expressed with other Cascade proteins, enable purification of the complex via either Nickel-nitriloacetic acid (Ni-NTA) resin or Strep-Tactin™ (GE Healthcare Bio-Sciences, Pittsburgh, Pa.) resin, respectively. The HRV3C (human rhinovirus 3C) protease recognition sequence (SEQ ID NO:420) is cleaved by an HRV3C protease and can be used to remove N-terminal fusions from a protein of interest. The NLS (nuclear localization signal; SEQ ID NO:421 peptide tag on the Cas6, Cas7, and/or Cas8 proteins enables nuclear trafficking in eukaryotic systems. The HA (hemagglutinin; SEQ ID NO:422) peptide tag on the Cas6 or Cas7 proteins enables detection of heterologous protein expression by Western blotting with an anti-HA antibody. The MBP (maltose binding protein; SEQ ID NO:423) peptide fusion is a solubilization tag that facilitates purification of the Cas8 protein. The TEV (tobacco etch virus) protease recognition sequence (SEQ ID NO:424) is cleaved by TEV protease and can be used to remove N-terminal fusions from a protein of interest. The FokI nuclease domain comprises the Sharkey variant described by Guo, et al. (Guo, J., et al., J. Mol. Biol. 400:96-107 (2010)), two monomeric FokI subunits associate to form a homodimer, and catalyze double-stranded DNA cleavage upon homo-dimerization. A linker sequence (SEQ ID NO:425) is used to fuse the FokI nuclease domain to the Cas8 protein.

Additional linker sequences of varying length and amino acid composition have been designed that connect the FokI nuclease domain to the Cas8 protein. These amino acid sequences can be found in Table 12.

TABLE 12

Amino Acid Linker Sequences

| SEQ ID NO: | Linker length (amino acids) | Amino acid sequence |
|---|---|---|
| SEQ ID NO: 426 | 5 | GGGGS |
| SEQ ID NO: 427 | 8 | TGPGAAAR |
| SEQ ID NO: 428 | 10 | GGSGSSGGSG |
| SEQ ID NO: 429 | 12 | TGPGAAARAASG |
| SEQ ID NO: 430 | 15 | GGSGSSGGSGSSGGS |
| SEQ ID NO: 431 | 16 | SGSETPGTSESATPES |
| SEQ ID NO: 432 | 20 | SGSETPGTSESATPESGGSG |
| SEQ ID NO: 433 | 30 | SGSETPGTSESATPESGGSGSSGGSGSSGG |

Table 13 contains the polynucleotide DNA sequence of four minimal CRISPR arrays that, when transcribed into precursor crRNA and processed by the RNA endonuclease protein of Cascade, generate mature crRNAs that function as the guide RNA to target complementary DNA sequences in biochemical assays and in cell culture gene editing experiments.

The minimal CRISPR array comprises two repeat sequences (underlined, lower case) flanking a spacer sequence, which represents the guide portion of the crRNA. RNA processing by the Cascade endonuclease protein generates a crRNA with repeat sequences on both the 5' and 3' ends, flanking the guide sequence. The CRISPR array may also be expanded to include three repeat sequences (underlined) flanking two spacer sequences, which represent the guide portions of two distinct crRNAs by RNA processing by the endonuclease Cascade protein. The arrays can be further expanded to include additional spacer sequences, if desired.

TABLE 13

CRISPR Array Sequences

| SEQ ID NO: | Cell type | Target | Minimal CRISPR array sequence |
|---|---|---|---|
| SEQ ID NO: 434 | E. coli | Bacteriophage λ J3 target | gagttccccgcgccagcggggataaaccgCCAGTGATAAGTGGAATGCCATGTGGGCTGTCgagttcccccgcgccagcggggataaaccg |
| SEQ ID NO: 435 | E. coli | Bacteriophage λ L3 target | gagttccccgcgccagcggggataaaccgAGTGGCAGATATAGCCTGGTGGTTCAGGCGGCgagttcccccgcgccagcggggataaaccg |
| SEQ ID NO: 436 | E. coli | Bacteriophage λ L3/J3 targets | gagttccccgcgccagcggggataaaccgCCAGTGATAAGTGGAATGCCATGTGGGCTGTCgagttcccccgcgccagcggggataaaccgAGTGGCAGATATAGCCTGGTGGTTCAGGCGGCgagttccccgcgccagcggggataaaccg |
| SEQ ID NO: 437 | H. sapiens | TRAC gene | gagttccccgcgccagcggggataaaccgGTTGATTTGCCTGCATTGGTGTTACACAGTCTgagttcccccgcgccagcggggataaaccgTAAGTTGTGTTCTTCTTTGCCTAGGCCTTCAGgagttccccgcgccagcggggataaaccg |

Example 2

Design of Bacterial Expression Vectors for Production of Cascade Effector Complexes This Example describes the design of bacterial expression vectors that encode the Cascade-associated proteins, as well as a minimal CRISPR array comprising the guide sequence as described in Example 1. The construction of Cascade subunit protein expression systems for use with plasmids encoding minimal CRISPR arrays is described.

A single-plasmid Cascade protein expression system was constructed to express the proteins of either a complex of Cascade in *E. coli*, known as the CasBCDE complex (which contains the Cse2, Cas7, Cas5, and Cas6 proteins, but not the Cas8 protein), or the entire functional Cascade complex in *E. coli*. The single plasmid system comprises either the cse2-cas7-cas5-cas6 operon, or the entire cas8-cse2-cas7-cas5-cas6 operon on a single expression plasmid. The Cas8 protein can be expressed from its own expression plasmid, for use in biochemical experiments where it is mixed together with the CasBCDE complex to reconstitute Cascade.

A starting plasmid for expression vector construction was used (see Brouns, S. J. J. et al., Science 321:960-964 (2008)). The single plasmid Cascade protein expression system comprising a Cas operon was assembled as follows. The coding sequences for the cas genes were arranged in the order cse2-cas7-cas5-cas6 (CasBCDE complex or cas8-cse2-cas7-cas5-cas6 (full Cascade complex), and were separated by sequences corresponding to the wild-type bacterial gene arrangement (see NCBI Reference Sequence NZ_CP014225.1).

In order to append a polynucleotide sequence encoding an affinity tag (His6 or Strep-tag™ II), the corresponding coding sequence was inserted at the junction of the 3' end of the cas8 gene and the 5' end of the cse2 gene; these two open reading frames overlap in the wild-type genomic DNA sequence.

In order to append polynucleotide sequences encoding N-terminal NLS and/or NLS-HA tags onto the 5' end of the cas6 gene, additional spacing was introduced between the cas6 and upstream cas5 genes, because these open reading frames overlap in the wild-type genomic DNA sequence, such that the Shine-Dalgarno sequence for the cas6 gene is within the 3' portion of the cas5 gene. A new Shine-Dalgarno sequence was inserted upstream of the new NLS-Cas6 or NLS-HA-Cas6 open reading frames, to improve translational efficiency.

In order to append polynucleotide sequences encoding C-terminal NLS and/or HA-NLS tags onto the 3' end of the cas7 gene, additional spacing was introduced between the cas7 and downstream cas5 genes, because these open reading frames are in close proximity in the wild-type genomic DNA sequence, such that the Shine-Dalgarno sequence for the cas5 gene is within the 3' portion of the cas7 gene. A new Shine-Dalgarno sequence was inserted downstream of the new Cas7-NLS or Cas7-HA-NLS open reading frames, to improve translational efficiency for the cas5 gene.

In order to append polynucleotide sequences encoding N-terminal NLS-FokI-linker fusions to the Cas8 protein, the corresponding coding sequences were inserted at the 5' end of the cas8 gene.

The cse2-cas7-cas5-cas6 and cas8-cse2-cas7-cas5-cas6 operons were cloned into the pCDF (MilliporeSigma, Hayward, Calif.) vector backbone, which confers spectinomycin resistance due to the presence of the aadA gene. Transcription of the operon is driven by a T7 promoter and is under control of the Lac operator; the vector also encodes the LacI repressor. A T7 terminator was cloned downstream of the cse2-cas7-cas5-cas6 or cas8-cse2-cas7-cas5-cas6 operon. The vector contains a CDF origin of replication.

For expression of Cas8 or FokI-Cas8 fusion proteins, the cas8 gene was cloned into a pET (MilliporeSigma, Hayward, Calif.) family vector backbone, which confers kanamycin resistance due to the presence of the kanR gene. Transcription of the operon is driven by a T7 promoter ($P_{T7}$), and is under control of the Lac operator (lacO); the vector also encodes the LacI repressor (lacI gene). A T7 terminator was cloned downstream of the cas8 gene. The vector contains a ColE1 origin of replication.

FIG. 24A, FIG. 24B, FIG. 24C, FIG. 24D, and FIG. 24E present schematic diagrams of overexpression vectors for the cas8, fokI-cas8, the cse2-cas7-cas5-cas6 operon, the cas8-cse2-cas7-cas5-cas6 operon, and the fokI-cas8-cse2-cas7-cas5-cash operon. The designations in FIG. 24A, FIG. 24B, FIG. 24C, FIG. 24D, and FIG. 24E are described in this Example and in Example 1 and are as follows: $P_{T7}$ (T7 promoter), lacO (Lac operator), His6 (hexahistidine), MBP (maltose binding protein), Strep-tag™ II, HRV3C (human rhinovirus 3C) protease recognition sequence, TEV (tobacco etch virus) protease recognition sequence, NLS (nuclear localization signal), kanR (kanamycin resistance gene), lacI (LacI repressor gene), colE1 ori (origin of replication), CDF ori (CloDF13 origin of replication), FokI nuclease domain (Sharkey variant), and aadA (gene encoding aminoglycoside resistance protein).

Table 14 provides sequences of bacterial expression plasmids encoding the Cas8 protein, the 4 proteins of the CasBCDE complex (cse2-cas7-cas5-cas6 operon), and all 5 proteins of the Cascade complex (cas8-cse2-cas7-cas5-cas6 operon). Polynucleotide sequences are provided with and without the N-terminal FokI fusion on the Cas8 protein.

TABLE 14

Bacterial Plasmid Sequences

| SEQ ID NO: | Vector designation | Arrangement of protein coding sequences (N to C) | Notable characteristics |
| --- | --- | --- | --- |
| SEQ ID NO: 438 | Cas8 expression vector | His6-MBP-TEV-Cas8 | Can be added to CasBCDE complex to reconstitute Cascade |
| SEQ ID NO: 439 | FokI-Cas8 expression vector | His6-MBP-TEV-NLS-FokI-linker-Cas8 | FokI confers the ability to cleave double-stranded DNA |
| SEQ ID NO: 440 | CasBCDE complex expression vector | Strep-tag™ II-HRV3C-Cse2_Cas7_Cas5_Cas6 | When co-expressed with a CRISPR array, generates CasBCDE complex |

TABLE 14-continued

Bacterial Plasmid Sequences

| SEQ ID NO: | Vector designation | Arrangement of protein coding sequences (N to C) | Notable characteristics |
|---|---|---|---|
| SEQ ID NO: 441 | Cascade complex expression vector | Cas8__His6-HRV3C-Cse2__Cas7__Cas5__Cas6 | When co-expressed with a CRISPR array, generates Cascade complex |
| SEQ ID NO: 442 | FokI-Cascade expression vector | NLS-FokI-linker-Cas8__His6-HRV3C-Cse2__Cas7__Cas5__Cas6 | FokI confers the ability to cleave double-stranded DNA targeted by crRNA |
| SEQ ID NO: 443 | FokI-Cascade expression vector, extra NLS tag | NLS-FokI-linker-Cas8__His6-HRV3C-Cse2__Cas7-NLS__Cas5__Cas6 | FokI confers the ability to cleave double-stranded DNA targeted by crRNA; extra NLS tag on Cas7 protein improves nuclear trafficking |

In order to purify the CasBCDE complex and Cascade complex containing a crRNA, the protein expression vectors encoding the cse2-cas7-cas5-cas6 operon or the cas8-cse2-cas7-cas5-cas6 operon are combined with a vector containing a minimal CRISPR array.

CRISPR arrays were cloned into the pACYC-Duet1 vector backbone, which confers chloramphenicol resistance due to the camR gene. Transcription of the array is driven by a T7 promoter and is under control of the Lac operator (lacO); the vector also encodes the LacI repressor. A T7 terminator was cloned downstream of the CRISPR array. The vector contains a p15A origin of replication.

Figure 25:
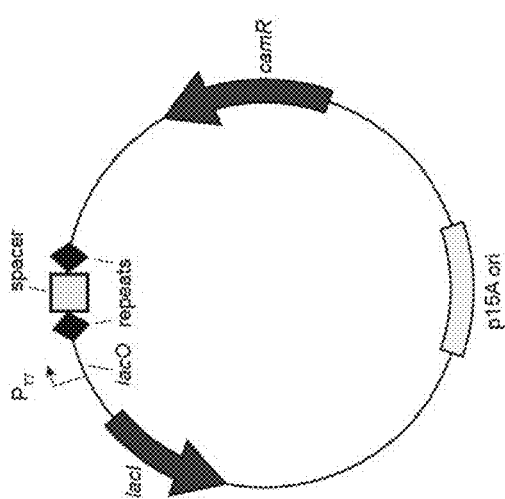

FIG. 25 contains a schematic diagram of an expression vector containing a CRISPR array with 2 repeats (FIG. 25, "repeats") and 1 spacer (FIG. 25, "spacer"). The array can be expanded, as described herein. The designations in FIG. 25 are described in this Example and in Example 1 and are as follows: $P_{T7}$ (T7 promoter), lacO (Lac operator), lacI (LacI repressor gene), p15A ori (origin of replication), and camR (chloramphenicol resistance gene).

Table 15 provides the sequences of bacterial expression plasmids encoding examples of minimal CRISPR arrays.

TABLE 15

Bacterial Plasmid Sequences

| SEQ ID NO: | Vector designation | DNA targeted by spacer | Notable characteristics |
|---|---|---|---|
| SEQ ID NO: 444 | CRISPR(J3) expression vector | Bacteriophage λ J3 target | Two repeats, one spacer |
| SEQ ID NO: 445 | CRISPR(L3) expression vector | Bacteriophage λ L3 target | Two repeats, one spacer |
| SEQ ID NO: 446 | CRISPR(J3/L3) expression vector | Bacteriophage λ L3/J3 targets | Three repeats, two spacers |
| SEQ ID NO: 447 | CRISPR(TRAC) expression vector | TRAC gene | Three repeats, two spacers |

Example 3

Design of Eukaryotic Expression Vectors for Production of Cascade Effector Complexes in Mammalian Cells This Example describes the design of eukaryotic expression plasmid vectors that encode Cascade-associated proteins, as well as minimal CRISPR arrays comprising the component sequences as described in Example 1.

A. Separate Plasmids Expressing Each Cascade Protein and Minimal CRISPR Array

Cascade proteins can be expressed in mammalian cells by encoding each of the protein components on a separate expression vector driven by the human cytomegalovirus (CMV) immediate-early promoter/enhancer and encoding the crRNA on a separate expression vector driven by the human U6 promoter.

The starting plasmid for each expression plasmid was a derivative of pcDNA3.1 (Thermo Scientific, Wilmington, Del.). Coding sequences for the Cascade proteins, codon optimized for expression in human cells (see Example 1), were inserted into the vector downstream of the CMV promoter and upstream of a bovine growth hormone (bGH) polyadenylation signal. The cse2 gene was fused to polynucleotide sequences at the 5' end coding for an N-terminal NLS and 3x-FLAG epitope tag. The cas5 gene was fused to polynucleotide sequences at the 5' end coding for an N-terminal NLS. The cash gene was fused to polynucleotide sequences at the 5' end coding for an N-terminal NLS and HA epitope tag. The cas7 gene was fused to polynucleotide sequences at the 5' end coding for an N-terminal NLS and Myc epitope tag. The cas8 gene was fused to polynucleotide sequences at the 5' end coding for an N-terminal NLS; in another embodiment, the cas8 gene was fused to polynucleotide sequences at the 5' end coding for an N-terminal NLS, HA epitope tag, and FokI nuclease domain.

Each gene or gene fusion was cloned into a pcDNA3.1 derivative vector backbone, which confers ampicillin resistance due to the presence of the ampR gene. The vector also encodes neomycin resistance due to the presence of the neoR gene, which is downstream of an SV40 early promoter ($P_{SV40}$) and origin (SV40 ori), and upstream of an SV40 early polyadenylation signal (SV40 pA). In addition to the human CMV immediate-early promoter/enhancer ($P_{CMV}$) and bGH (bovine growth hormone) polyadenylation signal, the vector contains a T7 promoter upstream of the gene of interest, allowing for in vitro transcription of mRNA. The vector contains an f1 origin of replication as well as a ColE1 origin of replication.

Figure 26:
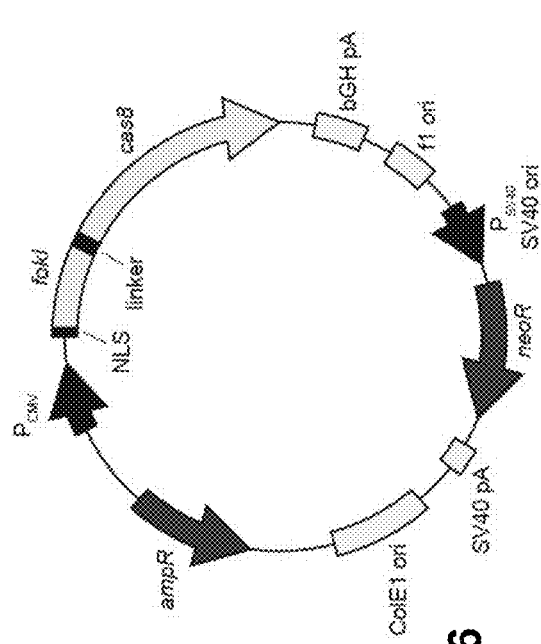

FIG. 26 contains a schematic diagram of a mammalian expression vector encoding the FokI-Cas8 fusion protein. The designations in FIG. 26 are described in this Example and in Example 1 and are as follows: the human CMV immediate-early promoter/enhancer ($P_{CMV}$), NLS (nuclear localization signal), FokI (FokI nuclease domain (Sharkey variant)), Cas8 protein coding sequence, bGH pA (bovine growth hormone polyadenylation signal), f1 ori (f1 phage origin of replication), $P_{SV40}$ (SV40 early promoter), SV40 ori (SV40 origin), neoR (neomycin resistance gene), SV40 pA (SV40 early polyadenylation signal), colE1 ori (origin of replication), and ampR (ampicillin resistance gene). Vectors encoding the other Cascade proteins were designed similarly.

Table 16 provides the sequences of individual mammalian expression vectors encoding each of Cse2, Cas5, Cas6, Cas7, Cas8, and FokI-Cas8.

TABLE 16

Mammalian Expression Vectors

| SEQ ID NO: | Vector designation | Notable characteristics |
|---|---|---|
| SEQ ID NO: 448 | Mammalian Cse2 expression vector | Cse2 contains N-terminal NLS-3xFLAG tag |
| SEQ ID NO: 449 | Mammalian Cas5 expression vector | Cas5 contains N-terminal NLS |
| SEQ ID NO: 450 | Mammalian Cas6 expression vector | Cas6 contains N-terminal NLS-Ha tag |
| SEQ ID NO: 451 | Mammalian Cas7 expression vector | Cas7 contains N-terminal NLS-Myc tag |
| SEQ ID NO: 452 | Mammalian Cas8 expression vector | Cas8 contains N-terminal NLS |
| SEQ ID NO: 453 | Mammalian FokI-Cas8 expression vector | Cas8 contains N-terminal NLS-HA-FokI; FokI confers the ability to cleave double-stranded DNA |

The CRISPR RNA was encoded with a minimal CRISPR array containing three repeats flanking two spacer sequences. The construct generating CRISPR RNA can be designed with additional sequences flanking the outermost repeats in the minimal array. Processing of the precursor CRISPR RNA is enabled by the RNA processing protein of the Cascade complex (Cas6 protein), which can be expressed on a separate plasmid.

The CRISPR array was cloned into the same pcDNA3.1 derivative vector backbone described above, except the human CMV promoter was replaced with the human U6 promoter ($P_{U6}$), and the bGH polyadenylation signal was replaced with a poly-T termination signal.

Figure 27:
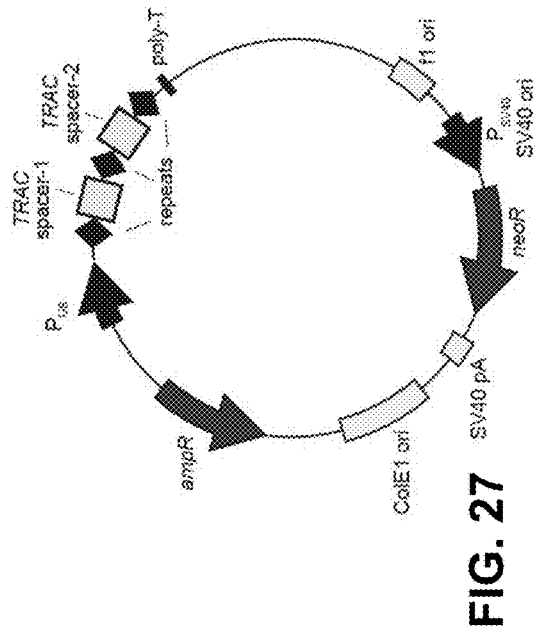

FIG. 27 contains a schematic diagram of a eukaryotic expression vector encoding a representative CRISPR array targeting the TRAC gene. The designations in FIG. 27 are described in this Example and in Example 1 and are as follows: $P_{U6}$ (human U6 promoter), repeats (CRISPR RNA repeats), TRAC spacer-1 (first spacer targeting the TRAC gene), TRAC spacer-2 (second spacer targeting the TRAC gene), polyT (poly-T termination signal), f1 ori (f1 phage origin of replication), $P_{SV40}$ (SV40 early promoter), SV40 ori (SV40 origin), neoR (neomycin resistance gene), SV40 pA (SV40 early polyadenylation signal), colE1 ori (origin of replication), and ampR (ampicillin resistance gene).

Table 17 provides the sequence of a representative mammalian expression vector encoding a CRISPR array targeting the TRAC gene; a spacer sequence that targets matching DNA sequences in the TRAC gene can be found in Table 13.

B. Cascade Protein Expression System Wherein Multiple Cascade Protein Coding Sequences are Expressed from a Single Promoter In order to express components of the Cascade complex off of fewer expression vectors, polycistronic expression vectors were constructed. On each, a single CMV promoter drives expression of multiple coding sequences simultaneously that are separated by a 2A viral peptide sequence. The *Thosea asigna* virus 2A peptide sequence induces ribosomal skipping (Liu, Z., et al., Sci. Rep. 7:2193 (2017)), thus enabling multiple protein-coding genes to be concatenated within a single polycistronic construct.

The starting plasmid for the polycistronic expression plasmid was the same derivative of pcDNA3.1 described above, containing the CMV promoter and bGH polyadenylation signal. Coding sequences for the Cascade proteins, codon optimized for expression in human cells (see Example 1), were joined in the order cas7-cse2-cas5-cas6-cas8, with a polynucleotide sequence coding for the *Thosea asigna* virus 2A (T2A) peptide inserted in between each pair of genes. In addition, polynucleotide sequences encoding NLS tags were appended to the 5' end of each Cascade protein gene, and a polynucleotide sequence encoding the FokI nuclease domain was appended to the 5' end of the cas8 gene, connecting by a 30-amino acid linker sequence. The final construct has the following order of elements: NLS-cas7-T2A-NLS-cse2-T2A-NLS-cas5-T2A-NLS-cash-T2A-NLS-fokI-linker-cas8.

Figure 28:
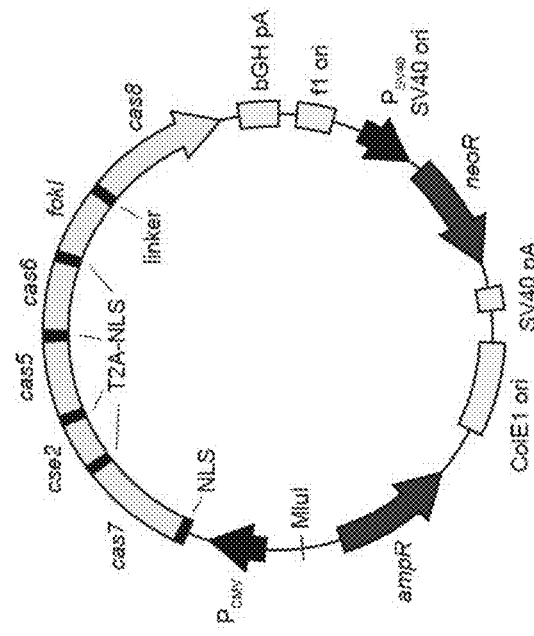

FIG. 28 contains a schematic diagram of an exemplary polycistronic mammalian expression vector encoding all the Cascade proteins. The designations in FIG. 28 are described in this Example and in Example 1 and are as follows: the human CMV immediate-early promoter/enhancer ($P_{CMV}$), NLS (nuclear localization signal), T2A (polynucleotide sequence coding for the *Thosea asigna* virus 2A peptide),

TABLE 17

Mammalian Expression Vector

| SEQ ID NO: | Vector designation | Spacer complementary to target | Notable characteristics |
|---|---|---|---|
| SEQ ID NO: 454 | Mammalian CRISPR RNA expression vector | TRAC gene | Three repeats, two spacers | coding sequences for the Cas7, Cse2, Cas5, and Cas6 proteins, fokI (FokI nuclease domain (Sharkey variant) a linker sequence, coding sequence for Cas8 protein, bGH pA (bovine growth hormone polyadenylation signal), f1 ori (f1 phage origin of replication), $P_{SV40}$ (SV40 early promoter), SV40 ori (SV40 origin), neoR (neomycin resistance gene), SV40 pA (SV40 early polyadenylation signal), colE1 ori (origin of replication), ampR (ampicillin resistance gene), and an MluI restriction site.

Table 18 provides the sequence of an exemplary polycistronic mammalian expression vector encoding all the Cascade proteins. This vector can be combined with the mammalian expression vector encoding CRISPR RNA described above to produce functional Cascade complexes in mammalian cells.

TABLE 18

Mammalian Expression Vectors

| SEQ ID NO: | Vector designation | Arrangement of protein coding sequences (N to C) | Notable characteristics |
| --- | --- | --- | --- |
| SEQ ID NO: 455 | Polycistronic mammalian expression vector encoding all 5 Cascade proteins | NLS-Cas7-T2A_NLS-Cse2-T2A_NLS-Cas5-T2A_NLS-Cas6-T2A_NLS-FokI-Cas8 | Single protein expression vector encoding all Cascade proteins, each with N-terminal NLS tag. Cas8 contains N-terminal NLS-HA-FokI; FokI confers the ability to cleave double-stranded DNA |

C. Single Plasmid Expression System

A single plasmid Cascade expression system was constructed to express the complete Cascade complex in human cells. The plasmid encodes the entire cas8-cse2-cas7-cas5-cas6 operon and a minimal CRISPR array on a single plasmid. This plasmid was constructed from the polycistronic protein expression vector (described above in Table 18 and FIG. 28) by inserting the minimal CRISPR array along with the upstream human U6 promoter and downstream poly-T termination signal into the MluI restriction site.

Table 19 provides the sequence of the single plasmid for expression of all five Cascade proteins together with the crRNA to facilitate formation of Cascade complexes in human cells.

TABLE 19

Mammalian Expression Vector

| SEQ ID NO: | Vector designation | Arrangement of protein coding sequences (N to C) | Notable characteristics |
| --- | --- | --- | --- |
| SEQ ID NO: 456 | Polycistronic mammalian expression vector encoding all 5 Cascade proteins and crRNA | hU6_CRISPR(TRAC), CMV_NLS-Cas7-T2A_NLS-Cse2-T2A_NLS-Cas5-T2A_NLS-Cas6_NLS-FokI-Cas8 | Single protein expression vector encoding crRNA and all Cascade proteins, each with N-terminal NLS tag. Cas8 contains N-terminal NLS-HA-FokI; FokI confers the ability to cleave double-stranded DNA |

Plasmids were also designed for the expression of the Cas3 protein (SEQ ID NO:21; monomer Cas3 nuclease/helicase *E. coli* K-12 substr. MG1655) in *E. coli* and in mammalian cells. Table 20 provides the constructs and sequences of these plasmids.

TABLE 20

Cas3 Protein Fusions

| SEQ ID NO: | Protein | Notable characteristics |
| --- | --- | --- |
| SEQ ID NO: 457 | Cas3 | Genomic DNA gene sequence |
| SEQ ID NO: 458 | Cas3 | Protein amino acid sequence |
| SEQ ID NO: 459 | His6-MBP-TEV-Cas3 | Derived from genomic DNA gene sequence |
| SEQ ID NO: 460 | His6-MBP-TEV-Cas3 | Protein amino acid sequence |
| SEQ ID NO: 461 | His6-MBP-TEV-Cas3 | Cas3 *E. coli* expression vector |

TABLE 20-continued

Cas3 Protein Fusions

| SEQ ID NO: | Protein | Notable characteristics |
|---|---|---|
| SEQ ID NO: 462 | Cas3, human codon-optimized | *Homo sapiens* codon-optimized DNA gene sequence |
| SEQ ID NO: 463 | Cas3-NLS | *Homo sapiens* codon-optimized DNA gene sequence |
| SEQ ID NO: 464 | Cas3-NLS | Protein amino acid sequence |
| SEQ ID NO: 465 | Cas3-NLS | Cas3 mammalian expression vector |

Example 4

Introduction of Polynucleotides Encoding Cascade Components into a Bacterial Production Strain This Example describes for introduction and expression of Cas8 subunit protein coding sequences, as well as coding sequences for components of engineered Type I CRISPR-Cas effector complexes in bacterial cells using *E. coli* expression systems.

A. Expression of Cas8 Protein

*E. coli* Type I-E Cas8 protein was expressed from a plasmid (Example 2, SEQ ID NO:438, Table 14, FIG. 24A) containing an operon for the IPTG inducible expression of His6-MBP-TEV-Cas8 from a T7 promoter. The expression plasmid conferred resistance to kanamycin.

In order to express Cas8 protein, *E. coli* cells were transformed with the expression plasmid. Briefly, a 100 μL aliquot of chemically competent *E. coli* cells (*E. coli* BL21 Star™ cells (Thermofisher, Waltham, Mass.)) in a microcentrifuge tube was thawed on ice for 10 minutes. 35 ng of plasmid DNA was added to the thawed cells and the cells were incubated with the DNA on ice for 8 minutes. Heat shock was performed by a placing the microcentrifuge tube in a 42° C. water bath for 30 seconds and then immediately placing the tube in ice for 2 minutes. 900 μL of 2×YT media were added to the microcentrifuge tube, and the microcentrifuge tube was placed in a tube rotator at 37° C. for 1 hour. Finally, 100 μL of the recovered cells were plated on LB solid kanamycin (50 μg/mL) and incubated overnight at 37° C.

A single colony was picked from the colonies that grew on the antibiotic selection plates and was inoculated into 10 mL of 2×YT media supplemented with kanamycin (50 μg/mL). The culture was grown overnight at 37° C. while shaking in an orbital shaker at 200 RPMs. 6 mL of the overnight culture were transferred to a 2 L baffled flask having 1 L of 2×YT media supplemented with chloramphenicol (34 μg/mL) and spectinomycin (100 μg/mL). The 1 L culture was grown at 37° C. while shaking in an orbital shaker at 200 RPM until the optical density at 600 nm was 0.56.

Expression from both plasmids was then induced by the addition of IPTG to a final concentration of 1 mM. The induced cultures were grown overnight at 16° C. while shaking in an orbital shaker at 200 RPM. Cells were harvested by centrifugation at 4,000 RCF for 15 minutes at 4° C. The cell pellet was re-suspended in 15 mL of a lysis buffer composed of 50 mM Tris pH 7.5, 100 mM NaCl, 5% glycerol, and 1 mM TCEP supplemented with 1 Complete™ protease inhibitor tablet (Roche, Basel, Switzerland) per 50 mL of lysis buffer. The re-suspended cells were transferred to a 50 mL conical tube for immediate downstream processing. The Cas8 protein was purified and the purified protein characterized essentially as described below for the FokI-Cas8 fusion protein (Example 5C).

B. Expression of the Components of Cascade RNP Complexes

A complete set of the five *E. coli* Cascade proteins and RNA guides were co-expressed in *E. coli* cells using a two-plasmid system to produce Cascade RNP complexes. One plasmid (Example 2, SEQ ID NO:441, Table 14, FIG. 24D) contained an operon for IPTG inducible expression of the Cse2, Cas5, Cash, Cas7, and Cas8 proteins from a T7 promoter. A His6 affinity tag was included as a translational fusion to the N-terminus of Cse2 (Example 1, SEQ ID NO:392, Table 11). The second plasmid coded for the IPTG inducible expression of the J3 guide (Example 2, SEQ ID NO:444, Table 15, FIG. 25). The Cascade protein expression plasmid conferred spectinomycin resistance, and the Cascade RNA guide expression plasmid conferred chloramphenicol resistance.

In order to co-express the Cascade proteins and RNA components in the same cell, *E. coli* cells were simultaneously transformed with the two plasmids. A 100 μL aliquot of chemically competent *E. coli* cells (*E. coli*, BL21 Star™ (DE3) (Thermofisher, Waltham, Mass.)) in a microcentrifuge tube was thawed on ice for 10 minutes. 35 ng of each plasmid was added to the thawed cells and the cells were incubated with the DNA on ice for 8 minutes. Heat shock was performed by a placing the microcentrifuge tube in a 42° C. water bath for 30 seconds and then immediately placing the microcentrifuge tube in ice for 2 minutes. 900 μL of 2×YT media were added to the microcentrifuge tube and the microcentrifuge tube placed in a tube rotator at 37° C. for 1 hour. Finally, 100 μL of the recovered cells were plated on LB solid media with chloramphenicol (34 μg/mL) and spectinomycin (50 μg/mL) and incubated overnight at 37° C.

A single colony was picked from the colonies that grew on the antibiotic selection plates and was inoculated into 10 mL of 2×YT media supplemented with chloramphenicol (34 μg/mL) and spectinomycin (100 μg/mL). The culture was grown overnight at 37° C. while shaking in an orbital shaker at 200 RPMs. 6 mL of the overnight culture were transferred to a 2 L baffled flask having 1 L of 2×YT media supplemented with chloramphenicol (34 μg/mL) and spectinomycin (100 μg/mL). The 1 L culture was grown at 37° C. while shaking in an orbital shaker at 200 RPM until the optical density at 600 nm was 0.56.

Expression from both plasmids was induced by the addition of IPTG to a final concentration of 1 mM. The induced cultures were grown overnight at 16° C. while shaking in an orbital shaker at 200 RPM. Cells were harvested by centrifugation for at 4,000 RCF for 15 minutes at 4° C. The cell pellet was re-suspended in 15 mL of lysis buffer composed of 50 mM Tris pH 7.5, 100 mM NaCl, 5% glycerol, and 1 mM TCEP supplemented with 1 Complete™ protease inhibitor tablet (Roche, Basel, Switzerland) per 50 mL of lysis buffer. The re-suspended cells were transferred to a 50 mL conical tube for immediate downstream processing. Cascade RNP complexes were purified and characterized as described below.

Example 5

Purification of Cascade Components and Cascade RNP Complexes

This Example describes a method to purify *E. coli* Type I-E Cascade ribonucleoprotein (RNP) complexes produced by overexpression in bacteria as described in Example 4. The method uses immobilized metal affinity chromatography followed by size exclusion chromatography. This Example also describes the methods used to assess the quality of the purified Cascade RNP product. In addition, this Example describes purification and characterization of Cascade components.

A. Purification of Cas8, Cas7, Cash, Cas5, and Cse2 Cascade RNP Complexes

*E. coli* Type I-E Cascade RNP complexes were produced as described in Example 4. The Cascade complexes were captured using immobilized metal affinity chromatography. Briefly, the re-suspended cell pellets, produced as described in Example 4, were thawed on ice and the volume was brought to 35 mL by of an additional 15 mL of lysis buffer composed of 50 mM Tris pH 7.5, 100 mM NaCl, 5% glycerol, and 1 mM TCEP supplemented with 1 Complete™ protease inhibitor tablet (Roche, Basel, Switzerland) per 50 mL of lysis buffer.

The 50 mL conical tube was placed in an ice water bath and the cells were lysed by two rounds of sonication using a Q500 sonicator with a ½ inch tip (Qsonica, Newtown, Conn.). Each round of sonication consisted of a treatment cycle of 2.5 minutes with repeating cycles of 10 seconds of sonication at 50% amplitude followed by 20 seconds of rest. The tube was allowed to cool in the ice water bath for one minute between rounds of sonication. The lysates were clarified by centrifugation at 48,384 RCF for 30 minutes at 4° C. The clarified supernatant was then added to a Hispur™ Ni-NTA resin (Thermofisher, Waltham, Mass.), that had been pre-equilibrated with Ni-wash buffer composed of 50 mM Tris pH 7.5, 100 mM NaCl, 10 mM imidazole, 5% glycerol, and 1 mM TCEP. A 1.5 mL bed volume of nickel affinity resin was used for each 1 L of *E. coli* expression culture. After one hour of incubation at 4° C. with gentle mixing, the resin was pelleted by centrifugation at 500 RCF for 2 minutes at 4° C. The supernatant was aspirated and the resin was washed 5 times with 5 bed volumes of Ni-wash buffer. After each wash the resin was pelleted at 500 RCF for 2 minutes at 4° C. and the supernatant was removed by aspiration. Finally, bound proteins (including the Cascade RNP complexes) were eluted by the addition of five bed volumes of Ni-elution buffer composed of 50 mM Tris pH 7.5, 100 mM NaCl, 300 mM imidazole, 5% glycerol, and 1 mM tris(2-carboxyethyl)phosphine (TCEP). After centrifugation at 500 RCF for 2 minutes at 4° C., the nickel affinity eluate was aspirated into a clean 50 mL conical tube.

The nickel affinity eluate was further purified by size exclusion chromatography (SEC). The nickel affinity eluate was concentrated to a final volume of 0.5 mL by ultrafiltration at 12° C. using an Amicon® ultrafiltration spin concentrator (Millipore Sigma, Billerica, Mass.) with an Ultracel®-50 membrane (Millipore Sigma, Billerica, Mass.). The concentrated sample was filtered using a 0.22 µM Ultrafree-MC GV Centrifugal Filter (Millipore Sigma, Billerica, Mass.) before being further purified by separation at 4° C. with a flow rate of 0.5 mL/minute on a HiPrep™ 16/60 Sephacryl® S-300 column (GE Healthcare, Uppsala, Sweden) equilibrated with SEC buffer composed of 50 mM Tris pH 7.5, 500 mM NaCl, 5% glycerol, 0.1 mM EDTA, and 1 mM TCEP. Proteins were eluted with SEC buffer and 1 ml fractions were collected. The earliest eluting peak, as judged by UV 280, was assumed to be high molecular weight aggregated material and the corresponding fractions were discarded. Subsequent elution fractions were analyzed by Coomassie stained SDS-PAGE. Each properly formed complex contained one molecule of Cas8, six molecules of Cas7, one molecule each of Cas6 and Cas5, and two molecules of Cse2. Elution fractions that had the approximate expected stoichiometry of Cascade proteins, when visualized on the SDS-PAGE gel, were pooled. Pooled fractions were analyzed spectrophotometrically to confirm they contained a significant nucleic acid component, as evidenced by an absorbance at 260 nm that is greater than the absorbance at 280 nm.

The pooled samples were exchanged into storage buffer composed of 50 mM Tris pH 7.5, 100 mM NaCl, 5% glycerol, 0.1 mM EDTA, and 1 mM TCEP by concentrating the pooled samples to 100 uL with an Amicon® spin concentrator with an Ultracel®-50 membrane (Millipore Sigma, Billerica, Mass.) and then diluting 50-fold with the storage buffer. Finally, the sample was concentrated to 10 mg/mL using the same ultrafiltration device and stored at −80° C.

The final purified product was analyzed spectrophotometrically to determine the final concentration of the Cascade RNP complexes and to confirm the presence of a nucleic acid component as evidenced by an absorbance at 260 nm that is greater than the absorbance at 280 nM. The concentration of the Cascade RNP complexes was determined by dividing the absorbance at 280 nm by the calculated absorbance of a 0.1% solution of the intact complex with a 1 cm path length. The predicted absorbance of a 0.1% solution of the purified complex is 2.03 $cm^{-1}$ and was calculated by dividing the sum of the calculated extinction coefficients at 280 nm for each of the molecules in the complex (916940 $M^{-1}$ $cm^{-1}$) by the sum of the molecular weights of each of the molecules in the complex (450832 g/mole).

Additionally, the final product was analyzed by SDS-PAGE with Coomassie blue staining to confirm that each protein component was present in approximately the correct stoichiometry, and to assess the presence of contaminating proteins. SDS-PAGE gels were stained with a Coomassie InstantBlue™ (Expedeon, San Diego, Calif.) stain. Gels were imaged using a Gel Doc™ EZ imager (Bio-Rad, Hercules, Calif.) and annotated using ImageLab software (Bio-Rad, Hercules, Calif.).

In view of the teachings of the Specification and the Examples, this method for purification of *E. coli* Type I-E Cascade complexes can be applied to the production of other purified Type I Cascade complexes.

B. Purification of Cascade Complexes Comprising Cas7, Cas6, Cas5, and Cse2 Proteins A Cascade complex composed of the and the protein components Cas7, Cas6, Cas5, and Cse2 was purified. The L3 guide RNA (Example 2, SEQ ID NO:445, Table 15) was expressed from a first plasmid (Example 2, FIG. 25) essentially as described in Example 4.B. The Cascade proteins were expressed from a second plasmid (Example 2, SEQ ID NO:440, Table 14, FIG. 24C) essentially as described in Example 4B.

The complex was captured using affinity chromatography. Re-suspended cell pellets were thawed on ice. In a 50 mL conical tube, the volume was brought up to 35 mL with an additional 15 mL of lysis buffer composed of 50 mM Tris pH 7.5, 100 mM NaCl, 5% glycerol, 1 mM TCEP, and supplemented with 1 Complete™ protease inhibitor tablet (Roche, Basel, Switzerland) per 50 mL of lysis buffer. The 50 mL conical tube was placed in an ice water bath, and the cells were lysed by six rounds of sonication using a Q500 sonicator with a ½ inch tip (Qsonica, Newtown, Conn.). Each round of sonication consisted of a 1 minute treatment cycle with repeating cycles of 3 seconds of sonication at 90% amplitude followed by 9 seconds of rest. The tube was allowed to cool in the ice water bath for one minute between rounds of sonication. The lysate was clarified by centrifugation at 48,384 RCF for 30 minutes at 4° C. The clarified supernatant was affinity purified by addition of Strep-Tactin® Sepharose® resin (IBA Life Sciences, Gottingen, Germany) that had been pre-equilibrated with Strep-wash buffer composed of 50 mM Tris pH 7.5, 100 mM NaCl, 1 mM EDTA, 5% glycerol, and 1 mM TCEP. A 0.55 mL bed volume of affinity resin was used for each 1 L of *E. coli* expression culture. After one hour of incubation at 4° C. with gentle mixing, the sample was poured onto a 30 mL disposable gravity flow column (Bio-Rad, Hercules, Calif.) allowing the unbound material to flow through the column. The resin was washed five times with five bed volumes of Strep-wash buffer. Finally, the bound proteins were eluted with two sequential additions of five bed volumes of Strep-elution buffer composed of 50 mM Tris pH 7.5, 100 mM NaCl, 2.5 mM Desthiobiotin, 5% glycerol, 1 mM EDTA, and 1 mM TCEP.

The affinity eluate was further purified by SEC. The affinity eluate was concentrated to a final volume of 550 uL by ultrafiltration at 12° C. using an Amicon® spin concentrator with an Ultracel®-50 membrane (Millipore Sigma, Billerica, Mass.). The concentrated sample was filtered using a 0.22 µm 13 mm UltraCruz® PVDF syringe filter (Santa Cruz Biotechnology, Dallas, Tex.) before being further purified by separation at 4° C. with a flow rate of 0.4 mL/minute on a HiPrep™ 16/60 Sephacryl® S-300 column (GE Healthcare, Uppsala, Sweden) equilibrated with SEC buffer composed of 50 mM Tris pH 7.5, 500 mM NaCl, 5% glycerol, 0.1 mM EDTA, and 1 mM TCEP. Protein was eluted with SEC buffer and 0.75 ml fractions were collected. The earliest eluting peak, as judged by UV 280, was assumed to be high molecular weight aggregated material and the corresponding fractions were discarded. Fractions corresponding to the second peak (a shoulder on the back side of the first UV 280 peak) were pooled.

The pooled samples were exchanged into storage buffer composed of 50 mM Tris pH 7.5, 100 mM NaCl, 5% glycerol, 0.1 mM EDTA, and 1 mM TCEP by concentrating down to 200 uL with an Amicon® spin concentrator with an Ultracel®-50 membrane (Millipore Sigma, Billerica, Mass.) and then diluting 75-fold with storage buffer. The sample was concentrated a second time to 700 uL and again diluted 20-fold with storage buffer. Finally, the sample was concentrated to 4.7 mg/mL in the same ultrafiltration device and stored at −80° C.

The final purified product was analyzed spectrophotometrically to determine the final concentration of the Cascade RNP complexes and to confirm the presence of a nucleic acid component as evidenced by an absorbance at 260 nm that is greater than the absorbance at 280 nM. The concentration of the Cascade RNP complexes was determined by dividing the absorbance at 280 nm by the calculated absorbance of a 0.1% solution of the intact complex with a 1 cm path length. The predicted absorbance of a 0.1% solution of the purified complex is 2.18 cm$^{-1}$ and was calculated by dividing the sum of the calculated extinction coefficients at 280 nm for each molecule in the complex (762240 M$^{-1}$ cm$^{-1}$) by the sum of the molecular weights of each molecule in the complex (348952.07 g/mole).

Additionally, the final product was analyzed by SDS-PAGE with Coomassie blue staining to confirm that each Cascade protein was present in approximately the correct stoichiometry, and to assess the presence of contaminating proteins. SDS-PAGE gels were stained with Coomassie InstantBlue™ (Expedeon, San Diego, Calif.) stain. Gels were imaged using a Gel Doc™ EZ imager (Bio-Rad, Hercules, Calif.) and annotated using ImageLab software (Bio-Rad, Hercules, Calif.). Each properly formed complex contained six molecules of Cas7, one molecule each of Cas6 and Cas5, and two molecules of Cse2.

C. Purification of FokI-Cas8 Fusion Protein

A method used to purify a fusion protein comprising a FokI nuclease fusion to the *E. coli* Type I-E Cas8 protein from bacterial over-expression pellets using immobilized metal affinity chromatography, cation exchange chromatography (CIEX), and finally size exclusion chromatography (SEC) is described herein.

The *E. coli* Type I-E FokI-Cas8 fusion protein, including a linker sequence, is described in Example 1 (SEQ ID NO:413, Table 11). The expression plasmid is described in Example 2 (SEQ ID NO:439, Table 14, FIG. 24B). Cells comprising the fusion protein were produced essentially as described in Example 4A. The Cas8 fusion protein contained a N-terminal His6 tag, a Maltose binding protein domain, a TEV cleavage site, a FokI nuclease domain, and a 30 amino acid linker. The protein was captured using immobilized metal affinity chromatography. A 50 mL conical tube containing the re-suspended cell pellets was thawed on ice. The tube was then placed in an ice water bath, and the cells were lysed by sonication using a Q500 sonicator with a ¼ inch tip (Qsonica, Newtown, Conn.) for a treatment cycle of three minutes with repeating cycles of 10 seconds of sonication at 40% amplitude followed by 20 seconds of rest. The lysates were clarified by centrifugation at 30,970 RCF for 30 minutes at 4° C. The clarified supernatant was then added to Hispur™ Ni-NTA resin (Thermofisher, Waltham, Mass.), that had been pre-equilibrated with Ni-wash buffer composed of 50 mM Tris pH 7.5, 100 mM NaCl, 10 mM imidazole, 5% glycerol, and 1 mM TCEP. A 2 mL bed volume of nickel affinity resin was used for 1 L of *E. coli* expression culture. After one hour of incubation at 4° C. with gentle mixing, the sample was poured onto a 30 mL disposable gravity flow column (Bio-Rad, Hercules, Calif.), allowing the unbound material to flow through the column. The resin was washed five times with five bed volumes of Ni-wash buffer. Finally, the bound proteins were eluted with five bed volumes of Ni-elution buffer composed of 50 mM Tris pH 7.5, 100 mM NaCl, 300 mM imidazole, 5% glycerol, and 1 mM TCEP.

The nickel affinity eluate was treated with TEV protease to remove the affinity tag. TEV protease was added to the eluate at a ratio of 1:25 (w/w). The sample, including TEV, was dialyzed overnight against Ni-wash buffer using a 12 mL Slid-A-Lyzer™, 10K MWCO dialysis cassette (Thermofisher, Waltham, Mass.).

The TEV protease and the cleaved His6-MBP fragment were removed from the dialyzed sample by Ni affinity chromatography. The dialyzed sample was poured over a clean Hispur™ Ni-NTA resin (Thermofisher, Waltham, Mass.) column equilibrated with Ni-wash buffer. The resin was then washed with 1 column volume of Ni-NTA wash buffer. The flow through and wash were combined, concentrated, and exchanged into storage buffer (50 mM Tris pH 7.5, 500 mM NaCl, 5% glycerol, and 1 mM TCEP) using an Amicon® spin concentrator with an Ultracel®-10 membrane (Millipore Sigma, Billerica, Mass.). This sample was then frozen at −80C for storage.

The sample was thawed and further purified by cation exchange chromatography (CIEX). The sample was thawed on ice and diluted 10-fold from 0.475 mL to 4.75 mL with Cold CIEX_A buffer composed of 50 mM Tris pH 7.5, 5% glycerol, and 1 mM TCEP, resulting in a final concentration of 50 mM NaCl. A 10 mL capillary loop was used to load the sample onto a 1 mL Hitrap™ SP HP column (GE Healthcare, Uppsala, Sweden), equilibrated with a buffer comprising CIEX_A buffer and 5% CIEX_B buffer (50 mM Tris pH 7.5, 1 M NaCl, 5% glycerol, and 1 mM TCEP). The flow rate throughout the separation was of 0.75 mL/min. The loop was emptied onto the column with 15 mL of with 5% CIEX_B buffer. The unbound sample was washed out with an additional 2 mL of 5% CIEX_B buffer. 500 μL fractions were collected as the bound proteins were eluted with an 8 mL linear gradient from 5% to 65% CIEX_B buffer. There were two major UV280 elution peaks. The four fractions corresponding to the first of those two peaks were pooled. The total pooled volume was 2 mL.

The pooled CIEX fractions were further purified by SEC. The pooled CIEX fractions were concentrated to a final volume of 0.3 mL by ultrafiltration at 12° C. using an Amicon® spin concentrator with an Ultracel®-10 membrane (Millipore Sigma, Billerica, Mass.). The concentrated sample was filtered using a 0.22 μm Ultrafree-MC GV Centrifugal spin filter (Millipore Sigma, Billerica, Mass.), and further purified by separation at 4° C. with a flow rate of 0.6 mL/minute on a 10/300 Superdex™ 200 GL Increase column (GE Healthcare, Uppsala, Sweden) equilibrated with a Cas8 SEC buffer (50 mM Tris pH 7.5, 200 mM NaCl, 5% glycerol, and 1 mM TCEP). The protein was eluted with the Cas8 SEC buffer and 0.5 ml fractions were collected. The earliest eluting peak, as judged by UV 280, was assumed to be high molecular weight aggregated material and the corresponding fractions were discarded. A second major UV 280 peak was eluted after about 14 mL. The fractions corresponding to this second peak were pooled. The pooled samples were concentrated to 40 μL with an Amicon® spin concentrator with an Ultracel®-3 membrane (Millipore Sigma, Billerica, Mass.) The concentrated sample was stored at −80° C.

The final purified product was analyzed spectrophotometrically to determine the final concentration of the fusion protein and to confirm the absence of a significant nucleic acid component as evidenced by an absorbance at 280 nm that is greater than the absorbance at 260 nm. The concentration of the FokI-Cas8 fusion was determined by dividing the absorbance at 280 nm by the calculated absorbance of a 0.1% solution of the intact complex. The predicted absorbance of a 0.1% solution of the purified complex is 1.05 cm$^{-1}$ and was calculated by dividing extinction coefficient at 280 nm for the FokI-Cas8 fusion (86290 M$^{-1}$ cm$^{-1}$) by its molecular weight (82171.32 g/mole). Additionally, the final product was analyzed by SDS-PAGE gels stained with InstantBlue™ stain (Expedeon, San Diego, Calif.). Gels were imaged using a Gel Doc™ EZ imager (Bio-Rad, Hercules, Calif.) and annotated using ImageLab software (Bio-Rad, Hercules, Calif.). This analysis demonstrates that the purified fusion protein was the expected size and that only a low level of contaminating proteins were present.

Example 6

Production of Double-stranded DNA (dsDNA) Target Sequences for Use in Biochemical Cleavage Assays Double-stranded DNA (dsDNA) target sequences for use in in vitro DNA binding or cleavage assays with Cascade or Cascade-fusion effector complexes can be produced using several different methods. This Example describes three methods to produce target sequences, including annealing of synthetic single-stranded DNA (ssDNA) oligonucleotides, PCR amplification of selected nucleic acid target sequences from genomic DNA, and/or cloning of nucleic acid target sequences into bacterial plasmids. The dsDNA target sequences were used in Cascade binding or cleavage assays.

A. Production of dsDNA Target Sequences by Annealing Synthetic Single-stranded DNA Oligonucleotides DNA oligonucleotides encoding the target region of interest comprising the target sequence, also known as the protospacer, that is recognized by the guide portion of CRISPR RNA, the neighboring protospacer adjacent motif (PAM), and additional 5' and 3' flanking sequences were purchased from a commercial manufacturer (Integrated DNA Technologies, Coralville, Iowa). Two oligonucleotides were ordered per construct, one comprising the sense strand and one comprising the nonsense strand. Table 21 lists oligonucleotide sequences that were ordered to contain a target sequence denoted J3, which is derived from bacteriophage lambda genomic DNA. The target and PAM sequences are flanked by 20-bp of additional sequence on both the 5' and 3' ends.

TABLE 21

Single-stranded DNA Oligonucleotides

| Seq ID NO: | Description | Sequence |
|---|---|---|
| SEQ ID NO: 466 | Foward oligo, J3 target sequence | ATCATCCTCCTGACAATTTTGACAGCCCACATGGC ATTCCACTTATCACTGGCATCTTTAAAAGCCAGGA CGGTC |
| SEQ ID NO: 467 | Reverse oligo, J3 target sequence | GACCGTCCTGGCTTTTAAAGATGCCAGTGATAAGT GGAATGCCATGTGGGCTGTCAAAATTGTCAGGAG GATGAT |

The oligonucleotides were annealed by mixing both oligonucleotides at equimolar concentration (10 μM) in 1× annealing buffer (6 mM HEPES, pH 7.0, and 60 mM KCl), heating at 95° C. for 2 minutes, and then slow cooling. Annealed oligonucleotides were then used directly in DNA binding and/or DNA cleavage assays with Cascade and/or Cascade-effector domain fusion RNPs.

5' Cy5 fluorescently-labeled DNA oligonucleotides encoding the target region of interest comprising both the target sequence, also known as the protospacer, recognized by the guide portion of CRISPR RNA, as well as the flanking neighboring protospacer adjacent motif (PAM), and additional 5' and 3' flanking sequences, were purchased from a commercial manufacturer (Integrated DNA Technologies, Coralville, Iowa). Four oligonucleotides were ordered per construct, one comprising the 5' fluorescent-labeled sense strand, one comprising the 5' unlabeled sense strand, one comprising the 5' fluorescent-labeled nonsense strand, and one comprising the 5' unlabeled nonsense strand. The target and PAM sequences are flanked by 20-bp of additional sequence on both the 5' and 3' ends.

Table 22 lists oligonucleotide sequences that were ordered to contain a target sequence denoted J3, which was derived from bacteriophage lambda genomic DNA and a control target sequence denoted CCR5, which was derived from the human CCR5 locus.

The oligonucleotides were annealed by mixing a labeled and unlabeled or two labeled or two unlabeled oligonucleotides at equimolar concentration (1 µM) in 1× annealing buffer (6 mM HEPES, pH 7.0, 60 mM KCl), heating at 95° C. for 2 minutes, and then slow cooling. Annealed oligonucleotides were then used directly in DNA binding assays with Cascade and/or Cascade-effector domain fusion RNPs. Cy5 fluorescently-labeled DNA oligonucleotides were imaged with an AZURE c600 Bioimager (Azure BioSystems, Dublin, Calif.).

This method can be applied to produce additional labeled or unlabeled target or dual-target sequences, whereby a dual target is defined as a target that contains two protospacer sequences targeted by individual Cascade molecules, separated by an interspacer sequence.

B. Production of dsDNA Target Sequences by PCR Amplification from Genomic DNA

Double-stranded DNA target sequences for dual targets derived from human genomic DNA were produced using PCR amplification directly from genomic DNA template material. Specifically, PCR reactions contained human genomic DNA purified from K562 cells and Q5 Hot Start High-Fidelity 2× Master Mix (New England Biolabs, Ipswich, Mass.), as well as the primers listed in Table 23, where the underlined portions correspond to primer binding sites within genomic DNA.

TABLE 22

Single-stranded DNA (ssDNA) Oligonucleotides for Fluorescently Labeled dsDNA Target Sequence Formation

| SEQ ID NO: | Description | Sequence |
| --- | --- | --- |
| SEQ ID NO: 468 | target strand J3 | 5'CGCCGAGCTCGAATTCTTTTGACAGCCCACATG GCATTCCACTTATCACTGGCATGGATCCTGGCTG TGGTGATG |
| SEQ ID NO: 469 | non target strand J3 | 5'CATCACCACAGCCAGGATCCATGCCAGTGATA AGTGGAATGCCATGTGGGCTGTCAAAAGAATTC GAGCTCGGCG |
| SEQ ID NO: 470 | target strand CCR5 Site | 5'CGCCGAGCTCGAATTCTTTTTAGGTACCTGGCT GTCGTCCATGCTGTGTTTGCATGGATCCTGGCTG TGGTGATG |
| SEQ ID NO: 471 | non target strand CCR5 | 5'CATCACCACAGCCAGGATCCATGCAAACACAG CATGGACGACAGCCAGGTACCTAAAAAGAATTC GAGCTCGGCG |
| SEQ ID NO: 472 | target strand J3 | 5'Cy5-CGCCGAGCTCGAATTCTTTTGACAGCCCACATGG CATTCCACTTATCACTGGCATGGATCCTGGCTGT GGTGATG |
| SEQ ID NO: 473 | non target strand J3 | 5'Cy5-CATCACCACAGCCAGGATCCATGCCAGTGATAA GTGGAATGCCATGTGGGCTGTCAAAAGAATTCG AGCTCGGCG |
| SEQ ID NO: 474 | target strand CCR5 Site | 5'Cy5-CGCCGAGCTCGAATTCTTTTTAGGTACCTGGCTG TCGTCCATGCTGTGTTTGCATGGATCCTGGCTGT GGTGATG |

TABLE 23

Primers for PCR Amplification

| SEQ ID NO: | Description | Sequence |
|---|---|---|
| SEQ ID NO: 475 | Forward primer to amplify Hsa07 dual-target from human genomic DNA | CACTCTTTCCCTACACGACGCTCTT CCGAT<u>CTTTCCTCCCTAACCTCCAC CT</u> |
| SEQ ID NO: 476 | Reverse primer to amplify Hsa07 dual-target from human genomic DNA | GGAGTTCAGACGTGTGCTCTTCCG ATCTTA<u>AAGAGCCCAACCAGATGC</u> |

PCR was performed according to the manufacturer's instructions (New England Biolabs, Ipswich, Mass.), and the desired product DNA, 288-bp in length, was purified using a Nucleospin Gel and PCR Cleanup kit (Macherey-Nagel, Bethlehem, Pa.) This dsDNA was then used directly in DNA binding and/or DNA cleavage assays with Cascade and/or Cascade-effector domain fusion RNPs.

C. Production of dsDNA Target Sequences by Cloning Target Sequences into Bacterial Plasmids DNA oligonucleotides encoding the target region of interest comprising the target sequence, also known as the protospacer, that is recognized by the guide portion of CRISPR RNA, the neighboring protospacer adjacent motif (PAM), and additional 5' and 3' flanking sequences were purchased from a commercial manufacturer (Integrated DNA Technologies, Coralville, Iowa). The oligonucleotides were designed such that, when annealed, the termini regenerate sticky ends upon cleavage of their respective recognition sites by the restriction enzymes EcoRI and BlpI, or by BamHI and EcoRI. Oligonucleotides were designed to contain a single target sequence derived from the bacteriophage lambda genome, denoted J3. In addition, oligonucleotides were designed to contain two tandem target sequences derived from the bacteriophage lambda genome, denoted J3 and L3, separated from each other by a 15-bp interspacer sequence. Sequences of these oligonucleotides are listed in Table 24.

TABLE 24

Oligonucleotides Comprising Target Sequences

| SEQ ID NO: | Description | Restriction enzyme recognition sites | Sequence |
|---|---|---|---|
| SEQ ID NO: 477 | Forward oligonucleotide, J3 target sequence for cloning into PACYC-Duet1 | BamHI and EcoRI | GATCCATGCCAGTGATAAGTG GAATGCCATGTGGGCTGTCAA AAG |
| SEQ ID NO: 478 | Reverse oligonucleotide, J3 target sequence for cloning into PACYC-Duet1 | BamHI and EcoRI | AATTCTTTTGACAGCCCACATG GCATTCCACTTATCACTGGCAT G |
| SEQ ID NO: 479 | Foward oligonucleotide, J3-15bp-L3 target sequences for cloning into pACYC-Duet1 | EcoRI and BlpI | AATTCTTTTGACAGCCCACATG GCATTCCACTTATCACTGGCAT CCTAGGCCTCTCGAGATGAGTG GCAGATATAGCCTGGTGGTTCA GGCGGCGCATGC |
| SEQ ID NO: 480 | Reverse oligonucleotide, J3-15bp-L3 target sequences for cloning into pACYC-Duet1 | EcoRI and BlpI | TCAGCATGCGCCGCCTGAACCA CCAGGCTATATCTGCCACTCAT CTCGAGAGGCCTAGGATGCCA GTGATAAGTGGAATGCCATGT GGGCTGTCAAAAG |

The oligonucleotides contain 5'-phosphorylated ends, which were introduced by the commercial manufacturer or phosphorylated in-house using T4 polynucleotide kinase (New England Biolabs, Ipswich, Mass.). The oligonucleotides were then annealed at a final concentration of 1 µM by mixing together equimolar amounts in annealing buffer (6 mM HEPES, pH 7.0, 60 mM KCl), heating to 95° C. for 2 minutes, and then slow-cooling on the benchtop.

Separately, a pACYC-Duet1 (MilliporeSigma, Hayward, Calif.) plasmid was double-digested with the corresponding pair of restriction enzymes, either BamHI and EcoRI, or EcoRI and BlpI, whose sticky ends match the sticky ends formed by the termini of the hybridized oligonucleotides. The double-digested vector was separated from the removed insert using agarose gel electrophoresis.

In order to clone the hybridized oligonucleotides into the double-digested vector, the hybridized oligonucleotides were diluted to a 50 nM stock concentration, and then a 10 µL ligation reaction was formed using hybridized oligonucleotides, the double-digested vector, and Quick Ligase from New England Biolabs. The ligation reaction was then used to transform chemically competent E. coli strains, and after overnight growth on agarose plates, individual clones were isolated and grown in liquid culture to generate sufficient bacterial cultures from which to isolate plasmids. Sanger sequencing was then used to validate the desired plasmid sequence. Table 25 provides complete vector sequences for plasmids containing the J3 target sequence (SEQ ID NO:481) and plasmids containing the J3 and L3 targets sequences separated by the 15-bp interspacer sequence (SEQ ID NO:482).

TABLE 25

Complete Plasmid Sequences

| SEQ ID NO: | Description of plasmid |
|---|---|
| SEQ ID NO: 481 | J3 target sequence in pACYC-Duet1 |
| SEQ ID NO: 482 | J3-15bp-L3 target sequences in pACYC-Duet1 |
| SEQ ID NO: 483 | J3-30bp-L3 target sequences in pACYC-Duet1 |
| SEQ ID NO: 484 | multi-target plasmid |

Further cloning manipulations were used to generate additional double-target plasmid constructs. The 15-bp interspacer sequence of SEQ ID NO:482 contains unique AvrII and XhoI restriction sites. Thus, introduction of additional hybridized oligonucleotides into these restriction sites expands the interspacer to longer lengths, for biochemical testing with purified Cascade and Cascade-nuclease fusion RNPs. Because the crRNA-guided FokI-Cascade fusion complex targets two adjacent DNA site, dimerization of the FokI domains from adjacent DNA-bound complexes leads to DNA cleavage within the interspacer separating the two target sites. Variable interspacer lengths were designed and tested to evaluate a given interspacer length with a given tethering geometry between the FokI nuclease domain and its fused Cascade subunit protein. The complete vector sequence for a target DNA substrate containing an expanded interspacer sequence of 30-bp in length is given in Table 25 as SEQ ID NO:483.

In addition, the following cloning strategy provided a plasmid substrate that contains several target sequences serially connected along one large insert. A gene block was ordered from a commercial manufacturer (Integrated DNA Technologies, Coralville, Iowa) that contained 17 consecutive dual targets. The gene block contained 4 bp separating each dual target from a neighboring dual target, and contained 16 dual targets derived from Homo sapiens genomic DNA, as well as one control dual target containing J3/L3 targets derived from the bacteriophage lambda genome. The genomic coordinates of the 16 consecutive human dual targets are shown in Table 26. The gene block was ordered with flanking SacI and SbfI restriction sites on the ends, such that it could be cloned into SacI and SbfI sites in the pACYC-Duet1 vector. The full vector sequence of the multi-target plasmid substrate generated by cloning the gene block into pACYC-Duet1 is presented as SEQ ID NO:484 in Table 25. This multi-target sequence plasmid allowed for biochemical testing of multiple different FokI-Cascade preparations harboring crRNAs targeting one of the serially connected target sites within the plasmid.

TABLE 26

Human Dual Targets

| SEQ ID NO: | Target name | Gene | 5' spacer target genomic coordinates | 3' spacer target genomic coordinates |
|---|---|---|---|---|
| SEQ ID NO: 485 | Hsa01 | PDCD1 | chr2: 241850348-241850382 | chr2: 241850408-241850442 |
| SEQ ID NO: 486 | Hsa02 | CTLA4 | chr2: 203870664-203870698 | chr2: 203870724-203870758 |
| SEQ ID NO: 487 | Hsa03 | TRAC | chr14: 22509340-22509374 | chr14: 22509405-22509439 |
| SEQ ID NO: 488 | Hsa04 | TRAC | chr14: 22509785-22509819 | chr14: 22509850-22509884 |
| SEQ ID NO: 489 | Hsa05 | TRAC | chr14: 22513932-22513966 | chr14: 22513997-22514031 |
| SEQ ID NO: 490 | Hsa06 | TRAC | chr14: 22515993-22516027 | chr14: 22516058-22516092 |
| SEQ ID NO: 491 | Hsa07 | TRAC | chr14: 22516265-22516299 | chr14: 22516330-22516364 |
| SEQ ID NO: 492 | Hsa08 | CD52 | chr1: 26320402-26320436 | chr1: 26320467-26320501 |
| SEQ ID NO: 493 | Hsa09 | CTLA4 | chr2: 203873012-203873046 | chr2: 203873077-203873111 |
| SEQ ID NO: 494 | Hsa10 | CTLA4 | chr2: 203873195-203873229 | chr2: 203873260-203873294 |
| SEQ ID NO: 495 | Hsa11 | TRAC | chr14: 22551630-22551664 | chr14: 22551700-22551734 |
| SEQ ID NO: 496 | Hsa12 | CTLA4 | chr2: 203872758-203872792 | chr2: 203872828-203872862 |
| SEQ ID NO: 497 | Hsa13 | TRAC | chr14: 22551862-22551896 | chr14: 22551937-22551971 |
| SEQ ID NO: 498 | Hsa14 | TRBC2 | chr7: 142801112-142801146 | chr7: 142801187-142801221 |
| SEQ ID NO: 499 | Hsa15 | TRAC | chr14: 22551630-22551664 | chr14: 22551710-22551744 |
| SEQ ID NO: 500 | Hsa16 | CTLA4 | chr2: 203867814-203867848 | chr2: 203867894-203867928 |

Example 7

Use of Purified Cascade Complexes in Biochemical Cleavage Assays

This Example illustrates the use of FokI-Cascade fusion protein complexes in biochemical double-stranded DNA (dsDNA) cleavage assays. Protein reagents were compared in terms of their activity in dsDNA cleavage.

FokI-Cascade RNPs derived from the E. coli Type I-E Cascade system were designed, recombinantly expressed in E. coli, and purified for use, as outlined in Examples 1, 2, and 5. These RNPs were designed to contain either CRISPR RNAs that target the J3 and L3 target sequences derived from bacteriophage lambda genomic DNA, or that target an intron in the TRAC gene within human genomic DNA. Each RNP preparation is a heterogeneous mixture comprising two FokI-Cascade complexes that are otherwise identical except for the guide portion of the crRNA.

A FokI-Cascade complex was reconstituted by mixing together a CasBCDE complex (produced using SEQ ID NO:440 and SEQ ID NO:446, as described in Example 2) with purified FokI-Cas8 comprising a 16-aa linker (the general FokI-Cas8 expression vector sequence is described in Example 2, SEQ ID NO:439 in Table 14; the particular 16-aa linker is in Example 1, SEQ ID NO:431 in Table 12). Reconstitution was performed in 1× Cascade Cleavage Buffer (20 mM Tris-Cl, pH 7.5, 200 mM NaCl, 5 mM MgCl$_2$, 1 mM TCEP, 5% glycerol) with CasBCDE and FokI-Cas8 both at 1 µM final concentrations.

In order to perform DNA cleavage assays, reaction mixtures were as follows. A plasmid substrate comprising the J3/L3 double-target sequence with a 30-bp interspacer (SEQ ID NO:483 in Table 25) was incubated with varying concentrations of FokI-Cascade complex (3-100 nM) in a 15 µL reaction in 1× Cascade Cleavage Buffer, with the plasmid DNA at a final concentration of 13.3 ng/µL. Reactions were incubated for 30 minutes at 37° C., after which 3 µL of 6×SDS loading dye was added. The loading dye was added to denature bound FokI-Cascade complexes. The reaction mixture components were resolved by 0.8% agarose gel electrophoresis. Gels were stained after electrophoresis with SYBR™ Safe DNA Gel Stain (Thermo Scientific, Wilmington, Del.).

As a positive control, *Streptococcus pyogenes* Cas9 protein was programmed with a single-guide RNA (sgRNA) targeting a 20-bp portion of the Cascade J3 target sequence (sgRNA-J3; the spacer sequence is presented as SEQ ID NO:501). Cas9/sgRNA-J3 complexes were reconstituted by mixing Cas9 together with a 2-fold molar excess of sgRNA in 1×CCE buffer (20 mM HEPES pH 7.4, 10 mM MgCl2, 150 mM KCl, 5% glycerol). Cleavage by this Cas9/sgRNA-J3 complex was evaluated across the same concentration range (3-100 nM) by incubating reactions for 30 minutes at 37° C. Also included in the experiment were control lanes containing uncut plasmid DNA, as well as plasmid DNA linearized with the NheI restriction enzyme (New England Biolabs, Ipswich, Mass.). Target DNA cleavage is evidenced by a mobility shift in the plasmid, because uncut plasmid DNA is supercoiled and has a faster mobility than cleaved, linearized plasmid DNA. Nicked, open-circular plasmid DNA has a slower mobility than both supercoiled and linearized plasmid DNA.

The data obtained from these experiments demonstrate that, over the concentration range, the FokI-Cascade complex exhibited similar target DNA cleavage activity as Cas9-sgRNA. At the highest concentration tested (100 nM), the plasmid target was quantitatively linearized by the FokI-Cascade complex and Cas9-sgRNA.

FokI-Cascade complex reagents were also tested for their kinetics of target DNA cleavage. A plasmid substrate containing the J3/L3 double-target sequence with a 30-bp interspacer (SEQ ID NO:483) was incubated with 200 nM FokI-Cascade complex or 200 nM Cas9-sgRNA in a 15 µL reaction, with the plasmid DNA at a final concentration of 13.3 ng/µL. Reactions were quenched at either 0, 7, 10, 15, 20, 25, or 30 minutes, and reaction components were resolved by agarose gel electrophoresis as described above. The FokI-Cascade complex exhibited similar but slightly slower rates of target DNA cleavage activity as Cas9/sgRNA-J3 complex, with the target plasmid quantitatively linearized by the 25 minute time-point for the FokI-Cascade complex and by the 20 minute time point for the Cas9/sgRNA-J3 complex.

FokI-Cascade complex reagents were also tested for their non-specific DNA cleavage and/or nicking activity on the pACYC-Duet1 non-target plasmid substrate, versus specific DNA cleavage of a the J3/L3 double-target plasmid substrate. Table 27 contains the sequence of the pACYC-Duet1 non-target plasmid substrate used for this control (SEQ ID NO:502). Specifically, the dependence of non-specific and specific DNA target cleavage was investigated as a function of the monovalent salt concentration in the reaction buffer. Modified variants of the 1× Cascade Cleavage Buffer (20 mM Tris-Cl, pH 7.5, 200 mM NaCl, 5 mM MgCl$_2$, 1 mM TCEP, and 5% glycerol) were prepared, in which the NaCl concentration was dropped from 200 mM to either 150 mM, 100 mM or 50 mM, and the same cleavage reactions as described above were performed by incubating 200 nM FokI-Cascade complex with either 13.3 ng/µL of the J3/L3 target plasmid or 13.3 ng/µL of the pACYC-Duet1 non-target plasmid. Additional control reactions were performed, in which the NaCl concentration was maintained at 100 mM, but the 5 mM MgCl2 was replaced with 10 mM EDTA, which was expected to abrogate cleavage because of the requirement of FokI for divalent metal ions for DNA cleavage. Accordingly, non-target plasmid and J3/L3 target plasmid were subjected to the following reaction conditions: −FokI-Cascade complex; +FokI-Cascade complex, 100 mM NaCl buffer+10 mM EDTA; +FokI-Cascade complex, 50 mM NaCl buffer; +FokI-Cascade complex, 100 mM NaCl buffer; +FokI-Cascade complex, 150 mM NaCl buffer; +FokI-Cascade complex, 200 mM NaCl buffer. The data demonstrate that FokI-Cascade complex showed non-specific nicking of both the non-target and J3/L3 target plasmid at low salt concentrations <200 mM NaCl, but that at a monovalent salt concentration of 200 mM NaCl, the non-target plasmid remained intact, but the J3/L3 target plasmid was quantitatively linearized. Furthermore, buffer containing EDTA led to a complete abrogation of target cleavage, as expected.

In order to confirm that the FokI-Cascade complex cleaves the target plasmid at the expected position, that is, within the middle of the interspacer sequence separating the J3 and L3 targets, an experiment was performed in which the target plasmid was first incubated with FokI-Cascade complex, followed by incubation with the AfeI restriction enzyme (New England Biolabs, Ipswich, Mass.), which cleaves elsewhere in the plasmid substrate. Thus, cleavage by both FokI-Cascade 1 complex and AfeI converts the supercoiled, circular plasmid into two linear fragments migrating as distinct species on an agarose gel. Specifically, cleavage was expected to generate fragments that are 2427 bp and 1357 bp in length.

13.3 ng/µL J3/L3 target plasmid was incubated with 200 nM FokI-Cascade 1 complex for 30 minutes, after which 1 µL of AfeI (10 Units/µL; New England Biolabs, Ipswich, Mass.) was added to the reaction, followed by an additional 30-minute incubation at 37° C. Reaction products were resolved by agarose gel electrophoresis, as described above. Additionally, for control experiments, the target plasmid was incubated with only FokI-Cascade 1 complex or only AfeI, and the same reactions were performed with a non-target plasmid that can be cleaved by AfeI but not by FokI-Cascade 1 complex (because the plasmid lacks the J3/L3 dual target). Table 27 contains the sequence of the pACYC-Duet1 non-target plasmid substrate used for this control (SEQ ID NO:502). Accordingly, non-target plasmid and J3/L3 target plasmid were subjected to the following reaction conditions: −AfeI/−FokI-Cascade complex; −AfeI/+FokI-Cascade complex; +AfeI/+FokI-Cascade complex; and +AfeI/−FokI-Cascade complex. The data demonstrate that FokI-Cascade complex cleaved the target plasmid in the expected location, because co-incubation with FokI-Cascade 1 complex and AfeI lead to two linear products of the expected lengths.

In order to further confirm the sequence specificity of DNA cleavage by the FokI-Cascade complex, additional control plasmid substrates were generated that contain as follows: mutations in the PAM flanking the J3 target, mutations in the PAM flanking the L3 target, mutations in both PAMs flanking J3/L3 targets; mutations in the spacer sequence within the J3 target, mutations in the spacer sequence within the L3 target, mutations in both spacer sequences within J3/L3 targets; and the J3 target but not the L3 target, the L3 target but not the J3 target, and neither J3 nor L3 target. Accordingly, the plasmid substrates were as follows: J3 PAM mutant, L3 PAM mutant, J3/L3 PAM mutant, J3 spacer mutant, L3 spacer mutant, J3/L3 spacer mutant, non-target plasmid, J3-only target, L3-only target, and J3/L3 target plasmid. Each target was subjected to the following reaction conditions: −NdeI/−FokI-Cascade complex; +NdeI/−FokI-Cascade complex; and −NdeI/+FokI-Cascade 1 complex. Table 27 contains the sequences of all the mutated plasmid substrates described above (SEQ ID NO:502 through SEQ ID NO:510).

TABLE 27

Mutated Plasmid Substrate Sequences

| SEQ ID NO: | Description of plasmid |
| --- | --- |
| SEQ ID NO: 502 | pACYC-Duet1 non-target plasmid |
| SEQ ID NO: 503 | J3-30bp-L3 target plasmid, J3 PAM mutant |
| SEQ ID NO: 504 | J3-30bp-L3 target plasmid, L3 PAM mutant |
| SEQ ID NO: 505 | J3-30bp-L3 target plasmid, J3/L3 PAM mutants |
| SEQ ID NO: 506 | J3-30bp-L3 target plasmid, J3 spacer mutant |
| SEQ ID NO: 507 | J3-30bp-L3 target plasmid, L3 spacer mutant |
| SEQ ID NO: 508 | J3-30bp-L3 target plasmid, J3/L3 spacer mutants |
| SEQ ID NO: 509 | J3-only target plasmid |
| SEQ ID NO: 510 | L3-only target plasmid |

DNA cleavage reactions were performed as described above, using 200 nM FokI-Cascade complex and 13.3 ng/μL plasmid substrates; control reactions to linearize each plasmid substrate were performed with NdeI (New England Biolabs, Ipswich, Mass.). Agarose gel electrophoresis was performed as described above. The data demonstrate that efficient double-strand beak introduction and linearization of the target plasmid is only observed for the J3/L3 target plasmids, but not for control plasmids harboring PAM or seed mutations, or only one of the two target sites.

Components for various FokI-Cascade complexes were cloned and overexpressed. RNPs produced by these components were purified and tested for biochemical DNA cleavage, in order to compare activity for different FokI-Cascade complexes. Specifically, DNA cleavage activities were compared for reconstituted FokI-Cascade complexes comprising the following: separately purified CasBCDE complex (produced using SEQ ID NO:440 and SEQ ID NO:446) and FokI-Cas8 (produced using SEQ ID NO:439); FokI-Cascade harboring the J3/L3 guide crRNAs (produced using SEQ ID NO:442 and SEQ ID NO:446); FokI-Cascade harboring an additional nuclear localization signal on either the Cas7 subunit (produced using SEQ ID NO:443 and SEQ ID NO:446) or the Cas6 subunit; FokI-Cascade harboring an additional nuclear localization signal and HA tag on either the Cas7 subunit or the Cas6 subunit; FokI-Cascade that underwent a more stringent purification involving both size exclusion chromatography (SEC) and ion exchange chromatography (IEX); and FokI-Cascade that was purified only by immobilized metal affinity chromatography (IMAC), without further clean-up.

Accordingly, non-target plasmid and J3/L3 target plasmid were subjected to the following reaction conditions: negative control; AfeI; CasBCDE+FokI-Cas8 complex; FokI-Cascade complex; FokI-Cascade (NLS-Cas6) complex; FokI-Cascade (Cas7-NLS) complex; FokI-Cascade (NLS-HA-Cas6) complex; FokI-Cascade (Cas7-HA-NLS) complex; FokI-Cascade complex (IEX, SEC clean-up); and FokI-Cascade complex (no clean-up). DNA cleavage reactions were performed with these RNP reagents as described above, using either the non-target plasmid or the consensus J3/L3 target plasmids, and reaction products were resolved by agarose gel electrophoresis. The data demonstrate that all of the RNP reagents, with one exception, exhibit nearly identical and quantitative plasmid DNA cleavage, with no background cleavage of the non-target plasmid. The sole exception was the FokI-Cascade purified without further clean-up, which exhibited more non-specific nicking activity, as seen for the lane in which it was incubated with the non-target plasmid.

Finally, using the NLS-tagged Cas7 variant of the FokI-Cascade complex as a starting point, 16 different paired guide crRNA were tested for biochemical DNA cleavage of a plasmid substrate for *Homo sapiens* genomic sites Hsa01 through Hsa16 serially connected along one large insert (SEQ ID NO:484). Each pair of crRNAs contains two unique spacer sequences that correspond to two adjacent target sites in human genomic DNA, separated by an interspacer; the target sequences are described in SEQ ID NO:485 through SEQ ID NO:500. Table 28 contains sequences of both crRNAs within each pair that targets Hsa01 through Hsa16 genomic DNA sequences; the spacer of the crRNA is underlined and in lower case, and the sequences 5' and 3' of the guide region correspond to repeat sequences from the CRISPR array.

TABLE 28 crRNA Sequences

| SEQ ID NO: | DNA target | crRNA sequence |
| --- | --- | --- |
| SEQ ID NO: 511 | Hsa01-1 | AUAAACCGcgggcaggcagagcuggaggccuuucaggccc GAGUUCCCCGCGCCAGCGGGG |
| SEQ ID NO: 512 | Hsa01-2 | AUAAACCGggccugaggugcugccugggcauguguaaagg GAGUUCCCCGCGCCAGCGGGG |
| SEQ ID NO: 513 | Hsa02-1 | AUAAACCGcacugucacccggaccucagtggcuuugccug GAGUUCCCCGCGCCAGCGGGG |
| SEQ ID NO: 514 | Hsa02-2 | AUAAACCGucugugcggcaaccuacaugaugggaaugag GAGUUCCCCGCGCCAGCGGGG |

TABLE 28-continued crRNA Sequences

| SEQ ID NO: | DNA target | crRNA sequence |
|---|---|---|
| SEQ ID NO: 515 | Hsa03-1 | AUAAACCGaugagcuuguuuguagcaccaccauaauucacGAGUUCCCCGCGCCAGCGGGG |
| SEQ ID NO: 516 | Hsa03-2 | AUAAACCGuacguaaguaguggcaugugucaggugg auucGAGUUCCCCGCGCCAGCGGGG |
| SEQ ID NO: 517 | Hsa04-1 | AUAAACCGaaggcauuuggaccggcagacacauaauuguaGAGUUCCCCGCGCCAGCGGGG |
| SEQ ID NO: 518 | Hsa04-2 | AUAAACCGagacuccagagccauccuugggaagagugcugGAGUUCCCCGCGCCAGCGGGG |
| SEQ ID NO: 519 | Hsa05-1 | AUAAACCGacaagagguguguuuccugaauucccacagugGAGUUCCCCGCGCCAGCGGGG |
| SEQ ID NO: 520 | Hsa05-2 | AUAAACCGuaaguguuucuagccauccuugauuuugaucaGAGUUCCCCGCGCCAGCGGGG |
| SEQ ID NO: 521 | Hsa06-1 | AUAAACCGuggcuacugcucugucuccugggauccugccuGAGUUCCCCGCGCCAGCGGGG |
| SEQ ID NO: 522 | Hsa06-2 | AUAAACCGgcccauaccuucaaggaaaauuaaggcaaauaGAGUUCCCCGCGCCAGCGGGG |
| SEQ ID NO: 523 | Hsa07-1 | AUAAACCGguugauuugccugcauuggguguuacacagucuGAGUUCCCCGCGCCAGCGGGG |
| SEQ ID NO: 524 | Hsa07-2 | AUAAACCGuaaguuguguucuucuuugccuaggccuucagGAGUUCCCCGCGCCAGCGGGG |
| SEQ ID NO: 525 | Hsa08-1 | AUAAACCGgcacugccugucaacuucuacaaccuggugauGAGUUCCCCGCGCCAGCGGGG |
| SEQ ID NO: 526 | Hsa08-2 | AUAAACCGuaggggccaagcagugcccagcuggggg ucaaGAGUUCCCCGCGCCAGCGGGG |
| SEQ ID NO: 527 | Hsa09-1 | AUAAACCGcuuucacugaaagugg agcugaugugacagaaGAGUUCCCCGCGCCAGCGGGG |
| SEQ ID NO: 528 | Hsa09-2 | AUAAACCGauguggg ucaaggaauuaaguuagg g aauggcGAGUUCCCCGCGCCAGCGGGG |
| SEQ ID NO: 529 | Hsa10-1 | AUAAACCGgcauaaaauuuaacuugaaaagaucauuucggGAGUUCCCCGCGCCAGCGGGG |
| SEQ ID NO: 530 | Hsa10-2 | AUAAACCGgcuucaaaaauacucacaugg cuauguuuuagGAGUUCCCCGCGCCAGCGGGG |
| SEQ ID NO: 531 | Hsa11-1 | AUAAACCGaggggcaaugcagaggaaggagcgagggagcaGAGUUCCCCGCGCCAGCGGGG |
| SEQ ID NO: 532 | Hsa11-2 | AUAAACCGgaggugaaagcugcuaccaccucugugcccccGAGUUCCCCGCGCCAGCGGGG |
| SEQ ID NO: 533 | Hsa12-1 | AUAAACCGgcugaaauugcuuuucacauucggcucuguuGAGUUCCCCGCGCCAGCGGGG |
| SEQ ID NO: 534 | Hsa12-2 | AUAAACCGagaguccauauuucaauuccaagagcugaggGAGUUCCCCGCGCCAGCGGGG |
| SEQ ID NO: 535 | Hsa13-1 | AUAAACCGugcacagccaggggaggcugcagcagccuugcGAGUUCCCCGCGCCAGCGGGG |
| SEQ ID NO: 536 | Hsa13-2 | AUAAACCGauggaucuucagugggguucucuugggcucuagGAGUUCCCCGCGCCAGCGGGG |
| SEQ ID NO: 537 | Hsa14-1 | AUAAACCGccuguggccaggcacaccaguqUGGCCUUUUGGAGUUCCCCGCGCCAGCGGGG |
| SEQ ID NO: 538 | Hsa14-2 | AUAAACCGgaggugcacaguggggucagcacagacccgcaGAGUUCCCCGCGCCAGCGGGG |
| SEQ ID NO: 539 | Hsa15-1 | AUAAACCGaggggcaaugcagaggaaggagcgagggagcaGAGUUCCCCGCGCCAGCGGGG |

TABLE 28-continued crRNA Sequences

| SEQ ID NO: | DNA target | crRNA sequence |
|---|---|---|
| SEQ ID NO: 540 | Hsa15-2 | AUAAACCGcugcuaccaccucugugccccccggcaaugcGAGUUCCCCGCGCCAGCGGGG |
| SEQ ID NO: 541 | Hsa16-1 | AUAAACCGgacuuuauauagauagcuuugaucccagauauGAGUUCCCCGCGCCAGCGGGG |
| SEQ ID NO: 542 | Hsa16-2 | AUAAACCGguuuugcucuacuuccugaagaccugaacaccGAGUUCCCCGCGCCAGCGGGG |

After the 16 FokI-Cascade complexes were purified, cleavage reactions were performed as described above, wherein the FokI-Cascade complexes were incubated with the plasmid substrate containing *Homo sapiens* genomic sites Hsa01 through Hsa16, and the reaction products were resolved by agarose gel electrophoresis. The data demonstrate that, of the 16 RNP reagents, 14/16 (Hsa03-Hsa16) exhibited nearly quantitative DNA cleavage, as evidenced by conversion of the supercoiled, circular plasmid substrate into the cleaved, linear form. Only constructs Hsa01 and Hsa02 showed partial nicking activity.

Example 8

Introduction of FokI-Cascade RNP Complexes into Target Cells

This Example illustrates the design and delivery of *E. coli* Type I-E Cascade complexes comprising FokI fusion proteins to facilitate genome editing in human cells and describes their delivery into target cells as pre-assembled Cascade RNP complexes.

A. Production of Cascade RNP Complexes Comprising FokI for Transformation into Cells Minimal CRISPR arrays were designed to target eight distinct loci in the human genome. Each minimal CRISPR array contained two spacer sequences, both of which were flanked by CRISPR repeat sequences. The two spacer sequences targeted loci in the genome separated by 30 bp (i.e., a 30-bp interspacer region), and each spacer was designed to bind a target sequence adjacent to an AAG or ATG protospacer adjacent motif (PAM) sequence in the target cell genome. Plasmid vectors containing each minimal CRISPR array were produced by ligating annealed oligonucleotides (Integrated DNA Technologies, Coralville, Iowa) into a pACYC-Duet1 (Millipore Sigma, Billerica, Mass.) vector backbone for bacterial expression.

Overlapping primers to produce selected spacers in minimal CRISPR arrays are set forth in Table 29, and the sequences of the primers are described in Table 30.

TABLE 29

Overlapping Primers for Generation of Minimal CRISPR arrays

| Component | Gene target | Primers |
|---|---|---|
| Hsa03 Minimal CRISPR array | TRAC intron | A, B |
| Hsa04 Minimal CRISPR array | TRAC intron | C, D |
| Hsa05 Minimal CRISPR array | TRAC intron | E, F |
| Hsa06 Minimal CRISPR array | TRAC intron | G, H |
| Hsa07 Minimal CRISPR array | TRAC intron | I, J |
| Hsa08 Minimal CRISPR array | CD52 exon | K, L |
| Hsa09 Minimal CRISPR array | CTLA4 exon | M, N |
| Hsa10 Minimal CRISPR array | CTLA4 exon | O, P |

TABLE 30

DNA Primer Sequences

| SEQ ID NO: | Oligo-nucleotide | Sequence |
|---|---|---|
| SEQ ID NO: 543 | A | /5Phos/ACCGATGAGCTTGTTTGTAGCACCACCATAATTCACGAGTTCCCCGCGCCAGCGGGGATAAACCGTACGTAAGTAGTGGCATGTGTCAGGTGGATTC |
| SEQ ID NO: 544 | B | /5Phos/ACTCGAATCCACCTGACACATGCCACTACTTACGTACGGTTTATCCCCGCTGGCGCGGGGAACTCGTGAATTATGGTGGTGCTACAAACAAGCTCAT |
| SEQ ID NO: 545 | C | /5Phos/ACCGAAGGCATTTGGACCGGCAGACACATAATTGTAGAGTTCCCCGCGCCAGCGGGGATAAACCGAGACTCCAGAGCCATCCTTGGGAAGAGTGCTG |
| SEQ ID NO: 546 | D | /5Phos/ACTCCAGCACTCTTCCCAAGGATGGCTCTGGAGTCTCGGTTTATCCCCGCTGGCGCGGGGAACTCTACAATTATGTGTCTGCCGGTCCAAATGCCTT |

TABLE 30-continued

DNA Primer Sequences

| SEQ ID NO: | Oligo-nucleotide | Sequence |
|---|---|---|
| SEQ ID NO: 547 | E | /5Phos/ACCGACAAGAGGTGTGTTTCCTGAATTCCCACA GTGGAGTTCCCCGCGCCAGCGGGGATAAACCGTAAGT GTTTCTAGCCATCCTTGATTTTGATCA |
| SEQ ID NO: 548 | F | /5Phos/ACTCTGATCAAAATCAAGGATGGCTAGAAACAC TTACGGTTTATCCCCGCTGGCGCGGGGAACTCCACTGT GGGAATTCAGGAAACACACCTCTTGT |
| SEQ ID NO: 549 | G | /5Phos/ACCGTGGCTACTGCTCTGTCTCCTGGGATCCTGC CTGAGTTCCCCGCGCCAGCGGGGATAAACCGGCCCAT ACCTTCAAGGAAAATTAAGGCAAATA |
| SEQ ID NO: 550 | H | /5Phos/ACTCTATTTGCCTTAATTTTCCTTGAAGGTATGG GCCGGTTTATCCCCGCTGGCGCGGGGAACTCAGGCAG GATCCCAGGAGACAGAGCAGTAGCCA |
| SEQ ID NO: 551 | I | /5Phos/ACCGGTTGATTTGCCTGCATTGGTGTTACACAGT CTGAGTTCCCCGCGCCAGCGGGGATAAACCGTAAGTTG TGTTCTTCTTTGCCTAGGCCTTCAG |
| SEQ ID NO: 552 | J | /5Phos/ACTCCTGAAGGCCTAGGCAAAGAAGAACACAAC TTACGGTTTATCCCCGCTGGCGCGGGGAACTCAGACTG TGTAACACCAATGCAGGCAAATCAAC |
| SEQ ID NO: 553 | K | /5Phos/ACCGGCACTGCTGTCAACTTCTACAACCTGGTG ATGAGTTCCCCGCGCCAGCGGGGATAAACCGTAGGGG CCAAGCAGTGCCCAGCTGGGGGTCAA |
| SEQ ID NO: 554 | L | /5Phos/ACTCTTGACCCCCAGCTGGGCACTGCTTGGCCCC TACGGTTTATCCCCGCTGGCGCGGGGAACTCATCACCA GGTTGTAGAAGTTGACAGGCAGTGC |
| SEQ ID NO: 555 | M | /5Phos/ACCGCTTTCACTGAAAGTGGAGCTGATGTGACA GAAGAGTTCCCCGCGCCAGCGGGGATAAACCGATGTG GGTCAAGGAATTAAGTTAGGGAATGGC |
| SEQ ID NO: 556 | N | /5Phos/ACTCGCCATTCCCTAACTTAATTCCTTGACCCAC ATCGGTTTATCCCCGCTGGCGCGGGGAACTCTTCTGTC ACATCAGCTCCACTTTCAGTGAAAG |
| SEQ ID NO: 557 | O | /5Phos/ACCGGCATAAAATTTAACTTGAAAAGATCATTT CGGGAGTTCCCCGCGCCAGCGGGGATAAACCGGCTTC AAAAATACTCACATGGCTATGTTTTAG |
| SEQ ID NO: 558 | P | /5Phos/ACTCCTAAAACATAGCCATGTGAGTATTTTTGAA GCCGGTTTATCCCCGCTGGCGCGGGGAACTCCCGAAAT GATCTTTTCAAGTTAAATTTTATGC |
| SEQ ID NO: 559 | Q | CACTCTTTCCCTACACGACGCTCTTCCGATCTAGCCTGG AAAGACACAAAGC |
| SEQ ID NO: 560 | R | GGAGTTCAGACGTGTGCTCTTCCGATCTCAGCCATCCT TTCCACCTAA |
| SEQ ID NO: 561 | S | CACTCTTTCCCTACACGACGCTCTTCCGATCTATGCTGC AGGCTTTATGCTT |
| SEQ ID NO: 562 | T | GGAGTTCAGACGTGTGCTCTTCCGATCTTTAGGCCTGC CTGACTTCTC |
| SEQ ID NO: 563 | U | CACTCTTTCCCTACACGACGCTCTTCCGATCTGGGAAG AAGACCAACAAGAGG |
| SEQ ID NO: 564 | V | GGAGTTCAGACGTGTGCTCTTCCGATCTTTCAAGGGAA GAAGCCATTG |
| SEQ ID NO: 565 | W | CACTCTTTCCCTACACGACGCTCTTCCGATCTAAGGCA GGAATTGGATGAAA |
| SEQ ID NO: 566 | X | GGAGTTCAGACGTGTGCTCTTCCGATCTAACCTGAGAT GACTGCCCAT |
| SEQ ID NO: 567 | Y | CACTCTTTCCCTACACGACGCTCTTCCGATCTTTCCTCC CTAACCTCCACCT |

TABLE 30-continued

DNA Primer Sequences

| SEQ ID NO: | Oligo-nucleotide | Sequence |
|---|---|---|
| SEQ ID NO: 568 | Z | GGAGTTCAGACGTGTGCTCTTCCGATCTTAAAGAGCCC AACCAGATGC |
| SEQ ID NO: 569 | A2 | CACTCTTTCCCTACACGACGCTCTTCCGATCTGTCTCAG CCTTAGCCCTGTG |
| SEQ ID NO: 570 | B2 | GGAGTTCAGACGTGTGCTCTTCCGATCTCCCACTGCAA GTACAAGGGT |
| SEQ ID NO: 571 | C2 | CACTCTTTCCCTACACGACGCTCTTCCGATCTGGATGC GGAACCCAAATTA |
| SEQ ID NO: 572 | D2 | GGAGTTCAGACGTGTGCTCTTCCGATCTTAGTCTTCTCC CTCGCTCCC |
| SEQ ID NO: 573 | E2 | CACTCTTTCCCTACACGACGCTCTTCCGATCTTGCAGCA TTATGATGTGGGT |
| SEQ ID NO: 574 | F2 | GGAGTTCAGACGTGTGCTCTTCCGATCTCAACCTTTAG CATCACTGGCT |
| SEQ ID NO: 575 | G2 | CAAGCAGAAGACGGCATACGAGATNNNNNNNNNG TGACTGGAGTTCAGACGTGTGCTC |
| SEQ ID NO: 576 | H2 | AATGATACGGCGACCACCGAGATCTACACNNNNNN NNNACACTCTTTCCCTACACGACG |

The design of bacterial expression vectors for production of Cascade RNP complexes is detailed in Example 2. In brief, each cas gene was expressed from a single operon, and the coding sequences for the cas genes were arranged in the order of cas8-cse2-cas7-cas5-cas6. The FokI moiety was attached by a 30-aa linker to Cas8, and a nuclear localization signal (NLS) was attached to the N-terminus of FokI-Cas8 (FokI-Cascade complex) and the N-terminus of Cas6 (hereafter referred to as FokI-Cascade-NLS-Cas6 complex, SEQ ID NO:577).

FokI-Cascade-NLS-Cas6 complexes were purified as assembled complexes from *E. coli* essentially as described in Example 5A.

B. Transfection of Cascade RNP Complexes Comprising FokI into Eukaryotic Cells

HEK293 cells (ATCC, Manassas, Va.) were cultured in suspension in DMEM medium supplemented with 10% FBS and 1× Antibiotic-Antimycotic Solution (Mediatech, Inc., Manassas, Va.) at 37° C., 5%© $CO_2$ and 100% humidity. HEK293 cells were transfected using the Nucleofector® 96-well Shuttle System (Lonza, Allendale, N.J.). Prior to nucleofection, 5 µl of FokI-Cascade RNPs were transferred to individual wells of a 96-well plate. Each well contained ~225-500 pmol of FokI-Cascade-NLS-Cas6 complexes, depending on the RNP. HEK293 cells were transferred to a 50 ml conical centrifuge tube and centrifuged at 200×G for 3 minutes. The media was aspirated and the cell pellet was washed in calcium and magnesium-free PBS. The cells were centrifuged once more and re-suspended in Nucleofector SF buffer (Lonza, Allendale, N.J.) at a concentration of $1\times10^7$ cells/ml. 20 µl of this cell suspension was added to the FokI-Cascade-NLS-Cas6 complexes in the 96-well plate, mixed, and then the entire volume was transferred to a 96-well Nucleocuvette™ Plate. The plate was then loaded into the Nucleofector™ 96-well Shuttle™ and cells were nucleofected using the 96-CM-130 Nucleofector™ program (Lonza, Allendale, N.J.). Immediately following nucleofection, 80 µl of complete DMEM medium was added to each well of the 96-well Nucleocuvette™ Plate. The entire contents of the well were then transferred to a 96-well tissue culture plate containing 100 µl of complete DMEM medium. The cells were cultured at 37° C., 5% $CO_2$ and 100% humidity for ~72 hours.

After ~72 hours, the HEK293 cells were centrifuged at 500×G for 5 minutes and the medium was removed. The cells were washed in calcium and magnesium-free PBS. The cell pellets were then re-suspended in 50 µl of QuickExtract DNA Extraction solutions (Epicentre, Madison, Wis.). The gDNA samples obtained were then incubated at 37° C. for 10 minutes, 65° C. for 6 minutes, and 95° C. for 3 minutes to stop the reaction. gDNA samples were then diluted with 50 µl of water and stored at −20° C. for subsequent deep sequencing analysis.

C. Deep Sequencing of gDNA from Transfected Cells

Using the isolated gDNA, a first PCR was performed using Q5 Hot Start High-Fidelity 2× Master Mix (New England Biolabs, Ipswich, Mass.) at 1× concentration, primers at 0.5 µM each, 3.75 µL of gDNA in a final volume of 10 µL and amplified 98° C. for 1 minute, 35 cycles of 10 seconds at 98° C., 20 seconds at 60° C., 30 seconds at 72° C., and a final extension at 72° C. for 2 minutes. PCR reaction was diluted 1:100 in water. Target-specific primers are shown in Table 31. The target-specific primers contained Illumina-compatible sequences so that the amplification products could be analyzed using a MiSeq Sequencer (Illumina, San Diego).

TABLE 31

Target-specific Primers Used for Sequencing

| Target | Oligonucleotide* |
|---|---|
| Hsa03 on-target | Q, R |
| Hsa04 on-target | S, T |
| Hsa05 on-target | U, V |
| Hsa06 on-target | W, X |
| Hsa07 on-target | Y, Z |
| Hsa08 on-target | A2, B2 |

TABLE 31-continued

Target-specific Primers Used for Sequencing

| Target | Oligonucleotide* |
|---|---|
| Hsa09 on-target | C2, D2 |
| Hsa10 on-target | E2, F2 |

*DNA primer sequences are shown in Table 30

A second "barcoding" PCR was set up such that each target was amplified with primers (G2 and H2 in Table 30) that each contained unique 8 bp indices (denoted by "NNNNNNNN" in the primer sequence (see SEQ ID NO:575 and SEQ ID NO:576), thus allowing de-multiplexing of each amplicon during sequence analysis.

The second PCR was performed using Q5 Hot Start High-Fidelity 2× Master Mix (New England Biolabs, Ipswich, Mass.) at 1× concentration, primers at 0.5 µM each, 1 µL of 1:100 diluted first PCR, in a final volume of 10 µL and amplified 98° C. for 1 minute, 12 cycles of 10 seconds at 98° C., 20 seconds at 60° C., 30 seconds at 72° C., and a final extension at 72° C. for 2 minutes. PCR reactions were pooled into a single microfuge tube for SPRIselect bead (Beckman Coulter, Pasadena, Calif.)-based cleanup of amplicons for sequencing.

To pooled amplicons, 0.9× volumes of SPRIselect beads were added, mixed and incubated at room temperature for 10 minutes. The microfuge tube was placed on a magnetic tube stand (Beckman Coulter, Pasadena, Calif.) until solution had cleared. Supernatant was removed and discarded, and the residual beads were washed with 1 volume of 85% ethanol, and incubated at room temperature (RT) for 30 seconds. After incubation, ethanol was aspirated and beads were air dried at room temperature for 10 minutes. The microfuge tube was then removed from the magnetic stand and 0.25× volumes of water (Qiagen, Hilden, Germany) was added to the beads, mixed vigorously, and incubated for 2 min. at RT. The microfuge tube was spun in a microcentrifuge to collect the contents of the tube, and was then returned to the magnet, incubated until solution had cleared, and the supernatant containing the purified amplicons were dispensed into a clean microfuge tube. The purified amplicon library was quantified using the Nanodrop™ 2000 system (Thermo Scientific, Wilmington, Del.).

The amplicon library was normalized to 4 nM concentration as calculated from optical absorbance at 260 nm (Nanodrop™ 2000 system; Thermo Scientific, Wilmington, Del.) and size of the amplicons. Library was analyzed on MiSeq Sequencer with MiSeq Reagent Kit v2, 300 cycles (Illumina, San Diego), with two 151-cycle paired-end run plus two eight-cycle index reads.

D. Deep Sequencing Data Analysis

The identity of products in the sequencing data was analyzed based upon the index barcode sequences adapted onto the amplicons in the second round of PCR. A computational script executing the following tasks was used to process the MiSeq data:

Reads were aligned to the human genome (build GRCh38/38) using Bowtie (bowtie-bio.sourceforge.net/index.shtml) software.

Aligned reads were compared to wild-type loci; reads not aligning to any part of the loci were discarded.

Reads matching wild-type sequence were tallied. Reads with indels (surrounding 10 bp from the FokI-Cascade RNP putative cut site) were categorized by indel type and tallied.

Total indel reads were divided by the sum of wild-type reads and indel reads to give percent-mutated reads.

Figure 29:
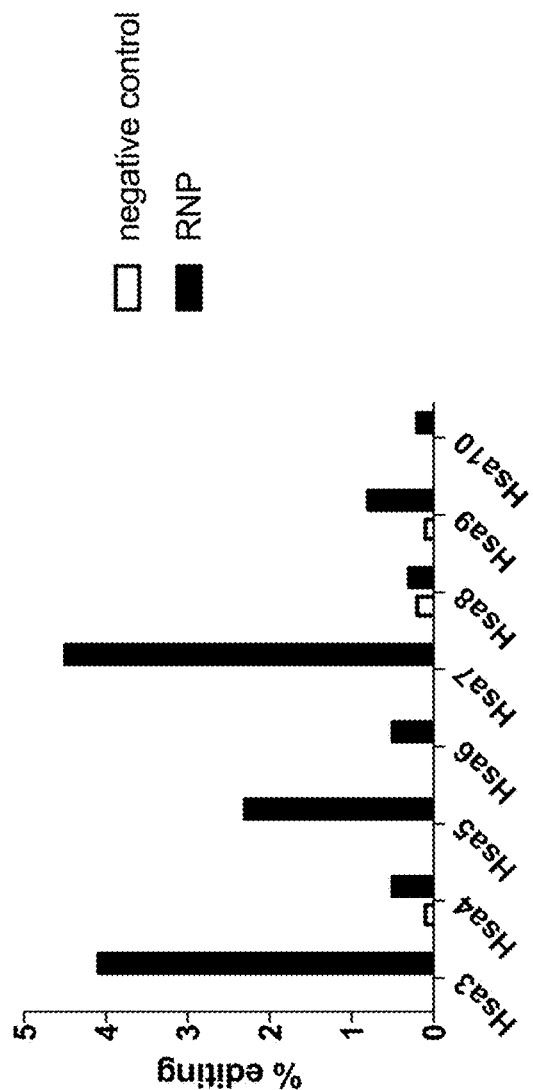

FIG. 29 shows genome editing as a function of FokI-Cascade-NLS-Cas6 complex nucleofection (n=1). FokI-Cascade-NLS-Cas6 complexes induced editing at all eight loci. Editing ranged from ~0.2-5% indels, and indels were centered around the predicted cut site, in the middle of the interspacer region.

Example 9

Introduction of Plasmids Encoding Components of FokI-Cascade RNP Complexes into Target Cells This Example illustrates the design and delivery of *E. coli* Type I-E Cascade complexes comprising FokI fusion proteins to facilitate genome editing in human cells. This Example also describes the delivery of plasmid vectors expressing Cascade complex components into eukaryotic cells.

A. Production of a Vector Encoding FokI-Cascade RNP Components to be Transfected into Target Cells A minimal CRISPR array was designed to target the TRAC locus in the human genome. The minimal CRISPR array contained two spacer sequences, both of which were flanked by CRISPR repeat sequences, as described in Examples 1 and 3. The two spacer sequences targeted loci in the genome separated by 30 bp and each spacer was complementary to a genomic sequence adjacent to an AAG PAM sequence. The plasmid vector containing the minimal CRISPR array was produced by ligating annealed oligonucleotides (Integrated DNA Technologies, Coralville, Iowa) encoding a CRISPR repeat flanked by two spacer sequences into a mammalian expression vector with two CRISPR repeat sequences. The resulting plasmid contained a "repeat-spacer-repeat-spacer-repeat" dual guide expressed from the human U6 (hU6) promoter (SEQ ID No:454).

FokI-Cascade RNP protein component-encoding genes were cloned into plasmid vectors containing CMV promoters to enable delivery and expression in mammalian cells. Cas genes were cloned into separate plasmids (SEQ ID NO:448 through SEQ ID NO:451 and SEQ ID NO:453) or in a single plasmid as a polycistronic construct with each gene linked via 2A viral peptide "ribosome-skipping" sequences (in SEQ ID NO:455). FokI-Cascade RNP complexes were delivered into eukaryotic cells via two different methods: cas genes and the minimal CRISPR array were supplied on separate plasmids ("six plasmid"-delivery system, SEQ ID NO:448 through SEQ ID NO:451, SEQ ID NO:453 and SEQ ID NO:454), or one plasmid encoding all cas genes as a polycistronic construct and a second plasmid encoding the minimal CRISPR array ("two plasmid"-delivery system, SEQ ID NO:454 and SEQ ID NO:455).

B. Transfection of Plasmid(s)-Encoding FokI-Cascade Complex RNPs

Transfection conditions for the six plasmid-delivery system and two plasmid-delivery systems were performed as detailed in Example 8 with the following modifications. Prior to nucleofection, 5 µl of plasmid vector solution was transferred to individual wells of a 96-well plate. The six plasmid-delivery system was initially tested by examining the necessity of each component for genome editing. More specifically, plasmid "cocktails" were added to each well such that there was a constant amount (420 ng) of five plasmids and a variable amount of the sixth plasmid (either 0 ng, 70 ng, 700 ng, or 1,400 ng). Next, the six plasmid delivery system and the two plasmid-delivery system were compared by nucleofecting in a fixed amount (3.5 µg) of total plasmid DNA while varying the ratio of minimal CRISPR array plasmid to cas-encoding plasmid(s). Finally, lysate was harvested ~72 hours after nucleofection for subsequent deep sequencing analysis.

C. Deep Sequencing of gDNA from Transfected Cells and Data Analysis

Deep sequencing was performed as detailed in Example 8, but only using target-specific primers Y and Z from Table 31.

D. Deep Sequencing Data Analysis

Figure 30:
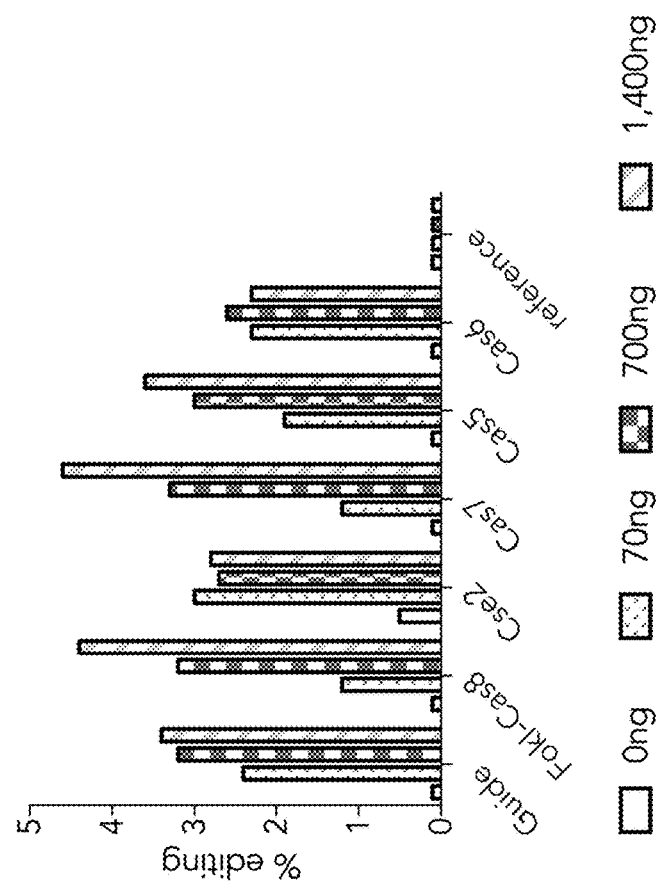

Deep sequencing data analysis was performed as detailed in Example 8. FIG. 30 shows genome editing at the TRAC locus as a function of each FokI-Cascade component in the six plasmid-delivery strategy (n=1). As is shown, editing was abolished or dramatically reduced (in the case of Cse2) if a given component was lacking. This confirms that each Cascade component is necessary for editing via plasmid delivery.

Figure 31:
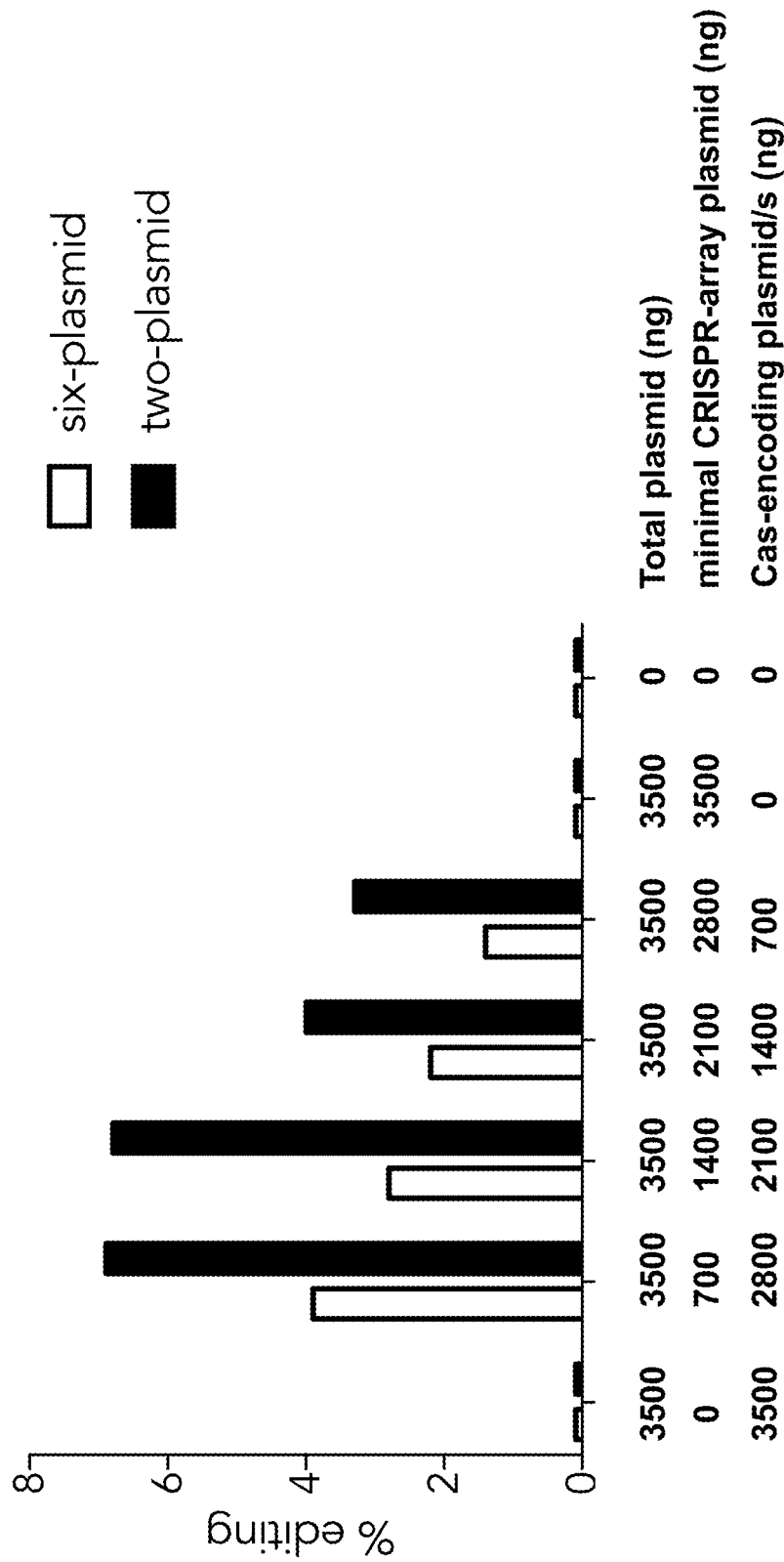

FIG. 31 shows data comparing genome editing with the six plasmid-delivery system or the two plasmid-delivery system. Across both methods, the highest levels of editing were achieved with the highest ratio of cas:minimal CRISPR array plasmids. Additionally, the polycistronic plasmid enabled higher levels of editing, potentially due to increased transcription perm of plasmid.

Example 10

Circular Permutations of Cascade Subunit Proteins

This Example illustrates in silico design, cloning, expression, and purification of a circularly-permuted (cp) *E. coli* Type I-E Cas7 protein using a structure-guided modelling approach.

A. In Silico Design

An *E. coli* Type I-E Cas7 protein (SEQ ID NO:18) was circularly permuted using a structure-guided approach based on the *E. coli* Cascade crystal structure 5H9E.pdb (www.rcsb.org/pdb/; Hayes, R. P, et al., Nature 530(7591):499-503 (2016)). The native Cas7 N-terminus and C-terminus were connected with a two-amino acid peptide linker having the sequence glycine-serine (G-S). The polypeptide sequence of this circularized Cas7 was opened at the position corresponding to the peptide bond between residues 301 and 302 in wild-type Cas7 polypeptide sequence to form a new N-terminus (residue 302) and a new C-terminus (residue 301), resulting in a circular permuted version of Cas7 protein (cp-Cas7 V1 protein). The new N-terminus and new C-terminus were designed to be positioned for connection with a fusion protein or linker region without disturbing the Cas7 protein fold or the Cascade complex assembly. A methionine residue was added to the new N-terminus (i.e., the amino acid residue corresponding to residue 302 of the wild-type Cas7 protein) of the cp-Cas7 V1 protein (SEQ ID NO:578).

A second cp-Ca.s7 protein, cp-Cas7 V2 protein, was similarly engineered using the G-S linker. The N-terminus and C-terminus of the cp-Cas7 V2 protein correspond to residues 338 and 339, respectively, in the wild-type Cas7 sequence. The new N-terminus and new C-terminus were designed to be positioned for connection with a fusion protein or linker region without disturbing the Cas7 protein fold or the Cascade complex assembly. A methionine residue was added to the N-terminus (i.e., the amino acid residue corresponding to residue 339 of the wild-type Cas7 protein) of the cp-Cas7 V2 protein (SEQ ID NO:579).

B. Cloning, Expression, and Purification of Cascade Complexes Comprising Cp-Cas7

DNA coding sequences of the in silico designed polypeptide sequences of cp-Cas7 V1 protein and cp-Cas7 V2 protein were codon optimized for expression in *E. coli*.

These DNA coding sequences were provided to a commercial manufacturer (GenScript, Piscataway, N.J.) for synthesis. The DNA sequences were individually introduced into a Cascade-operon expression vector (Table 14; SEQ ID NO:441) to replace the wild-type Cas7 protein in the expression vector as described in Example 2.

Each expression vector was transfected into *E. coli* BL21 Star™ cells (Thermofisher, Waltham, Mass.) with a second vector encoding a guide RNA for the J3 target (SEQ ID NO:444) Table 15, as described in Example 2. Cells were cultured as described in Example 4. *E. coli* Type I-E Cascade complexes containing Cas5, Cas6, cp-Cas7 V1, Cse2, and Cas8 proteins, as well as guide RNA/target J3; and Cas5, Cas6, cp-Cas7 V2, Cse2, and Cas8 proteins as well as guide RNA/target J3, were purified as described in Example 5.

Purification of the Cascade complexes comprising the circularly-permuted Cas7 variants demonstrate that circularly-permuted Type I-E CRISPR-Cas subunit proteins can be successfully used to form Cascade complexes having essentially the same composition (based on molecular weight) as Cascade complexes comprising wild-type proteins.

C. EMSA (Electrophoretic Mobility Shift Assays) of Cascade/cp-Cas7 and J3 Target Purified Cascade/cp-Cas7 complexes were purified as described in this Example and subjected to an EMSA to demonstrate specific binding to their respective target sequence. Briefly, Cascade/cp-Cas7 and Cascade/WT-Cas7 were purified and concentrated to 10 mg/mL. Cy5 double-stranded target DNA was produced as described in Example 6 and diluted to 1 μM in TE buffer (J3 target SEQ ID NO:469 and SEQ ID NO:472 and CCR5 target SEQ ID NO:474 and SEQ ID NO:470). Cascade complexes and labeled double-stranded target DNA were incubated for 30 min at 37° C. at different protein/target ratios. Immediately following the incubation, 2 μl of 50% glycerol was added to the samples and they were loaded on a 5% native PAA gel. Gels were run at 4° C. at 70V for 90 min in 0.5×TBE buffer and imaged on an AZURE c600 Bioimager (Azure BioSystems, Dublin, Calif.) and the bands were quantitated. The data are presented in Table 32.

TABLE 32

Results of Cascade/cp-Cas7 V2 EMSA

| Cascade ID and guide | Target DNA | Cascade:dsDNA ratio | Gel shift % |
| --- | --- | --- | --- |
| Cascade/WT-Cas7 J3 | J3 | 6.7 | 44 |
| Cascade/cp-Cas7 V2 J3 | J3 | 6.7 | 90 |
| Cascade/WT-Cas7 J3 | CCR5 | 6.7 | LOD* |
| Cascade/cp-Cas7 V2 J3 | CCR5 | 6.7 | LOD |

*LOD = below the limit of detection

Example 11

Cascade Subunit Fusion Proteins

A. Cascade Subunit Fusion with FokI

This Example illustrates in silico design, cloning, expression, and purification of a *E. coli* Type I-E Cas8 protein fused to a FokI nuclease domain to confer nuclease activity to the Cascade complex.

*E. coli* Type I-E Cas8 was fused N-terminally with a *Flavobacterium okeanokoites* FokI nuclease domain (GenBank no. AAA24927.1). The FokI nuclease domain comprises residues contained in the Sharkey variant described by Guo, et al. (Guo, J., et al., J. Mol. Biol. 400:96-107 (2010)), and catalyzes double-stranded DNA cleavage upon homodimerization. The amino acid sequence for the FokI nuclease (SEQ ID NO:580) contained residues Q384 to F579 (GenBank no. AAA24927.1) and had the following point mutations: E486Q, L499I, and D469N. Briefly, the FokI Sharkey nuclease domain (SEQ ID NO:581) was fused N-terminal to Cas8 using a linker sequence (SEQ ID NO:582). For purification purposes, a hexahistine tag (His6, SEQ ID NO:583), followed by a MBP tag (SEQ ID NO:584), followed by a TEV protease cleavage sequence (SEQ ID NO:585), a nuclear localization signal (NLS, SEQ ID NO:586), and a GGS linker were appended N-terminal to residue 384 of FokI. The final construct comprised NH3-His6-MBP-TEV-NLS-GGS-FokISharkey-30aa-linker-Cas8-COOH in the protein sequence (SEQ ID NO:413).

In silico designed DNA sequences were provided to a commercial manufacturer (GenScript, Piscataway, N.J.) for synthesis. The DNA sequences were cloned into a pET expression (MilliporeSigma, Hayward, Calif.) family vector backbone, which confers kanamycin resistance due to the presence of the kanR gene as described in Example 2 resulting in a vector carrying NH3-His6-MBP-TEV-NLS-GGS-FokISharkey-30aa-linker-Cas8-COOH (SEQ ID NO:439).

The *E. coli* Type I-E Cascade H3-His6-MBP-TEV-NLS-GGS-FokISharkey-30aa-linker-Cas8-COOH (SEQ ID NO:439) was expressed and purified as described in Example 4 and Example 5C. The protein sequence after TEV cleavage comprises NH3-NLS-GGS-FokISharkey-30aa-linker-Cas8-COOH (SEQ ID NO:587).

Similarly, a FokI-Cas8 fusion protein was constructed in a vector that carries NLS-FokI-linker-Cas8_His6-HRV3C-Cse2_Cas7_Cas5_Cas6_as described in Examples 1 and 2 (SEQ ID NO:442). Each expression vector was transfected into *E. coli* BL21 Star™ cells (Thermofisher, Waltham, Mass.) with a second vector encoding a guide RNA for the J3 target (SEQ ID NO:444), as described in Example 2. This construct was expressed and purified as described in Example 4B and Example 5A. Purification of the Cascade complexes comprising the fused FokI-Cas8 variants demonstrate that nuclease fused Type I-E CRISPR-Cas subunit proteins can be successfully used to form Cascade complexes having essentially the same composition (based on molecular weight) as Cascade complexes comprising wild-type proteins. FokI-Cas8 fusions were successfully used for biochemical cleavage of target nucleic acid (Example 7) and for in-cell cleavage of genomic sequences in eukaryotic cells (Examples 8 and 9).

Table 33 lists further examples of Cas subunit protein-enzyme fusions. In Table 33, APOBEC corresponds to a gene that is member of the cytidine deaminase pathway (human APOBEC I Genbank no. AB009426, human APOBEC 3F Genbank no. CH471095, human APOBEC 3G Genbank no. CR456472, rat APOBEC UCSC genome browser ID RGD:2133 rat); AID corresponds to an activation-induced cytidine deaminase (Genbank no. AY536516); PmCDA1 is an AID ortholog (Nishida, et al., Science 16:353 (2016); Iwamatsu, et al., J Biochem 110:151-158 (1991)); PvuIIHIFIT46G is a PvuII high fidelity variant T46G (Fonfara, et al., Nucleic Acids Res, 40:847-860 (2012)); PvuIIsinglechainT46G is described in pdbID 3KSK); I-TeeI is a site-specific, sequence-tolerant homing endonuclease from bacteriophage T4 and comprises an N-terminal catalytic domain as well as a C-terminal DNA-binding domain (the domains are connected by a long, flexible linker) (Van Roey, et al., EMBO J, 20:3631-3637 (2001)); BcnI (Sokolowska, et al., J Mol Biol 369:722-734 (2007)); and MvaI (Kaus-Drobek, et al., Nucleic Acids Res 35:2035-2046 (2007)) are restriction enzymes.

TABLE 33

Other Enzyme Fusions such as Nucleases and Cytidine Deaminases with Cas8

| SEQ ID NO: | Enzyme | Fusion to Cas8 |
|---|---|---|
| SEQ ID NO: 593 | Cas8_rAPOBEC1 | C terminal |
| SEQ ID NO: 594 | Cas8_AID | C terminal |
| SEQ ID NO: 595 | Cas8_PmCDA1 | C terminal |
| SEQ ID NO: 596 | Cas8_Human APOBEC1 | C terminal |
| SEQ ID NO: 597 | Cas8_APOBEC3F | C terminal |
| SEQ ID NO: 598 | Cas8_APOBEC3G | C terminal |
| SEQ ID NO: 599 | PvuIIHIFIT46G | N terminal |
| SEQ ID NO: 600 | PvuIIsinglechainT46G | N terminal |
| SEQ ID NO: 601 | I-TevI1-169Q158R | N terminal |
| SEQ ID NO: 602 | I-TevI1-169 | N terminal |
| SEQ ID NO: 603 | BcnI singlechain | N terminal |
| SEQ ID NO: 604 | MvaI singlechain | N terminal |
| SEQ ID NO: 605 | DNaseI | N terminal, C terminal |
| SEQ ID NO: 606 | Cas3 | N terminal |
| SEQ ID NO: 607 | S1*Aspergillus* | N terminal, C terminal |

B. Cascade Subunit Protein Fusion with Another Cascade Subunit Protein

The two Cse2 proteins of the Cascade complex were fused together using a structure-guided approach based on the *E. coli* Cascade crystal structure 5H9E.pdb (www.rcsb.org/pdb/; Hayes, R. P, et al., Nature 530(7591):499-503 (2016)). Briefly, the C-terminus of one Cse2 and the N-terminus of a second Cse2 were fused together using a 10-aa flexible linker (SEQ ID NO:589). The full sequence of the Cse2-Cse2 (CasB_CasB) fusion protein is shown in SEQ ID NO:588.

In silico designed DNA sequences were provided to a commercial manufacturer (GenScript, Piscataway, N.J.) for synthesis. The DNA sequences were cloned into the expression vector designed in Example 2 (SEQ ID NO:441). The Cse2 sequence was exchanged with SEQ ID NO:588.

Each expression vector was transfected into *E. coli* BL21 Star™ cells (Thermofisher, Waltham, Mass.) with a second vector encoding a guide RNA for the J3 target (SEQ ID NO:444), as described in Example 2. The *E. coli* Type I-E Cascade complex containing Cas5, Cash, Cas7, Cse2-Cse2, and Cas8 was expressed and purified as described in Example 4B and 5B. Purification of the Cascade complexes comprising the fused Cse2-Cse2 variant demonstrate that fused Type I-E CRISPR-Cas subunit proteins successfully formed Cascade complexes having essentially the same composition (based on molecular weight) as Cascade complexes comprising wild-type proteins.

C. Electrophoretic Mobility Shift Assays (EMSA) of Cascade/Cse2-Cse2 and J3 Target Purified Cascade/Cse2-Cse2 complexes were purified as described in this Example and subjected to an EMSA to demonstrate specific binding to their respective target sequence. Briefly, Cascade/Cse2-Cse2 and Cascade/WT-Cse2 were purified and concentrated to 10 mg/mL. Cy5 double-stranded target DNA was produced as described in Example 6 and diluted to 1M in TE buffer (J3 target SEQ ID NO:469 and SEQ ID NO:472 and CCR5 target SEQ ID NO:474 and SEQ ID NO:470). Cascade complexes and labeled double-stranded target DNA were incubated for 30 min at 37° C. at different protein/target ratios. Immediately following the incubation, 2 µl of 50% glycerol was added to the samples and they were loaded on a 5% native PAA gel. Gels were run at 4° C. at 70V for 90 min in 0.5×TBE buffer and imaged on an AZURE c600 Bioimager (Azure BioSystems, Dublin, Calif.) and the bands were quantitated. The data are presented in Table 34.

TABLE 34

Results of Cascade/Cse2-Cse2 EMSA

| Cascade ID and guide | Target DNA | Cascade:dsDNA ratio | Gel shift % |
|---|---|---|---|
| Cascade/WT-Cse2 J3 | J3 | 6.7 | 44 |
| Cascade/Cse2-Cse2 J3 | J3 | 6.7 | 46 |
| Cascade/WT-Cse2 J3 | CCR5 | 6.7 | LOD* |
| Cascade/Cse2-Cse2 J3 | CCR5 | 6.7 | LOD |

*LOD = below the limit of detection

D. Cascade Subunit Protein Fusion with Another Cascade Subunit Protein and an Enzymatic Protein Domain The cytidine deaminase rAPOBEC1 (apolipoprotein B mRNA editing enzyme catalytic subunit 1, *Rattus norvegicus*; NCBI Gene ID: 25383, uEnsembl:ENSRNOG00000015411) was selected for fusion. The Cse2-Cse2 protein was fused with rAPOBEC1 using a structure-guided approach based on the *E. coli* Cascade crystal structure 5H9E.pdb (www.rcsb.org/pdb/; Hayes, R. P, et al., Nature 530(7591):499-503 (2016)). Briefly, the C-terminus of rAPOBEC1 (SEQ ID NO:590) was fused to the N-terminus of the Cse2-Cse2 dimer (described above) using a 9-aa flexible linker (SEQ ID NO:591). The full sequence of the rAPOBEC1_Cse2-Cse2 fusion protein is shown in SEQ ID NO:592.

In silico designed DNA sequences were provided to a commercial manufacturer (GenScript, Piscataway, N.J.) for synthesis. The DNA sequences were cloned into the expression vector (SEQ ID NO:441), replacing the Cse2 sequence. Each expression vector was transfected into *E. coli* BL21 Star™ cells (Thermofisher, Waltham, Mass.) with a second vector encoding a guide RNA for the J3 target (SEQ ID NO:444), as described in Example 2. The *E. coli* Type I-E Cascade complex containing Cas5, Cash, Cas7, rAPOBEC1_Cse2-Cse2, and Cas8 was expressed and purified as described in Example 4B and 5B. Purification of the Cascade complexes comprising the fused rAPOBEC1_Cse2-Cse2 variant demonstrate that cytidine deaminase fusions to Type I-E CRISPR-Cas subunit proteins were successfully used to form Cascade complexes having essentially the same composition (based on molecular weight) as Cascade complexes comprising wild-type proteins. Table 35 presents examples of enzyme fusions with Cse2-Cse2.

TABLE 35

Other Enzyme Fusions Such as Cytidine Deaminases with Cse2-Cse2

| SEQ ID NO: | Enzyme | Fusion to Cse2-Cse2 |
|---|---|---|
| SEQ ID NO: 608 | rAPOBEC1 | N terminal |
| SEQ ID NO: 609 | AID | C terminal |
| SEQ ID NO: 610 | CPmCDA1 | C terminal |
| SEQ ID NO: 611 | Human APOBEC1 | N terminal |
| SEQ ID NO: 612 | Human APOBEC3F | N terminal |
| SEQ ID NO: 613 | APOBEC3G | N terminal |

Example 12

Cascade Subunit Protein Fusions to Transcription Activation/Repression Domains

This Example illustrates the design of a *E. coli* Type I-E cp-Cas7 protein fused to a VP64 activation domain to confer transcriptional activation activity to the Cascade complex.

VP64 is a transcriptional activator comprising four tandem copies of VP16 (herpes simplex viral protein 16, DALDDFDLDML (SEQ ID NO:614); amino acids 437-447, UNIPROT:UL48) connected with glycine-serine (GS) linkers. When fused to a protein domain that can bind near the promoter of a gene, VP64 (SEQ ID No:615) acts as a strong transcriptional activator. The *E. coli* Type I-E cp-Cas7 V2 (SEQ ID NO:616) can be selected for engineering.

The activation domain VP64 can be fused to the N-terminus of cpCas7 V2 (described in Example 10). A linker (e.g., 5 to 50 amino acids in length) can be selected to operably link cpCas7 V2 and the VP64 domain.

In silico designed DNA sequences can be provided to a commercial manufacturer for synthesis. The DNA sequences encoding a VP64-cpCas7 V2 fusion protein can be cloned into an expression vector (e.g., SEQ ID NO:455, wherein VP64-cpCas7 V2 can be substituted for Cas7). Each expression vector can be transfected into *E. coli* BL21 Star™ cells (Thermofisher, Waltham, Mass.) with a second vector encoding a guide RNA for the J3 target (SEQ ID NO:444), as described in Example 2. The *E. coli* Type I-E Cascade complex containing Cas5, Cas6, VP64 cpCas7 V2, Cse2, and Cas8 can be expressed and purified as described in Examples 4 and 5. Purification of the Cascade complexes comprising the fused VP64 cpCas7 V2 variant can be used to form Cascade complexes having essentially the same composition (based on molecular weight) as Cascade complexes comprising wild-type proteins.

Selection of a guide targeted to the promoter region of a particular gene can be used to verify the ability of the Cascade complex comprising the fused VP64 cpCas7 V2 to facilitate transcriptional activation of the gene.

Example 13

Site-Directed Recruitment of Functional Domains Fused to Cascade Subunit by dCas9/Guide Complex This Example describes a method of modifying a Class 2 Type II CRISPR sgRNA, crRNA, tracrRNA, or crRNA and tracrRNA sequence with a Class 1 Type I CRISPR repeat stem sequence (e.g., a Type I-F CRISPR repeat stem sequence) for the recruitment of one or more Cascade subunit proteins (i.e., Cas6, Cas5, etc.) fused to a functional domain, to a Type II CRISPR Cas protein/guide RNA complex binding site. This method here is adapted from Gilbert, Let. al., Cell 154(2):442-451 (2013) and Ferry, Q et. al., Nature Communication 8, 14633 doi: 10.1038/ncomms14633 (2017).

A. Modifying a Type II Guide RNA

A Type II CRISPR sgRNA, crRNA, tracrRNA, or crRNA and tracrRNA (collectively referred to a "Type II guide RNA") can be selected for engineering.

A Type II guide RNA sequence can be evaluated in silico for regions of incorporation of a Type I CRISPR repeat stem sequence. The Type I CRISPR repeat stem sequence can be attached at the 5' or 3' end of the Type II guide RNA, internal to the Type II guide RNA, or can replace secondary structure in the Type II guide RNA (e.g., 3' hairpin elements). Incorporation of the Type I CRISPR repeat stem sequence can be accompanied by a linker element nucleotide sequence. An example of a Type II tracrRNA 3' modified with a Type I CRISPR repeat stem sequence is presented in Table 36.

TABLE 36

Exemplary Type II tracrRNA with 3' Type I CRISPR Repeat Stem Sequence

| SEQ ID NO: | Sequence* |
|---|---|
| SEQ ID NO: 617 | 5'-AGCAUAGCAAGUUAAAAUAAGGCUAGUCCGUUAUCAAC UUGAAAAAGUGGCACCGAGUCGGUGCUUAAGUUCAcuq ccquauaqqcaqCUUU-3' |

*Type I CRISPR repeat stem sequence is underlined and in lower case letters. A corresponding DNA coding sequence is presented as SEQ ID NO: 618.

A mammalian gene, such as C-X-C chemokine receptor type 4 (CXCR4), can be selected for targeting. The junction between the 5' UTR and exon 1 can be scanned in silico for a Type II CRISPR Cas protein target sequence occurring adjacent a Type II CRISPR Cas protein PAM sequence (e.g., 5'-NGG). The 20-nucleotide target sequence occurring upstream, in a 5' direction, can be incorporated into the Type II crRNA. An example of a Type II crRNA targeting CXCR4 is shown in Table 37.

TABLE 37

Exemplary Type II crRNA Targeting CXCR4

| SEQ ID NO: | Sequence* |
|---|---|
| SEQ ID NO: 619 | 5'-GAACCAGCGGUUACCAUGGAGUUUUAGAGCUAUG CU-3' |

*A corresponding DNA coding sequence is presented as SEQ ID NO: 620.

Alternatively, the 3' end of the CXCR4 targeting spacer (RNA) (SEQ ID NO:619) can be covalently linked to the 5' end of the Type II tracrRNA with 3' Type I CRISPR repeat stem sequence (RNA) (SEQ ID NO:617) with a linker. A suitable linker element is 5'-GAAA-3'.

In silico designed Type II guide RNAs with the incorporated Type I CRISPR repeat stem sequence can be provided to a commercial manufacturer for synthesis.

A Type I Cascade subunit protein (e.g., Cas6) can be operably linked to a transcriptional activation or repression domain (e.g., KRAB) and c-terminally tagged with a nuclear localization signal (NLS) as described in Example 12.

A Type II Cas protein (e.g., Cas9) can be mutated such that it is catalytically inactive (e.g. dCas9) and tagged with a NLS sequence.

The Cas6-KRAB-NLS protein and the dCas9-NLS protein can be recombinantly expressed and purified from *E. coli*.

Ribonucleoprotein complexes can be formed at a concentration of 60 pmol dCas9 protein:60 pmol Cas6-KRAB-NLS:120 pmol:CXCR4 targeting crRNA:120 pmol tracrRNA 3' modified with a Type I CRISPR repeat stem sequence. Prior to assembly with the dCas9 and the Cas6-KRAB-NLS, each of the 120 pmol CXCR4 targeting crRNA and 120 pmol tracrRNA 3' modified with a Type I CRISPR repeat stem sequence (herein referred to as "modified Type II guide RNA") can be diluted to the desired total concentration (120 pmol) in a final volume of 2 μL, incubated for 2 minutes at 95° C., removed from a thermocycler, and allowed to equilibrate to room temperature. dCas9 and the Cas6-KRAB-NLS protein can be diluted to an appropriate concentration in binding buffer (20 mM HEPES, 100 mM KCl, 5 mM $MgCl_2$, and 5% glycerol at pH 7.4) to a final volume of 3 μL and mixed with the 2 μL of Type II guide RNA, followed by incubation at 37° C. for 30 minutes. A nontransfected control (e.g., buffer only), unmodified Type II guide RNA, or a Cas6 not linked to a repression domain, can be used to assemble negative control RNPs.

B. Cell Transfections Using dCas9:Cas6-KRAB-NLS: Modified Type II Guide RNA dCas9:Cas6-KRAB-NLS: modified Type II guide RNA nucleoprotein complexes can be transfected into HEK293 cells (ATCC, Manassas Va.), using the Nucleofector® 96-well Shuttle System (Lonza, Allendale, N.J.) and the following protocol: The complexes can be dispensed in a 5 μL final volume into individual wells of a 96-well plate. The cell culture medium can be removed from the HEK293 cell culture plate and the cells detached with TrypLE™ (Thermo Scientific, Wilmington, Del.). Suspended HEK293 cells can be pelleted by centrifugation for 3 minutes at 200×g, TrypLE reagents aspirated, and cells washed with calcium and magnesium-free phosphate buffered saline (PBS). Cells can be pelleted by centrifugation for 3 minutes at 200×g, the PBS aspirated, and the cell pellet re-suspended in 10 mL of calcium and magnesium-free PBS.

The cells can be counted using the Countess® II Automated Cell Counter (Life Technologies; Grand Island, N.Y.). $2.2 \times 10^7$ cells can be transferred to a 1.5 ml microfuge tube and pelleted. The PBS can be aspirated and the cells re-suspended in Nucleofector™ SF (Lonza, Allendale, N.J.) solution to a density of $1 \times 10^7$ cells/m. 20 μL of the cell suspension can be then added to each individual well containing 5 μL of ribonucleoprotein complexes, and the entire volume from each well can be transferred to a well of a 96-well Nucleocuvette™ Plate (Lonza, Allendale, N.J.). The plate can be loaded onto the Nucleofector™ 96-well Shuttle™ (Lonza, Allendale, N.J.) and cells nucleofected using the 96-CM-130 Nucleofector™ program (Lonza, Allendale, N.J.). Post-nucleofection, 70 μL Dulbecco's Modified Eagle Medium (DMEM; Thermo Scientific, Wilmington, Del.), supplemented with 10% Fetal Bovine Serum (FBS; Thermo Scientific, Wilmington, Del.), penicillin and streptomycin (Life Technologies, Grand Island, N.Y.) can be added to each well, and 50 μL of the cell suspension can be transferred to a 96-well cell culture plate containing 150 μL pre-warmed DMEM complete culture medium. The plate can be transferred to a tissue culture incubator and maintained at 37° C. in 5% $CO_2$ for 48 hours.

72 hours after nucleofection of the dCas9:Cas6-KRAB-NLS: modified Type II guide RNA nucleoprotein complexes, cells can be evaluated for repression of CXCR4 expression. Culture medium can be aspirated from the HEK293, and the cells can be washed once with calcium and magnesium-free PBS then are trypsinized by the addition of TrypLE (Life Technologies, Grand Island, N.Y.) followed by incubation at 37° C. for 3-5 minutes. Trypsinized cells can be gently pipetted up and down to form a single cell suspension, and the cells can then be pelleted by centrifugation for 3 minutes at 200×g. After centrifugation the culture medium can be aspirated and cells are re-suspended in a 10 mM EDTA/PBS buffer and gently mixed into a singles cell suspension. The single-cell suspension can be stained using 0.05% FITC conjugated to an anti-human CXCR4 antibodies (Medical & Biological Laboratories Co., Japan) in PBS containing 10% FBS for 1 hour at room temperature. Isotype controls and native RNP controls can be similarly stained for reference. Stained cells can then be sorted LSR II flow cytometer (BD laboratories, San Jose Calif.) and population of FITC positive fluorescent cells tallied.

Reduction in CXCR4 expression is measure by a decrease in detected fluorescence of a dCas9:Cas6-KRAB-NLS: modified Type II guide RNA nucleofected sample compared to the measured fluorescence of a non-transfected control. Decrease in fluorescence from the flow cytometer can be used to demonstrate that a modified Type II guide RNA with a Type I CRISPR repeat stem sequence can be used in combination with a nuclease-deficient Type II Cas9 protein to recruit and localize a Type I CRISPR Cascade subunit protein fused to repression domain to a gene target and repress transcription of said gene target.

Example 14

Identification and Screening of Type I Cas Genes

This Example describes a method to identify and screen Type I cas genes from different species. The method presented here is adapted from Shmakov, S., et al., Molecular Cell 60(3):385-397 (2015).

A. Identification of Type I CRISPR-Cas Genes

Using the Basic Local Alignment Search Tool (BLAST, blast.ncbi.nlm.nih.gov/Blast.cgi), a search of the genomes of various species can be conducted to identify one or more genes coding for the various gene component of the Type I CRISPR-Cas complex. The cas1 integrase gene is a component of both Class 1 and Class 2 CRISPR-Cas families, and upon identification of species containing the cas1 gene, subsequence searcher in these genomes can be conducted to isolate genomes comprising Type I-specific genes. Genome searches can be anchored upon the CRISPR-Cas integrase genes cas1, an exemplary cas1 sequence from the Type I-E system from *E. coli* K-12 MG1655 that can be used is SEQ ID. NO:621. Particular genes (e.g., cas7 and cas5) are core components of the interference complexes of the Type I systems and can be used to further differentiate species containing Type I systems. Exemplary sequences of *E. coli* K-12 MG1655 cas7 and cas5 genes that can be used are SEQ ID. NO:622 and SEQ ID. NO:623, respectively. Genomes identified possessing cas7 and cas5 genes can be further parsed through the identification of the Type I-specific nuclease-helicase cas3 gene or homologs thereof. An exemplary sequences of a *E. coli* K-12 MG1655 cas3 sequence that can be used is SEQ ID. NO:624.

Genomes containing CRISPR-Cas integrase genes cas1, Type I interference complex genes cas7 and cas5, and the nuclease-helicase cas3 gene, or some combination thereof, are likely candidates of Type I CRISPR-Cas system(s). Type I CRISPR-Cas genes are generally found in proximity to one in a single genomic locus, typically within 20 kilobases (kb). The area around the cas1, cas7, cas5, or cas3 genes can be searched for other open reading frames (ORFs) of the remaining cas genes that constitute a Type I interference complex. The amino acid sequence of putative ORFs can be compared to known Type I genes for homology or the presence of characteristic protein domains of the Type I protein components can be analyzed using the homology detection and structure prediction search tools available through the Max Planck Institute Bioinformatics Toolkit (https://toolkit.tuebingen.mpg.de/#/), or equivalent.

B. Screening of Identified Type I Components

Once a putative collection of Type I components (e.g., cas genes and the corresponding crRNA) have been identified, the Type I components can be tested for their ability to carry out programmable DNA targeting.

Putative cas genes and the crRNA can be encoded into expression vectors following the guidance of Examples 1, 2, and 3. Vectors encoding the various cas genes and crRNA can be introduced into a bacteria strain and the Type I interference complex expressed and purified as described in Examples 4 and 5. The elution fraction from the size-exclusion chromatography (SEC) column, can be analyzed via SDS-PAGE gel to determine the identity, based on weight, of the protein components comprising a complete Type I interference complex. An ethidium bromide gel can also be run to detect the presence of crRNA as part of the interference complex.

Purified Cascade complexes can be tested for their ability to support in vitro biochemical cleavage of a DNA target as described in Examples 6 and 7.

Control expressions and purification samples, where single putative cas gene are not expressed, can be used to determine the required cas genes that constitute a complete Type I interference complex capable of programmable DNA target.

For certain applications, identification of individual cas gene homologs (e.g., cas7) from a genomic sequence is sufficient and additional cas genes need not be identified nor screening performed.

Example 15

Identification of Type I crRNAs

This Example describes a method to identify Type I crRNAs in different species. The method presented here is adapted from Chylinski, K., et al., RNA Biology 10(5):726-737 (2013).

A search of genomes of various species can be conducted to identify Type I CRISPR-Cas genes as described in Example 17A. Genomes that comprise one of more Type I specific cas genes are candidate genomes that likely to contain CRISPR RNAs (crRNAs) encoded within the CRISPR repeat-spacer array. The sequences adjacent to the identified Type I cas genes (e.g., a cas7, cas5, or cas3 gene) can be probed for an associated CRISPR repeat-spacer array. Methods for in silico predictive screening can be used to extract the crRNA sequence from the repeat array following Grissa, I. V., et. al. Nucleic Acids Research 35 (Web Server issue):W52-W57 (2007). The crRNA sequence is contained within CRISPR repeat array and can be identified by its hallmark repeating sequences interspaced by foreign spacer sequences.

A. Preparation of RNA-Seq Library

The putative CRISPR array containing the individual crRNA identified in silico can be further validated using RNA sequencing (RNA-seq).

Cells from species identified as comprising putative Type I cas genes and crRNA components can be procured from a commercial repository (e.g., ATCC, Manassas, Va.; German Collection of Microorganisms and Cell Cultures GmbH (DSMZ), Braunschweig, Germany).

Cells can be grown to mid-log phase and total RNA prepped using Trizol reagent (SigmaAldrich, St. Louis, Mo.) and treated with DNaseI (Fermentas, Vilnius, Lithuania).

10 µg of the total RNA can be treated with Ribo-Zero rRNA Removal Kit (Illumina, San Diego, Calif.) and the remaining RNA purified using RNA Clean and Concentrators (Zymo Research, Irvine, Calif.).

A library can be prepared using a TRUSEQ™ Small RNA Library Preparation Kit (Illumina, San Diego, Calif.), following the manufacturer's instructions. This will result in cDNAs having adapter sequences.

The resulting cDNA library can be sequenced using MiSeq Sequencer (Illumina, San Diego, Calif.).

B. Processing of Sequencing Data

Sequencing reads of the cDNA library can be processed, for example, using the following method.

Adapter sequences can be removed using cutadapt 1.1 (pypi.python.org/pypi/cutadapt/1.1) and about 15 nucleotides trimmed from the 3' end of the read to improve read quality.

Reads can be aligned to the genome of the respective species (i.e., from which the putative crRNA is to be identified) using Bowtie 2 (http://bowtie-bio.sourceforge.net/bowtie2/index.shtml). The Sequence Alignment/Map (SAM) file, which is generated by Bowtie 2, can be converted into a Binary Alignment/Map (BAM) file using SAMTools (http://samtools.sourceforge.net/) for subsequent sequencing analysis steps.

Read coverage mapping to the CRISPR locus or loci can be calculated from the BAM file using BedTools (bedtools.readthedocs.org/en/latest/).

The BED file, as generated in the previous step, can be loaded into Integrative Genomics Viewer (IGV; www.broadinstitute.org/igv/) to visualize the sequencing read pileup. Read pile can be used to identify the 5' and 3' termini of the transcribed putative crRNA sequence. The RNA-seq data can be used to validate that a putative crRNA element is actively transcribed in vivo.

Putative crRNA can be tested with their cognate Type I cas genes for the ability to carry out programmable DNA targeting, following the guidance of Example 17.A of the present Specification.

Example 16

Probing for Sites Tolerant of Modification in Cascade Guide RNA Backbones

This Example describes the generation and testing of various modifications of Type I guide crRNAs and their suitability for use in constructing Cascade polynucleotide complexes. The method described below is adapted from Briner, A., et al., Molecular Cell 56(2):333-339 (2014).

Modifications can be introduced into the crRNA backbone, and the modified crRNA tested with a cognate Cascade complex to facilitate the identification of regions or positions in the Type I guide crRNA backbone amenable to modification.

A crRNA from a Type I CRISPR system (e.g., *E. coli* Cascade) can be selected for engineering. The crRNA sequence can be modified in silico to introduce one or more base substitutions, deletions, or insertions into nucleic acid sequences in regions selected from one or more of the following regions: nucleic acid sequences 5' of the spacer (5' handle), the spacer element, Type I CRISPR repeat stem sequence, or 3' of the Type I CRISPR repeat stem sequence (3' handle).

Base modification can also be used to introduce mismatches in the hydrogen base-pair interactions of any of the crRNA regions, or base-pair mutation introducing an alternative hydrogen base-pair interaction through substitution of two bases, wherein the alternative hydrogen base-pair interaction differs from the original hydrogen base-pair interaction (e.g., the original hydrogen base-pair interaction is Watson-Crick base pairing and the substitution of the two bases form a reverse Hoogsteen base pairing). Substitution of bases can also be used to introduce hydrogen base-pair interaction within the crRNA backbone.

Regions of the crRNA can be independently engineered to introduce secondary structure elements into the crRNA backbone. Such secondary structure elements include, but are not limited to, the following: stem-loop elements, stem elements, pseudo-knots, and ribozymes. Furthermore, the crRNA guide RNA backbone can be modified to delete portions of the crRNA backbone either through deletion at the 5' end, 3' end, or internal to the crRNA. Alternative backbone structures can also be introduced.

In silico designed crRNA sequences can be provided to a commercial manufacturer for synthesis.

Modified crRNAs can be evaluated for their ability to support binding by individual Cascade subunit proteins (i.e., Cas6, Cas5, etc.), or to support complete formation of the Cascade protein complex, or to support formation of the Cascade complex and modification of a double-stranded DNA target sequence through recruitment of a nuclease (e.g., Cas3). crRNA binding to individual Cascade subunit proteins and Cascade protein complex assembly can be evaluated by nano-ESI mass spectrometry in a manner similar to Jore, M., et al., Nature Structural & Molecular Biology 18:529-536 (2011). Biochemical characterization of crRNA and Cascade protein complex modification of a double-stranded DNA target sequence through recruitment of a nuclease can be carried out in a manner similar to those described in Examples 6 and 7. Modified crRNA that are capable of supporting formation of the Cascade complex and modification of a double-stranded DNA target sequence through recruitment of a nuclease can be validated for activity in cells using the method described in Example 8.

Example 17

Screening of Cascade Complex Guides Comprising DNA Target Binding Sequences

This Example illustrates the use of Type I CRISPR proteins and Type I guide crRNAs of the present invention to modify DNA target sequences present in human genomic DNA (gDNA) and to measure the level of cleavage activity at those sites.

Target sites (DNA target sequences) can be first selected from genomic DNA. Type I guide crRNAs can be designed to target the selected sequences. Assays (e.g., as described in Example 7) can be performed to determine the level of DNA target sequence cleavage.

A. Selecting DNA Target Sequences from Genomic DNA

PAM sequences (e.g., ATG) for a Cascade protein complex (e.g., *E. coli* Type I-E Cascade) can be identified within the selected genomic region.

One or more Cascade DNA target sequences (e.g., 32 nucleotides in length) that are 3' adjacent to a ATG PAM sequence can be identified.

Criteria for selection of nucleic acid target sequences can include, but are not limited to, the following: homology to other regions in the genome; percent G-C content; melting temperature; presences of homopolymer within the spacer; distance between the two sequences; and other criteria known to one skilled in the art.

A DNA target binding sequence that hybridizes to the Cascade DNA target sequence can be incorporated into a guide crRNAs. The nucleic acid sequence of a guide crRNA construct is typically provided to and synthesized by a commercial manufacturer.

A guide crRNA, as described herein, can be used with cognate Type I Cascade protein complex to form crRNA/Cascade protein complexes.

B. Determination of Cleavage Percentages and Specificity

In vitro cleavage percentages and specificity (i.e., the amount of off-target binding) related to a guide crRNA can be determined, for example, using the cleavage assays described in Example 7, and compared as follows:

(1) If only a single DNA target sequences is identified or selected for a guide crRNA, the cleavage percentage and specificity for each of the DNA target sequences can be determined. If so desired, cleavage percentage and/or specificity can be altered in further experiments using methods including, but not limited to, modifying the guide crRNA, or introducing effector proteins/effector protein-binding sequences to modify the guide crRNA or the Cascade subunit proteins, or ligand/ligand-binding moieties to modify the guide crRNA or the Cascade subunit proteins.

(2) If multiple DNA target sequences are identified or selected for guide crRNAs, the percentage cleavage data and site-specificity data obtained from the cleavage assays can be compared between different DNAs comprising the target binding sequence to identify the DNA target sequences having the desired cleavage percentage and specificity. Cleavage percentage data and specificity data provide criteria on which to base choices for a variety of applications. For example, in some situations the activity of the guide crRNA may be the most important factor. In other situations, the specificity of the cleavage site may be relatively more important than the cleavage percentage. If so desired, cleavage percentage and/or specificity can be altered in further experiments using methods including, but not limited to, modifying the guide crRNA, introducing effector proteins/effector protein-binding sequences to modify the guide crRNA or the Cascade subunit proteins, or ligand/ligand-binding moieties to modify the guide crRNA or the Cascade subunit proteins.

Alternatively, or in addition to the in vitro analysis, in-cell cleavage percentages and specificities of guide crRNAs can be obtained using, for example, the method described in Example 8, and compared as follows:

(1) If only a single DNA target sequences is identified or selected for a guide crRNA, the cleavage percentage and specificity for each of the DNA target sequences can be determined. If so desired, cleavage percentage and/or specificity can be altered in further experiments using methods including, but not limited to, modifying the guide crRNA, or introducing effector proteins/effector protein-binding sequences to modify the guide crRNA or the Cascade subunit proteins, or ligand/ligand-binding moieties to modify the guide crRNA or the Cascade subunit proteins.

(2) If multiple DNA target sequences are identified or selected for guide crRNAs, the percentage cleavage data and site-specificity data obtained from the cleavage assays can be compared between different DNAs comprising the target binding sequence to identify the DNA target sequences having the desired cleavage percentage and specificity. Cleavage percentage data and specificity data provide criteria on which to base choices for a variety of applications. For example, in some situations the activity of the guide crRNA may be the most important factor. In other situations, the specificity of the cleavage site may be relatively more important than the cleavage percentage. If so desired, cleavage percentage and/or specificity can be altered in further experiments using methods including, but not limited to, modifying the guide crRNA, introducing effector proteins/effector protein-binding sequences to modify the guide crRNA or the Cascade subunit proteins, or ligand/ligand-binding moieties to modify the guide crRNA or the Cascade subunit proteins.

Example 18

Varying FokI-Cas8 Linker Composition and Interspacer Distance for Efficient FokI-Cascade Complex Genome Editing This Example illustrates the design and testing of multiple fusion proteins comprising FokI-Cas8 and linker polypeptides of various lengths, as well as the effect of varying interspacer distances for efficient genome editing.

A. Production of a Vector Encoding *E. coli* Type I-E Cascade Complex Components Comprising FokI Fusion Proteins to be Transfected into Target Cells Minimal CRISPR arrays were designed to target a set of loci in the human genome at or near two different genes: ADAMTSL1 and PCSK9. Interspacer distances ranged from 14-60 bp, in increments of 2 bp. Four targets were designed for each interspacer distance. Targets were flanked by either AAG or ATG PAM sequences. Dual guides containing "repeat-spacer-repeat-spacer-repeat" sequences were cloned as described in Example 9 with SEQ ID NO:454. SEQ ID NO:625 through SEQ ID NO:816 provide the sequences for the full set of oligonucleotide sequences used to generate the minimal CRISPR arrays.

FokI-Cascade RNP subunit protein component-encoding genes were cloned into vectors comprising: CMV promoters to enable delivery and expression in mammalian cells; cas genes linked via 2A viral peptide "ribosome-skipping" sequences; a fusion protein comprising FokI and Cas8 connected with a 30-aa linker (SEQ ID NO:455 from Example 3). Additional linker polypeptide sequences of varying length and amino acid composition were designed and used to connect FokI to the Cas8 protein in these vectors. The additional linker polypeptide sequences are listed in Table 38.

TABLE 38

Amino Acid Linker Sequences

| SEQ ID NO: | Linker length (amino acids) | Amino acid sequence |
|---|---|---|
| SEQ ID NO: 817 | 5 | GGGGS |
| SEQ ID NO: 818 | 8 | TGPGAAAR |

TABLE 38-continued

Amino Acid Linker Sequences

| SEQ ID NO: | Linker length (amino acids) | Amino acid sequence |
|---|---|---|
| SEQ ID NO: 819 | 10 | GGSGSSGGSG |
| SEQ ID NO: 820 | 15 | GGSGSSGGSGSSGGS |
| SEQ ID NO: 821 | 17 | ADPTNRAKGLEAVSVAS |
| SEQ ID NO: 822 | 20 | SGSETPGTSESATPESGGSG |
| SEQ ID NO: 433 | 30 | SGSETPGTSESATPESGGSGSSGGSGSSGG |
| SEQ ID NO: 823 | 40 | SGSETPGTSESATPESGGSGSSGGSGSSGGSGSGGSGSS |
| SEQ ID NO: 824 | 50 | SGSETPGTSESATPESGGSGSSGGSGSSGGSGSGGSGSSGGSGSSGGSG |

B. Transfection of Vectors Encoding FokI-Cascade RNP Complex Components

Transfection conditions were essentially as described in Example 8 with the following modifications. Prior to nucleofection, 5 μl of plasmid vector solution was transferred to individual wells of a 96-well plate. Each well contained 2.4 μg of plasmid encoding FokI-Cascade RNP complex subunit protein components and ~1-2 μg of plasmid encoding the minimal CRISPR array.

C. Deep Sequencing of gDNA from Transfected Cells

Deep sequencing was performed essentially as described in Example 8 with the following modifications. Instead of primers Y and Z from Table 31 of Example 8, the target-specific primers were SEQ ID NO:825 to SEQ ID NO:1016.

D. Deep Sequencing Data Analysis

Figure 32A:
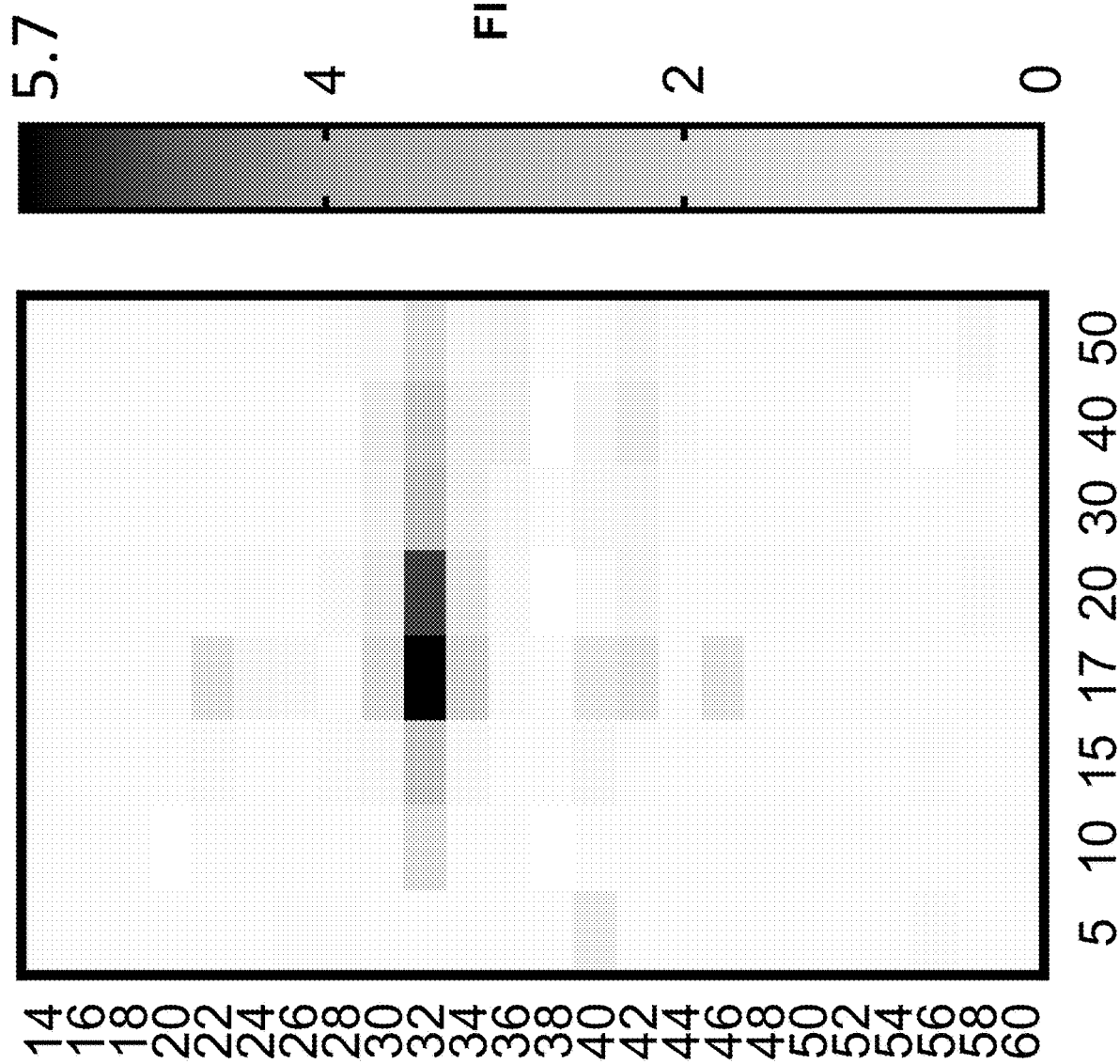

Deep sequencing data analysis was performed essentially as described in Example 8. FIG. 32A and FIG. 32B present the results of the data analysis. In FIG. 32A and FIG. 32B, percent genome editing is shown as a function of FokI-Cas8 linker type and interspacer distance (n=1); grey scale vertical bar to the right is percentage of indels. An initial analysis of the data showed genome editing was highest with FokI-Cas8 linkers of 17 and 20 amino acids (SEQ ID NO:821 and SEQ ID NO:822, respectively) and with interspacer distances of ~26 bp and ~30-32 bp. The data was reprocessed and samples with less than a thousand sequences reads were removed as they may contain inflated editing values due to low coverage (sites were only retained if all the associated samples contained >1000 reads). This data, presented in FIG. 32A and FIG. 32B, showed that genome editing was highest with FokI-Cas8 linkers of 17 and 20 amino acids (SEQ ID NO:821 and SEQ ID NO:822, respectively) and with interspacer distances of ~30-32 bp. Thus, efficient genome editing using Type I CRISPR-Cas complexes comprising FokI-Cas8 fusion proteins was achieved by varying the interspacer distance and the linker polypeptide length of the FokI-Cas8 fusion protein. The amino acid composition of the linker polypeptides is discussed herein.

Example 19

Identifying Cascade Homologs that Enable High-efficiency Genome Editing

This Example illustrates the design and testing of multiple homolog Cascade complexes to evaluate the efficiency of genome editing.

A. Identification of Sites for Testing with Homolog Cascade Complexes

A panel of sites was identified for testing additional homolog Cascade complexes. Specifically, minimal CRISPR arrays were designed to target a set of loci in the human genome with 30 bp interspacer distances and that were flanked by either AAG or ATG PAM sequences. Dual-guide polynucleotides containing "repeat-spacer-repeat-spacer-repeat" sequences were cloned following the method described in Example 9 with SEQ ID NO:454. The full set of oligonucleotide sequences used to generate the minimal CRISPR arrays are presented as SEQ ID NO:1017 to SEQ ID NO:1130 (Hsa33F, SEQ ID NO:1017, and Hsa33R, SEQ ID NO:1074, exemplify one pair). A positive control dual-guide targeting the TRAC locus was included (SEQ ID NO:454).

FokI-Cascade RNP subunit protein component-encoding genes were cloned into vectors comprising: CMV promoters to enable delivery and expression in mammalian cells; cas genes linked via 2A viral peptide "ribosome-skipping" sequences; a fusion protein comprisng FokI and Cas8 connected with a 30-aa linker (SEQ ID NO:455 from Example 3).

B. Transfection of Vectors Encoding FokI-Cascade RNP Complex Components

Transfection conditions were performed essentially as described in Example 8 with the following modifications. Prior to nucleofection, 5 μl of plasmid vector solution was transferred to individual wells of a 96-well plate. Each well contained 3 μg of plasmid encoding FokI-Cascade RNP subunit protein components and 0.3 μg of plasmid encoding the minimal CRISPR array.

C. Deep Sequencing of gDNA from Transfected Cells

Deep sequencing was performed essentially as described in Example 8 with the following modifications. Instead of primers Y and Z from Table 31 of Example 8, the target-specific primers used in this Example were SEQ ID NO:1131 to SEQ ID NO:1244.

D. Deep Sequencing Data Analysis

Figure 33:
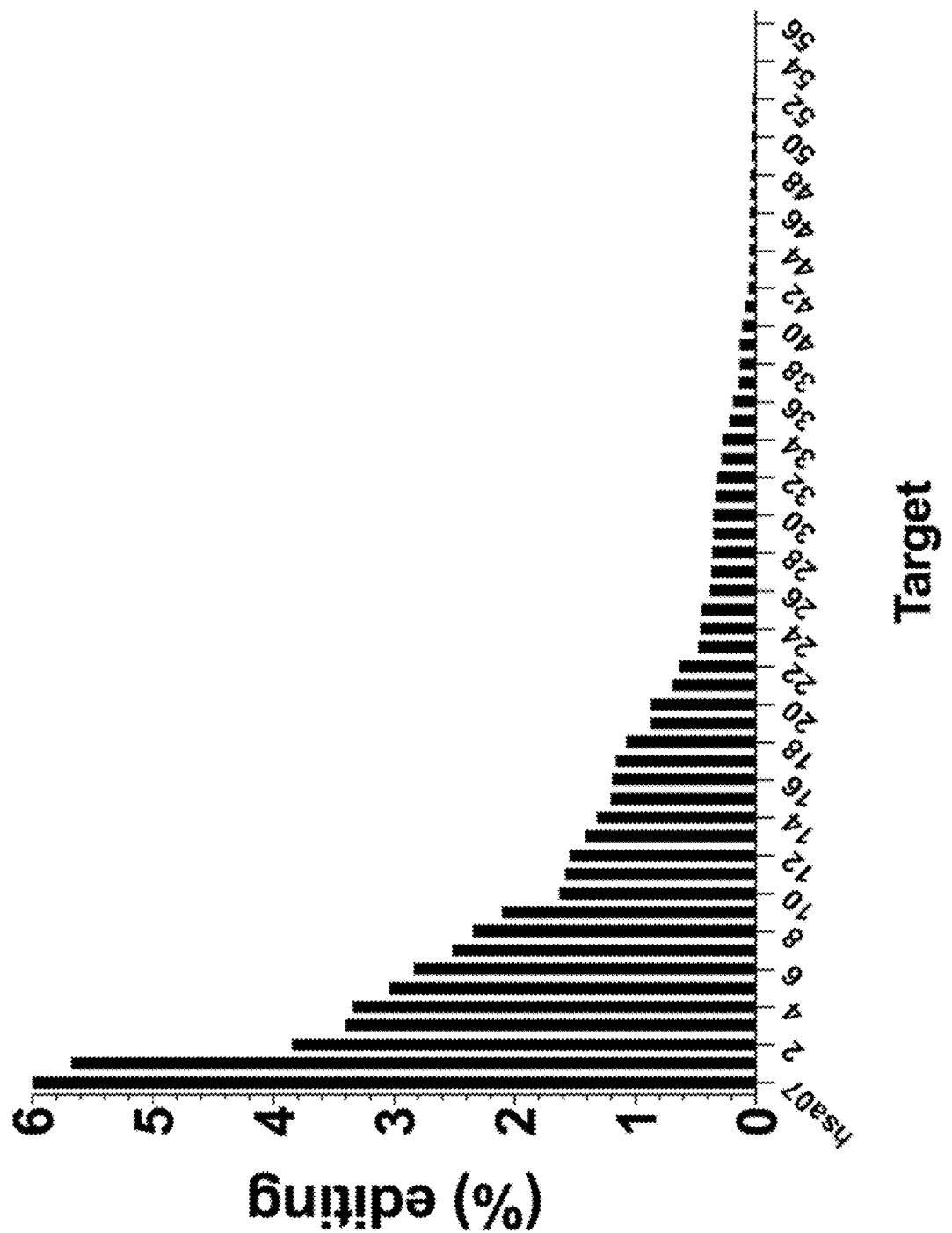

Deep sequencing data analysis was performed essentially as described in Example 8. FIG. 33 present the results of the data analysis. In FIG. 33, percent genome editing is plotted against 58 test sites (oligonucleotide sequences used to generate these minimal CRISPR arrays are discussed above) in addition to target Hsa07 from Example 8 (n=3). As is shown in FIG. 33, editing ranged from ~6% to below the limit of detection. From these data, a panel of eight sites (Hsa07 as well as targets 1, 3-5, 10, 13, and 16 corresponding to the following targets Hsa37, Hsa43, Hsa46, Hsa60, Hsa77, Hsa88, and Hsa126) with AAG PAMs were selected for testing homolog Cascade complexes for genome editing.

E. Identification of Homolog Cascade Complexes to Test with FokI Nuclease for Genome Editing Cas8 protein sequences from different Type I systems were used as queries for psi-BLASTp to generate phylogenetic trees for homolog selection. Specifically, Cas8 from organisms that grow at 37° C.; (2) their cas gene operons were intact and had all the expected Cascade subunit protein encoding genes, a cas3 gene, and intact acquisition genes (i.e., cas1 and cast); (3) their cas gene operon was flanked by one or more CRISPR arrays; and (4) their CRISPR arrays contained >10 spacers. For some homologs, the CRISPRfinder program (crispr.i2bc.paris-saclay.fr/Server/) was used to identify putative PAM sequences. Based on the above criteria, the 22 homolog Cascade complexes shown in Table 39 were selected.

TABLE 39

Homolog Cascade Complexes

| SEQ ID NO: | Cascade homolog organism | PAM | Spacer length | Type |
|---|---|---|---|---|
| SEQ ID NO: 1245 | Oceanicola sp. HL-35 | AAG | 32 | I-E |
| SEQ ID NO: 1246 | Pseudomonas sp. S-6-2 | AAG | 32 | I-E |
| SEQ ID NO: 1247 | Salmonella enterica subsp. enterica serovar Muenster strain | AAG | 32 | I-E |
| SEQ ID NO: 1248 | Atlantibacter hermannii NBRC 105704 | AAG | 32 | I-E |
| SEQ ID NO: 1249 | Geothermobacter sp. EPR-M | AAG | 32 | I-E |
| SEQ ID NO: 1250 | Methylocaldum sp. 14B | AAG | 32 | I-E |
| SEQ ID NO: 1251 | Methanocella arvoryzae MRE50 | AAG | 32 | I-E |
| SEQ ID NO: 1252 | Pseudomonas aeruginosa DHS01 | AAG | 32 | I-E |
| SEQ ID NO: 1253 | Lachnospiraceae bacterium KH1T2 | GAA | 35 | I-E |
| SEQ ID NO: 1254 | Klebsiella pneumoniae strain VRCO0172 | GAA | 33 | I-E |
| SEQ ID NO: 1255 | Streptococcus thermophilus strain ND07 | GAA | 33 | I-E |
| SEQ ID NO: 1256 | Streptomyces sp. S4 | GAA | 33 | I-E |
| SEQ ID NO: 1257 | Campylobacter fetus subsp. testudinum Sp3 | TCA | 36 | I-B |
| SEQ ID NO: 1258 | Odoribacter splanchnicus DSM 20712 | TCA | 36 | I-B |
| SEQ ID NO: 1259 | Bacillus halodurans C-125 | TTC | 34 | I-C |
| SEQ ID NO: 1260 | Desulfovibrio vulgaris RCH1 plasmid pDEVAL01 | TTC | 34 | I-C |
| SEQ ID NO:1261 | Geobacillus thermocatenulatus strain KCTC 3921 | TTC | 35 | I-C |
| SEQ ID NO: 1262 | Vibrio cholerae strain L15 L15_contig8 | CC | 32 | I-F |
| SEQ ID NO: 1263 | Pseudomonas aeruginosa UCBPP-PA14 | CC | 32 | I-F |
| SEQ ID NO: 1264 | Shewanella putrefaciens CN-32 | CC | 32 | I-Fv2 |
| SEQ ID NO: 1265 | Acinetobacter sp. 869535 | CC | 32 | I-Fv2 |
| SEQ ID NO: 1266 | Vibrio cholerae HE48 vcoHE48.contig.11 | CC | 32 | I-Fv2 |

*Fusobacterium nucleatum* (WP_008798978.1) was used for Type I-B, Cas8 from *Bacillus halodurans* (WP_010896519.1) was used for Type I-C, Cas8 from *E. coli* (WP_001050401.1) was used for Type I-E, Cas8 from *Pseudomonas aeruginosa* (WP_003139224.1) was used for Type I-F, and Cas5 from *Shewanella putrefaciens* (WP_011919226.1) was used for Type I-Fv2.

Next, psi-BLASTp was iterated multiple times until thousands of homologs were identified for each Type I system. From this information, phylogenetic trees were built using the interactive Tree of Life online software (iTOL, accessible at itol.embl.de/login.cgi). The trees were visually inspected after auto-collapsing clades using variable branch lengths.

Lists of organisms falling within major clades were then outputted and manually inspected for selection. In this step, priority was placed on selecting homologs that sampled from different regions of the phylogenetic tree, both for the 12 homologs within the Type I-E as well as 2-3 representative homologs for Types I-B, I-C, I-F, and I-Fv2. cas8 and cas5 candidates, based on the above phylogenetic analysis, were inputted into NCBI, and the genomic context within the endogenous host bacterium was visually inspected within NCBI's genome graphics browser. Cascade homologs were selected only if (1) they were found in F. Production of Vectors Encoding FokI-Cascade RNP Components from 22 Distinct Species for Transfection into Target Cells Sequences for each cas gene from each homolog were synthesized as part of a polycistronic construct that included a fusion protein comprising FokI nuclease and Cas8. For each Type I-E Cascade complex homolog, a set of ~7-8 guides targeting loci with the appropriate PAM sequences were generated. For each Type I-B, I-C, I-F, and I-Fv2 Cascade homolog, a set of ~2-7 guides targeting loci with appropriate PAM sequences were generated. Each Cascade complex homolog system required unique repeat sequences to process their cognate guide (SEQ ID NO:1267 to SEQ ID NO:1288). Dual guides containing "repeat-spacer-repeat-spacer-repeat" sequences were cloned using the method described in Example 9 for SEQ ID NO:454. Oligonucleotides were phosphorylated on the 5' end and appended with overhang sequences to enable cloning into plasmid vectors with the appropriate repeat sequences. The full set of oligonucleotide sequences used to generate the minimal CRISPR arrays for the 22 Cascade complex homologs are presented as (SEQ ID NO:1289 to SEQ ID NO:1400).

FokI-Cascade RNP subunit protein component-encoding genes were cloned into vectors comprising: CMV promoters to enable delivery and expression in mammalian cells; cas genes linked via 2A viral peptide "ribosome-skipping" sequences; a fusion protein comprising FokI and Cas8 connected with a 30-aa linker.

G. Transfection of Plasmids Encoding FokI-Cascade Complex RNPs

Transfection conditions were essentially as described in Example 8 with the following modifications. Prior to nucleofection, 5 µl of plasmid vector solution was transferred to individual wells of a 96-well plate. Each well contained 1.5 µg of plasmid encoding FokI-Cascade RNP subunit protein components and ~0.5-1.5 µg of plasmid encoding the minimal CRISPR array. Experiments were performed in triplicate and included FokI-Cascade RNP complexes from E. coli (SEQ ID NO:455) targeted to eight sites (Hsa07 from Example 8 and Hsa37, Hsa43, Hsa46, Hsa60, Hsa77, Hsa88, Hsa126 from section D of this Example) as positive controls. As previously described, the following oligonucleotides were used to generate the minimal CRISPR arrays used with the E. coli positive control: Hsa37 (SEQ ID NO:1019; SEQ ID NO:1076), Hsa43 (SEQ ID NO:1024; SEQ ID NO:1081), Hsa46 (SEQ ID NO:1027; SEQ ID NO:1084), Hsa60 (SEQ ID NO:1037; SEQ ID NO:1094), Hsa77 (SEQ ID NO:1045; SEQ ID NO:1102), Hsa88 (SEQ ID NO:1050; SEQ ID NO:1107), Hsa126 (SEQ ID NO:1072; SEQ ID NO:1129).

H. Deep Sequencing of gDNA from Transfected Cells

Deep sequencing was performed essentially as described in Example 8 with the following modifications. Instead of primers Y and Z from Table 31 of Example 8, the target-specific primers used in this Example were SEQ ID NO:1401 to SEQ ID NO:1512. For both Type I-E RNP complexes and Type I-B, I-C, I-F, and I-Fv2 RNP complexes, control samples comprising E. coli Type I-E Cascade were included for comparison and sequenced with target-specific primers corresponding to targets Hsa07 from Example 8 and Hsa37, Hsa43, Hsa46, Hsa60, Hsa77, Hsa88, Hsa126 from this Example. More specifically, the following target-specific amplification primers were used for these targets: Hsa37 (SEQ ID NO:1133; SEQ ID NO:1190), Hsa43 (SEQ ID NO:1138; SEQ ID NO:1195), Hsa46 (SEQ ID NO:1141; SEQ ID NO:1198), Hsa60 (SEQ ID NO:1151; SEQ ID NO:1208), Hsa77 (SEQ ID NO:1159; SEQ ID NO:1216), Hsa88 (SEQ ID NO:1164; SEQ ID NO:1221), Hsa126 (SEQ ID NO:1186; SEQ ID NO:1243).

I. Deep Sequencing Data Analysis

Deep sequencing data analysis was performed essentially as described in Example 8. FIG. 34A and FIG. 34B show results from these experiments. Editing was observed with many of the Type I-E FokI-Cascade homologs (FIG. 34A). The highest editing was observed with the variant from Pseudomonas sp. S-6-2, while other homologs (i.e., Salmonella enterica, Geothermobacter sp. EPR-M, Methanocella arvoryzae MRE50, and S. thermophilus (strain ND07)) showed editing approximately equivalent to E. coli. Editing with FokI-Cascade RNPs derived from Types I-B, I-C, I-F, and I-Fv2 was not observed and therefore may be below the limit of detection (FIG. 34B).

Example 20

Varying FokI-Cas8 Linker Length and Interspacer Distances in Pseudomonas sp S-6-2 for Efficient Genome Editing This Example illustrates the design and testing of multiple fusion proteins comprising FokI-Cas8 and linker polypeptides of various lengths, as well as the effect of varying interspacer distances for efficient genome editing with Pseudomonas sp S-6-2 Type I-E CRISPR-Cas systems.

A. Production of a Vector Encoding FokI-Cascade RNP Components to be Transfected into Target Cells Minimal CRISPR arrays were designed to target a set of loci in the human genome. Interspacer distances ranged from 23-34 bp, in increments of 1 bp. Eight targets were designed for each of the interspacer distances, and targets were flanked by AAG PAM sequences. Dual guides were generated with PCR-based assembly using three oligonucleotides (SEQ ID NO:1513 to SEQ ID NO:1515) and a unique primer encoding a "repeat-spacer-repeat-spacer-repeat" sequence to enable FokI-Cascade targeting. The full set of unique oligonucleotide sequences to generate the minimal CRISPR arrays were SEQ ID NO:1516 to SEQ ID NO:1704. PCR-assembled guides were purified and concentrated using SPRIselect® beads (Beckman Coulter, Pasadena, Calif.) essentially according to the manufacturer's instructions.

FokI-Cascade RNP subunit protein component-encoding genes were cloned into vectors comprising: CMV promoters to enable delivery and expression in mammalian cells, cas genes linked via 2A "ribosome-skipping" sequences, and FokI attached to Cas8 with a 30-aa linker (SEQ ID NO:1748). Additional linker polypeptide sequences of varying length were designed and used to connect FokI to the Cas8 protein to form fusion proteins. The linker polypeptide sequences are listed in Table 40.

TABLE 40

| Amino Acid Linker Sequences | | |
| --- | --- | --- |
| Linker length (amino acids) | Amino acid sequence | SEQ ID NO: |
| 17 | ADPTNRAKGLEAVSVAS | SEQ ID NO: 821 |
| 20 | SGSETPGTSESATPESGGSG | SEQ ID NO: 822 |

B. Transfection of Vectors Encoding FokI-Cascade RNP Complex Components

Transfection conditions were performed essentially as described in Example 8 except for with the following modifications. Prior to nucleofection, 5 µl of plasmid vector solution was transferred to individual wells of a 96-well plate. Each well contained 5 µg of plasmid encoding FokI-Cascade RNP protein components and ~0.1-0.5 µg of linear PCR product encoding the minimal CRISPR array.

C. Deep Sequencing of gDNA from Transfected Cells

Deep sequencing was performed essentially as described in Example 8. Instead of primers Y and Z from Table 31 of Example 8, the target-specific primers were SEQ ID NO:1705 to SEQ ID NO:1803.

D. Deep Sequencing Data Analysis

Figure 35:
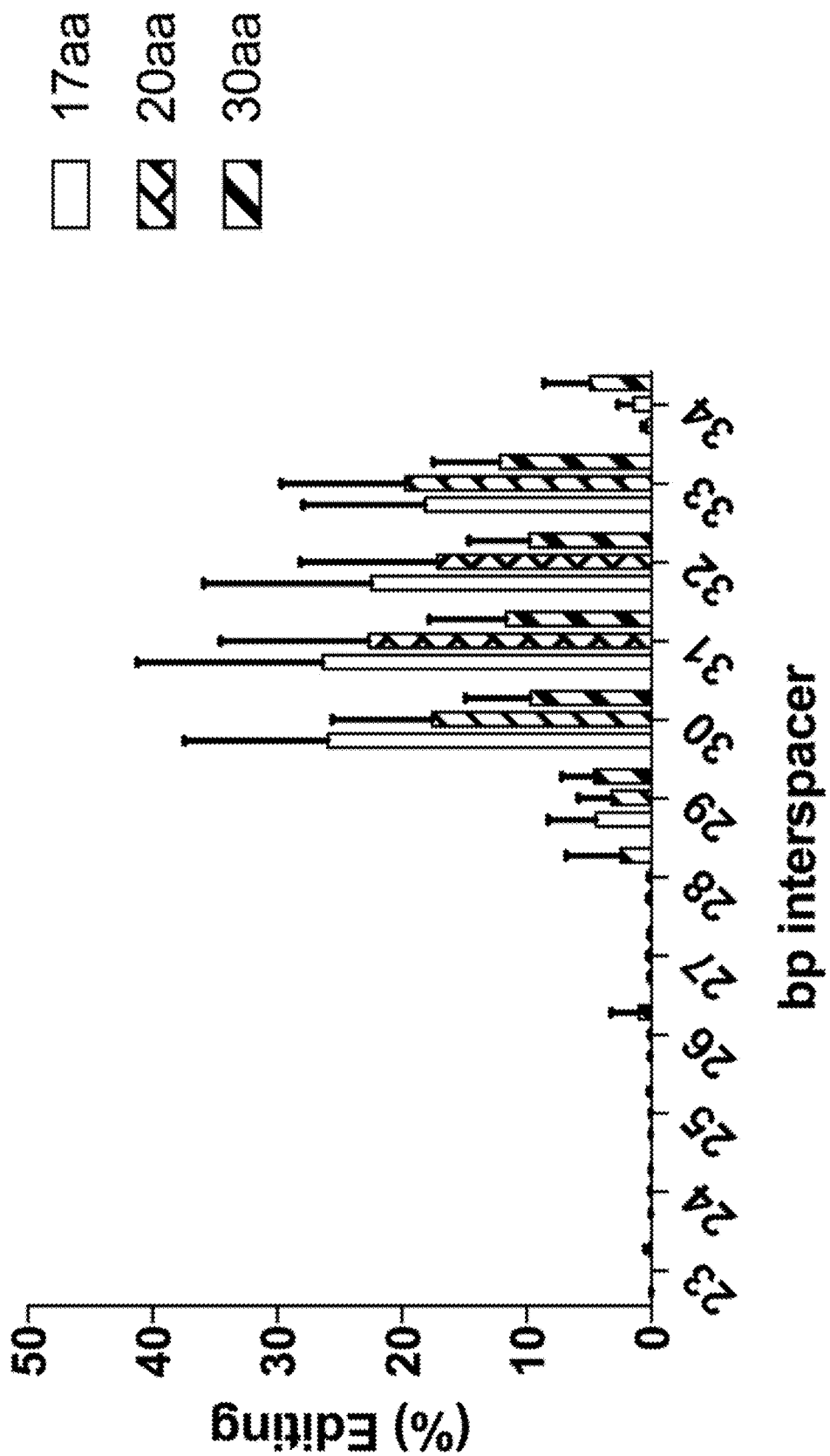

Deep sequencing data analysis was performed essentially as described in Example 8. FIG. 35 shows genome editing at 95 sites (n=1). Editing ranged from ~50% (FIG. 35 shows the mean+/−1 standard deviation) to below the limit of detection, and was related to the interspacer distance and linker polypeptide length. The amino acid composition of the linker polypeptides is discussed herein. Interspacer distances of ~30-33 bp and linker polypeptide lengths of 17 and 20 amino acids provided very efficient editing.

Example 21

Utilizing Cas3-FokI and FokI-Cas8 to Enable FokI-Cascade Genome Editing

Figure 17A:
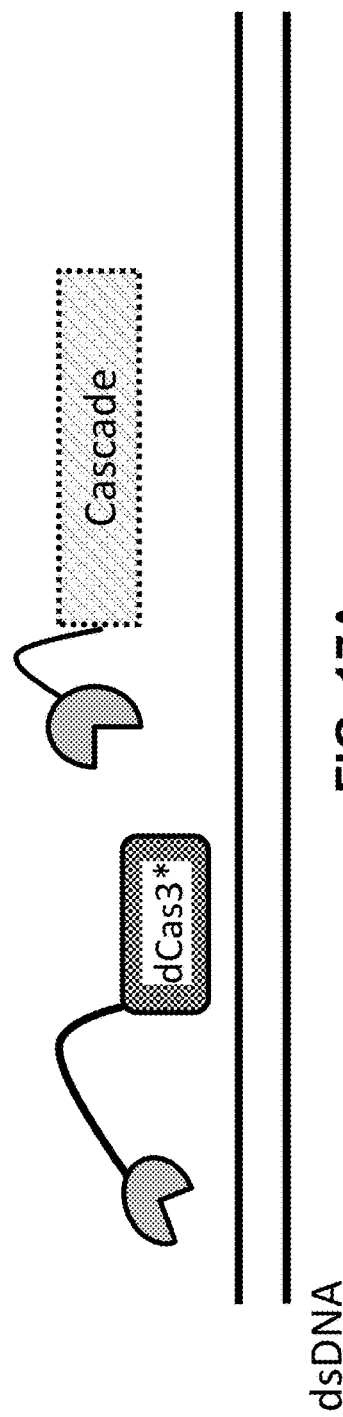
Figure 17B:
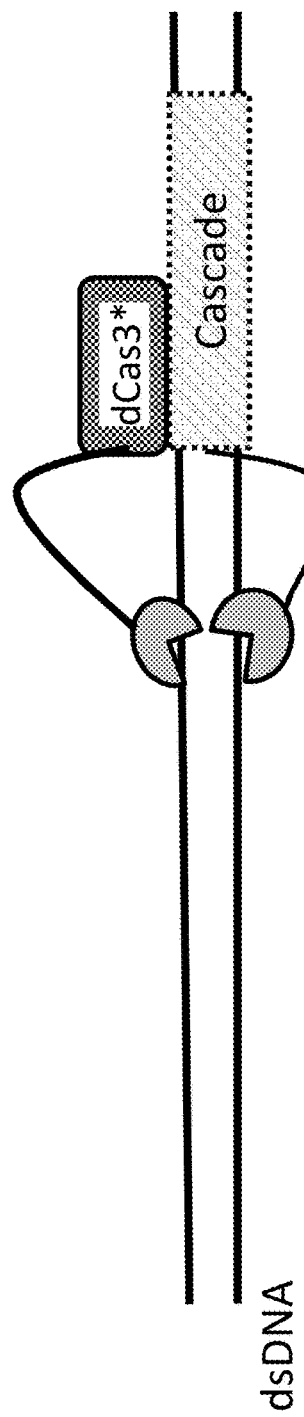
Figure 17C:
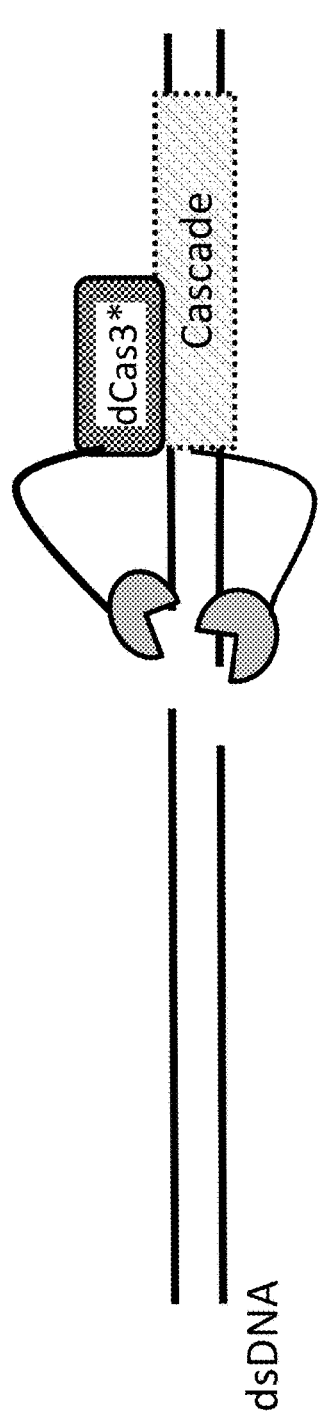

This Example illustrates the use of Cas3-FokI and FokI-Cascade to induce dimerization of FokI to generate a double-strand break at a locus in the human genome (see e.g., FIG. 17A, FIG. 17B, and FIG. 17C). More specifically, this Example details the design and testing of multiple Cas3-FokI linker compositions and lengths and FokI-Cas8 linker compositions and lengths for affecting genome editing efficiency.

A. Production of a Vectors Encoding FokI-Cas3 and FokI-Cascade RNP Components to be Transfected into Target Cells Minimal CRISPR arrays are designed to target three distinct sites flanked by AAG PAMs in the human genome. Sites are selected that were previously shown to support interspacer editing with *E. coli* FokI-Cascade dimers directed by dual-guides and are therefore known to be permissive for FokI-Cascade binding (e.g., Hsa37, Hsa43, and Hsa46).

The FokI-Cascade systems described in the Examples above used two FokI Cascade complexes (see e.g., FIG. 16A, FIG. 16B, and FIG. 16C); accordingly, dual-guides comprising a first guide sequence specifying a first nucleic acid target site and a second guide sequence specifying a second nucleic acid target site can be used. Because the Cas3-FokI-FokI-Cascade system only requires a single PAM, a guide comprising "repeat-spacer-repeat" should be sufficient to facilitate binding of the functional Cascade complex to a nucleic acid target site. A dual-guide containing "repeat-spacer-repeat-spacer-repeats" can also be used but, typically in this embodiment, the two spacer sequences direct binding of the Cascade complex to the same nucleic acid target sequence; that is, the two spacers can have the same sequence. The guides are cloned essentially as described in Example 9 with SEQ ID No:454. The following annealed oligonucleotides are used for generation of the minimal CRISPR arrays: Hsa37 (SEQ ID NO:1019; SEQ ID NO:1076), Hsa43 (SEQ ID NO:1024; SEQ ID NO:1081), and Hsa46 (SEQ ID NO:1027; SEQ ID NO:1084).

As described in Example 9, FokI-Cascade RNP protein component-encoding genes are cloned into plasmid vectors containing CMV promoters to enable delivery and expression in mammalian cells. cas genes are linked via 2A "ribosome-skipping" sequences. Furthermore, FokI is fused to Cas8 with a 30-aa linker (SEQ ID NO:455 from Example 3). Additional linkers sequences of varying length and composition are designed and used to connect FokI to the Cas8 protein. Example of such sequences are listed in Table 41.

Cas3 protein from *E. coli* is fused with FokI on the C-terminus using a 30-aa linker. This fusion is further modified with an NLS sequence on the N-terminus (SEQ ID NO:1806). Additional linkers sequences of varying length and composition are designed and used to connect FokI to the Cas3 protein (Table 41 and SEQ ID NO:1804 to SEQ ID NO:1807).

Additional Cas3-FokI fusion constructs are generated wherein the helicase or nuclease activity of the Cas3 protein is inactivated (SEQ ID NO:1808 to SEQ ID NO:1815). Helicase and nuclease activities are impaired by making D452A and D75A modifications, respectively, of the Cas3 protein (Mulepati, S., et al., J. Biol. Chem. 288(31):22184-22192 (2013)).

TABLE 41

Amino Acid Linker Sequences

| Linker length (amino acids) | Amino acid sequence | SEQ ID NO: |
|---|---|---|
| 5 | GGGGS | SEQ ID NO: 817 |
| 10 | GGSGSSGGSG | SEQ ID NO: 819 |
| 17 | ADPTNRAKGLEAVSVAS | SEQ ID NO: 821 |
| 20 | SGSETPGTSESATPESGGSG | SEQ ID NO: 822 |
| 40 | SGSETPGTSESATPESGGSGSSGGSGSSGG SGSSGGSGSS | SEQ ID NO: 823 |

B. Transfection of Plasmids Encoding FokI-Cascade Complex RNPs

Transfection conditions are performed as described in Example 8 with the following modifications. Prior to nucleofection, 5 µl of plasmid vector solution are transferred to individual wells of a 96-well plate. Each well comprises the following three components: 3 µg of a plasmid encoding a set of FokI-Cascade RNP protein components, 3 µg of a plasmid encoding a Cas3-FokI, and 0.5 µg of a plasmid encoding a minimal CRISPR array. The 96-well plate is set up as a matrix to provide all combinations of the three components.

C. Deep Sequencing of gDNA from Transfected Cells

Deep sequencing is performed as described in Example 8 with the following modifications. Instead of primers Y and Z from Table 4 of Example 8, the target-specific primers used in this Example are as follows: SEQ ID NO:1133 and SEQ ID NO:1190 (Hsa37 target site), SEQ ID NO:1138 and SEQ ID NO:1195 (Hsa43 target site), and SEQ ID NO:1141 and SEQ ID NO:1198 (Hsa46 target site).

D. Deep Sequencing Data Analysis

Deep sequencing data analysis is performed as described in Example 8 with the exception that indels ~1 bp to ~25 bp upstream of the FokI-Cascade binding site PAM sequence are tallied. In this manner, the combinations of FokI-Cas8 linker sequences, Cas3-FokI linker sequences, and Cas3 variants that support the most efficient editing can be determined.

As is apparent to one of skill in the art, various modification and variations of the above embodiments can be made without departing from the spirit and scope of this invention. Such modifications and variations are within the scope of this invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10597648B2). An electronic copy of the "Sequence Listing" will also be available from the USPTO upon request and payment of the fee set forth in 37 CFR 1.19(b)(3).

The invention claimed is:

1. A composition comprising:
   a first engineered Class 1 Type I CRISPR-Cas effector complex comprising,
      a first Cas5 subunit protein and a first Cas7 subunit protein,
      a first fusion protein comprising a first Cas8 subunit protein and a first FokI, wherein the N-terminus of the first Cas8 subunit protein or the C-terminus of the first Cas8 subunit protein is covalently connected by a first linker polypeptide to the C-terminus or N-terminus of the first FokI, and wherein the first linker polypeptide has a length of between 10 amino acids to 40 amino acids, and
      a first guide polynucleotide comprising a first spacer capable of binding a first nucleic acid target sequence; and
   a second engineered Class 1 Type I CRISPR-Cas effector complex comprising,
      a second Cas5 subunit protein and a second Cas7 subunit protein,
      a second fusion protein comprising a second Cas8 subunit protein and a second FokI, wherein the N-terminus of the second Cas8 subunit protein or the C-terminus of the second Cas8 subunit protein is covalently connected by a second linker polypeptide to the C-terminus or N-terminus of the second FokI, and wherein the second linker polypeptide has a length of between 10 amino acids to 40 amino acids, and
      a second guide polynucleotide comprising a second spacer capable of binding a second nucleic acid target sequence, wherein a protospacer adjacent motif (PAM) of the second nucleic acid target sequence and a PAM of the first nucleic acid target sequence have an interspacer distance between 20 base pairs to 42 base pairs.

2. The composition of claim 1, wherein the first engineered Class 1 Type I CRISPR-Cas effector complex further comprises a first Cas6 subunit protein and the second engineered Class 1 Type I CRISPR-Cas effector complex further comprises a second Cas6 subunit protein.

3. The composition of claim 1, wherein the first linker polypeptide has a length of between 15 amino acids and 30 amino acids.

4. The composition of claim 3, wherein the first linker polypeptide has a length of between 17 amino acids and 20 amino acids.

5. The composition of claim 1, wherein the second linker polypeptide has a length of between 15 amino acids and 30 amino acids.

6. The composition of claim 5, wherein the second linker polypeptide has a length of between 17 amino acids and 20 amino acids.

7. The composition of claim 1, wherein the length of the first linker polypeptide and the second linker polypeptide are the same.

8. The composition of claim 1, wherein the interspacer distance of the PAM of the second nucleic acid target sequence and the PAM of the first nucleic acid target sequence is between 22 base pairs to 40 base pairs.

9. The composition of claim 8, wherein the interspacer distance of the PAM of the second nucleic acid target sequence and the PAM of the first nucleic acid target sequence is between 26 base pairs to 36 base pairs.

10. The composition of claim 9, wherein the interspacer distance of the PAM of the second nucleic acid target sequence and the PAM of the first nucleic acid target sequence is between 30 base pairs to 34 base pairs.

11. The composition of claim 1, wherein the first FokI and the second FokI comprise monomeric subunits capable of associating to form a homodimer.

12. The composition of claim 1, wherein the first FokI and the second FokI comprise distinct monomeric subunits capable of associating to form a heterodimer.

13. The composition of claim 1, wherein the N-terminus of the first Cas8 subunit protein is covalently connected by the first linker polypeptide to the C-terminus of the first FokI.

14. The composition of claim 1, wherein the C-terminus of the first Cas8 subunit protein is covalently connected by the first linker polypeptide to the N-terminus of the first FokI.

15. The composition of claim 1, wherein the N-terminus of the second Cas8 subunit protein is covalently connected by the second linker polypeptide to the C-terminus of the second FokI.

16. The composition of claim 1, wherein the C-terminus of the second Cas8 subunit protein is covalently connected by the second linker polypeptide to the N-terminus of the second FokI.

17. The composition of claim 1, wherein the first Cas5 subunit protein and the second Cas5 subunit protein comprise identical amino acid sequences, the first Cas7 subunit protein and the second Cas7 subunit protein comprise identical amino acid sequences, and the first Cas8 subunit protein and the second Cas8 subunit protein comprise identical amino acid sequences.

18. The composition of claim 2, wherein the first Cas6 subunit protein and the second Cas6 subunit protein comprise identical amino acid sequences.

19. The composition of claim 1, wherein the first guide polynucleotide comprises RNA.

20. The composition of claim 1, wherein the second guide polynucleotide comprises RNA.

* * * * *

UNITED STATES PATENT AND TRADEMARK OFFICE
CERTIFICATE OF CORRECTION

PATENT NO.          : 10,597,648 B2
APPLICATION NO.     : 16/665316
DATED               : March 24, 2020
INVENTOR(S)         : Peter Sean Cameron, Sanne Eveline Klompe and Samuel Henry Sternberg Page 1 of 1

It is certified that error appears in the above-identified patent and that said Letters Patent is hereby corrected as shown below:

In the Specification
Column 2, Line 22, delete "cash" and insert --cas6--
Column 2, Line 34, delete "Cash" and insert --Cas6--
Column 10, Line 45, delete "Cash" and insert --Cas6--
Column 14, Line 29, delete "Cash" and insert --Cas6--
Column 31, Line 13, delete "Cash" and insert --Cas6--
Column 32, Line 55, delete "cash" and insert --cas6--
Column 37, Line 33, delete "Cash" and insert --Cas6--
Column 38, Line 37, delete "Cash" and insert --Cas6--
Column 39, Line 22, delete "Cash" and insert --Cas6--
Column 61, Line 15, delete "Cash" and insert --Cas6--
Column 62, Line 35, delete "cash" and insert --cas6--
Column 64, Line 35, delete "cash" and insert --cas6--
Column 66, Line 48, delete "cash" and insert --cas6--
Column 67, Line 1, delete "Cash" and insert --Cas6--
Column 70, Line 23, delete "Cash" and insert --Cas6--
Column 71, Line 20, delete "Cash" and insert --Cas6--
Column 100, Line 49, delete "Cash" and insert --Cas6--
Column 101, Line 44, delete "Cash" and insert --Cas6--

Signed and Sealed this
Fifth Day of May, 2020

Andrei Iancu
*Director of the United States Patent and Trademark Office*